(12) United States Patent
Hilpert et al.

(10) Patent No.: US 8,202,885 B2
(45) Date of Patent: Jun. 19, 2012

(54) BRIDGED SIX-MEMBERED RING COMPOUNDS

(75) Inventors: Kurt Hilpert, Hofstetten (CH); Francis Hubler, Hegenheim (FR); Dorte Renneberg, Basel (CH)

(73) Assignee: Actelion Pharmaceuticals Ltd., Allschwil (CH)

( * ) Notice: Subject to any disclaimer, the term of this patent is extended or adjusted under 35 U.S.C. 154(b) by 192 days.

(21) Appl. No.: 12/597,817

(22) PCT Filed: Apr. 25, 2008

(86) PCT No.: PCT/IB2008/051599
§ 371 (c)(1),
(2), (4) Date: Oct. 27, 2009

(87) PCT Pub. No.: WO2008/132679
PCT Pub. Date: Nov. 6, 2008

(65) Prior Publication Data
US 2010/0130545 A1 May 27, 2010

(30) Foreign Application Priority Data

Apr. 27, 2007 (WO) .................. PCT/IB2007/051581

(51) Int. Cl.
| | |
|---|---|
| A61K 31/47 | (2006.01) |
| A61K 31/44 | (2006.01) |
| A61K 31/4184 | (2006.01) |
| A61K 31/417 | (2006.01) |
| C07D 217/12 | (2006.01) |
| C07D 215/14 | (2006.01) |
| C07D 215/12 | (2006.01) |
| C07D 401/12 | (2006.01) |
| C07D 213/24 | (2006.01) |

(52) U.S. Cl. ........ 514/307; 514/311; 514/339; 514/357; 514/394; 548/309.7; 548/340.1; 549/467

(58) Field of Classification Search .................. None
See application file for complete search history.

(56) References Cited

U.S. PATENT DOCUMENTS
| | | | |
|---|---|---|---|
| 4,808,605 A | 2/1989 | Branca et al. | |
| 5,120,759 A | 6/1992 | Hengartner et al. | |
| 6,268,377 B1 | 7/2001 | Waldstreicher et al. | |
| 6,608,097 B2 | 8/2003 | Druzgala et al. | |

FOREIGN PATENT DOCUMENTS
| | | |
|---|---|---|
| EP | 388739 | 9/1990 |
| EP | 609058 | 8/1994 |
| GB | 2289276 | 11/1995 |
| WO | PCT/IB2009/051668 | 10/2008 |
| WO | WO 2008/132679 | 11/2008 |

OTHER PUBLICATIONS

Hamden et al. in the Journal of Medicinal Chemistry (1970), 13(2), 305-308.*
Norris, James F. in Experimental Organic Chemistry, 2nd Edition, McGraw-Hill Book Company, Inc. New York, 1924.*
Foti et al. in Drug Metabolism and Disposition, 39:1188-1185, 2011.*
Kobrin, I. in J Hypertens Suppl. 1997 15(5):S33-40 (Abstract).*
U.S. Appl. No. 13/125,443, filed Apr. 21, 2011, Actelion Pharmaceuticals Ltd.
Villame, J., et al., Effects of Milbefradil, a T- and L-Type Calcium Channel Blocker, on Cardiac Remodeling in the UM-X7.1 Cardiomyopathic Hamster, Cardiovascular Drugs and Therapy, vol. 15, pp. 41-48 (2001).
Ramires, F.J.A., et al., Myocardial Fibrosis Associated with Aldosterone or Angiotensin II Administration: Attenuation by Calcium Channel Blockade, J. Mol. Cell. Cardiol., vol. 30, pp. 475-483, (1998).
Honda, M., et al., Divergent Renal Vasodilator Action of L- and T-type Calcium Antagonists in vivo, J. Hypertens, vol. 19, Issue 11, pp. 2031-2037, (2001).
Clozel, J., et al., Voltage-Gated T-Type Ca2+ Channels and Heart Failure, Proceedings of the Association of American Physicians, vol. 111, No. 5, pp. 429-437, (1999).
Du Souich, P., et al., Nonlinear kinetics and pharmacologic response to miberfradil, Clinical Pharmacology & Therapeutics, vol. 67, No. 3, pp. 249-257, (2000).
Wandel, C., et al., Mibefradil is a P-Glycoprotein Substrate and a Potent Inhibitor of Both P-Glcycoprotein and CYP3A In Vitro, Drug Metabolism and Disposition, vol. 28, No. 8, pp. 895-898, (2000).
Gould, P.L., Salt Selection for Basic Drugs, International Journal of Pharmaceutics, vol. 33, pp. 201-217, (1986).
Remington, The Science and Practice of Pharmacy, 21st Edition, The University of the Sciences in Philadelphia, Part 5, Pharmaceutical Manufacturing, published by Lippincott Williams and Wilkins (2005).
Greene, T.W., et al., Protective Groups in Organic Synthesis, Wiley-Interscience, (1999).
Werstiuk, N. H., et al., Synthesis of bicyclic diones and thiones. Facile methylation of the enolates of bicyclo[2.2.1]heptane-2,s-dione and bicyclo[2.2.2]octane-2,5-dione. An AM1 computational study of bicyclic enolates; Can. J. Chem., vol. 70, (1992).
Wood, G., et al., Bicyclic analogues of cyclohexane-1,4-dione. I. Bicyclo[3•2•2]nonan-6,8-dione[1], Canadian Journal of Chemistry, vol. 46, pp. 3713-3717, (1968).

(Continued)

Primary Examiner — Timothy Thomas
Assistant Examiner — Dennis Heyer
(74) Attorney, Agent, or Firm — Hoxie & Associates LLC

(57) ABSTRACT

The invention relates to compounds of formula (I), wherein $R^1, R^2, R^{1a}, R^{2a}, R^3, R^4, A, B, X, W$ and n are as defined in the description, and pharmaceutically acceptable salts of such compounds. These compounds are useful as calcium channel blockers.

(I)

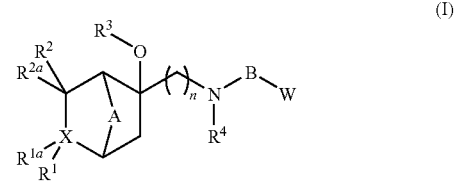

27 Claims, No Drawings

OTHER PUBLICATIONS

Hawkins, R.T., et al., Bicyclo [2.2.1] heptane-2,5-dione: Its Preparation and Reaction with Nucleophiles, J. Org. Chem. vol. 43., No. 24, pp. 4648-4650, (1978).

Jung, M.E., et al., Synthesis of bicyclo [2.2.2]oct-5-en-2-ones via a tandem intermolecular Michael addition intramolecular aldol process (a bridged Robinson annulation), Tetrahedron Letters, vol. 46, pp. 5057-5061, (2005).

Sunden, H., et al., Direct Catalytic Enantioselective Aza-Diels-Alder Reactions, Angewandte Chemie, vol. 44, pp. 4877-4880, (2005).

Musso, D.L., et al., Indanylidenes. 1. Design and Synthesis of (E)-2-(4,6-Difluoro-1-indanylidene)acetamide, a Potent, Centrally Acting Muscle Relaxant with Antiinflammatory and Analgesic Activity, Journal of Medicinal Chemistry, vol. 46, pp. 399-408, (2003).

Katritzky, A.R., et al., Comprehensive Heterocyclic Chemistry, vol. 5, pp. 469-498, (1984).

Grimmett, M.R., Imidazole and Benzimidazole Synthesis, Academic Press, (1997).

Gilchrist, T.L., Heterocyclic Chemistry, The Bath Press, (1985).

Fischer, A., et al., ipso Nitration XXIX. [1] Nitration of substituted 4-methylanisoles and phenols, Canadian Journal of Chemistry, vol. 65, pp. 1233-1240, (1987).

White, A.W., et al., Resistance-Modifying Agents. 9.1 Synthesis and Biological Properties of Benzimidazole Inhibitors of the DNA Repair Enzyme Poly(ADP-ribose) Polymerase, J. Med. Chem., 43, pp. 4084-4097, (2000).

Kitbunnadaj, R., et al., Identification of 4-(1H-Imidazol-4(5)-ylmethyl)pyridine (Immethridine) as a Novel, Potent, and Highly Selective Histamine H3 Receptor Agonist, J. Med. Chem., 47, pp. 2414-2417, (2004).

Cai, W., et al., Metal-assisted Assembly and Stabilization of Collagen-like Triple Helices, J. Am. Chem. Soc., vol. 126, pp. 15030-15031, (2004).

Wolf, C., et al., Use of Highly Active Palladium-Phosphinous Acid Catalysts in Stille, Heck, Amination, and Thiation Reactions of Chloroquinolines, J. Org. Chem., vol. 68, No. 18, pp. 7077-7084, (2003).

Jimonet, P., et al., Riluzole Series. Synthesis and in Vivo "Antiglutamate" Activity of 6-Substituted-2-benzothiazolamines and 3-Substituted-2-imino-benzothiazolines, J. Med. Chem., vol. 42, pp. 2828-2843, (1999).

Hammershoj, P., et al., Synthesis and Properties of 2,3-Dialkynyl-1,4-benzoquinones, Eur. J. Org. Chem., pp. 2786-2794, (2006).

Richardson, W.H., et al., Multi-Bond Fragmentation of tert-Butyl2-Methyl-2- tert-butylperoxyperpropanoate, J. Org. Chem., vol. 41, No. 19, pp. 3182-3187(1976).

Doring, H.J., The Isolated Perfused Heart According to Langendorff Technique—Function—Application, Physiologie Bohemoslovaca, vol. 39, No. 6, pp. 481-504, (1990).

Kligfield, P., et al., A Model of Graded Ischemia in the isolated Perfused Rat Heart, Journal of Applied Physiology, vol. 40, No. 6, pp. 1004-1008, (1976).

* cited by examiner

BRIDGED SIX-MEMBERED RING COMPOUNDS

CROSS REFERENCE TO RELATED APPLICATIONS

This application is a United States Application under 35 U.S.C. 371 claiming benefit of PCT Application No. PCT/IB2008/051599, filed on Apr. 25, 2008, which claims the benefit of PCT Application No. PCT/IB2007/051581, filed on Apr. 27, 2007 the contents of each of which are incorporated herein by reference.

The present invention relates to novel bridged six-membered ring compounds and their use as potent calcium channel blockers in the treatment or prevention of chronic stable angina, hypertension, ischemia (renal and cardiac), cardiac arrhythmias including atrial fibrillation, cardiac hypertrophy, or congestive heart failure, to pharmaceutical compositions containing these derivatives and to processes for their preparation. The bridged six-membered ring compounds derivatives of the present invention may also be used, alone or in pharmaceutical compositions, for the treatment of renal diseases, diabetes and its complications, hyperaldosteronism, epilepsy, neuropathic pain, or cancer in humans and other mammals.

Many cardiovascular disorders have been associated with a 'calcium overload' resulting from an abnormal elevated calcium influx through the plasma membrane of cardiac and vascular smooth muscle cells. There are 3 major pathways through which extracellular calcium can enter these cells: 1) receptor-activated calcium channels, 2) ligand-gated calcium channels and 3) voltage-operated calcium channels (VOCs).

VOCs have been classified into 6 main categories: L (Long-lasting), T (Transient), N (Neuronal), P (Purkinje cells), Q (after P) and R (Remaining or Resistant).

L-type calcium channels are responsible for the inward movement of calcium that initiates contraction in cardiac and smooth muscle cells suggesting a putative application for blockers of these channels in the cardiovascular field. In this view, L-type calcium channel blockers have been used in clinic since the early 60s and are now recommended as a first line of treatment for systolic-diastolic hypertension and angina pectoris.

T-type calcium channels are found in various tissues such as coronary and peripheral vasculature, sinoatrial node and Purkinje fibres, brain, adrenal glands and in the kidney. This broad distribution suggests a T-type channel blocker to have a putative cardiovascular protection, to have en effect on sleep disorders, mood disorders, depression, migraine, hyperaldosteroneemia, preterm labor, urinary incontinence, brain aging or neurodegenerative disorders such as Alzheimers disease.

Mibefradil (Posicor®), the first L-type and T-type calcium channels blocker demonstrated a superior effect over calcium channel blockers, which target the L channel predominantly. Mibefradil was used for the treatment of hypertension and angina without showing negative side-effects often seen by L channel blockers like inotropy, reflex tachycardia, vasoconstrictive hormone release or peripheral edema. Additionally, mibefradil showed a potentially cardioprotective effect (Villame, Cardiovascular Drugs and Therapy 15, 41-28, 2001; Ramires, J Mol Cell Cardiol 1998, 30, 475-83), a renal protective effect (Honda, Hypertension 19, 2031-37, 2001), and showed a positive effect in the treatment of heart failure (Clozel, Proceedings Association American Physicians 1999, 111, 429-37).

Despite the enormous demand for a compound of this profile, mibefradil was withdrawn from the market in 1998 (one year after its launch), due to unacceptable CYP 3A4 drug interactions. Moreover, ECG abnormalities (i.e. QT prolongations) and interaction with the MDR-1 mediated digoxin efflux were also reported (du Souich, Clin Pharmacol Ther 67, 249-57, 2000; Wandel, Drug Metab Dispos 2000, 28, 895-8).

There clearly is a demand for novel compounds, which act as T/L-type calcium channel blockers but have an improved safety profile with respect to mibefradil.

The compounds of the present invention are potent T/L channel blockers and therefore useful in diseases where both, T and L channels are involved.

Various embodiments of the invention are presented hereafter:

1) A first embodiment of the invention relates to bridged six-membered ring compounds of formula (I)

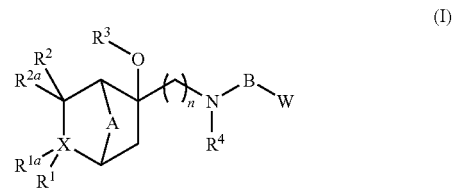

wherein
  X represents a carbon atom, and $R^{1a}$ and $R^{2a}$ together form a bond; or
  X represents a carbon atom, $R^{1a}$ and $R^{2a}$ together form a bond, and $R^1$ and $R^2$ together form the fragment

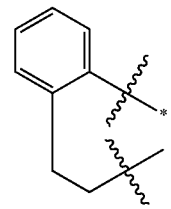

wherein the asterisk indicates the point of attachment of $R^2$; or
  X represents a carbon atom, $R^{1a}$ represents hydrogen or $(C_{1-4})$alkoxy, and $R^{2a}$ represents hydrogen; or
  X represents a carbon atom, $R^1$ and $R^{1a}$ together form a 3H-benzofuran-2,2-diyl group, and $R^2$ and $R^{2a}$ both represent hydrogen; or
  X represents a nitrogen atom, $R^{1a}$ is absent, and $R^2$ and $R^{2a}$ both represent hydrogen or $R^2$ and $R^{2a}$ together form a carbonyl group; and
$R^1$ and $R^2$, if not indicated otherwise, independently represent hydrogen; $(C_{1-5})$alkyl; aryl, which is unsubstituted, or independently mono-, di-, or tri-substituted wherein the substituents are independently selected from the group consisting of $(C_{1-4})$alkyl, $(C_{1-4})$alkoxy, halogen, trifluoromethyl, trifluoromethoxy, cyano, and $(C_{3-6})$cycloalkyl; or heteroaryl, which is unsubstituted, or independently mono-, di-, or tri-substituted wherein the substituents are independently selected from the group consisting of $(C_{1-4})$alkyl, $(C_{1-4})$alkoxy, halogen, cyano, trifluoromethyl, and trifluoromethoxy; with the proviso that in the case $R^2$ represents aryl or heteroaryl, $R^1$ may not represent aryl or heteroaryl, wherein the aryl and heteroaryl independently are unsubstituted or substituted as defined before;

$R^3$ represents hydrogen, or —CO—$R^{31}$;
$R^{31}$ represents ($C_{1-5}$)alkyl, ($C_{1-3}$)fluoroalkyl, ($C_{3-6}$)cycloalkyl, ($C_{3-6}$)cycloalkyl-($C_{1-3}$)alkyl, ($C_{1-5}$)alkoxy, ($C_{1-2}$)alkoxy-($C_{1-3}$)alkyl, or $R^{32}R^{33}$N—;
$R^{32}$ represents ($C_{1-5}$)alkyl;
$R^{33}$ represents hydrogen, or ($C_{1-5}$)alkyl;
n represents the integer 1, 2, 3, or 4;
B represents a group —(CH$_2$)$_m$—, wherein m represents the integer 1, 2, 3, 4, or 5; or B together with $R^4$ and the nitrogen atom to which B and $R^4$ are attached forms a 4- to 6-membered saturated ring;
A represents a linear ($C_{1-3}$)alkan-diyl chain, wherein said linear ($C_{1-3}$)alkan-diyl chain is optionally substituted with one or more methyl;
$R^4$ represents hydrogen; ($C_{1-5}$)alkyl; ($C_{1-2}$)alkoxy-($C_{1-3}$)alkyl; ($C_{1-3}$)fluoroalkyl; ($C_{3-6}$)cycloalkyl; ($C_{3-6}$)cycloalkyl-($C_{1-3}$)alkyl; or $R^4$ together with B and the nitrogen atom to which $R^4$ and B are attached forms a 4- to 6-membered saturated ring;
W represents aryl, which is unsubstituted, mono-, di-, or tri-substituted (especially unsubstituted or di-substituted), wherein the substituents are independently selected from the group consisting of ($C_{1-4}$)alkyl, ($C_{1-4}$)alkoxy, halogen, trifluoromethyl, trifluoromethoxy, cyano, and ($C_{3-6}$)cycloalkyl (especially from ($C_{1-4}$)alkoxy);
or W represents heteroaryl, which is unsubstituted, mono-, di-, or tri-substituted, wherein the substituents are independently selected from the group consisting of ($C_{1-4}$)alkyl, ($C_{1-4}$)alkoxy, halogen, cyano, trifluoromethyl, and trifluoromethoxy;
or W represents a group selected from:

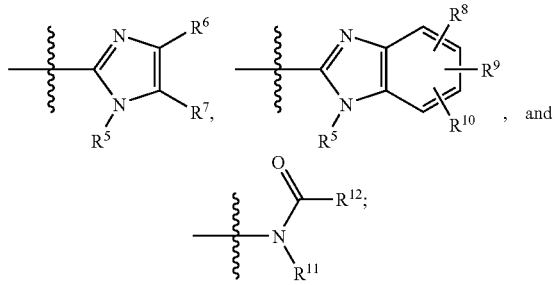

wherein
$R^5$ represents hydrogen, or ($C_{1-5}$)alkyl;
$R^6$ and $R^7$ independently represent hydrogen; ($C_{1-5}$)alkyl; or phenyl, which is independently unsubstituted, mono-, or di-substituted, wherein each substituent is independently selected from the group consisting of ($C_{1-4}$)alkyl, ($C_{1-4}$)alkoxy, halogen and trifluoromethyl;
$R^8$, $R^9$ and $R^{10}$ independently represent hydrogen, halogen, ($C_{1-5}$)alkyl, hydroxy, ($C_{1-5}$)alkoxy, —O—CO—($C_{1-5}$)alkyl, ($C_{1-3}$)fluoroalkyl, ($C_{1-3}$)fluoroalkoxy, —COOH, —CO—($C_{1-5}$)alkoxy, ($C_{1-2}$)alkoxy-($C_{1-4}$)alkoxy, or —NH—CO—($C_{1-5}$)alkyl;
$R^{11}$ represents hydrogen, or ($C_{1-5}$)alkyl;
$R^{12}$ represents ($C_{1-5}$)alkyl, which is unsubstituted, mono-, or di-substituted, wherein each substituent is independently selected from the group consisting of hydroxy and ($C_{1-2}$)alkoxy;
or $R^{12}$ represents a saturated four- to eight-membered carbon ring optionally containing two oxygen ring atoms, whereby the two oxygen ring atoms are not adjacent to each other.

2) Another embodiment of the invention consists of compounds of formula (I) according to embodiment 1), wherein at least one, preferably all of the following characteristics are present:
X represents a carbon atom, and $R^1$, $R^{1a}$, $R^2$ and $R^{2a}$ are as defined for formula (I) according to embodiment 1); or
X represents a nitrogen atom, $R^{1a}$ is absent, $R^2$ and $R^{2a}$ both represent hydrogen, and $R^1$ is as defined for formula (I) according to embodiment 1);
$R^{31}$ represents ($C_{1-5}$)alkyl, ($C_{1-3}$)fluoroalkyl, ($C_{3-6}$)cycloalkyl, ($C_{1-5}$)alkoxy, ($C_{1-2}$)alkoxy-($C_{1-3}$)alkyl or $R^{32}R^{33}$N—;
B represents a group —(CH$_2$)$_m$—, wherein m represents the integer 1, 2, 3, 4, or 5;
$R^4$ represents hydrogen; or ($C_{1-5}$)alkyl.

3) Another embodiment of the invention relates to compounds of formula (I$_P$), which are also compounds of formula (I) according to embodiment 1);

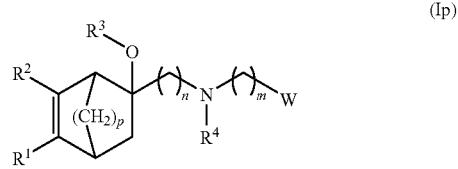

wherein
$R^1$ represents ($C_{1-5}$)alkyl; aryl, which is unsubstituted, mono-, di-, or tri-substituted wherein the substituents are independently selected from the group consisting of ($C_{1-4}$)alkyl, ($C_{1-4}$)alkoxy, halogen, trifluoromethyl, trifluoromethoxy, cyano, and ($C_{3-6}$)cycloalkyl; or heteroaryl, which is unsubstituted, mono-, di-, or tri-substituted wherein the substituents are independently selected from the group consisting of ($C_{1-4}$)alkyl, ($C_{1-4}$)alkoxy, halogen, cyano, trifluoromethyl, and trifluoromethoxy;
$R^2$ represents hydrogen; ($C_{1-5}$)alkyl; aryl, which is unsubstituted, mono-, or di-substituted, wherein each substituent is independently selected from the group consisting of ($C_{1-4}$)alkyl, ($C_{1-4}$)alkoxy, halogen and trifluoromethyl;
with the proviso that in the case $R^2$ represents aryl $R^1$ may not represent aryl or heteroaryl, wherein aryl and heteroaryl are unsubstituted or substituted as defined before;
or $R^1$ and $R^2$ together form the fragment

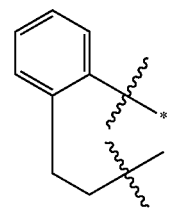

wherein the asterisk indicates the point of attachment of $R^2$;
$R^3$ represents hydrogen, or especially —CO—$R^{31}$;
$R^{31}$ represents ($C_{1-5}$)alkyl, ($C_{1-3}$)fluoroalkyl, ($C_{3-6}$)cycloalkyl, ($C_{1-5}$)alkoxy, or $R^{32}R^{33}$N—;
$R^{32}$ represents ($C_{1-5}$)alkyl;
$R^{33}$ represents hydrogen, or ($C_{1-5}$)alkyl;
n represents the integer 2;
m represents the integer 1, 2, 3, 4, or 5;
p represents the integer 2, or 3;
$R^4$ represents hydrogen, or ($C_{1-5}$)alkyl;

W represents aryl, which is unsubstituted, mono-, di-, or tri-substituted (especially unsubstituted or di-substituted), wherein the substituents are independently selected from the group consisting of $(C_{1-4})$alkyl, $(C_{1-4})$alkoxy, halogen, trifluoromethyl, trifluoromethoxy, cyano, and $(C_{3-6})$cycloalkyl (especially from $(C_{1-4})$alkoxy);

or W represents heteroaryl, which is unsubstituted, mono-, di-, or tri-substituted, wherein the substituents are independently selected from the group consisting of $(C_{1-4})$alkyl, $(C_{1-4})$alkoxy, halogen, cyano, trifluoromethyl, and trifluoromethoxy;

or W represents a group selected from:

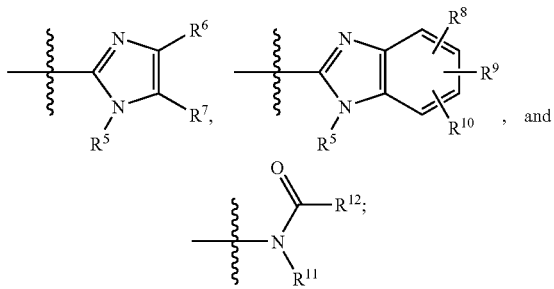

wherein
$R^5$ represents hydrogen, or $(C_{1-5})$alkyl;
$R^6$ and $R^7$ independently represent phenyl, which is unsubstituted, mono-, or di-substituted, wherein each substituent is independently selected from the group consisting of $(C_{1-4})$alkyl, $(C_{1-4})$alkoxy, halogen and trifluoromethyl;
$R^8$, $R^9$ and $R^{10}$ independently represent hydrogen, halogen, $(C_{1-5})$alkyl, hydroxy, $(C_{1-5})$alkoxy, —O—CO—$(C_{1-5})$alkyl, $(C_{1-3})$fluoroalkyl, —COOH, or —CO—$(C_{1-5})$alkoxy;
$R^{11}$ represents hydrogen, or $(C_{1-5})$alkyl;
$R^{12}$ represents $(C_{1-5})$alkyl, which is unsubstituted, mono-, or di-substituted, wherein each substituent is independently selected from the group consisting of hydroxy and $(C_{1-2})$alkoxy;
or $R^{12}$ represents a saturated four- to eight-membered carbon ring optionally containing two oxygen ring atoms, whereby the two oxygen ring atoms are not adjacent to each other.

The following paragraphs provide definitions of the various chemical moieties for the compounds according to the invention and are intended to apply uniformly throughout the specification and claims, unless an otherwise expressly set out definition provides a broader or narrower definition.

In this patent application, a bond interrupted by a wavy line shows the point of attachment of the radical drawn. For example, the radical drawn below

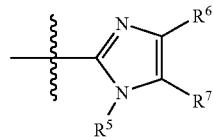

is an imidazol-2-yl group which is further substituted with $R^5$, $R^6$, and $R^7$.

Further, if in a compound of formula (I) "X represents a carbon atom, and $R^{1a}$ and $R^{2a}$ together form a bond", this means that the carbon atom represented by X and the carbon atom to which $R^2$ is attached are linked by a double bond.

The term "$(C_{1-5})$alkyl" means a straight-chain or branched-chain alkyl group with 1 to 5 carbon atoms. Preferred are groups with 1 to 4 carbon atoms. The term "$(C_{x-y})$alkyl" (x and y being an integer) refers to a straight or branched chain alkyl group containing x to y carbon atoms. Examples of $(C_{1-5})$alkyl groups are methyl, ethyl, n-propyl, isopropyl, n-butyl, sec.-butyl, tert.-butyl, isobutyl, n-pentyl, and isopentyl. Preferred are methyl, ethyl, n-propyl, and isopropyl. Most preferred is methyl. For the substituent $R^4$, $R^5$, and $R^{11}$ a preferred example of a $(C_{1-5})$alkyl group is methyl. For the substituent $R^{31}$ a preferred example of a $(C_{1-5})$alkyl group is isopropyl.

Preferred examples of $R^{12}$ representing unsubstituted $(C_{1-5})$alkyl are isopropyl and tert.-butyl. In preferred examples of $R^{12}$ representing "$(C_{1-5})$alkyl, which is mono-, or di-substituted, wherein each substituent is independently selected from the group consisting of hydroxy and $(C_{1-2})$alkoxy" the substituent(s) is/are selected from $(C_{1-2})$alkoxy. Particular examples of such groups are 1,3-dimethoxy-2-methyl-propane-2-yl and 2-methoxy-propane-2-yl.

Preferred examples of $R^{12}$ representing "a saturated four- to eight-membered carbon ring optionally containing two oxygen ring atoms, whereby the two oxygen ring atoms are not adjacent to each other" are 1,3-dioxolan-2-yl, and 1,3-dioxan-2-yl.

The term "linear $(C_{1-3})$alkan-diyl chain, wherein said linear $(C_{1-3})$alkan-diyl chain is optionally substituted with one or more methyl" as used for the substituent A means a straight-chain alkan-diyl group with 1 to 3 carbon atoms which is unsubstituted, or wherein 1 up to the maximum of hydrogen atoms have been replaced by methyl. Examples of such groups are methylen, ethane-1,1-diyl, propane-2,2-diyl, ethane-1,2-diyl, 1,2-dimethyl-ethane-1,2-diyl, 1,1-dimethyl-ethane-1,2-diyl, 2,2-dimethyl-ethane-1,2-diyl, 1,1,2,2-tetramethyl-ethane-1,2-diyl, propane-1,3-diyl, and 2,2-dimethyl-propane-1,3-diyl. Preferred are methylen, propane-2,2-diyl, ethane-1,2-diyl, and propane-1,3-diyl. Most preferred are ethane-1,2-diyl, and propane-1,3-diyl.

The term "$(C_{1-3})$fluoroalkyl" means a straight-chain or branched-chain $(C_{1-3})$alkyl group which is substituted with 1 to 7 fluorine atoms. Examples of $(C_{1-3})$fluoroalkyl groups are 2-trifluoromethyl, 2-fluoroethyl, 2,2-difluoroethyl, 2,2,2-trifluoroethyl, and pentafluoroethyl. Preferred are trifluoromethyl, 2,2,2-trifluoroethyl, and pentafluoroethyl. Most preferred are (especially) trifluoromethyl and 2,2,2-trifluoroethyl. For the substituent $R^{31}$, 2,2,2-trifluoroethyl is preferred. For the substituent $R^4$, 2-fluoroethyl, 2,2-difluoroethyl and 2,2,2-trifluoroethyl are preferred.

The term "$(C_{1-3})$fluoroalkoxy" means a straight-chain or branched-chain $(C_{1-3})$alkyl-O-group which is substituted with 1 to 7 fluorine atoms. Examples of $(C_{1-3})$fluoroalkoxy groups are trifluoromethoxy, and 2,2,2-trifluoroethoxy. Preferred is trifluoromethoxy.

The term "$(C_{3-6})$cycloalkyl" means a saturated cyclic alkyl group with 3 to 6 carbon atoms. Examples of $(C_{3-6})$cycloalkyl groups are cyclopropyl, cyclobutyl, cyclopentyl and cyclohexyl. Preferred is cyclopropyl.

The term "$(C_{3-6})$cycloalkyl-$(C_{1-3})$alkyl" means a $(C_{3-6})$cycloalkyl group as defined before which is attached to the rest of the molecule via a $(C_{1-3})$alkyl group as defined before. Examples are cyclopropyl-methyl, cyclopentyl-methyl and cyclohexyl-methyl; preferred is cyclopropyl-methyl.

Examples of rings wherein "$R^4$ together with B and the nitrogen atom to which $R^4$ and B are attached forms a 4- to 6-membered saturated ring" are azetidin-3-yl, pyrrolidin-3-yl, piperidin-3-yl and piperidin-4-yl.

The term "$(C_{1-5})$alkoxy" means a group of the formula $(C_{1-5})$alkyl-O— in which the term $(C_{1-5})$alkyl has the previously given significance. The term "$(C_{x-y})$alkoxy" (x and y being an integer) refers to a straight or branched chain alkoxy group containing x to y carbon atoms. Examples of $(C_{1-5})$ alkoxy groups are methoxy, ethoxy, n-propoxy, isopropoxy, n-butoxy, isobutoxy, sec-butoxy and tert.-butoxy. Preferred are methoxy and ethoxy.

The term "$(C_{1-2})$alkoxy-$(C_{1-3})$alkyl" means a $(C_{1-2})$ alkoxy-group as defined before which is attached to the rest of the molecule via a $(C_{1-3})$alkyl group as defined before. Examples are 2-methoxy-ethyl, 2-methoxy-2-methyl-ethyl and 3-methoxy-propyl. For the substituent $R^{31}$, 2-methoxy-2-methyl-ethyl is preferred.

An example of a "$(C_{1-2})$alkoxy-$(C_{1-4})$alkoxy" group is 2-methoxy-ethoxy.

An example of a "—O—CO—$(C_{1-5})$alkyl" group is —O—CO—CH(CH$_3$)$_2$.

An example of a "—CO—$(C_{1-5})$alkoxy" group is —CO—OCH$_3$.

An example of a "—NH—CO—$(C_{1-5})$alkyl" group is acetamido.

The term "halogen" means fluoro, chloro, bromo or iodo, especially fluoro or chloro.

The term "aryl" means a phenyl or a naphthyl group. Preferred is a phenyl group. The aryl group may be unsubstituted or mono-, di-, or tri-substituted wherein the substituents are independently selected from the group consisting of $(C_{1-4})$alkyl, $(C_{1-4})$alkoxy, halogen, trifluoromethyl, trifluoromethoxy, cyano, and $(C_{3-6})$cycloalkyl.

Examples of "aryl" groups are phenyl, naphthyl, 2-methylphenyl, 3-methylphenyl, 4-methylphenyl, 3,4-dimethylphenyl, 2,3-dimethylphenyl, 2,4-dimethylphenyl, 2,6-dimethylphenyl, 3,4-dimethylphenyl, 3,5-dimethylphenyl, 2-methoxyphenyl, 3-methoxyphenyl, 4-methoxyphenyl, 2,3-dimethoxyphenyl, 3,4-dimethoxyphenyl, 3,4-diethoxyphenyl, 2-fluorophenyl, 3-fluorophenyl, 4-fluorophenyl, 3,4-difluorophenyl, 3-chlorophenyl, 2,3-dichlorophenyl, 3,4-dichlorophenyl, 2-trifluoromethylphenyl, 3-trifluoromethylphenyl, 4-trifluoromethylphenyl, 2-trifluoromethoxyphenyl, 3-trifluoromethoxyphenyl, 4-trifluoromethoxyphenyl, 2-cyanophenyl, 3-cyanophenyl and 4-cyanophenyl.

In case $R^1$ represents "aryl" the term preferably means the above-mentioned groups which are unsubstituted, mono-, di-, or tri-substituted (preferred mono- or di-substituted), wherein the substituents are independently selected from the group consisting of $(C_{1-4})$alkyl, $(C_{1-4})$alkoxy, halogen and trifluoromethyl. More preferably, the term means the above-mentioned groups which are unsubstituted, mono-, or di-substituted, wherein the substituents are independently selected from the group consisting of $(C_{1-4})$alkyl, $(C_{1-4})$alkoxy and halogen. In a sub-embodiment the aryl group as used for the substituent $R^1$ is preferably unsubstituted. Examples wherein $R^1$ represents "aryl" are phenyl, naphthyl, 2-methylphenyl, 3-methylphenyl, 4-methylphenyl, 2,6-dimethylphenyl, 2-methoxyphenyl, 3-methoxyphenyl, 4-methoxyphenyl, 3-fluorophenyl and 4-fluorophenyl. Preferred is phenyl.

In case $R^2$ represents "aryl" the term preferably means the above-mentioned groups (especially phenyl) which are unsubstituted, mono-, or di-substituted, wherein the substituents are independently selected from the group consisting of $(C_{1-4})$alkyl, $(C_{1-4})$alkoxy, halogen and trifluoromethyl. More preferably, the term means the above-mentioned groups (especially phenyl) which are unsubstituted, mono-, or di-substituted, wherein the substituents are independently selected from the group consisting of $(C_{1-4})$alkyl, $(C_{1-4})$alkoxy and halogen. In a sub-embodiment the aryl group as used for the substituent $R^2$ is preferably unsubstituted.

In case W represents "aryl" the term preferably means the above-mentioned groups (especially phenyl) which are unsubstituted, mono-, di-, or tri-substituted (preferred di-substituted), wherein the substituents are independently selected from the group consisting of $(C_{1-4})$alkyl, $(C_{1-4})$alkoxy, halogen and trifluoromethyl. More preferably, the term means the above-mentioned groups (especially phenyl) which are unsubstituted or di-substituted, wherein the substituents are independently selected from $(C_{1-4})$alkoxy. Examples wherein W represents "aryl" are phenyl, 3,4-dimethoxyphenyl, and 3,4-diethoxyphenyl.

The term "heteroaryl" means a 5- to 14-membered (preferably a 5- to 10-membered) mono-, bi- or tricyclic (preferably mono- or bicyclic) ring or ring system; wherein at least one (preferably all) ring(s) is/are aromatic; wherein said ring or ring system contains 1 to 4 (preferably 1, 2 or 3) heteroatoms independently selected from oxygen, nitrogen and sulfur. Especially, the term "heteroaryl" means a 5- to 10-membered monocyclic or bicyclic aromatic ring containing 1, 2 or 3 heteroatoms independently selected from oxygen, nitrogen and sulfur.

Examples of such heteroaryl groups are pyridyl, pyrimidinyl, pyrazinyl, triazinyl (especially 1,3,4-triazinyl and 1,2,3-triazinyl), furyl, thienyl, pyrrolyl, oxazolyl, isoxazolyl, thiazolyl, isothiazolyl, pyrazolyl, imidazolyl, oxadiazolyl (especially 1,2,3-oxadiazolyl, 1,2,4-oxadiazolyl, 1,2,5-oxadiazolyl and 1,3,4-oxadiazolyl), thiadiazolyl (especially 1,2,4-thiadiazolyl and 1,3,4-thiadiazolyl), triazolyl (especially 1,2,3-triazolyl and 1,2,4-triazolyl), tetrazolyl, benzofuryl, [2,3-dihydro]benzofuryl, isobenzofuryl, benzothiophenyl (especially benzo[b]thiophenyl and benzo[c]thiophenyl), indolyl, isoindolyl, 3H-indolyl, benzoxazolyl, benzisoxazolyl, benzothiazolyl, benzisothiazolyl, benzimidazolyl, indazolyl, benzotriazolyl, thienoimidazolyl (especially 3H-thieno[2,3-d]imidazolyl and 3H-thieno[3,4-d]imidazolyl), imidazooxazolyl (especially 6H-imidazo[4,5-d]oxazolyl), imidazothiazolyl (especially 6H-imidazo[4,5-d]thiazolyl and imidazo[2,1-b]thiazolyl), imidazoimidazolyl (especially 1,4-dihydro-imidazo[4,5-d]imidazolyl and 1,6-dihydro-imidazo[4,5-d]imidazolyl), quinolyl, isoquinolyl, quinolizinyl, quinazolinyl, naphthyridinyl, phthalazinyl, quinoxalinyl, cinnolinyl, pyridopyridyl (especially pyrido[3,4-b]pyridyl, pyrido[3,2-b]pyridyl and pyrido[4,3-b]pyridyl), pyridopyrimidinyl (especially pyrido[4,3-d]pyrimidinyl, pyrido[3,4-d]pyrimidinyl, pyrido[3,2-d]pyrimidinyl and pyrido[2,3-d]pyrimidinyl), pteridinyl, furo[2,3-b]pyridyl, imidazopyridyl (especially imidazo[1,2-a]pyridyl, imidazo[4,5-b]pyridyl and imidazo[4,5-c]pyridyl), purinyl, carbazolyl, xanthenyl and benzoquinolyl.

Preferred examples are pyridyl, pyrimidinyl, pyrazinyl, triazinyl (especially 1,3,4-triazinyl and 1,2,3-triazinyl), furyl, thienyl, pyrrolyl, oxazolyl, isoxazolyl, thiazolyl, isothiazolyl, pyrazolyl, imidazolyl, oxadiazolyl (especially 1,2,3-oxadiazolyl, 1,2,4-oxadiazolyl, 1,2,5-oxadiazolyl and 1,3,4-oxadiazolyl), thiadiazolyl (especially 1,2,4-thiadiazolyl and 1,3,4-thiadiazolyl), triazolyl (especially 1,2,3-triazolyl and 1,2,4-triazolyl), benzofuryl, isobenzofuryl, benzothiophenyl (especially benzo[b]thiophenyl and benzo[c]thiophenyl), indolyl, isoindolyl, benzoxazolyl, benzisoxazolyl, benzothiazolyl, benzisothiazolyl, benzimidazolyl, indazolyl, benzotriazolyl, thienoimidazolyl (especially 3H-thieno[2,3-d]imidazolyl and 3H-thieno[3,4-d]imidazolyl), imidazooxazolyl (especially 6H-imidazo[4,5-d]oxazolyl), imidazothiazolyl (especially 6H-imidazo[4,5-d]thiazolyl and imidazo[2,1-b]

thiazolyl), quinolyl, isoquinolyl, quinazolinyl, naphthyridinyl, phthalazinyl, quinoxalinyl, cinnolinyl, pyridopyridyl (especially pyrido[3,4-b]pyridyl, pyrido[3,2-b]pyridyl and pyrido[4,3-b]pyridyl), furo[2,3-b]pyridyl, imidazopyridyl (especially imidazo[1,2-a]pyridyl, imidazo[4,5-b]pyridyl and imidazo[4,5-c]pyridyl).

In another embodiment, preferred examples of such heteroaryl groups are pyridyl, pyrrolyl, furyl, thienyl, imidazolyl, oxazolyl, isoxazolyl, thiazolyl, isothiazolyl, pyrazolyl, 1,2,3-triazolyl, 1,2,4-triazolyl, 1,2,3-oxadiazolyl, 1,2,4-oxadiazolyl, 1,2,5-oxadiazolyl, 1,3,4-oxadiazolyl, 1,3,4-triazinyl, 1,2,3-triazinyl, benzofuryl, [2,3-dihydro]benzofuryl, isobenzofuryl, benzothienyl, benzotriazolyl, isobenzothienyl, indolyl, isoindolyl, 3H-indolyl, benzimidazolyl, imidazo[1,2-a]pyridyl, benzothiazolyl, benzoxazolyl, quinolizinyl, quinazolinyl, phthalazinyl, quinoxalinyl, cinnolinyl, naphthyridinyl, pyrido[3,4-b]pyridyl, pyrido[3,2-b]pyridyl, pyrido[4,3-b]pyridyl, quinolyl, isoquinolyl, furo[2,3-b]pyridyl, tetrazolyl, purinyl, pteridinyl, carbazolyl, xanthenyl and benzoquinolyl. Most preferred examples of such heteroaryl groups are pyridyl (especially 3-pyridyl), thienyl (especially 2-thienyl), oxazolyl (especially 2-oxazolyl), thiazolyl (especially 2-thiazolyl), quinolyl (especially 3- or 4-quinolyl), isoquinolyl (especially 4-isoquinolyl), and furo[2,3-b]pyridyl (especially 5-furo[2,3-b]pyridyl); and in addition to the above mentioned most preferred groups imidazolyl (especially imidazol-2-yl) and benzimidazolyl (especially benzimidazol-2-yl).

The above-mentioned heteroaryl groups are unsubstituted, mono-, di-, or tri-substituted (especially unsubstituted, mono- or di-substituted), wherein the substituents are independently selected from the group consisting of $(C_{1-4})$alkyl, $(C_{1-4})$alkoxy, halogen, cyano, trifluoromethyl, and trifluoromethoxy (preferably from $(C_{1-4})$alkyl, $(C_{1-4})$alkoxy, and halogen). In another embodiment the above-mentioned heteroaryl groups are preferably unsubstituted.

In case $R^1$ or $R^2$ represent heteroaryl, examples are the above-mentioned heteroaryl groups, especially examples are pyridyl, pyrimidinyl, pyrazinyl, furyl, thienyl, oxazolyl, isoxazolyl, thiazolyl, isothiazolyl, pyrazolyl, oxadiazolyl thiadiazolyl benzofuryl, benzothiophenyl, benzoxazolyl, benzisoxazolyl, benzothiazolyl, benzisothiazolyl, quinolyl, and isoquinolyl. In a sub-embodiment preferred examples of $R^1$ or $R^2$ representing heteroaryl are pyridyl, thienyl, oxazolyl and thiazolyl. In case $R^1$ or $R^2$ represent heteroaryl, said heteroaryl is preferably unsubstituted.

In case W represents heteroaryl, examples are the above-mentioned heteroaryl groups, especially examples are pyridyl, pyrimidinyl, pyrazinyl, imidazolyl, triazolyl, indolyl, benzoxazolyl, benzothiazolyl, benzimidazolyl, thienoimidazolyl, imidazooxazolyl, imidazothiazolyl, quinolyl, isoquinolyl, pyridopyridyl, furo[2,3-b]pyridyl, and imidazopyridyl. Preferred examples are benzimidazolyl, pyridyl, quinolyl, isoquinolyl, and furo[2,3-b]pyridyl. In a sub-embodiment a preferred example of W representing heteroaryl is benzimidazolyl. In another sub-embodiment preferred examples of W representing heteroaryl are pyridyl, quinolyl, isoquinolyl, and furo[2,3-b]pyridyl. In case W represents heteroaryl, said heteroaryl is preferably unsubstituted; with the exception of furo[2,3-b]pyridyl groups which are preferably unsubstituted or mono-substituted with methyl, and imidazolyl and benzimidazolyl groups which are substituted as indicated specifically in the description.

In case W represents an imidazolyl group, said imidazolyl is unsubstituted, mono-, di-, or tri-substituted, wherein the substituents are independently selected from the group consisting of $(C_{1-4})$alkyl, $(C_{1-4})$alkoxy, halogen, cyano, trifluoromethyl, and trifluoromethoxy; or said imidazolyl is substituted by $R^5$, $R^6$ and $R^7$ as defined for formula (I) or for formula $(I_P)$ according to embodiment 1) or 3), respectively.

Preferably, in case W represents an imidazolyl group, said imidazolyl group is

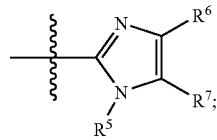

wherein
$R^5$ represents hydrogen (preferred), or $(C_{1-5})$alkyl; and $R^6$ and $R^7$ independently represent hydrogen; $(C_{1-5})$alkyl; or phenyl, which is independently unsubstituted, mono-, or di-substituted, wherein each substituent is independently selected from the group consisting of $(C_{1-4})$alkyl, $(C_{1-4})$alkoxy, halogen and trifluoromethyl.

In case W represents a benzimidazolyl group, said benzimidazolyl is unsubstituted, mono-, di-, or tri-substituted, wherein the substituents are independently selected from the group consisting of $(C_{1-4})$alkyl, $(C_{1-4})$alkoxy, halogen, cyano, trifluoromethyl, and trifluoromethoxy (preferably from $(C_{1-4})$alkyl, $(C_{1-4})$alkoxy, halogen, trifluoromethyl, and trifluoromethoxy); or said benzimidazolyl is substituted by $R^5$, $R^8$, $R^9$ and $R^{10}$ as defined for formula (I) or for formula $(I_P)$ according to embodiment 1) or 3), respectively.

Preferably, in case W represents a benzimidazolyl group, said benzimidazolyl group is

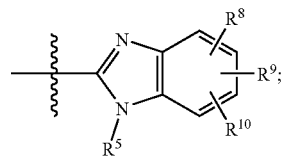

wherein $R^5$ represents hydrogen, or $(C_{1-5})$alkyl; and $R^8$, $R^9$ and $R^{10}$ independently represent hydrogen, halogen, $(C_{1-5})$alkyl, hydroxy, $(C_{1-5})$alkoxy, —O—CO—$(C_{1-5})$alkyl, $(C_{1-3})$fluoroalkyl, $(C_{1-3})$fluoroalkoxy, —COOH, —CO—$(C_{1-5})$alkoxy, $(C_{1-2})$alkoxy-$(C_{1-4})$alkoxy, or —NH—CO—$(C_{1-5})$alkyl.

In the following, further embodiments of the invention are described:

4) A further embodiment of the invention relates to compounds of formula (I) according to embodiments 1) or 2), wherein the configuration of the bridged cyclohexane, cyclohexene or piperidine moiety is such that the $R^3$—O— substituent and the bridge A of the cyclohexane, cyclohexene or piperidine moiety are in cis relation (i.e. the absolute configuration is as depicted in either formula $(I_{E1})$ or formula $(I_{E2})$ below).

5) A further embodiment of the invention relates to compounds of formula (I) according to embodiments 1), 2) or 4), wherein the absolute configuration is as depicted in formula $(I_{E1})$

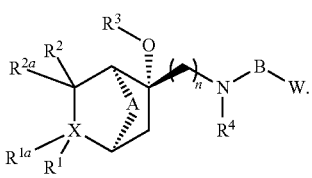

(I$_{E1}$)

6) A further embodiment of the invention relates to compounds of formula (I) according to embodiments 1), 2) or 4), wherein the absolute configuration depicted is as in formula (I$_{E2}$)

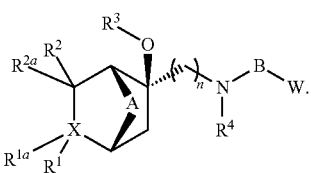

(I$_{E2}$)

7) A further embodiment of the invention relates to compounds of formula (I) according to any one of embodiments 1), 2) or 4) to 6), wherein
X represents a carbon atom, and R$^{1a}$ and R$^{2a}$ together form a bond; or
X represents a carbon atom, R$^{1a}$ and R$^{2a}$ together form a bond, and R$^1$ and R$^2$ together form the fragment

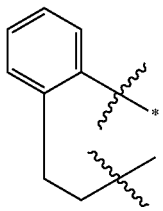

wherein the asterisk indicates the point of attachment of R$^2$; or
X represents a carbon atom, R$^{1a}$ represents hydrogen or (C$_{1-4}$)alkoxy, and R$^{2a}$ represents hydrogen.

8) A further embodiment of the invention relates to compounds of formula (I) according to any one of embodiments 1), 2) or 4) to 7), wherein
X represents a carbon atom, and R$^{1a}$ and R$^{2a}$ together form a bond; or
X represents a carbon atom, R$^{1a}$ and R$^{2a}$ together form a bond, and R$^1$ and R$^2$ together form the fragment

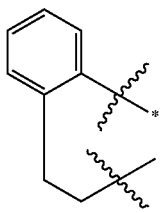

wherein the asterisk indicates the point of attachment of R$^2$.

9) A further embodiment of the invention relates to compounds of formula (I) according to any one of embodiments 1), 2) or 4) to 8), wherein X represents a carbon atom, and R$^{1a}$ and R$^{2a}$ a together form a bond.

10) A further embodiment of the invention relates to compounds of formula (I) according to any one of embodiments 1), 2) or 4) to 6), wherein
X represents a nitrogen atom, R$^{1a}$ is absent, and R$^2$ and R$^{2a}$ both represent hydrogen.

11) A further embodiment of the invention relates to compounds of formula (I) according to any one of embodiments 1), 2), or 4) to 10), wherein R$^1$ and R$^2$, if not indicated otherwise, independently represent hydrogen; (C$_{1-5}$)alkyl; aryl, which is unsubstituted, or independently mono-, di-, or tri-substituted, wherein the substituents are independently selected from the group consisting of (C$_{1-4}$)alkyl, (C$_{1-4}$)alkoxy, halogen and trifluoromethyl; or unsubstituted heteroaryl; with the proviso that in the case R$^2$ represents aryl or heteroaryl, R$^1$ may not represent aryl or heteroaryl, wherein the aryl independently is unsubstituted or substituted as defined before.

12) A further embodiment of the invention relates to compounds of formula (I) according to any one of embodiments 1) to 11), wherein R$^1$ represents aryl (preferred), which is unsubstituted, mono-, di-, or tri-substituted wherein the substituents are independently selected from the group consisting of (C$_{1-4}$)alkyl, (C$_{1-4}$)alkoxy, halogen and trifluoromethyl; or R$^1$ represents unsubstituted heteroaryl.

13) A further embodiment of the invention relates to compounds of formula (I) according to any one of embodiments 1) to 12), wherein R$^2$ represents hydrogen (preferred), or (C$_{1-5}$)alkyl.

14) A further embodiment of the invention relates to compounds of formula (I) according to any one of embodiments 1) to 9), or 11), wherein R$^1$ represents (C$_{1-5}$)alkyl; and R$^2$ represents aryl, which is unsubstituted (preferred), or mono-, or di-substituted, wherein the substituents are independently selected from the group consisting of (C$_{1-4}$)alkyl, (C$_{1-4}$)alkoxy, halogen and trifluoromethyl.

15) A further embodiment of the invention relates to compounds of formula (I) according to any one of embodiments 1), 2) or 4) to 14), wherein A represents —(CH$_2$)$_p$—, wherein p represents the integer 2 or 3.

16) A further embodiment of the invention relates to compounds of formula (I) according to embodiments 3) or 15), wherein p represents the integer 2.

17) A further embodiment of the invention relates to compounds of formula (I) according to embodiments 3) or 15), wherein p represents the integer 3.

18) A further embodiment of the invention relates to compounds of formula (I) according to any one of embodiments 1) to 17), wherein R$^3$ represents —CO—R$^{31}$; and R$^{31}$ represents (C$_{1-5}$)alkyl, (C$_{1-3}$)fluoroalkyl, or (C$_{3-6}$)cycloalkyl.

19) A further embodiment of the invention relates to compounds of formula (I) according to any one of embodiments 1) to 18), wherein
R$^{31}$ represents (C$_{1-5}$)alkyl (preferred), or (C$_{3-6}$)cycloalkyl.

20) A further embodiment of the invention relates to compounds of formula (I) according to any one of embodiments 1) to 17), wherein R$^3$ represents hydrogen.

21) A further embodiment of the invention relates to compounds of formula (I) according to any one of embodiments 1) or 4) to 20), wherein B represents a group —(CH$_2$)$_m$—.

22) A further embodiment of the invention relates to compounds of formula (I) according to any one of embodiments 1) to 21), wherein m represents the integer 1 to 3 (preferably 2 or 3).

23) A further embodiment of the invention relates to compounds of formula (I) according to any one of embodiments 1) to 21), wherein m represents the integer 3.

24) A further embodiment of the invention relates to compounds of formula (I) according to any one of embodiments 1) to 23), wherein n represents the integer 2.

25) A further embodiment of the invention relates to compounds of formula (I) according to any one of embodiments 1) to 24), wherein $R^4$ represents $(C_{1-5})$alkyl.

26) A further embodiment of the invention relates to compounds of formula (I) according to any one of embodiments 1) to 25), wherein
W represents heteroaryl, which is unsubstituted, mono-, di-, or tri-substituted, wherein the substituents are independently selected from the group consisting of $(C_{1-4})$alkyl, $(C_{1-4})$alkoxy, halogen, cyano, trifluoromethyl, and trifluoromethoxy;
or W represents a group selected from:

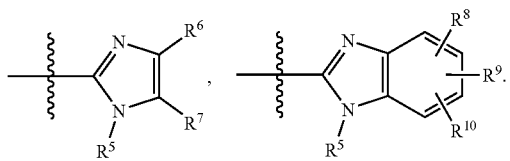

27) A further embodiment of the invention relates to compounds of formula (I) according to any one of embodiments 1), 2) or 4) to 26), wherein W represents a benzimidazolyl group which is unsubstituted, mono-, di-, or tri-substituted, wherein the substituents are independently selected from the group consisting of $(C_{1-4})$alkyl, $(C_{1-4})$alkoxy, halogen, cyano, trifluoromethyl, and trifluoromethoxy; or said benzimidazolyl is substituted by $R^5$, $R^8$, $R^9$ and $R^{10}$, wherein $R^5$, $R^8$, $R^9$ and $R^{10}$ are as defined for formula (I).

28) A further embodiment of the invention relates to compounds of formula (I) according to any one of embodiments 1) to 27), wherein W represents

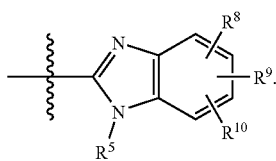

29) A further embodiment of the invention relates to compounds of formula (I) according to any one of embodiments 1), 2), or 4) to 28), wherein
$R^5$ represents hydrogen, or $(C_{1-5})$alkyl; and
$R^8$, $R^9$ and $R^{10}$ independently represent hydrogen, halogen, $(C_{1-5})$alkyl, $(C_{1-5})$alkoxy, $(C_{1-3})$fluoroalkyl, or $(C_{1-3})$fluoroalkoxy.

30) A further embodiment of the invention relates to compounds of formula (I) according to any one of embodiments 1) to 29), wherein W represents

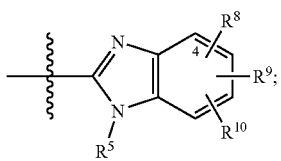

wherein one of $R^8$, $R^9$ or $R^{10}$ is $(C_{1-5})$alkoxy in position 4 of the benzimidazole ring.

31) A further embodiment of the invention relates to compounds of formula (I) according to embodiment 30), wherein W represents

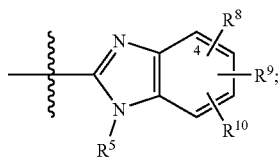

wherein one of $R^8$, $R^9$ or $R^{10}$ is $(C_{1-5})$alkoxy (especially methoxy) in position 4 of the benzimidazole ring, one of $R^8$, $R^9$ or $R^{10}$ is hydrogen and the remaining is selected from the group consisting of hydrogen, halogen, $(C_{1-5})$alkyl, and $(C_{1-5})$alkoxy (especially from hydrogen and $(C_{1-5})$alkyl).

32) A further embodiment of the invention relates to compounds of formula (I) according to embodiment 30), wherein W represents

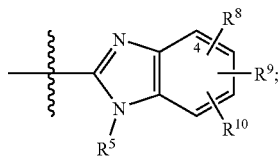

wherein one of $R^8$, $R^9$ or $R^{10}$ is $(C_{1-5})$alkoxy (especially methoxy) in position 4 of the benzimidazole ring, one of $R^8$, $R^9$ or $R^{10}$ is hydrogen and the remaining is selected from $(C_{1-5})$alkoxy (especially methoxy).

33) A further embodiment of the invention relates to compounds of formula (I) according to any one of embodiments 28) to 32), wherein W represents

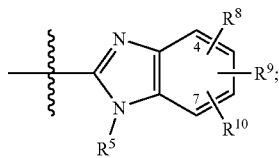

wherein two of $R^8$, $R^9$ or $R^{10}$ are in position 4 and 7, respectively, of the benzimidazole ring; wherein said two of $R^8$, $R^9$ or $R^{10}$ are preferably different from hydrogen.

34) A further embodiment of the invention relates to compounds of formula (I) according to any one of embodiments 1) to 33), wherein W represents

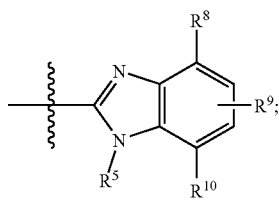

wherein $R^8$ and $R^{10}$ are independently $(C_{1-5})$alkoxy (especially methoxy), and $R^9$ represents hydrogen.

35) A further embodiment of the invention relates to compounds of formula (I) according to any one of embodiments 1) to 26), wherein W represents

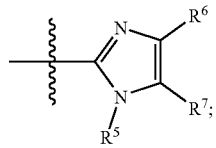

wherein $R^5$ represents hydrogen (preferred) or $(C_{1-5})$alkyl; and $R^6$ and $R^7$ independently represent hydrogen; $(C_{1-5})$alkyl; or phenyl, which is independently unsubstituted, mono-, or di-substituted, wherein each substituent is independently selected from the group consisting of $(C_{1-4})$alkyl, $(C_{1-4})$alkoxy, halogen and trifluoromethyl (especially $R^6$ and $R^7$ both represent unsubstituted phenyl).

36) A further embodiment of the invention relates to compounds of formula (I) according to any one of embodiments 1) to 35), wherein $R^5$ represents hydrogen.

37) A further embodiment of the invention relates to compounds of formula (I) according to any one of embodiments 1) to 35), wherein $R^5$ represents $(C_{1-5})$alkyl.

38) A further embodiment of the invention relates to compounds of formula (I) according to any one of embodiments 1) to 25), wherein W represents —$NR^{11}$—CO—$R^{12}$.

39) A further embodiment of the invention relates to compounds of formula (I) according to any one of embodiments 1) to 25), wherein W represents —$NR^{11}$—CO—$R^{12}$ and $R^{12}$ represents $(C_{1-5})$alkyl, which is unsubstituted, mono-, or di-substituted, wherein each substituent is independently selected from the group consisting of $(C_{1-2})$alkoxy.

40) A further embodiment of the invention relates to compounds of formula (I) according to embodiment 1), wherein at least one, preferably all of the following characteristics are present:
X represents a carbon atom, and $R^{1a}$ and $R^{2a}$ together form a bond; or
X represents a carbon atom, $R^{1a}$ and $R^{2a}$ together form a bond, and $R^1$ and $R^2$ together form the fragment

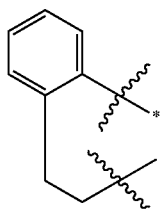

wherein the asterisk indicates the point of attachment of $R^2$;
$R^1$, if not indicated otherwise, represents $(C_{1-5})$alkyl; aryl, which is unsubstituted, mono-, or di-substituted wherein the substituents are independently selected from the group consisting of $(C_{1-4})$alkyl, $(C_{1-4})$alkoxy, and halogen; or unsubstituted heteroaryl;
$R^2$, if not indicated otherwise, represents hydrogen; $(C_{1-5})$alkyl; or phenyl;
$R^3$ represents hydrogen, or —CO—$R^{31}$;
$R^{31}$ represents $(C_{1-5})$alkyl, $(C_{1-3})$fluoroalkyl, or $(C_{3-6})$cycloalkyl;
n represents the integer 2;

B represents a group —$(CH_2)_m$—, wherein m represents the integer 1, 2, or 3;
A represents —$(CH_2)_p$—, wherein p represents the integer 2 or 3;
$R^4$ represents $(C_{1-5})$alkyl;
W represents unsubstituted phenyl, phenyl di-substituted with $(C_{1-4})$alkoxy, or heteroaryl which is unsubstituted or mono-substituted with $(C_{1-4})$alkyl;
or W represents a group selected from:

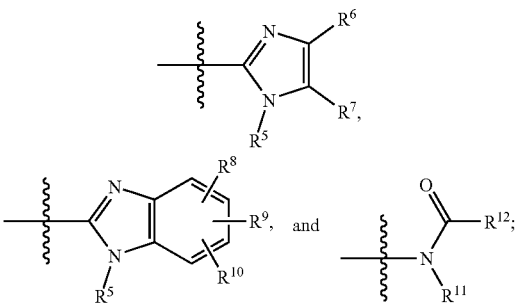

wherein
$R^5$ represents hydrogen, or $(C_{1-5})$alkyl;
$R^6$ and $R^7$ independently represent hydrogen; $(C_{1-5})$alkyl; or phenyl, which is independently unsubstituted, or mono-substituted, wherein the substituent is independently selected from $(C_{1-4})$alkoxy (especially $R^6$ and $R^7$ both represent unsubstituted phenyl);
$R^8$, $R^9$ and $R^{10}$ independently represent hydrogen, halogen, $(C_{1-5})$alkyl, hydroxy, $(C_{1-5})$alkoxy, —O—CO—$(C_{1-5})$alkyl, $(C_{1-3})$fluoroalkyl, $(C_{1-3})$fluoroalkoxy, —CO—$(C_{1-5})$alkoxy, $(C_{1-2})$alkoxy-$(C_{1-4})$alkoxy, or —NH—CO—$(C_{1-5})$alkyl (especially $R^8$, $R^9$ and $R^{10}$ independently represent hydrogen, halogen, $(C_{1-5})$alkyl, hydroxy, $(C_{1-5})$alkoxy, —O—CO—$(C_{1-5})$alkyl, or —CO—$(C_{1-5})$alkoxy);
$R^{11}$ represents hydrogen, or $(C_{1-5})$alkyl; and
$R^{12}$ represents $(C_{1-5})$alkyl, which is unsubstituted, mono-, or di-substituted, wherein each substituent is independently selected from the group consisting of $(C_{1-2})$alkoxy.

The compounds of formula (I) contain stereogenic or asymmetric centers, such as asymmetric carbon atoms. The compounds of formula (I) may thus be present as mixtures of stereoisomers or preferably as pure stereoisomers. Mixtures of stereoisomers may be separated in a manner known to a person skilled in the art.

Where the plural form is used for compounds, salts, pharmaceutical compositions, diseases and the like, this is intended to mean also a single compound, salt, or the like.

Any reference to a compound of formulae (I), ($I_P$), ($I_{E1}$), and/or ($I_{E2}$) is to be understood as referring also to the salts (and especially the pharmaceutically acceptable salts) of such compounds, as appropriate and expedient.

The term "pharmaceutically acceptable salts" refers to non-toxic, inorganic or organic acid and/or base addition salts. Reference can be made to "Salt selection for basic drugs", *Int. J. Pharm.* 1986, 33, 201-217.

In one embodiment examples of preferred compounds of formula (I) are selected from the group consisting of:
(1S,2S,4S)-2-(2-{[3-(1H-Benzoimidazol-2-yl)-propyl]-methyl-amino}-ethyl)-5-phenyl-bicyclo[2.2.2]oct-5-en-2-ol;
(1R,2R,4R)-2-(2-{[3-(1H-Benzoimidazol-2-yl)-propyl]-methyl-amino}-ethyl)-5-phenyl-bicyclo[2.2.2]oct-5-en-2-ol;

(1S,2S,4S)-2-(2-{[3-(1H-Benzoimidazol-2-yl)-propyl]-methyl-amino}-ethyl)-5-(3-methoxy-phenyl)-bicyclo[2.2.2]oct-5-en-2-ol;
(1R,2R,4R)-2-(2-{[3-(1H-Benzoimidazol-2-yl)-propyl]-methyl-amino}-ethyl)-5-(3-methoxy-phenyl)-bicyclo[2.2.2]oct-5-en-2-ol;
(1S,2S,4S)-2-(2-{[3-(1H-Benzoimidazol-2-yl)-propyl]-methyl-amino}-ethyl)-5-(2,6-dimethyl-phenyl)-bicyclo[2.2.2]oct-5-en-2-ol;
(1R,2R,4R)-2-(2-{[3-(1H-Benzoimidazol-2-yl)-propyl]-methyl-amino}-ethyl)-5-(2,6-dimethyl-phenyl)-bicyclo[2.2.2]oct-5-en-2-ol;
(1S,2S,4S)-2-(2-{[3-(1H-Benzoimidazol-2-yl)-propyl]-methyl-amino}-ethyl)-5-o-tolyl-bicyclo[2.2.2]oct-5-en-2-ol;
(1R,2R,4R)-2-(2-{[3-(1H-Benzoimidazol-2-yl)-propyl]-methyl-amino}-ethyl)-5-o-tolyl-bicyclo[2.2.2]oct-5-en-2-ol;
(1S,2S,4S)-2-(2-{[3-(1H-Benzoimidazol-2-yl)-propyl]-methyl-amino}-ethyl)-5-m-tolyl-bicyclo[2.2.2]oct-5-en-2-ol;
(1R,2R,4R)-2-(2-{[3-(1H-Benzoimidazol-2-yl)-propyl]-methyl-amino}-ethyl)-5-m-tolyl-bicyclo[2.2.2]oct-5-en-2-ol;
(1S,2S,4S)-2-(2-{[3-(1H-Benzoimidazol-2-yl)-propyl]-methyl-amino}-ethyl)-5-p-tolyl-bicyclo[2.2.2]oct-5-en-2-ol;
(1R,2R,4R)-2-(2-{[3-(1H-Benzoimidazol-2-yl)-propyl]-methyl-amino}-ethyl)-5-p-tolyl-bicyclo[2.2.2]oct-5-en-2-ol;
(1S,2S,4S)-2-(2-{[3-(1H-Benzoimidazol-2-yl)-propyl]-methyl-amino}-ethyl)-5-(3-fluoro-phenyl)-bicyclo[2.2.2]oct-5-en-2-ol;
(1R,2R,4R)-2-(2-{[3-(1H-Benzoimidazol-2-yl)-propyl]-methyl-amino}-ethyl)-5-(3-fluoro-phenyl)-bicyclo[2.2.2]oct-5-en-2-ol;
(1S,2S,4S)-2-(2-{[3-(1H-Benzoimidazol-2-yl)-propyl]-methyl-amino}-ethyl)-5-(4-fluoro-phenyl)-bicyclo[2.2.2]oct-5-en-2-ol;
(1R,2R,4R)-2-(2-{[3-(1H-Benzoimidazol-2-yl)-propyl]-methyl-amino}-ethyl)-5-(4-fluoro-phenyl)-bicyclo[2.2.2]oct-5-en-2-ol;
(1S,2S,4S)-2-(2-{[3-(1H-Benzoimidazol-2-yl)-propyl]-methyl-amino}-ethyl)-5-pyridin-3-yl-bicyclo[2.2.2]oct-5-en-2-ol;
(1R,2R,4R)-2-(2-{[3-(1H-Benzoimidazol-2-yl)-propyl]-methyl-amino}-ethyl)-5-pyridin-3-yl-bicyclo[2.2.2]oct-5-en-2-ol;
(1S,2S,4S)-2-(2-{[3-(1H-Benzoimidazol-2-yl)-propyl]-methyl-amino}-ethyl)-5-naphthalen-2-yl-bicyclo[2.2.2]oct-5-en-2-ol;
(1R,2R,4R)-2-(2-{[3-(1H-Benzoimidazol-2-yl)-propyl]-methyl-amino}-ethyl)-5-naphthalen-2-yl-bicyclo[2.2.2]oct-5-en-2-ol;
(1S,2S,4S)-2-(2-{[2-(1H-Benzoimidazol-2-yl)-ethyl]-methyl-amino}-ethyl)-5-phenyl-bicyclo[2.2.2]oct-5-en-2-ol;
(1R,2R,4R)-2-(2-{[2-(1H-Benzoimidazol-2-yl)-ethyl]-methyl-amino}-ethyl)-5-phenyl-bicyclo[2.2.2]oct-5-en-2-ol;
(1S,2S,4S)-2-{2-[(1H-Benzoimidazol-2-ylmethyl)-methyl-amino]-ethyl}-5-phenyl-bicyclo[2.2.2]oct-5-en-2-ol;
(1R,2R,4R)-2-{2-[(1H-Benzoimidazol-2-ylmethyl)-methyl-amino]-ethyl}-5-phenyl-bicyclo[2.2.2]oct-5-en-2-ol;
(1S,2S,4S)-2-{2-[Methyl-(3-phenyl-propyl)-amino]-ethyl}-5-phenyl-bicyclo[2.2.2]oct-5-en-2-ol;
(1R,2R,4R)-2-{2-[Methyl-(3-phenyl-propyl)-amino]-ethyl}-5-phenyl-bicyclo[2.2.2]oct-5-en-2-ol;
(1S,2S,4S)-2-(2-{[3-(1H-Benzoimidazol-2-yl)-propyl]-methyl-amino}-ethyl)-6-methyl-5-propyl-bicyclo[2.2.2]oct-5-en-2-ol;
(1R,2R,4R)-2-(2-{[3-(1H-Benzoimidazol-2-yl)-propyl]-methyl-amino}-ethyl)-6-methyl-5-propyl-bicyclo[2.2.2]oct-5-en-2-ol;
(1S,2S,4S)-2-(2-{[3-(1H-Benzoimidazol-2-yl)-propyl]-methyl-amino}-ethyl)-5-methyl-6-phenyl-bicyclo[2.2.2]oct-5-en-2-ol;
(1R,2R,4R)-2-(2-{[3-(1H-Benzoimidazol-2-yl)-propyl]-methyl-amino}-ethyl)-5-methyl-6-phenyl-bicyclo[2.2.2]oct-5-en-2-ol;
(1S,3S,4S)-1,2,3,4,9,10-Hexahydro-3-hydroxy-3-{N-methyl-N-(3-benzimidazol-2-ylpropyl)aminoethyl}-1,4-ethanophenanthrene;
(1R,3R,4R)-1,2,3,4,9,10-Hexahydro-3-hydroxy-3-{N-methyl-N-(3-benzimidazol-2-ylpropyl)aminoethyl}-1,4-ethanophenanthrene;
2-(3-{[2-((1S,2S,4S)-2-Hydroxy-5-phenyl-bicyclo[2.2.2]oct-5-en-2-yl)-ethyl]-methyl-amino}-propyl)-1H-benzoimidazole-4-carboxylic acid methyl ester;
2-(3-{[2-((1R,2R,4R)-2-Hydroxy-5-phenyl-bicyclo[2.2.2]oct-5-en-2-yl)ethyl]-methyl-amino}-propyl)-1H-benzoimidazole-4-carboxylic acid methyl ester;
2-(3-{[2-((1S,2S,4S)-2-Hydroxy-5-phenyl-bicyclo[2.2.2]oct-5-en-2-yl)ethyl]-methyl-amino}-propyl)-1H-benzoimidazole-5-carboxylic acid methyl ester;
2-(3-{[2-((1R,2R,4R)-2-Hydroxy-5-phenyl-bicyclo[2.2.2]oct-5-en-2-yl)ethyl]-methyl-amino}-propyl)-1H-benzoimidazole-5-carboxylic acid methyl ester;
(1S,2S,4S)-2-(2-{[3-(1H-Benzoimidazol-2-yl)-propyl]-methyl-amino}-ethyl)-5-thiophen-2-yl-bicyclo[2.2.2]oct-5-en-2-ol;
(1R,2R,4R)-2-(2-{[3-(1H-Benzoimidazol-2-yl)-propyl]-methyl-amino}-ethyl)-5-thiophen-2-yl-bicyclo[2.2.2]oct-5-en-2-ol;
(1S,2S,4S)-2-(2-{[3-(1H-Benzoimidazol-2-yl)-propyl]-methyl-amino}-ethyl)-5-(4-methoxy-phenyl)-bicyclo[2.2.2]oct-5-en-2-ol;
(1R,2R,4R)-2-(2-{[3-(1H-Benzoimidazol-2-yl)-propyl]-methyl-amino}-ethyl)-5-(4-methoxy-phenyl)-bicyclo[2.2.2]oct-5-en-2-ol;
(1S,2S,4S)-2-(2-{[3-(1H-Benzoimidazol-2-yl)-propyl]-methyl-amino}-ethyl)-5-(2-methoxy-phenyl)-bicyclo[2.2.2]oct-5-en-2-ol;
(1R,2R,4R)-2-(2-{[3-(1H-Benzoimidazol-2-yl)-propyl]-methyl-amino}-ethyl)-5-(2-methoxy-phenyl)-bicyclo[2.2.2]oct-5-en-2-ol;
(1S,2S,4S)-2-(2-{[3-(1H-Benzoimidazol-2-yl)-propyl]-methyl-amino}-ethyl)-5-thiazol-2-yl-bicyclo[2.2.2]oct-5-en-2-ol;
(1R,2R,4R)-2-(2-{[3-(1H-Benzoimidazol-2-yl)-propyl]-methyl-amino}-ethyl)-5-thiazol-2-yl-bicyclo[2.2.2]oct-5-en-2-ol;
(1S,2S,4S)-2-(2-{[3-(1H-Benzoimidazol-2-yl)-propyl]-methyl-amino}-ethyl)-5-oxazol-2-yl-bicyclo[2.2.2]oct-5-en-2-ol;
(1R,2R,4R)-2-(2-{[3-(1H-Benzoimidazol-2-yl)-propyl]-methyl-amino}-ethyl)-5-oxazol-2-yl-bicyclo[2.2.2]oct-5-en-2-ol;
(1S,2S,4S)-2-(2-{[3-(4-Methoxy-1H-benzoimidazol-2-yl)-propyl]-methyl-amino}-ethyl)-5-phenyl-bicyclo[2.2.2]oct-5-en-2-ol;
(1R,2R,4R)-2-(2-{[3-(4-Methoxy-1H-benzoimidazol-2-yl)-propyl]-methyl-amino}-ethyl)-5-phenyl-bicyclo[2.2.2]oct-5-en-2-ol;
(1S,2S,4S)-2-(2-{[3-(5,6-Dichloro-1H-benzoimidazol-2-yl)-propyl]-methyl-amino}-ethyl)-5-phenyl-bicyclo[2.2.2]oct-5-en-2-ol;

(1R,2R,4R)-2-(2-{[3-(5,6-Dichloro-1H-benzoimidazol-2-yl)-propyl]-methyl-amino}-ethyl)-5-phenyl-bicyclo[2.2.2]oct-5-en-2-ol;

(1S,2S,4S)-2-(2-{[3-(5,6-Dimethoxy-1H-benzoimidazol-2-yl)-propyl]-methyl-amino}-ethyl)-5-phenyl-bicyclo[2.2.2]oct-5-en-2-ol;

(1R,2R,4R)-2-(2-{[3-(5,6-Dimethoxy-1H-benzoimidazol-2-yl)-propyl]-methyl-amino}-ethyl)-5-phenyl-bicyclo[2.2.2]oct-5-en-2-ol;

(1S,2S,4S)-2-(2-{[3-(5-Methoxy-1H-benzoimidazol-2-yl)-propyl]-methyl-amino}-ethyl)-5-phenyl-bicyclo[2.2.2]oct-5-en-2-ol;

(1R,2R,4R)-2-(2-{[3-(5-Methoxy-1H-benzoimidazol-2-yl)-propyl]-methyl-amino}-ethyl)-5-phenyl-bicyclo[2.2.2]oct-5-en-2-ol;

(1S,2S,4S)-2-(2-{[3-(7-Methoxy-4-methyl-1H-benzoimidazol-2-yl)-propyl]-methyl-amino}-ethyl)-5-phenyl-bicyclo[2.2.2]oct-5-en-2-ol;

(1R,2R,4R)-2-(2-{[3-(7-Methoxy-4-methyl-1H-benzoimidazol-2-yl)-propyl]-methyl-amino}-ethyl)-5-phenyl-bicyclo[2.2.2]oct-5-en-2-ol;

(1S,2S,4S)-2-(2-{[3-(7-Ethoxy-1H-benzoimidazol-2-yl)-propyl]-methyl-amino}-ethyl)-5-phenyl-bicyclo[2.2.2]oct-5-en-2-ol;

(1R,2R,4R)-2-(2-{[3-(7-Ethoxy-1H-benzoimidazol-2-yl)-propyl]-methyl-amino}-ethyl)-5-phenyl-bicyclo[2.2.2]oct-5-en-2-ol;

(1S,2S,4S)-2-(2-{[2-(4-Methoxy-1H-benzoimidazol-2-yl)-ethyl]-methyl-amino}-ethyl)-5-phenyl-bicyclo[2.2.2]oct-5-en-2-ol;

(1R,2R,4R)-2-(2-{[2-(4-Methoxy-1H-benzoimidazol-2-yl)-ethyl]-methyl-amino}-ethyl)-5-phenyl-bicyclo[2.2.2]oct-5-en-2-ol;

(1S,2S,4S)-2-(2-{[3-(7-Isopropoxy-1H-benzoimidazol-2-yl)-propyl]-methyl-amino}-ethyl)-5-phenyl-bicyclo[2.2.2]oct-5-en-2-ol;

(1R,2R,4R)-2-(2-{[3-(7-Isopropoxy-1H-benzoimidazol-2-yl)-propyl]-methyl-amino}-ethyl)-5-phenyl-bicyclo[2.2.2]oct-5-en-2-ol;

2-(3-{[2-((1S,2S,4S)-2-Hydroxy-5-phenyl-bicyclo[2.2.2]oct-5-en-2-yl)-ethyl]-methyl-amino}-propyl)-3H-benzoimidazol-4-ol;

2-(3-{[2-((1R,2R,4R)-2-Hydroxy-5-phenyl-bicyclo[2.2.2]oct-5-en-2-yl)-ethyl]-methyl-amino}-propyl)-3H-benzoimidazol-4-ol;

(1S,5S,6S)-6-(2-{[3-(7-Methoxy-1H-benzoimidazol-2-yl)-propyl]-methyl-amino}-ethyl)-8-phenyl-bicyclo[3.2.2]non-8-en-6-ol;

(1R,5R,6R)-6-(2-{[3-(7-Methoxy-1H-benzoimidazol-2-yl)-propyl]-methyl-amino}-ethyl)-8-phenyl-bicyclo[3.2.2]non-8-en-6-ol;

(1S,2S,4S)-2-(2-{[3-(4-Methoxy-1-methyl-1H-benzoimidazol-2-yl)-propyl]-methyl-amino}-ethyl)-5-phenyl-bicyclo[2.2.2]oct-5-en-2-ol;

(1R,2R,4R)-2-(2-{[3-(4-Methoxy-1-methyl-1H-benzoimidazol-2-yl)-propyl]-methyl-amino}-ethyl)-5-phenyl-bicyclo[2.2.2]oct-5-en-2-ol;

(1S,2S,4S)-2-(2-{[2-(3,4-Diethoxy-phenyl)-ethyl]-ethyl-amino}-ethyl)-5-phenyl-bicyclo[2.2.2]oct-5-en-2-ol;

(1R,2R,4R)-2-(2-{[2-(3,4-Diethoxy-phenyl)-ethyl]-ethyl-amino}-ethyl)-5-phenyl-bicyclo[2.2.2]oct-5-en-2-ol;

(1S,2S,4S)-2-(2-{[3-(3,4-Dimethoxy-phenyl)-propyl]-methyl-amino}-ethyl)-5-phenyl-bicyclo[2.2.2]oct-5-en-2-ol;

(1R,2R,4R)-2-(2-{[3-(3,4-Dimethoxy-phenyl)-propyl]-methyl-amino}-ethyl)-5-phenyl-bicyclo[2.2.2]oct-5-en-2-ol;

(1S,2S,4S)-2-(2-{[3-(3,4-Diethoxy-phenyl)-propyl]-methyl-amino}-ethyl)-5-phenyl-bicyclo[2.2.2]oct-5-en-2-ol;

(1R,2R,4R)-2-(2-{[3-(3,4-Diethoxy-phenyl)-propyl]-methyl-amino}-ethyl)-5-phenyl-bicyclo[2.2.2]oct-5-en-2-ol;

(1S,2S,4S)-2-{2-[(3-Furo[2,3-b]pyridin-5-yl-propyl)-methyl-amino]ethyl}-5-phenyl-bicyclo[2.2.2]oct-5-en-2-ol;

(1R,2R,4R)-2-{2-[(3-Furo[2,3-b]pyridin-5-yl-propyl)-methyl-amino]ethyl}-5-phenyl-bicyclo[2.2.2]oct-5-en-2-ol;

(1S,2S,4S)-2-(2-{Methyl-[3-(2-methyl-furo[2,3-b]pyridin-5-yl)-propyl]-amino}-ethyl)-5-phenyl-bicyclo[2.2.2]oct-5-en-2-ol;

(1R,2R,4R)-2-(2-{Methyl-[3-(2-methyl-furo[2,3-b]pyridin-5-yl)-propyl]-amino}-ethyl)-5-phenyl-bicyclo[2.2.2]oct-5-en-2-ol;

N-(3-{[2-((1S,2S,4S)-2-Hydroxy-5-phenyl-bicyclo[2.2.2]oct-5-en-2-yl)-ethyl]-methyl-amino}-propyl)-3-methoxy-2-methoxymethyl-2-methyl-propionamide;

N-(3-{[2-((1R,2R,4R)-2-Hydroxy-5-phenyl-bicyclo[2.2.2]oct-5-en-2-yl)-ethyl]-methyl-amino}-propyl)-3-methoxy-2-methoxymethyl-2-methyl-propionamide;

N-(3-{[2-((1S,2S,4S)-2-Hydroxy-5-phenyl-bicyclo[2.2.2]oct-5-en-2-yl)-ethyl]-methyl-amino}-propyl)-2-methoxy-2-methyl-propionamide;

N-(3-{[2-((1R,2R,4R)-2-Hydroxy-5-phenyl-bicyclo[2.2.2]oct-5-en-2-yl)-ethyl]-methyl-amino}-propyl)-2-methoxy-2-methyl-propionamide;

N-(3-{[2-((1S,2S,4S)-2-Hydroxy-5-phenyl-bicyclo[2.2.2]oct-5-en-2-yl)-ethyl]-methyl-amino}-propyl)-2,2-dimethyl-propionamide;

N-(3-{[2-((1R,2R,4R)-2-Hydroxy-5-phenyl-bicyclo[2.2.2]oct-5-en-2-yl)-ethyl]-methyl-amino}-propyl)-2,2-dimethyl-propionamide;

(1S,2S,4S)-2-{2-[Methyl-(3-pyridin-3-yl-propyl)-amino]-ethyl}-5-phenyl-bicyclo[2.2.2]oct-5-en-2-ol;

(1R,2R,4R)-2-{2-[Methyl-(3-pyridin-3-yl-propyl)-amino]-ethyl}-5-phenyl-bicyclo[2.2.2]oct-5-en-2-ol;

(1S,2S,4S)-2-{2-[(3-Isoquinolin-4-yl-propyl)-methyl-amino]-ethyl}-5-phenyl-bicyclo[2.2.2]oct-5-en-2-ol;

(1R,2R,4R)-2-{2-[(3-Isoquinolin-4-yl-propyl)-methyl-amino]-ethyl}-5-phenyl-bicyclo[2.2.2]oct-5-en-2-ol;

(1S,2S,4S)-2-{2-[Methyl-(3-quinolin-3-yl-propyl)-amino]-ethyl}-5-phenyl-bicyclo[2.2.2]oct-5-en-2-ol;

(1R,2R,4R)-2-{2-[Methyl-(3-quinolin-3-yl-propyl)-amino]-ethyl}-5-phenyl-bicyclo[2.2.2]oct-5-en-2-ol;

(1S,2S,4S)-2-{2-[Methyl-(3-quinolin-4-yl-propyl)-amino]-ethyl}-5-phenyl-bicyclo[2.2.2]oct-5-en-2-ol;

(1R,2R,4R)-2-{2-[Methyl-(3-quinolin-4-yl-propyl)-amino]-ethyl}-5-phenyl-bicyclo[2.2.2]oct-5-en-2-ol;

N-(3-{[2-((1S,2S,4S)-2-Hydroxy-5-phenyl-bicyclo[2.2.2]oct-5-en-2-yl)-ethyl]-methyl-amino}-propyl)-3-methoxy-2-methoxymethyl-2,N-dimethyl-propionamide;

N-(3-{[2-((1R,2R,4R)-2-Hydroxy-5-phenyl-bicyclo[2.2.2]oct-5-en-2-yl)-ethyl]-methyl-amino}-propyl)-3-methoxy-2-methoxymethyl-2,N-dimethyl-propionamide;

N-(3-{[2-((1S,2S,4S)-2-Hydroxy-6-methyl-5-propyl-bicyclo[2.2.2]oct-5-en-2-yl)-ethyl]-methyl-amino}-propyl)-3-methoxy-2-methoxymethyl-2, N-dimethyl-propionamide;

N-(3-{[2-((1R,2R,4R)-2-Hydroxy-6-methyl-5-propyl-bicyclo[2.2.2]oct-5-en-2-yl)-ethyl]-methyl-amino}-propyl)-3-methoxy-2-methoxymethyl-2, N-dimethyl-propionamide;

N-(3-{[2-((1S,2S,4S)-2-Hydroxy-5-methyl-6-phenyl-bicyclo[2.2.2]oct-5-en-2-yl)-ethyl]-methyl-amino}-propyl)-3-methoxy-2-methoxymethyl-2, N-dimethyl-propionamide;

N-(3-{[2-((1R,2R,4R)-2-Hydroxy-5-methyl-6-phenyl-bicyclo[2.2.2]oct-5-en-2-yl)-ethyl]-methyl-amino}-propyl)-3-methoxy-2-methoxymethyl-2, N-dimethyl-propionamide;

(1S,2R,4S)-2-(2-{[3-(1H-Benzoimidazol-2-yl)-propyl]-methyl-amino}-ethyl)-5-methyl-6-phenyl-bicyclo[2.2.2]oct-5-en-2-ol;

(1R,2S,4R)-2-(2-{[3-(1H-Benzoimidazol-2-yl)-propyl]-methyl-amino}-ethyl)-5-methyl-6-phenyl-bicyclo[2.2.2]oct-5-en-2-ol;

N-(3-{[2-((1S,2R,4S)-2-Hydroxy-5-methyl-6-phenyl-bicyclo[2.2.2]oct-5-en-2-yl)-ethyl]-methyl-amino}-propyl)-3-methoxy-2-methoxymethyl-2, N-dimethyl-propionamide;

N-(3-{[2-((1R,2S,4R)-2-Hydroxy-5-methyl-6-phenyl-bicyclo[2.2.2]oct-5-en-2-yl)-ethyl]-methyl-amino}-propyl)-3-methoxy-2-methoxymethyl-2, N-dimethyl-propionamide;

N-[2-(3-{[2-((1S,2S,4S)-2-Hydroxy-5-phenyl-bicyclo[2.2.2]oct-5-en-2-yl)-ethyl]-methyl-amino}-propyl)-1H-benzoimidazol-4-yl]-acetamide;

N-[2-(3-{[2-((1R,2R,4R)-2-Hydroxy-5-phenyl-bicyclo[2.2.2]oct-5-en-2-yl)-ethyl]-methyl-amino}-propyl)-1H-benzoimidazol-4-yl]-acetamide;

(1S,2S,4S)-2-(2-{[3-(4-Chloro-1H-benzoimidazol-2-yl)-propyl]-methyl-amino}-ethyl)-5-phenyl-bicyclo[2.2.2]oct-5-en-2-ol;

(1R,2R,4R)-2-(2-{[3-(4-Chloro-1H-benzoimidazol-2-yl)-propyl]-methyl-amino}-ethyl)-5-phenyl-bicyclo[2.2.2]oct-5-en-2-ol;

(1S,2S,4S)-2-(2-{[3-(7-Chloro-4-methoxy-1H-benzoimidazol-2-yl)-propyl]-methyl-amino}-ethyl)-5-phenyl-bicyclo[2.2.2]oct-5-en-2-ol;

(1R,2R,4R)-2-(2-{[3-(7-Chloro-4-methoxy-1H-benzoimidazol-2-yl)-propyl]-methyl-amino}-ethyl)-5-phenyl-bicyclo[2.2.2]oct-5-en-2-ol;

(1S,2S,4S)-2-(2-{[3-(4,6-Dimethoxy-1H-benzoimidazol-2-yl)-propyl]-methyl-amino}-ethyl)-5-phenyl-bicyclo[2.2.2]oct-5-en-2-ol;

(1R,2R,4R)-2-(2-{[3-(4,6-Dimethoxy-1H-benzoimidazol-2-yl)-propyl]-methyl-amino}-ethyl)-5-phenyl-bicyclo[2.2.2]oct-5-en-2-ol;

(1S,2S,4S)-2-(2-{[3-(4,7-Dimethoxy-1H-benzoimidazol-2-yl)-propyl]-methyl-amino}-ethyl)-5-phenyl-bicyclo[2.2.2]oct-5-en-2-ol;

(1R,2R,4R)-2-(2-{[3-(4,7-Dimethoxy-1H-benzoimidazol-2-yl)-propyl]-methyl-amino}-ethyl)-5-phenyl-bicyclo[2.2.2]oct-5-en-2-ol;

(1S,2S,4S)-2-(2-{[3-(4,6-Bis-trifluoromethyl-1H-benzoimidazol-2-yl)-propyl]-methyl-amino}-ethyl)-5-phenyl-bicyclo[2.2.2]oct-5-en-2-ol;

(1R,2R,4R)-2-(2-{[3-(4,6-Bis-trifluoromethyl-1H-benzoimidazol-2-yl)-propyl]-methyl-amino}-ethyl)-5-phenyl-bicyclo[2.2.2]oct-5-en-2-ol;

(1S,2S,4S)-2-[2-({3-[4-(2-Methoxy-ethoxy)-1H-benzoimidazol-2-yl]-propyl}-methyl-amino)-ethyl]-5-phenyl-bicyclo[2.2.2]oct-5-en-2-ol;

(1R,2R,4R)-2-[2-({3-[4-(2-Methoxy-ethoxy)-1H-benzoimidazol-2-yl]-propyl}-methyl-amino)-ethyl]-5-phenyl-bicyclo[2.2.2]oct-5-en-2-ol;

(1S,2S,4S)-2-(2-{[3-(4,5-Dimethoxy-7-methyl-1H-benzoimidazol-2-yl)-propyl]-methyl-amino}-ethyl)-5-phenyl-bicyclo[2.2.2]oct-5-en-2-ol;

(1R,2R,4R)-2-(2-{[3-(4,5-Dimethoxy-7-methyl-1H-benzoimidazol-2-yl)-propyl]-methyl-amino}-ethyl)-5-phenyl-bicyclo[2.2.2]oct-5-en-2-ol;

(1S,5S,6S)-6-(2-{[3-(7-Methoxy-4-methyl-1H-benzoimidazol-2-yl)-propyl]-methyl-amino}-ethyl)-8-phenyl-bicyclo[3.2.2]non-8-en-6-ol;

(1R,5R,6R)-6-(2-{[3-(7-Methoxy-4-methyl-1H-benzoimidazol-2-yl)-propyl]-methyl-amino}-ethyl)-8-phenyl-bicyclo[3.2.2]non-8-en-6-ol;

(1S,2S,4S)-2-(2-{Methyl-[3-(4-trifluoromethoxy-1H-benzoimidazol-2-yl)-propyl]-amino}-ethyl)-5-phenyl-bicyclo[2.2.2]oct-5-en-2-ol;

(1R,2R,4R)-2-(2-{Methyl-[3-(4-trifluoromethoxy-1H-benzoimidazol-2-yl)-propyl]-amino}-ethyl)-5-phenyl-bicyclo[2.2.2]oct-5-en-2-ol;

(1S,5S,6S)-6-(2-{[3-(4,7-Dimethoxy-1H-benzoimidazol-2-yl)-propyl]-methyl-amino}-ethyl)-8-phenyl-bicyclo[3.2.2]non-8-en-6-ol;

(1R,5R,6R)-6-(2-{[3-(4,7-Dimethoxy-1H-benzoimidazol-2-yl)-propyl]-methyl-amino}-ethyl)-8-phenyl-bicyclo[3.2.2]non-8-en-6-ol;

(1R,2R,4R)-2-(2-{[3-(1H-Benzoimidazol-2-yl)-propyl]-methyl-amino}-ethyl)-bicyclo[2.2.2]oct-5-en-2-ol;

(1S,2S,4S)-2-(2-{[3-(1H-Benzoimidazol-2-yl)-propyl]-methyl-amino}-ethyl)-bicyclo[2.2.2]oct-5-en-2-ol;

(1R,2R,4R,5R)-2-(2-{[3-(1H-Benzoimidazol-2-yl)-propyl]-methyl-amino}-ethyl)-5-methoxy-5-phenyl-bicyclo[2.2.2]octan-2-ol;

(1S,2S,4S,5S)-2-(2-{[3-(1H-Benzoimidazol-2-yl)-propyl]-methyl-amino}-ethyl)-5-methoxy-5-phenyl-bicyclo[2.2.2]octan-2-ol;

(1R,2S,4R,5S)-2-(2-{[3-(1H-Benzoimidazol-2-yl)-propyl]-methyl-amino}-ethyl)-5-methoxy-5-phenyl-bicyclo[2.2.2]octan-2-ol;

(1S,2R,4S,5R)-2-(2-{[3-(1H-Benzoimidazol-2-yl)-propyl]-methyl-amino}-ethyl)-5-methoxy-5-phenyl-bicyclo[2.2.2]octan-2-ol;

(1R,2R,4R,5S)-2-(2-{[3-(1H-Benzoimidazol-2-yl)-propyl]-methyl-amino}-ethyl)-5-methoxy-5-phenyl-bicyclo[2.2.2]octan-2-ol;

(1S,2S,4S,5R)-2-(2-{[3-(1H-Benzoimidazol-2-yl)-propyl]-methyl-amino}-ethyl)-5-methoxy-5-phenyl-bicyclo[2.2.2]octan-2-ol;

(1R,2R,4R,5R)-5-(2-{[3-(1H-Benzoimidazol-2-yl)-propyl]-methyl-amino}-ethyl)-3'H-spiro(bicyclo[2.2.2]octane-2,1'-isobenzofuran)-5-ol;

(1S,2S,4S,5S)-5-(2-{[3-(1H-Benzoimidazol-2-yl)-propyl]-methyl-amino}-ethyl)-3'H-spiro(bicyclo[2.2.2]octane-2,1'-isobenzofuran)-5-ol;

(1R,2S,4R,5R)-5-(2-{[3-(1H-Benzoimidazol-2-yl)-propyl]-methyl-amino}-ethyl)-3'H-spiro(bicyclo[2.2.2]octane-2,1'-isobenzofuran)-5-ol; and (1S,2R,4S,5S)-5-(2-{[3-(1H-Benzoimidazol-2-yl)-propyl]-methyl-amino}-ethyl)-3'H-spiro(bicyclo[2.2.2]octane-2,1'-isobenzofuran)-5-ol;

wherein the first 102 compounds of the above list constitute a particular sub-embodiment.

In addition to the compounds of the above list, further examples of preferred compounds of formula (I) are selected from the group consisting of:

Isobutyric acid (1S,2S,4S)-2-(2-{[3-(1H-benzoimidazol-2-yl)-propyl]-methyl-amino}-ethyl)-5-phenyl-bicyclo[2.2.2]oct-5-en-2-yl ester;

Isobutyric acid (1R,2R,4R)-2-(2-{[3-(1H-benzoimidazol-2-yl)-propyl]-methyl-amino}-ethyl)-5-phenyl-bicyclo[2.2.2]oct-5-en-2-yl ester;

Isobutyric acid (1S,2S,4S)-2-(2-{[3-(1H-benzoimidazol-2-yl)-propyl]-methyl-amino}-ethyl)-5-(3-methoxy-phenyl)-bicyclo[2.2.2]oct-5-en-2-yl ester;

Isobutyric acid (1R,2R,4R)-2-(2-{[3-(1H-benzoimidazol-2-yl)-propyl]-methyl-amino}-ethyl)-5-(3-methoxy-phenyl)-bicyclo[2.2.2]oct-5-en-2-yl ester;
Isobutyric acid (1S,2S,4S)-2-(2-{[3-(1H-benzoimidazol-2-yl)-propyl]-methyl-amino}-ethyl)-5-(2,6-dimethyl-phenyl)-bicyclo[2.2.2]oct-5-en-2-yl ester;
Isobutyric acid (1R,2R,4R)-2-(2-{[3-(1H-benzoimidazol-2-yl)-propyl]-methyl-amino}-ethyl)-5-(2,6-dimethyl-phenyl)-bicyclo[2.2.2]oct-5-en-2-yl ester;
Isobutyric acid (1S,2S,4S)-2-(2-{[3-(1H-benzoimidazol-2-yl)-propyl]-methyl-amino}-ethyl)-5-o-tolyl-bicyclo[2.2.2]oct-5-en-2-yl ester;
Isobutyric acid (1R,2R,4R)-2-(2-{[3-(1H-benzoimidazol-2-yl)-propyl]-methyl-amino}-ethyl)-5-o-tolyl-bicyclo[2.2.2]oct-5-en-2-yl ester;
Isobutyric acid (1S,2S,4S)-2-(2-{[3-(1H-benzoimidazol-2-yl)-propyl]-methyl-amino}-ethyl)-5-m-tolyl-bicyclo[2.2.2]oct-5-en-2-yl ester;
Isobutyric acid (1R,2R,4R)-2-(2-{[3-(1H-benzoimidazol-2-yl)-propyl]-methyl-amino}-ethyl)-5-m-tolyl-bicyclo[2.2.2]oct-5-en-2-yl ester;
Isobutyric acid (1S,2S,4S)-2-(2-{[3-(1H-benzoimidazol-2-yl)-propyl]-methyl-amino}-ethyl)-5-p-tolyl-bicyclo[2.2.2]oct-5-en-2-yl ester;
Isobutyric acid (1R,2R,4R)-2-(2-{[3-(1H-benzoimidazol-2-yl)-propyl]-methyl-amino}-ethyl)-5-p-tolyl-bicyclo[2.2.2]oct-5-en-2-yl ester;
Isobutyric acid (1S,2S,4S)-2-(2-{[3-(1H-benzoimidazol-2-yl)-propyl]-methyl-amino}-ethyl)-5-(3-fluoro-phenyl)-bicyclo[2.2.2]oct-5-en-2-yl ester;
Isobutyric acid (1R,2R,4R)-2-(2-{[3-(1H-benzoimidazol-2-yl)-propyl]-methyl-amino}-ethyl)-5-(3-fluoro-phenyl)-bicyclo[2.2.2]oct-5-en-2-yl ester;
Isobutyric acid (1S,2S,4S)-2-(2-{[3-(1H-benzoimidazol-2-yl)-propyl]-methyl-amino}-ethyl)-5-(4-fluoro-phenyl)-bicyclo[2.2.2]oct-5-en-2-yl ester;
Isobutyric acid (1R,2R,4R)-2-(2-{[3-(1H-benzoimidazol-2-yl)-propyl]-methyl-amino}-ethyl)-5-(4-fluoro-phenyl)-bicyclo[2.2.2]oct-5-en-2-yl ester;
Isobutyric acid (1S,2S,4S)-2-(2-{[3-(1H-benzoimidazol-2-yl)-propyl]-methyl-amino}-ethyl)-5-pyridin-3-yl-bicyclo[2.2.2]oct-5-en-2-yl ester;
Isobutyric acid (1R,2R,4R)-2-(2-{[3-(1H-benzoimidazol-2-yl)-propyl]-methyl-amino}-ethyl)-5-pyridin-3-yl-bicyclo[2.2.2]oct-5-en-2-yl ester;
Isobutyric acid (1S,2S,4S)-2-(2-{[3-(1H-benzoimidazol-2-yl)-propyl]-methyl-amino}-ethyl)-5-naphthalen-2-yl-bicyclo[2.2.2]oct-5-en-2-yl ester;
Isobutyric acid (1R,2R,4R)-2-(2-{[3-(1H-benzoimidazol-2-yl)-propyl]-methyl-amino}-ethyl)-5-naphthalen-2-yl-bicyclo[2.2.2]oct-5-en-2-yl ester;
Isobutyric acid (1S,2S,4S)-2-(2-{[2-(1H-benzoimidazol-2-yl)-ethyl]-methyl-amino}-ethyl)-5-phenyl-bicyclo[2.2.2]oct-5-en-2-yl ester;
Isobutyric acid (1R,2R,4R)-2-(2-{[2-(1H-benzoimidazol-2-yl)-ethyl]-methyl-amino}-ethyl)-5-phenyl-bicyclo[2.2.2]oct-5-en-2-yl ester;
Isobutyric acid (1S,2S,4S)-2-{2-[(1H-benzoimidazol-2-ylmethyl)-methyl-amino]-ethyl}-5-phenyl-bicyclo[2.2.2]oct-5-en-2-yl ester;
Isobutyric acid (1R,2R,4R)-2-{2-[(1H-benzoimidazol-2-ylmethyl)-methyl-amino]-ethyl}-5-phenyl-bicyclo[2.2.2]oct-5-en-2-yl ester;
Isobutyric acid (1S,2S,4S)-2-{2-[methyl-(3-phenyl-propyl)-amino]-ethyl}-5-phenyl-bicyclo[2.2.2]oct-5-en-2-yl ester;
Isobutyric acid (1R,2R,4R)-2-{2-[methyl-(3-phenyl-propyl)-amino]-ethyl}-5-phenyl-bicyclo[2.2.2]oct-5-en-2-yl ester;
Isobutyric acid (1S,2S,4S)-2-(2-{[3-(1H-benzoimidazol-2-yl)-propyl]-methyl-amino}-ethyl)-6-methyl-5-propyl-bicyclo[2.2.2]oct-5-en-2-yl ester;
Isobutyric acid (1R,2R,4R)-2-(2-{[3-(1H-benzoimidazol-2-yl)-propyl]-methyl-amino}-ethyl)-6-methyl-5-propyl-bicyclo[2.2.2]oct-5-en-2-yl ester;
Isobutyric acid (1S,2S,4S)-2-(2-{[3-(1H-benzoimidazol-2-yl)-propyl]-methyl-amino}-ethyl)-5-methyl-6-phenyl-bicyclo[2.2.2]oct-5-en-2-yl ester;
Isobutyric acid (1R,2R,4R)-2-(2-{[3-(1H-benzoimidazol-2-yl)-propyl]-methyl-amino}-ethyl)-5-methyl-6-phenyl-bicyclo[2.2.2]oct-5-en-2-yl ester;
Isobutyric acid (1S,2R,4S)-2-(2-{[3-(1H-benzoimidazol-2-yl)-propyl]-methyl-amino}-ethyl)-5-methyl-6-phenyl-bicyclo[2.2.2]oct-5-en-2-yl ester;
Isobutyric acid (1R,2S,4R)-2-(2-{[3-(1H-benzoimidazol-2-yl)-propyl]-methyl-amino}-ethyl)-5-methyl-6-phenyl-bicyclo[2.2.2]oct-5-en-2-yl ester;
Isobutyric acid (1S,3S,4S)-1,2,3,4,9,10-hexahydro-3-hydroxy-3-{N-methyl-N-(3-benzimidazol-2-ylpropyl)aminoethyl}-1,4-ethanophenanthrene ester;
Isobutyric acid (1R,3R,4R)-1,2,3,4,9,10-hexahydro-3-hydroxy-3-{N-methyl-N-(3-benzimidazol-2-ylpropyl)aminoethyl}-1,4-ethanophenanthrene ester;
2-(3-{[2-((1S,2S,4S)-2-Isobutyryloxy-5-phenyl-bicyclo[2.2.2]oct-5-en-2-yl)-ethyl]-methyl-amino}-propyl)-1H-benzoimidazole-4-carboxylic acid methyl ester;
2-(3-{[2-((1R,2R,4R)-2-Isobutyryloxy-5-phenyl-bicyclo[2.2.2]oct-5-en-2-yl)-ethyl]-methyl-amino}-propyl)-1H-benzoimidazole-4-carboxylic acid methyl ester;
2-(3-{[2-((1S,2S,4S)-2-Isobutyryloxy-5-phenyl-bicyclo[2.2.2]oct-5-en-2-yl)-ethyl]-methyl-amino}-propyl)-1H-benzoimidazole-5-carboxylic acid methyl ester;
2-(3-{[2-((1R,2R,4R)-2-Isobutyryloxy-5-phenyl-bicyclo[2.2.2]oct-5-en-2-yl)-ethyl]-methyl-amino}-propyl)-1H-benzoimidazole-5-carboxylic acid methyl ester;
Isobutyric acid (1S,2S,4S)-2-(2-{[3-(1H-benzoimidazol-2-yl)-propyl]-methyl-amino}-ethyl)-5-thiophen-2-yl-bicyclo[2.2.2]oct-5-en-2-yl ester;
Isobutyric acid (1R,2R,4R)-2-(2-{[3-(1H-benzoimidazol-2-yl)-propyl]-methyl-amino}-ethyl)-5-thiophen-2-yl-bicyclo[2.2.2]oct-5-en-2-yl ester;
Isobutyric acid (1S,2S,4S)-2-(2-{[3-(1H-benzoimidazol-2-yl)-propyl]-methyl-amino}-ethyl)-5-(4-methoxy-phenyl)-bicyclo[2.2.2]oct-5-en-2-yl ester;
Isobutyric acid (1R,2R,4R)-2-(2-{[3-(1H-benzoimidazol-2-yl)-propyl]-methyl-amino}-ethyl)-5-(4-methoxy-phenyl)-bicyclo[2.2.2]oct-5-en-2-yl ester;
Isobutyric acid (1S,2S,4S)-2-(2-{[3-(1H-benzoimidazol-2-yl)-propyl]-methyl-amino}-ethyl)-5-(2-methoxy-phenyl)-bicyclo[2.2.2]oct-5-en-2-yl ester;
Isobutyric acid (1R,2R,4R)-2-(2-{[3-(1H-benzoimidazol-2-yl)-propyl]-methyl-amino}-ethyl)-5-(2-methoxy-phenyl)-bicyclo[2.2.2]oct-5-en-2-yl ester;
Isobutyric acid (1S,2S,4S)-2-(2-{[3-(1H-benzoimidazol-2-yl)-propyl]-methyl-amino}-ethyl)-5-thiazol-2-yl-bicyclo[2.2.2]oct-5-en-2-yl ester;
Isobutyric acid (1R,2R,4R)-2-(2-{[3-(1H-benzoimidazol-2-yl)-propyl]-methyl-amino}-ethyl)-5-thiazol-2-yl-bicyclo[2.2.2]oct-5-en-2-yl ester;
Isobutyric acid (1S,2S,4S)-2-(2-{[3-(1H-benzoimidazol-2-yl)-propyl]-methyl-amino}-ethyl)-5-oxazol-2-yl-bicyclo[2.2.2]oct-5-en-2-yl ester;

Isobutyric acid (1R,2R,4R)-2-(2-{[3-(1H-benzoimidazol-2-yl)-propyl]-methyl-amino}-ethyl)-5-oxazol-2-yl-bicyclo[2.2.2]oct-5-en-2-yl ester;
Isobutyric acid (1S,2S,4S)-2-(2-{[3-(4-methoxy-1H-benzoimidazol-2-yl)-propyl]-methyl-amino}-ethyl)-5-phenyl-bicyclo[2.2.2]oct-5-en-2-yl ester;
Isobutyric acid (1R,2R,4R)-2-(2-{[3-(4-methoxy-1H-benzoimidazol-2-yl)-propyl]-methyl-amino}-ethyl)-5-phenyl-bicyclo[2.2.2]oct-5-en-2-yl ester;
Cyclobutanecarboxylic acid (1S,2S,4S)-2-(2-{[3-(4-methoxy-1H-benzoimidazol-2-yl)-propyl]-methyl-amino}-ethyl)-5-phenyl-bicyclo[2.2.2]oct-5-en-2-yl ester;
Cyclobutanecarboxylic acid (1R,2R,4R)-2-(2-{[3-(4-methoxy-1H-benzoimidazol-2-yl)-propyl]-methyl-amino}-ethyl)-5-phenyl-bicyclo[2.2.2]oct-5-en-2-yl ester;
3,3,3-Trifluoro-propionic acid (1S,2S,4S)-2-(2-{[3-(4-methoxy-1H-benzoimidazol-2-yl)-propyl]-methyl-amino}-ethyl)-5-phenyl-bicyclo[2.2.2]oct-5-en-2-yl ester;
3,3,3-Trifluoro-propionic acid (1R,2R,4R)-2-(2-{[3-(4-methoxy-1H-benzoimidazol-2-yl)-propyl]-methyl-amino}-ethyl)-5-phenyl-bicyclo[2.2.2]oct-5-en-2-yl ester;
Isobutyric acid (1S,2S,4S)-2-(2-{[3-(5,6-dichloro-1H-benzoimidazol-2-yl)-propyl]-methyl-amino}-ethyl)-5-phenyl-bicyclo[2.2.2]oct-5-en-2-yl ester;
Isobutyric acid (1R,2R,4R)-2-(2-{[3-(5,6-dichloro-1H-benzoimidazol-2-yl)-propyl]-methyl-amino}-ethyl)-5-phenyl-bicyclo[2.2.2]oct-5-en-2-yl ester;
Cyclopropanecarboxylic acid (1S,2S,4S)-2-(2-{[3-(5,6-dichloro-1H-benzoimidazol-2-yl)-propyl]-methyl-amino}-ethyl)-5-phenyl-bicyclo[2.2.2]oct-5-en-2-yl ester;
Cyclopropanecarboxylic acid (1R,2R,4R)-2-(2-{[3-(5,6-dichloro-1H-benzoimidazol-2-yl)-propyl]-methyl-amino}-ethyl)-5-phenyl-bicyclo[2.2.2]oct-5-en-2-yl ester;
Isobutyric acid (1S,2S,4S)-2-(2-{[3-(5,6-dimethoxy-1H-benzoimidazol-2-yl)-propyl]-methyl-amino}-ethyl)-5-phenyl-bicyclo[2.2.2]oct-5-en-2-yl ester;
Isobutyric acid (1R,2R,4R)-2-(2-{[3-(5,6-dimethoxy-1H-benzoimidazol-2-yl)-propyl]-methyl-amino}-ethyl)-5-phenyl-bicyclo[2.2.2]oct-5-en-2-yl ester;
Isobutyric acid (1S,2S,4S)-2-(2-{[3-(5-methoxy-1H-benzoimidazol-2-yl)-propyl]-methyl-amino}-ethyl)-5-phenyl-bicyclo[2.2.2]oct-5-en-2-yl ester;
Isobutyric acid (1R,2R,4R)-2-(2-{[3-(5-methoxy-1H-benzoimidazol-2-yl)-propyl]-methyl-amino}-ethyl)-5-phenyl-bicyclo[2.2.2]oct-5-en-2-yl ester;
Isobutyric acid (1S,2S,4S)-2-(2-{[3-(7-methoxy-4-methyl-1H-benzoimidazol-2-yl)-propyl]-methyl-amino}-ethyl)-5-phenyl-bicyclo[2.2.2]oct-5-en-2-yl ester;
Isobutyric acid (1R,2R,4R)-2-(2-{[3-(7-methoxy-4-methyl-1H-benzoimidazol-2-yl)-propyl]-methyl-amino}-ethyl)-5-phenyl-bicyclo[2.2.2]oct-5-en-2-yl ester;
Isobutyric acid (1S,2S,4S)-2-(2-{[3-(7-ethoxy-1H-benzoimidazol-2-yl)-propyl]-methyl-amino}-ethyl)-5-phenyl-bicyclo[2.2.2]oct-5-en-2-yl ester;
Isobutyric acid (1R,2R,4R)-2-(2-{[3-(7-ethoxy-1H-benzoimidazol-2-yl)-propyl]-methyl-amino}-ethyl)-5-phenyl-bicyclo[2.2.2]oct-5-en-2-yl ester;
Isobutyric acid (1S,2S,4S)-2-(2-{[2-(7-methoxy-1H-benzoimidazol-2-yl)-ethyl]-methyl-amino}-ethyl)-5-phenyl-bicyclo[2.2.2]oct-5-en-2-yl ester;
Isobutyric acid (1R,2R,4R)-2-(2-{[2-(7-methoxy-1H-benzoimidazol-2-yl)-ethyl]-methyl-amino}-ethyl)-5-phenyl-bicyclo[2.2.2]oct-5-en-2-yl ester;
Isobutyric acid (1S,2S,4S)-2-(2-{[3-(7-isopropoxy-1H-benzoimidazol-2-yl)-propyl]-methyl-amino}-ethyl)-5-phenyl-bicyclo[2.2.2]oct-5-en-2-yl ester;
Isobutyric acid (1R,2R,4R)-2-(2-{[3-(7-isopropoxy-1H-benzoimidazol-2-yl)-propyl]-methyl-amino}-ethyl)-5-phenyl-bicyclo[2.2.2]oct-5-en-2-yl ester;
Isobutyric acid (1S,2S,4S)-2-(2-{[3-(7-isobutyryloxy-1H-benzoimidazol-2-yl)-propyl]-methyl-amino}-ethyl)-5-phenyl-bicyclo[2.2.2]oct-5-en-2-yl ester;
Isobutyric acid (1R,2R,4R)-2-(2-{[3-(7-isobutyryloxy-1H-benzoimidazol-2-yl)-propyl]-methyl-amino}-ethyl)-5-phenyl-bicyclo[2.2.2]oct-5-en-2-yl ester;
Isobutyric acid (1S,2S,4S)-2-(2-{[3-(7-hydroxy-1H-benzoimidazol-2-yl)-propyl]-methyl-amino}-ethyl)-5-phenyl-bicyclo[2.2.2]oct-5-en-2-yl ester;
Isobutyric acid (1R,2R,4R)-2-(2-{[3-(7-hydroxy-1H-benzoimidazol-2-yl)-propyl]-methyl-amino}-ethyl)-5-phenyl-bicyclo[2.2.2]oct-5-en-2-yl ester;
Isobutyric acid (1S,5S,6S)-6-(2-{[3-(7-methoxy-1H-benzoimidazol-2-yl)-propyl]-methyl-amino}-ethyl)-8-phenyl-bicyclo[3.2.2]non-8-en-6-yl ester;
Isobutyric acid (1R,5R,6R)-6-(2-{[3-(7-methoxy-1H-benzoimidazol-2-yl)-propyl]-methyl-amino}-ethyl)-8-phenyl-bicyclo[3.2.2]non-8-en-6-yl ester;
3,3,3-Trifluoro-propionic acid (1S,5S,6S)-6-(2-{[3-(4-methoxy-1H-benzoimidazol-2-yl)-propyl]-methyl-amino}-ethyl)-8-phenyl-bicyclo[3.2.2]non-8-en-6-yl ester;
3,3,3-Trifluoro-propionic acid (1R,5R,6R)-6-(2-{[3-(4-methoxy-1H-benzoimidazol-2-yl)-propyl]-methyl-amino}-ethyl)-8-phenyl-bicyclo[3.2.2]non-8-en-6-yl ester;
Isobutyric acid (1S,2S,4S)-2-(2-{[3-(4-methoxy-1-methyl-1H-benzoimidazol-2-yl)-propyl]-methyl-amino}-ethyl)-5-phenyl-bicyclo[2.2.2]oct-5-en-2-yl ester;
Isobutyric acid (1R,2R,4R)-2-(2-{[3-(4-methoxy-1-methyl-1H-benzoimidazol-2-yl)-propyl]-methyl-amino}-ethyl)-5-phenyl-bicyclo[2.2.2]oct-5-en-2-yl ester;
Isobutyric acid (1S,2S,4S)-2-(2-{[2-(3,4-diethoxy-phenyl)-ethyl]-ethyl-amino}-ethyl)-5-phenyl-bicyclo[2.2.2]oct-5-en-2-yl ester;
Isobutyric acid (1R,2R,4R)-2-(2-{[2-(3,4-diethoxy-phenyl)-ethyl]-ethyl-amino}-ethyl)-5-phenyl-bicyclo[2.2.2]oct-5-en-2-yl ester;
Isobutyric acid (1S,2S,4S)-2-(2-{[3-(3,4-dimethoxy-phenyl)-propyl]-methyl-amino}-ethyl)-5-phenyl-bicyclo[2.2.2]oct-5-en-2-yl ester;
Isobutyric acid (1R,2R,4R)-2-(2-{[3-(3,4-dimethoxy-phenyl)-propyl]-methyl-amino}-ethyl)-5-phenyl-bicyclo[2.2.2]oct-5-en-2-yl ester;
Isobutyric acid (1S,2S,4S)-2-(2-{[3-(3,4-diethoxy-phenyl)-propyl]-methyl-amino}-ethyl)-5-phenyl-bicyclo[2.2.2]oct-5-en-2-yl ester;
Isobutyric acid (1R,2R,4R)-2-(2-{[3-(3,4-diethoxy-phenyl)-propyl]-methyl-amino}-ethyl)-5-phenyl-bicyclo[2.2.2]oct-5-en-2-yl ester;
Isobutyric acid (1S,2S,4S)-2-{2-[(3-furo[2,3-b]pyridin-5-yl-propyl)-methyl-amino]-ethyl}-5-phenyl-bicyclo[2.2.2]oct-5-en-2-yl ester;
Isobutyric acid (1R,2R,4R)-2-{2-[(3-furo[2,3-b]pyridin-5-yl-propyl)-methyl-amino]-ethyl}-5-phenyl-bicyclo[2.2.2]oct-5-en-2-yl ester;
Isobutyric acid (1S,2S,4S)-2-(2-{methyl-[3-(2-methyl-furo[2,3-b]pyridin-5-yl)-propyl]-amino}-ethyl)-5-phenyl-bicyclo[2.2.2]oct-5-en-2-yl ester;
Isobutyric acid (1R,2R,4R)-2-(2-{methyl-[3-(2-methyl-furo[2,3-b]pyridin-5-yl)-propyl]-amino}-ethyl)-5-phenyl-bicyclo[2.2.2]oct-5-en-2-yl ester;

Isobutyric acid (1S,2S,4S)-2-(2-{[3-(3-methoxy-2-methoxymethyl-2-methyl-propionylamino)-propyl]-methyl-amino}-ethyl)-5-phenyl-bicyclo[2.2.2]oct-5-en-2-yl ester;

Isobutyric acid (1R,2R,4R)-2-(2-{[3-(3-methoxy-2-methoxymethyl-2-methyl-propionylamino)-propyl]-methyl-amino}-ethyl)-5-phenyl-bicyclo[2.2.2]oct-5-en-2-yl ester;

Isobutyric acid (1S,2S,4S)-2-(2-{[3-(2-methoxy-2-methyl-propionylamino)-propyl]-methyl-amino}-ethyl)-5-phenyl-bicyclo[2.2.2]oct-5-en-2-yl ester;

Isobutyric acid (1R,2R,4R)-2-(2-{[3-(2-methoxy-2-methyl-propionylamino)-propyl]-methyl-amino}-ethyl)-5-phenyl-bicyclo[2.2.2]oct-5-en-2-yl ester;

Isobutyric acid (1S,2S,4S)-2-(2-{[3-(2,2-dimethyl-propionylamino)-propyl]-methyl-amino}-ethyl)-5-phenyl-bicyclo[2.2.2]oct-5-en-2-yl ester;

Isobutyric acid (1R,2R,4R)-2-(2-{[3-(2,2-dimethyl-propionylamino)-propyl]-methyl-amino}-ethyl)-5-phenyl-bicyclo[2.2.2]oct-5-en-2-yl ester;

Isobutyric acid (1S,2S,4S)-2-{2-[methyl-(3-pyridin-3-yl-propyl)-amino]-ethyl}-5-phenyl-bicyclo[2.2.2]oct-5-en-2-yl ester;

Isobutyric acid (1R,2R,4R)-2-{2-[methyl-(3-pyridin-3-yl-propyl)-amino]-ethyl}-5-phenyl-bicyclo[2.2.2]oct-5-en-2-yl ester;

Isobutyric acid (1S,2S,4S)-2-(2-{[3-(4,5-diphenyl-1H-imidazol-2-yl)-propyl]-methyl-amino}-ethyl)-5-phenyl-bicyclo[2.2.2]oct-5-en-2-yl ester;

Isobutyric acid (1R,2R,4R)-2-(2-{[3-(4,5-diphenyl-1H-imidazol-2-yl)-propyl]-methyl-amino}-ethyl)-5-phenyl-bicyclo[2.2.2]oct-5-en-2-yl ester;

Isobutyric acid (1S,2S,4S)-2-{2-[(3-isoquinolin-4-yl-propyl)-methyl-amino]-ethyl}-5-phenyl-bicyclo[2.2.2]oct-5-en-2-yl ester;

Isobutyric acid (1R,2R,4R)-2-{2-[(3-isoquinolin-4-yl-propyl)-methyl-amino]-ethyl}-5-phenyl-bicyclo[2.2.2]oct-5-en-2-yl ester;

Isobutyric acid (1S,2S,4S)-2-{2-[methyl-(3-quinolin-3-yl-propyl)-amino]-ethyl}-5-phenyl-bicyclo[2.2.2]oct-5-en-2-yl ester;

Isobutyric acid (1R,2R,4R)-2-{2-[methyl-(3-quinolin-3-yl-propyl)-amino]-ethyl}-5-phenyl-bicyclo[2.2.2]oct-5-en-2-yl ester;

Isobutyric acid (1S,2S,4S)-2-{2-[methyl-(3-quinolin-4-yl-propyl)-amino]-ethyl}-5-phenyl-bicyclo[2.2.2]oct-5-en-2-yl ester;

Isobutyric acid (1R,2R,4R)-2-{2-[methyl-(3-quinolin-4-yl-propyl)-amino]-ethyl}-5-phenyl-bicyclo[2.2.2]oct-5-en-2-yl ester;

Isobutyric acid (1S,2S,4S)-2-[2-({3-[(3-methoxy-2-methoxymethyl-2-methyl-propionyl)-methyl-amino]-propyl}-methyl-amino)-ethyl]-5-phenyl-bicyclo[2.2.2]oct-5-en-2-yl ester;

Isobutyric acid (1R,2R,4R)-2-[2-({3-[(3-methoxy-2-methoxymethyl-2-methyl-propionyl)-methyl-amino]-propyl}-methyl-amino)-ethyl]-5-phenyl-bicyclo[2.2.2]oct-5-en-2-yl ester;

Isobutyric acid (1S,2S,4S)-2-[2-({3-[(3-methoxy-2-methoxymethyl-2-methyl-propionyl)-methyl-amino]-propyl}-methyl-amino)-ethyl]-6-methyl-5-propyl-bicyclo[2.2.2]oct-5-en-2-yl ester;

Isobutyric acid (1R,2R,4R)-2-[2-({3-[(3-methoxy-2-methoxymethyl-2-methyl-propionyl)-methyl-amino]-propyl}-methyl-amino)-ethyl]-6-methyl-5-propyl-bicyclo[2.2.2]oct-5-en-2-yl ester;

Isobutyric acid (1S,2S,4S)-2-[2-({3-[(3-methoxy-2-methoxymethyl-2-methyl-propionyl)-methyl-amino]-propyl}-methyl-amino)-ethyl]-5-methyl-6-phenyl-bicyclo[2.2.2]oct-5-en-2-yl ester;

Isobutyric acid (1R,2R,4R)-2-[2-({3-[(3-methoxy-2-methoxymethyl-2-methyl-propionyl)-methyl-amino]-propyl}-methyl-amino)-ethyl]-5-methyl-6-phenyl-bicyclo[2.2.2]oct-5-en-2-yl ester;

Isobutyric acid (1S,2R,4S)-2-[2-({3-[(3-methoxy-2-methoxymethyl-2-methyl-propionyl)-methyl-amino]-propyl}-methyl-amino)-ethyl]-5-methyl-6-phenyl-bicyclo[2.2.2]oct-5-en-2-yl ester;

Isobutyric acid (1R,2S,4R)-2-[2-({3-[(3-methoxy-2-methoxymethyl-2-methyl-propionyl)-methyl-amino]-propyl}-methyl-amino)-ethyl]-5-methyl-6-phenyl-bicyclo[2.2.2]oct-5-en-2-yl ester;

2,2-Dimethyl-propionic acid (1S,2S,4S)-2-(2-{[3-(4-methoxy-1H-benzoimidazol-2-yl)-propyl]-methyl-amino}-ethyl)-5-phenyl-bicyclo[2.2.2]oct-5-en-2-yl ester;

2,2-Dimethyl-propionic acid (1R,2R,4R)-2-(2-{[3-(4-methoxy-1H-benzoimidazol-2-yl)-propyl]-methyl-amino}-ethyl)-5-phenyl-bicyclo[2.2.2]oct-5-en-2-yl ester;

Isopropyl-carbamic acid (1S,2S,4S)-2-(2-{[3-(4-methoxy-1H-benzoimidazol-2-yl)-propyl]-methyl-amino}-ethyl)-5-phenyl-bicyclo[2.2.2]oct-5-en-2-yl ester;

Isopropyl-carbamic acid (1R,2R,4R)-2-(2-{[3-(4-methoxy-1H-benzoimidazol-2-yl)-propyl]-methyl-amino}-ethyl)-5-phenyl-bicyclo[2.2.2]oct-5-en-2-yl ester;

2-Methoxy-2-methyl-propionic acid (1S,2S,4S)-2-(2-{[3-(4-methoxy-1H-benzoimidazol-2-yl)-propyl]-methyl-amino}-ethyl)-5-phenyl-bicyclo[2.2.2]oct-5-en-2-yl ester;

2-Methoxy-2-methyl-propionic acid (1R,2R,4R)-2-(2-{[3-(4-methoxy-1H-benzoimidazol-2-yl)-propyl]-methyl-amino}-ethyl)-5-phenyl-bicyclo[2.2.2]oct-5-en-2-yl ester;

Carbonic acid isopropyl ester (1S,2S,4S)-2-(2-{[3-(4-methoxy-1H-benzoimidazol-2-yl)-propyl]-methyl-amino}-ethyl)-5-phenyl-bicyclo[2.2.2]oct-5-en-2-yl ester;

Carbonic acid isopropyl ester (1R,2R,4R)-2-(2-{[3-(4-methoxy-1H-benzoimidazol-2-yl)-propyl]-methyl-amino}-ethyl)-5-phenyl-bicyclo[2.2.2]oct-5-en-2-yl ester;

Isobutyric acid (1S,2S,4S)-2-(2-{[3-(4-acetylamino-1H-benzoimidazol-2-yl)-propyl]-methyl-amino}-ethyl)-5-phenyl-bicyclo[2.2.2]oct-5-en-2-yl ester;

Isobutyric acid (1R,2R,4R)-2-(2-{[3-(4-acetylamino-1H-benzoimidazol-2-yl)-propyl]-methyl-amino}-ethyl)-5-phenyl-bicyclo[2.2.2]oct-5-en-2-yl ester;

Isobutyric acid (1S,2S,4S)-2-(2-{[3-(4-chloro-1H-benzoimidazol-2-yl)-propyl]-methyl-amino}-ethyl)-5-phenyl-bicyclo[2.2.2]oct-5-en-2-yl ester;

Isobutyric acid (1R,2R,4R)-2-(2-{[3-(4-chloro-1H-benzoimidazol-2-yl)-propyl]-methyl-amino}-ethyl)-5-phenyl-bicyclo[2.2.2]oct-5-en-2-yl ester;

Isobutyric acid (1S,2S,4S)-2-(2-{[3-(7-chloro-4-methoxy-1H-benzoimidazol-2-yl)-propyl]-methyl-amino}-ethyl)-5-phenyl-bicyclo[2.2.2]oct-5-en-2-yl ester;

Isobutyric acid (1R,2R,4R)-2-(2-{[3-(7-chloro-4-methoxy-1H-benzoimidazol-2-yl)-propyl]-methyl-amino}-ethyl)-5-phenyl-bicyclo[2.2.2]oct-5-en-2-yl ester;

Isobutyric acid (1S,2S,4S)-2-(2-{[3-(4,6-dimethoxy-1H-benzoimidazol-2-yl)-propyl]-methyl-amino}-ethyl)-5-phenyl-bicyclo[2.2.2]oct-5-en-2-yl ester;

Isobutyric acid (1R,2R,4R)-2-(2-{[3-(4,6-dimethoxy-1H-benzoimidazol-2-yl)-propyl]-methyl-amino}-ethyl)-5-phenyl-bicyclo[2.2.2]oct-5-en-2-yl ester;

Isobutyric acid (1S,2S,4S)-2-(2-{[3-(4,7-dimethoxy-1H-benzoimidazol-2-yl)-propyl]-methyl-amino}-ethyl)-5-phenyl-bicyclo[2.2.2]oct-5-en-2-yl ester;
Isobutyric acid (1R,2R,4R)-2-(2-{[3-(4,7-dimethoxy-1H-benzoimidazol-2-yl)-propyl]-methyl-amino}-ethyl)-5-phenyl-bicyclo[2.2.2]oct-5-en-2-yl ester;
Isobutyric acid (1S,2S,4S)-2-(2-{[3-(4,6-bis-trifluoromethyl-1H-benzoimidazol-2-yl)-propyl]-methyl-amino}-ethyl)-5-phenyl-bicyclo[2.2.2]oct-5-en-2-yl ester;
Isobutyric acid (1R,2R,4R)-2-(2-{[3-(4,6-bis-trifluoromethyl-1H-benzoimidazol-2-yl)-propyl]-methyl-amino}-ethyl)-5-phenyl-bicyclo[2.2.2]oct-5-en-2-yl ester;
Isobutyric acid (1S,2S,4S)-2-[2-({3-[4-(2-methoxy-ethoxy)-1H-benzoimidazol-2-yl]-propyl}-methyl-amino)-ethyl]-5-phenyl-bicyclo[2.2.2]oct-5-en-2-yl ester;
Isobutyric acid (1R,2R,4R)-2-[2-({3-[4-(2-methoxy-ethoxy)-1H-benzoimidazol-2-yl]-propyl}-methyl-amino)-ethyl]-5-phenyl-bicyclo[2.2.2]oct-5-en-2-yl ester;
Isobutyric acid (1S,2S,4S)-2-(2-{[3-(4,5-dimethoxy-7-methyl-1H-benzoimidazol-2-yl)-propyl]-methyl-amino}-ethyl)-5-phenyl-bicyclo[2.2.2]oct-5-en-2-yl ester;
Isobutyric acid (1R,2R,4R)-2-(2-{[3-(4,5-dimethoxy-7-methyl-1H-benzoimidazol-2-yl)-propyl]-methyl-amino}-ethyl)-5-phenyl-bicyclo[2.2.2]oct-5-en-2-yl ester;
Isobutyric acid (1S,5S,6S)-6-(2-{[3-(7-methoxy-4-methyl-1H-benzoimidazol-2-yl)-propyl]-methyl-amino}-ethyl)-8-phenyl-bicyclo[3.2.2]non-8-en-6-yl ester;
Isobutyric acid (1R,5R,6R)-6-(2-{[3-(7-methoxy-4-methyl-1H-benzoimidazol-2-yl)-propyl]-methyl-amino}-ethyl)-8-phenyl-bicyclo[3.2.2]non-8-en-6-yl ester;
Isobutyric acid (1S,2S,4S)-2-(2-{methyl-[3-(4-trifluoromethoxy-1H-benzoimidazol-2-yl)-propyl]-amino}-ethyl)-5-phenyl-bicyclo[2.2.2]oct-5-en-2-yl ester;
Isobutyric acid (1R,2R,4R)-2-(2-{methyl-[3-(4-trifluoromethoxy-1H-benzoimidazol-2-yl)-propyl]amino}-ethyl)-5-phenyl-bicyclo[2.2.2]oct-5-en-2-yl ester;
Isobutyric acid (1S,5S,6S)-6-(2-{[3-(4,7-dimethoxy-1H-benzoimidazol-2-yl)-propyl]-methyl-amino}-ethyl)-8-phenyl-bicyclo[3.2.2]non-8-en-6-yl ester;
Isobutyric acid (1R,5R,6R)-6-(2-{[3-(4,7-dimethoxy-1H-benzoimidazol-2-yl)-propyl]-methyl-amino}-ethyl)-8-phenyl-bicyclo[3.2.2]non-8-en-6-yl ester;
Isobutyric acid (1S,2S,4S)-2-(2-{methyl-[3-(4-methyl-5-phenyl-1H-imidazol-2-yl)-propyl]-amino}-ethyl)-5-phenyl-bicyclo[2.2.2]oct-5-en-2-yl ester;
Isobutyric acid (1R,2R,4R)-2-(2-{methyl-[3-(4-methyl-5-phenyl-1H-imidazol-2-yl)-propyl]-amino}-ethyl)-5-phenyl-bicyclo[2.2.2]oct-5-en-2-yl ester;
Isobutyric acid (1S,2S,4S)-2-[2-({3-[5-(2-methoxy-phenyl)-1H-imidazol-2-yl]-propyl}-methyl-amino)-ethyl]-5-phenyl-bicyclo[2.2.2]oct-5-en-2-yl ester;
Isobutyric acid (1R,2R,4R)-2-[2-({3-[5-(2-methoxy-phenyl)-1H-imidazol-2-yl]-propyl}-methyl-amino)-ethyl]-5-phenyl-bicyclo[2.2.2]oct-5-en-2-yl ester;
Isobutyric acid (1R,2R,4R,5R)-2-(2-{[3-(1H-benzoimidazol-2-yl)-propyl]-methyl-amino}-ethyl)-5-phenyl-bicyclo[2.2.2]oct-2-yl ester;
Isobutyric acid (1S,2S,4S,5R)-2-(2-{[3-(1H-benzoimidazol-2-yl)-propyl]-methyl-amino}-ethyl)-5-phenyl-bicyclo[2.2.2]oct-2-yl ester;
Isobutyric acid (1R,2R,4R,5S)-2-(2-{[3-(1H-benzoimidazol-2-yl)-propyl]-methyl-amino}-ethyl)-5-phenyl-bicyclo[2.2.2]oct-2-yl ester;
Isobutyric acid (1S,2S,4S,5S)-2-(2-{[3-(1H-benzoimidazol-2-yl)-propyl]-methyl-amino}-ethyl)-5-phenyl-bicyclo[2.2.2]oct-2-yl ester;
Isobutyric acid (1R,2R,4R)-2-(2-{[3-(1H-benzoimidazol-2-yl)-propyl]-methyl-amino}-ethyl)-bicyclo[2.2.2]oct-5-en-2-yl ester;
Isobutyric acid (1S,2S,4S)-2-(2-{[3-(1H-benzoimidazol-2-yl)-propyl]-methyl-amino}-ethyl)-bicyclo[2.2.2]oct-5-en-2-yl ester;
Isobutyric acid (1R,2R,4R,5R)-2-(2-{[3-(1H-benzoimidazol-2-yl)-propyl]-methyl-amino}-ethyl)-5-methoxy-5-phenyl-bicyclo[2.2.2]oct-2-yl ester;
Isobutyric acid (1S,2S,4S,5S)-2-(2-{[3-(1H-benzoimidazol-2-yl)-propyl]-methyl-amino}-ethyl)-5-methoxy-5-phenyl-bicyclo[2.2.2]oct-2-yl ester;
Isobutyric acid (1R,2S,4R,5S)-2-(2-{[3-(1H-benzoimidazol-2-yl)-propyl]-methyl-amino}-ethyl)-5-methoxy-5-phenyl-bicyclo[2.2.2]oct-2-yl ester;
Isobutyric acid (1S,2R,4S,5R)-2-(2-{[3-(1H-benzoimidazol-2-yl)-propyl]-methyl-amino}-ethyl)-5-methoxy-5-phenyl-bicyclo[2.2.2]oct-2-yl ester; Isobutyric acid (1R,2R,4R,5R)-5-(2-{[3-(1H-benzoimidazol-2-yl)-propyl]-methyl-amino}-ethyl)-3'H-spiro(bicyclo[2.2.2]octane-2,1'-isobenzofuran)-5-yl ester;
Isobutyric acid (1S,2S,4S,5S)-5-(2-{[3-(1H-benzoimidazol-2-yl)-propyl]-methyl-amino}-ethyl)-3'H-spiro(bicyclo[2.2.2]octane-2,1'-isobenzofuran)-5-yl ester;
Isobutyric acid (1R,2S,4R,5R)-5-(2-{[3-(1H-benzoimidazol-2-yl)-propyl]-methyl-amino}-ethyl)-3'H-spiro(bicyclo[2.2.2]octane-2,1'-isobenzofuran)-5-yl ester; and
Isobutyric acid (1S,2R,4S,5S)-5-(2-{[3-(1H-benzoimidazol-2-yl)-propyl]-methyl-amino}-ethyl)-3'H-spiro(bicyclo[2.2.2]octane-2,1'-isobenzofuran)-5-yl ester;
wherein the first 114 compounds of the above list constitute a particular sub-embodiment.

In another embodiment examples of preferred compounds of formula (I) are selected from the group consisting of:
(1R*,2R*,4R*)-2-(2-{[3-(1H-Benzoimidazol-2-yl)-propyl]-methyl-amino}-ethyl)-5-phenyl-bicyclo[2.2.2]oct-5-en-2-ol;
(1R*,2R*,4R*)-2-(2-{[3-(1H-Benzoimidazol-2-yl)-propyl]-methyl-amino}-ethyl)-5-(3-methoxy-phenyl)-bicyclo[2.2.2]oct-5-en-2-ol;
(1R*,2R*,4R*)-2-(2-{[3-(1H-Benzoimidazol-2-yl)-propyl]-methyl-amino}-ethyl)-5-(2,6-dimethyl-phenyl)-bicyclo[2.2.2]oct-5-en-2-ol;
(1R*,2R*,4R*)-2-(2-{[3-(1H-Benzoimidazol-2-yl)-propyl]-methyl-amino}-ethyl)-5-o-tolyl-bicyclo[2.2.2]oct-5-en-2-ol;
(1R*,2R*,4R*)-2-(2-{[3-(1H-Benzoimidazol-2-yl)-propyl]-methyl-amino}-ethyl)-5-m-tolyl-bicyclo[2.2.2]oct-5-en-2-ol;
(1R*,2R*,4R*)-2-(2-{[3-(1H-Benzoimidazol-2-yl)-propyl]-methyl-amino}-ethyl)-5-p-tolyl-bicyclo[2.2.2]oct-5-en-2-ol;
(1R*,2R*,4R*)-2-(2-{[3-(1H-Benzoimidazol-2-yl)-propyl]-methyl-amino}-ethyl)-5-(3-fluoro-phenyl)-bicyclo[2.2.2]oct-5-en-2-ol;
(1R*,2R*,4R*)-2-(2-{[3-(1H-Benzoimidazol-2-yl)-propyl]-methyl-amino}-ethyl)-5-(4-fluoro-phenyl)-bicyclo[2.2.2]oct-5-en-2-ol;
(1R*,2R*,4R*)-2-(2-{[3-(1H-Benzoimidazol-2-yl)-propyl]-methyl-amino}-ethyl)-5-pyridin-3-yl-bicyclo[2.2.2]oct-5-en-2-ol;
(1R*,2R*,4R*)-2-(2-{[3-(1H-Benzoimidazol-2-yl)-propyl]-methyl-amino}-ethyl)-5-naphthalen-2-yl-bicyclo[2.2.2]oct-5-en-2-ol;
(1R*,2R*,4R*)-2-(2-{[2-(1H-Benzoimidazol-2-yl)-ethyl]-methyl-amino}-ethyl)-5-phenyl-bicyclo[2.2.2]oct-5-en-2-ol;

(1R*,2R*,4R*)-2-{2-[(1H-Benzoimidazol-2-ylmethyl)-methyl-amino]-ethyl}-5-phenyl-bicyclo[2.2.2]oct-5-en-2-ol;
(1R*,2R*,4R*)-2-{2-[Methyl-(3-phenyl-propyl)-amino]-ethyl}-5-phenyl-bicyclo[2.2.2]oct-5-en-2-ol;
(1R*,2R*,4R*)-2-(2-{[3-(1H-Benzoimidazol-2-yl)-propyl]-methyl-amino}-ethyl)-6-methyl-5-propyl-bicyclo[2.2.2]oct-5-en-2-ol;
(1R*,2R*,4R*)-2-(2-{[3-(1H-Benzoimidazol-2-yl)-propyl]-methyl-amino}-ethyl)-5-methyl-6-phenyl-bicyclo[2.2.2]oct-5-en-2-ol;
(1R*,3R*,4R*)-1,2,3,4,9,10-Hexahydro-3-hydroxy-3-{N-methyl-N-(3-benzimidazol-2-ylpropyl)aminoethyl}-1,4-ethanophenanthrene;
2-(3-{[2-((1R*,2R*,4R*)-2-Hydroxy-5-phenyl-bicyclo[2.2.2]oct-5-en-2-yl)-ethyl]-methyl-amino}-propyl)-1H-benzoimidazole-4-carboxylic acid methyl ester;
2-(3-{[2-((1R*,2R*,4R*)-2-Hydroxy-5-phenyl-bicyclo[2.2.2]oct-5-en-2-yl)-ethyl]-methyl-amino}-propyl)-1H-benzoimidazole-5-carboxylic acid methyl ester;
(1R*,2R*,4R*)-2-(2-{[3-(1H-Benzoimidazol-2-yl)-propyl]-methyl-amino}-ethyl)-5-thiophen-2-yl-bicyclo[2.2.2]oct-5-en-2-ol;
(1R*,2R*,4R*)-2-(2-{[3-(1H-Benzoimidazol-2-yl)-propyl]-methyl-amino}-ethyl)-5-(4-methoxy-phenyl)-bicyclo[2.2.2]oct-5-en-2-ol;
(1R*,2R*,4R*)-2-(2-{[3-(1H-Benzoimidazol-2-yl)-propyl]-methyl-amino}-ethyl)-5-(2-methoxy-phenyl)-bicyclo[2.2.2]oct-5-en-2-ol;
(1R*,2R*,4R*)-2-(2-{[3-(1H-Benzoimidazol-2-yl)-propyl]-methyl-amino}-ethyl)-5-thiazol-2-yl-bicyclo[2.2.2]oct-5-en-2-ol;
(1R*,2R*,4R*)-2-(2-{[3-(1H-Benzoimidazol-2-yl)-propyl]-methyl-amino}-ethyl)-5-oxazol-2-yl-bicyclo[2.2.2]oct-5-en-2-ol;
(1R*,2R*,4R*)-2-(2-{[3-(4-Methoxy-1H-benzoimidazol-2-yl)-propyl]-methyl-amino}-ethyl)-5-phenyl-bicyclo[2.2.2]oct-5-en-2-ol;
(1R*,2R*,4R*)-2-(2-{[3-(5,6-Dichloro-1H-benzoimidazol-2-yl)-propyl]-methyl-amino}-ethyl)-5-phenyl-bicyclo[2.2.2]oct-5-en-2-ol;
(1R*,2R*,4R*)-2-(2-{[3-(5,6-Dimethoxy-1H-benzoimidazol-2-yl)-propyl]-methyl-amino}-ethyl)-5-phenyl-bicyclo[2.2.2]oct-5-en-2-ol;
(1R*,2R*,4R*)-2-(2-{[3-(5-Methoxy-1H-benzoimidazol-2-yl)-propyl]-methyl-amino}-ethyl)-5-phenyl-bicyclo[2.2.2]oct-5-en-2-ol;
(1R*,2R*,4R*)-2-(2-{[3-(7-Methoxy-4-methyl-1H-benzoimidazol-2-yl)-propyl]-methyl-amino}-ethyl)-5-phenyl-bicyclo[2.2.2]oct-5-en-2-ol;
(1R*,2R*,4R*)-2-(2-{[3-(7-Ethoxy-1H-benzoimidazol-2-yl)-propyl]-methyl-amino}-ethyl)-5-phenyl-bicyclo[2.2.2]oct-5-en-2-ol;
(1R*,2R*,4R*)-2-(2-{[2-(4-Methoxy-1H-benzoimidazol-2-yl)-ethyl]-methyl-amino}-ethyl)-5-phenyl-bicyclo[2.2.2]oct-5-en-2-ol;
(1R*,2R*,4R*)-2-(2-{[3-(7-Isopropoxy-1H-benzoimidazol-2-yl)-propyl]-methyl-amino}-ethyl)-5-phenyl-bicyclo[2.2.2]oct-5-en-2-ol;
2-(3-{[2-((1R*,2R*,4R*)-2-Hydroxy-5-phenyl-bicyclo[2.2.2]oct-5-en-2-yl)-ethyl]-methyl-amino}-propyl)-3H-benzoimidazol-4-ol;
(1R*,5R*,6R*)-6-(2-{[3-(7-Methoxy-1H-benzoimidazol-2-yl)-propyl]-methyl-amino}-ethyl)-8-phenyl-bicyclo[3.2.2]non-8-en-6-ol;
(1R*,2R*,4R*)-2-(2-{[3-(4-Methoxy-1-methyl-1H-benzoimidazol-2-yl)-propyl]-methyl-amino}-ethyl)-5-phenyl-bicyclo[2.2.2]oct-5-en-2-ol;
(1R*,2R*,4R*)-2-(2-{[2-(3,4-Diethoxy-phenyl)-ethyl]-ethyl-amino}-ethyl)-5-phenyl-bicyclo[2.2.2]oct-5-en-2-ol;
(1R*,2R*,4R*)-2-(2-{[3-(3,4-Dimethoxy-phenyl)-propyl]-methyl-amino}-ethyl)-5-phenyl-bicyclo[2.2.2]oct-5-en-2-ol;
(1R*,2R*,4R*)-2-(2-{[3-(3,4-Diethoxy-phenyl)-propyl]-methyl-amino}-ethyl)-5-phenyl-bicyclo[2.2.2]oct-5-en-2-ol;
(1R*,2R*,4R*)-2-{2-[(3-Furo[2,3-b]pyridin-5-yl-propyl)-methyl-amino]-ethyl}-5-phenyl-bicyclo[2.2.2]oct-5-en-2-ol;
(1R*,2R*,4R*)-2-(2-{Methyl-[3-(2-methyl-furo[2,3-b]pyridin-5-yl)-propyl]-amino}-ethyl)-5-phenyl-bicyclo[2.2.2]oct-5-en-2-ol;
N-(3-{[2-((1R*,2R*,4R*)-2-Hydroxy-5-phenyl-bicyclo[2.2.2]oct-5-en-2-yl)-ethyl]-methyl-amino}-propyl)-3-methoxy-2-methoxymethyl-2-methyl-propionamide;
N-(3-{[2-((1R*,2R*,4R*)-2-Hydroxy-5-phenyl-bicyclo[2.2.2]oct-5-en-2-yl)-ethyl]-methyl-amino}-propyl)-2-methoxy-2-methyl-propionamide;
N-(3-{[2-((1R*,2R*,4R*)-2-Hydroxy-5-phenyl-bicyclo[2.2.2]oct-5-en-2-yl)-ethyl]-methyl-amino}-propyl)-2,2-dimethyl-propionamide;
(1R*,2R*,4R*)-2-{2-[Methyl-(3-pyridin-3-yl-propyl)-amino]-ethyl}-5-phenyl-bicyclo[2.2.2]oct-5-en-2-ol;
(1R*,2R*,4R*)-2-{2-[(3-Isoquinolin-4-yl-propyl)-methyl-amino]-ethyl}-5-phenyl-bicyclo[2.2.2]oct-5-en-2-ol;
(1R*,2R*,4R*)-2-{2-[Methyl-(3-quinolin-3-yl-propyl)-amino]-ethyl}-5-phenyl-bicyclo[2.2.2]oct-5-en-2-ol;
(1R*,2R*,4R*)-2-{2-[Methyl-(3-quinolin-4-yl-propyl)-amino]-ethyl}-5-phenyl-bicyclo[2.2.2]oct-5-en-2-ol;
N-(3-{[2-((1R*,2R*,4R*)-2-Hydroxy-5-phenyl-bicyclo[2.2.2]oct-5-en-2-yl)-ethyl]-methyl-amino}-propyl)-3-methoxy-2-methoxymethyl-2, N-dimethyl-propionamide;
N-(3-{[2-((1R*,2R*,4R*)-2-Hydroxy-6-methyl-5-propyl-bicyclo[2.2.2]oct-5-en-2-yl)-ethyl]-methyl-amino}-propyl)-3-methoxy-2-methoxymethyl-2, N-dimethyl-propionamide;
N-(3-{[2-((1R*,2R*,4R*)-2-Hydroxy-5-methyl-6-phenyl-bicyclo[2.2.2]oct-5-en-2-yl)-ethyl]-methyl-amino}-propyl)-3-methoxy-2-methoxymethyl-2, N-dimethyl-propionamide;
(1R*,2S*,4R*)-2-(2-{[3-(1H-Benzoimidazol-2-yl)-propyl]-methyl-amino}-ethyl)-5-methyl-6-phenyl-bicyclo[2.2.2]oct-5-en-2-ol;
N-(3-{[2-((1R*,2S*,4R*)-2-Hydroxy-5-methyl-6-phenyl-bicyclo[2.2.2]oct-5-en-2-yl)-ethyl]-methyl-amino}-propyl)-3-methoxy-2-methoxymethyl-2, N-dimethyl-propionamide;
(1S,2S,4S)-2-(2-{[3-(4-Methoxy-1H-benzoimidazol-2-yl)-propyl]-methyl-amino}-ethyl)-5-phenyl-bicyclo[2.2.2]oct-5-en-2-ol;
(1R,2R,4R)-2-(2-{[3-(4-Methoxy-1H-benzoimidazol-2-yl)-propyl]-methyl-amino}-ethyl)-5-phenyl-bicyclo[2.2.2]oct-5-en-2-ol;
N-[2-(3-{[2-((1S*,2S*,4S*)-2-Hydroxy-5-phenyl-bicyclo[2.2.2]oct-5-en-2-yl)-ethyl]-methyl-amino}-propyl)-1H-benzoimidazol-4-yl]-acetamide;
(1S*,2S*,4S*)-2-(2-{[3-(4-Chloro-1H-benzoimidazol-2-yl)-propyl]-methyl-amino}-ethyl)-5-phenyl-bicyclo[2.2.2]oct-5-en-2-ol;
(1S*,2S*,4S*)-2-(2-{[3-(7-Chloro-4-methoxy-1H-benzoimidazol-2-yl)-propyl]-methyl-amino}-ethyl)-5-phenyl-bicyclo[2.2.2]oct-5-en-2-ol;

(1S*,2S*,4S*)-2-(2-{[3-(4,6-Dimethoxy-1H-benzoimidazol-2-yl)-propyl]-methyl-amino}-ethyl)-5-phenyl-bicyclo[2.2.2]oct-5-en-2-ol;

(1S,2S,4S)-2-(2-{[3-(4,6-Dimethoxy-1H-benzoimidazol-2-yl)-propyl]-methyl-amino}-ethyl)-5-phenyl-bicyclo[2.2.2]oct-5-en-2-ol;

(1S*,2S*,4S*)-2-(2-{[3-(4,7-Dimethoxy-1H-benzoimidazol-2-yl)-propyl]-methyl-amino}-ethyl)-5-phenyl-bicyclo[2.2.2]oct-5-en-2-ol;

(1S*,2S*,4S*)-2-(2-{[3-(4,6-Bis-trifluoromethyl-1H-benzoimidazol-2-yl)-propyl]-methyl-amino}-ethyl)-5-phenyl-bicyclo[2.2.2]oct-5-en-2-ol;

(1S*,2S*,4S*)-2-[2-({3-[4-(2-Methoxy-ethoxy)-1H-benzoimidazol-2-yl]-propyl}-methyl-amino)-ethyl]-5-phenyl-bicyclo[2.2.2]oct-5-en-2-ol;

(1S*,2S*,4S*)-2-(2-{[3-(4,5-Dimethoxy-7-methyl-1H-benzoimidazol-2-yl)-propyl]-methyl-amino}-ethyl)-5-phenyl-bicyclo[2.2.2]oct-5-en-2-ol;

(1S,2S,4S)-2-(2-{[3-(4,5-Dimethoxy-7-methyl-1H-benzoimidazol-2-yl)-propyl]-methyl-amino}-ethyl)-5-phenyl-bicyclo[2.2.2]oct-5-en-2-ol;

(1S*,5S*,6S*)-6-(2-{[3-(7-Methoxy-4-methyl-1H-benzoimidazol-2-yl)-propyl]-methyl-amino}-ethyl)-8-phenyl-bicyclo[3.2.2]non-8-en-6-ol;

(1R,2R,4R)-2-(2-{[3-(4,7-Dimethoxy-1H-benzoimidazol-2-yl)-propyl]-methyl-amino}-ethyl)-5-phenyl-bicyclo[2.2.2]oct-5-en-2-ol;

(1S*,2S*,4S*)-2-(2-{Methyl-[3-(4-trifluoromethoxy-1H-benzoimidazol-2-yl)-propyl]-amino}-ethyl)-5-phenyl-bicyclo[2.2.2]oct-5-en-2-ol;

(1S*,5S*,6S*)-6-(2-{[3-(4,7-Dimethoxy-1H-benzoimidazol-2-yl)-propyl]-methyl-amino}-ethyl)-8-phenyl-bicyclo[3.2.2]non-8-en-6-ol;

(1S,2S,4S)-2-(2-{[3-(4,7-Dimethoxy-1H-benzoimidazol-2-yl)-propyl]-methyl-amino}-ethyl)-5-phenyl-bicyclo[2.2.2]oct-5-en-2-ol;

(1S,4S,5R)-5-(2-{[3-(1H-Benzoimidazol-2-yl)-propyl]-methyl-amino}-ethyl)-2-phenyl-2-aza-bicyclo[2.2.2]octan-5-ol;

(1R*,2R*,4R*)-2-(2-{[3-(1H-Benzoimidazol-2-yl)-propyl]-methyl-amino}-ethyl)-bicyclo[2.2.2]oct-5-en-2-ol;

(1R*,2R*,4R*,5R*)-2-(2-{[3-(1H-Benzoimidazol-2-yl)-propyl]-methyl-amino}-ethyl)-5-methoxy-5-phenyl-bicyclo[2.2.2]octan-2-ol;

(1R*,2S*,4R*,5S*)-2-(2-{[3-(1H-Benzoimidazol-2-yl)-propyl]-methyl-amino}-ethyl)-5-methoxy-5-phenyl-bicyclo[2.2.2]octan-2-ol;

(1R*,2R*,4R*,5S*)-2-(2-{[3-(1H-Benzoimidazol-2-yl)-propyl]-methyl-amino}-ethyl)-5-methoxy-5-phenyl-bicyclo[2.2.2]octan-2-ol;

(1R*,2R*,4R*,5R*)-5-(2-{[3-(1H-Benzoimidazol-2-yl)-propyl]-methyl-amino}-ethyl)-3'H-spiro(bicyclo[2.2.2]octane-2,1'-isobenzofuran)-5-ol;

(1R*,2S*,4R*,5R*)-5-(2-{[3-(1H-Benzoimidazol-2-yl)-propyl]-methyl-amino}-ethyl)-3'H-spiro(bicyclo[2.2.2]octane-2,1l-isobenzofuran)-5-ol;

wherein the first 51 compounds of the above list constitute a particular sub-embodiment.

In addition to the compounds of the above list, further examples of preferred compounds of formula (I) are selected from the group consisting of:

Isobutyric acid (1R*,2R*,4R*)-2-(2-{[3-(1H-benzoimidazol-2-yl)-propyl]-methyl-amino}-ethyl)-5-phenyl-bicyclo[2.2.2]oct-5-en-2-yl ester;

Isobutyric acid (1R*,2R*,4R*)-2-(2-{[3-(1H-benzoimidazol-2-yl)-propyl]-methyl-amino}-ethyl)-5-(3-methoxyphenyl)-bicyclo[2.2.2]oct-5-en-2-yl ester;

Isobutyric acid (1R*,2R*,4R*)-2-(2-{[3-(1H-benzoimidazol-2-yl)-propyl]-methyl-amino}-ethyl)-5-(2,6-dimethylphenyl)-bicyclo[2.2.2]oct-5-en-2-yl ester;

Isobutyric acid (1R*,2R*,4R*)-2-(2-{[3-(1H-benzoimidazol-2-yl)-propyl]-methyl-amino}-ethyl)-5-o-tolyl-bicyclo[2.2.2]oct-5-en-2-yl ester;

Isobutyric acid (1R*,2R*,4R*)-2-(2-{[3-(1H-benzoimidazol-2-yl)-propyl]-methyl-amino}-ethyl)-5-m-tolyl-bicyclo[2.2.2]oct-5-en-2-yl ester;

Isobutyric acid (1R*,2R*,4R*)-2-(2-{[3-(1H-benzoimidazol-2-yl)-propyl]-methyl-amino}-ethyl)-5-p-tolyl-bicyclo[2.2.2]oct-5-en-2-yl ester;

Isobutyric acid (1R*,2R*,4R*)-2-(2-{[3-(1H-benzoimidazol-2-yl)-propyl]-methyl-amino}-ethyl)-5-(3-fluoro-phenyl)-bicyclo[2.2.2]oct-5-en-2-yl ester;

Isobutyric acid (1R*,2R*,4R*)-2-(2-{[3-(1H-benzoimidazol-2-yl)-propyl]-methyl-amino}-ethyl)-5-(4-fluoro-phenyl)-bicyclo[2.2.2]oct-5-en-2-yl ester;

Isobutyric acid (1R*,2R*,4R*)-2-(2-{[3-(1H-benzoimidazol-2-yl)-propyl]-methyl-amino}-ethyl)-5-pyridin-3-yl-bicyclo[2.2.2]oct-5-en-2-yl ester;

Isobutyric acid (1R*,2R*,4R*)-2-(2-{[3-(1H-benzoimidazol-2-yl)-propyl]-methyl-amino}-ethyl)-5-naphthalen-2-yl-bicyclo[2.2.2]oct-5-en-2-yl ester;

Isobutyric acid (1R*,2R*,4R*)-2-(2-{[2-(1H-benzoimidazol-2-yl)-ethyl]-methyl-amino}-ethyl)-5-phenyl-bicyclo[2.2.2]oct-5-en-2-yl ester;

Isobutyric acid (1R*,2R*,4R*)-2-{2-[(1H-benzoimidazol-2-ylmethyl)-methyl-amino]-ethyl}-5-phenyl-bicyclo[2.2.2]oct-5-en-2-yl ester;

Isobutyric acid (1R*,2R*,4R*)-2-{2-[methyl-(3-phenyl-propyl)-amino]-ethyl}-5-phenyl-bicyclo[2.2.2]oct-5-en-2-yl ester;

Isobutyric acid (1R*,2R*,4R*)-2-(2-{[3-(1H-benzoimidazol-2-yl)-propyl]-methyl-amino}-ethyl)-6-methyl-5-propyl-bicyclo[2.2.2]oct-5-en-2-yl ester;

Isobutyric acid (1R*,2R*,4R*)-2-(2-{[3-(1H-benzoimidazol-2-yl)-propyl]-methyl-amino}-ethyl)-5-methyl-6-phenyl-bicyclo[2.2.2]oct-5-en-2-yl ester;

Isobutyric acid (1R*,2S*,4R*)-2-(2-{[3-(1H-benzoimidazol-2-yl)-propyl]-methyl-amino}-ethyl)-5-methyl-6-phenyl-bicyclo[2.2.2]oct-5-en-2-yl ester;

Isobutyric acid (1R*,3R*,4R*)-1,2,3,4,9,10-hexahydro-3-hydroxy-3-{N-methyl-N-(3-benzimidazol-2-ylpropyl) aminoethyl}-1,4-ethanophenanthrene ester;

2-(3-{[2-((1R*,2R*,4R*)-2-Isobutyryloxy-5-phenyl-bicyclo[2.2.2]oct-5-en-2-yl)-ethyl]-methyl-amino}-propyl)-1H-benzoimidazole-4-carboxylic acid methyl ester;

2-(3-{[2-((1R*,2R*,4R*)-2-Isobutyryloxy-5-phenyl-bicyclo[2.2.2]oct-5-en-2-yl)-ethyl]-methyl-amino}-propyl)-1H-benzoimidazole-5-carboxylic acid methyl ester;

Isobutyric acid (1R*,2R*,4R*)-2-(2-{[3-(1H-benzoimidazol-2-yl)-propyl]-methyl-amino}-ethyl)-5-thiophen-2-yl-bicyclo[2.2.2]oct-5-en-2-yl ester;

Isobutyric acid (1R*,2R*,4R*)-2-(2-{[3-(1H-benzoimidazol-2-yl)-propyl]-methyl-amino}-ethyl)-5-(4-methoxyphenyl)-bicyclo[2.2.2]oct-5-en-2-yl ester;

Isobutyric acid (1R*,2R*,4R*)-2-(2-{[3-(1H-benzoimidazol-2-yl)-propyl]-methyl-amino}-ethyl)-5-(2-methoxyphenyl)-bicyclo[2.2.2]oct-5-en-2-yl ester;

Isobutyric acid (1R*,2R*,4R*)-2-(2-{[3-(1H-benzoimidazol-2-yl)-propyl]-methyl-amino}-ethyl)-5-thiazol-2-yl-bicyclo[2.2.2]oct-5-en-2-yl ester;

Isobutyric acid (1R*,2R*,4R*)-2-(2-{[3-(1H-benzoimidazol-2-yl)-propyl]-methyl-amino}-ethyl)-5-oxazol-2-yl-bicyclo[2.2.2]oct-5-en-2-yl ester;

Isobutyric acid (1R*,2R*,4R*)-2-(2-{[3-(4-methoxy-1H-benzoimidazol-2-yl)-propyl]-methyl-amino}-ethyl)-5-phenyl-bicyclo[2.2.2]oct-5-en-2-yl ester;
Cyclobutanecarboxylic acid (1R*,2R*,4R*)-2-(2-{[3-(4-methoxy-1H-benzoimidazol-2-yl)-propyl]-methyl-amino}-ethyl)-5-phenyl-bicyclo[2.2.2]oct-5-en-2-yl ester;
3,3,3-Trifluoro-propionic acid (1R*,2R*,4R*)-2-(2-{[3-(4-methoxy-1H-benzoimidazol-2-yl)-propyl]-methyl-amino}-ethyl)-5-phenyl-bicyclo[2.2.2]oct-5-en-2-yl ester;
Isobutyric acid (1R*,2R*,4R*)-2-(2-{[3-(5,6-dichloro-1H-benzoimidazol-2-yl)-propyl]-methyl-amino}-ethyl)-5-phenyl-bicyclo[2.2.2]oct-5-en-2-yl ester;
Cyclopropanecarboxylic acid (1R*,2R*,4R*)-2-(2-{[3-(5,6-dichloro-1H-benzoimidazol-2-yl)-propyl]-methyl-amino}-ethyl)-5-phenyl-bicyclo[2.2.2]oct-5-en-2-yl ester;
Isobutyric acid (1R*,2R*,4R*)-2-(2-{[3-(5,6-dimethoxy-1H-benzoimidazol-2-yl)-propyl]-methyl-amino}-ethyl)-5-phenyl-bicyclo[2.2.2]oct-5-en-2-yl ester;
Isobutyric acid (1R*,2R*,4R*)-2-(2-{[3-(5-methoxy-1H-benzoimidazol-2-yl)-propyl]-methyl-amino}-ethyl)-5-phenyl-bicyclo[2.2.2]oct-5-en-2-yl ester;
Isobutyric acid (1R*,2R*,4R*)-2-(2-{[3-(7-methoxy-4-methyl-1H-benzoimidazol-2-yl)-propyl]-methyl-amino}-ethyl)-5-phenyl-bicyclo[2.2.2]oct-5-en-2-yl ester;
Isobutyric acid (1R*,2R*,4R*)-2-(2-{[3-(7-ethoxy-1H-benzoimidazol-2-yl)-propyl]-methyl-amino}-ethyl)-5-phenyl-bicyclo[2.2.2]oct-5-en-2-yl ester;
Isobutyric acid (1R*,2R*,4R*)-2-(2-{[2-(7-methoxy-1H-benzoimidazol-2-yl)-ethyl]-methyl-amino}-ethyl)-5-phenyl-bicyclo[2.2.2]oct-5-en-2-yl ester;
Isobutyric acid (1R*,2R*,4R*)-2-(2-{[3-(7-isopropoxy-1H-benzoimidazol-2-yl)-propyl]-methyl-amino}-ethyl)-5-phenyl-bicyclo[2.2.2]oct-5-en-2-yl ester;
Isobutyric acid (1R*,2R*,4R*)-2-(2-{[3-(7-isobutyryloxy-1H-benzoimidazol-2-yl)-propyl]-methyl-amino}-ethyl)-5-phenyl-bicyclo[2.2.2]oct-5-en-2-yl ester;
Isobutyric acid (1R*,2R*,4R*)-2-(2-{[3-(7-hydroxy-1H-benzoimidazol-2-yl)-propyl]-methyl-amino}-ethyl)-5-phenyl-bicyclo[2.2.2]oct-5-en-2-yl ester;
Isobutyric acid (1R*,5R*,6R*)-6-(2-{[3-(7-methoxy-1H-benzoimidazol-2-yl)-propyl]-methyl-amino}-ethyl)-8-phenyl-bicyclo[3.2.2]non-8-en-6-yl ester;
3,3,3-Trifluoro-propionic acid (1R*,5R*,6R*)-6-(2-{[3-(4-methoxy-1H-benzoimidazol-2-yl)-propyl]-methyl-amino}-ethyl)-8-phenyl-bicyclo[3.2.2]non-8-en-6-yl ester;
Isobutyric acid (1R*,2R*,4R*)-2-(2-{[3-(4-methoxy-1-methyl-1H-benzoimidazol-2-yl)-propyl]-methyl-amino}-ethyl)-5-phenyl-bicyclo[2.2.2]oct-5-en-2-yl ester;
Isobutyric acid (1R*,2R*,4R*)-2-(2-{[2-(3,4-diethoxy-phenyl)-ethyl]-ethyl-amino}-ethyl)-5-phenyl-bicyclo[2.2.2]oct-5-en-2-yl ester;
Isobutyric acid (1R*,2R*,4R*)-2-(2-{[3-(3,4-dimethoxy-phenyl)-propyl]-methyl-amino}-ethyl)-5-phenyl-bicyclo[2.2.2]oct-5-en-2-yl ester;
Isobutyric acid (1R*,2R*,4R*)-2-(2-{[3-(3,4-diethoxy-phenyl)-propyl]-methyl-amino}-ethyl)-5-phenyl-bicyclo[2.2.2]oct-5-en-2-yl ester;
Isobutyric acid (1R*,2R*,4R*)-2-(2-{2-[(3-furo[2,3-b]pyridin-5-yl)-propyl]-methyl-amino]-ethyl}-5-phenyl-bicyclo[2.2.2]oct-5-en-2-yl ester;
Isobutyric acid (1R*,2R*,4R*)-2-(2-{methyl-[3-(2-methyl-furo[2,3-b]pyridin-5-yl)-propyl]-amino}-ethyl)-5-phenyl-bicyclo[2.2.2]oct-5-en-2-yl ester;
Isobutyric acid (1R*,2R*,4R*)-2-(2-{[3-(3-methoxy-2-methoxymethyl-2-methyl-propionylamino)-propyl]-methyl-amino}-ethyl)-5-phenyl-bicyclo[2.2.2]oct-5-en-2-yl ester;
Isobutyric acid (1R*,2R*,4R*)-2-(2-{[3-(2-methoxy-2-methyl-propionylamino)-propyl]-methyl-amino}-ethyl)-5-phenyl-bicyclo[2.2.2]oct-5-en-2-yl ester;
Isobutyric acid (1R*,2R*,4R*)-2-(2-{[3-(2,2-dimethyl-propionylamino)-propyl]-methyl-amino}-ethyl)-5-phenyl-bicyclo[2.2.2]oct-5-en-2-yl ester;
Isobutyric acid (1R*,2R*,4R*)-2-{2-[methyl-(3-pyridin-3-yl-propyl)-amino]-ethyl}-5-phenyl-bicyclo[2.2.2]oct-5-en-2-yl ester;
Isobutyric acid (1R*,2R*,4R*)-2-(2-{[3-(4,5-diphenyl-1H-imidazol-2-yl)-propyl]-methyl-amino}-ethyl)-5-phenyl-bicyclo[2.2.2]oct-5-en-2-yl ester;
Isobutyric acid (1R*,2R*,4R*)-2-{2-[(3-isoquinolin-4-yl-propyl)-methyl-amino]-ethyl}-5-phenyl-bicyclo[2.2.2]oct-5-en-2-yl ester;
Isobutyric acid (1R*,2R*,4R*)-2-{2-[methyl-(3-quinolin-3-yl-propyl)-amino]-ethyl}-5-phenyl-bicyclo[2.2.2]oct-5-en-2-yl ester;
Isobutyric acid (1R*,2R*,4R*)-2-{2-[methyl-(3-quinolin-4-yl-propyl)-amino]-ethyl}-5-phenyl-bicyclo[2.2.2]oct-5-en-2-yl ester;
Isobutyric acid (1R*,2R*,4R*)-2-[2-({3-[(3-methoxy-2-methoxymethyl-2-methyl-propionyl)-methyl-amino]-propyl}-methyl-amino)-ethyl]-5-phenyl-bicyclo[2.2.2]oct-5-en-2-yl ester;
Isobutyric acid (1R*,2R*,4R*)-2-[2-({3-[(3-methoxy-2-methoxymethyl-2-methyl-propionyl)-methyl-amino]-propyl}-methyl-amino)-ethyl]-6-methyl-5-propyl-bicyclo[2.2.2]oct-5-en-2-yl ester;
Isobutyric acid (1R*,2R*,4R*)-2-[2-({3-[(3-methoxy-2-methoxymethyl-2-methyl-propionyl)-methyl-amino]-propyl}-methyl-amino)-ethyl]-5-methyl-6-phenyl-bicyclo[2.2.2]oct-5-en-2-yl ester;
Isobutyric acid (1R*,2S*,4R*)-2-[2-({3-[(3-methoxy-2-methoxymethyl-2-methyl-propionyl)-methyl-amino]-propyl}-methyl-amino)-ethyl]-5-methyl-6-phenyl-bicyclo[2.2.2]oct-5-en-2-yl ester;
2,2-Dimethyl-propionic acid (1S*,2S*,4S*)-2-(2-{[3-(4-methoxy-1H-benzoimidazol-2-yl)-propyl]-methyl-amino}-ethyl)-5-phenyl-bicyclo[2.2.2]oct-5-en-2-yl ester;
Isopropyl-carbamic acid (1S*,2S*,4S*)-2-(2-{[3-(4-methoxy-1H-benzoimidazol-2-yl)-propyl]-methyl-amino}-ethyl)-5-phenyl-bicyclo[2.2.2]oct-5-en-2-yl ester;
2-Methoxy-2-methyl-propionic acid (1S*,2S*,4S*)-2-(2-{[3-(4-methoxy-1H-benzoimidazol-2-yl)-propyl]-methyl-amino}-ethyl)-5-phenyl-bicyclo[2.2.2]oct-5-en-2-yl ester;
Carbonic acid isopropyl ester (1S*,2S*,4S*)-2-(2-{[3-(4-methoxy-1H-benzoimidazol-2-yl)-propyl]-methyl-amino}-ethyl)-5-phenyl-bicyclo[2.2.2]oct-5-en-2-yl ester;
Isobutyric acid (1S,2S,4S)-2-(2-{[3-(4-methoxy-1H-benzoimidazol-2-yl)-propyl]-methyl-amino}-ethyl)-5-phenyl-bicyclo[2.2.2]oct-5-en-2-yl ester;
Isobutyric acid (1R,2R,4R)-2-(2-{[3-(4-methoxy-1H-benzoimidazol-2-yl)-propyl]-methyl-amino}-ethyl)-5-phenyl-bicyclo[2.2.2]oct-5-en-2-yl ester;
Isobutyric acid (1S*,2S*,4S*)-2-(2-{[3-(4-acetylamino-1H-benzoimidazol-2-yl)-propyl]-methyl-amino}-ethyl)-5-phenyl-bicyclo[2.2.2]oct-5-en-2-yl ester;

Isobutyric acid (1S*,2S*,4S*)-2-(2-{[3-(4-chloro-1H-benzoimidazol-2-yl)-propyl]-methyl-amino}-ethyl)-5-phenyl-bicyclo[2.2.2]oct-5-en-2-yl ester;
Isobutyric acid (1S*,2S*,4S*)-2-(2-{[3-(7-chloro-4-methoxy-1H-benzoimidazol-2-yl)-propyl]-methyl-amino}-ethyl)-5-phenyl-bicyclo[2.2.2]oct-5-en-2-yl ester;
Isobutyric acid (1S*,2S*,4S*)-2-(2-{[3-(4,6-dimethoxy-1H-benzoimidazol-2-yl)-propyl]-methyl-amino}-ethyl)-5-phenyl-bicyclo[2.2.2]oct-5-en-2-yl ester;
Isobutyric acid (1S,2S,4S)-2-(2-{[3-(4,6-dimethoxy-1H-benzoimidazol-2-yl)-propyl]-methyl-amino}-ethyl)-5-phenyl-bicyclo[2.2.2]oct-5-en-2-yl ester;
Isobutyric acid (1S*,2S*,4S*)-2-(2-{[3-(4,7-dimethoxy-1H-benzoimidazol-2-yl)-propyl]-methyl-amino}-ethyl)-5-phenyl-bicyclo[2.2.2]oct-5-en-2-yl ester;
Isobutyric acid (1S*,2S*,4S*)-2-(2-{[3-(4,6-bis-trifluoromethyl-1H-benzoimidazol-2-yl)-propyl]-methyl-amino}-ethyl)-5-phenyl-bicyclo[2.2.2]oct-5-en-2-yl ester;
Isobutyric acid (1S*,2S*,4S*)-2-[2-({3-[4-(2-methoxy-ethoxy)-1H-benzoimidazol-2-yl]-propyl}-methyl-amino)-ethyl]-5-phenyl-bicyclo[2.2.2]oct-5-en-2-yl ester;
Isobutyric acid (1S*,2S*,4S*)-2-(2-{[3-(4,5-dimethoxy-7-methyl-1H-benzoimidazol-2-yl)-propyl]-methyl-amino}-ethyl)-5-phenyl-bicyclo[2.2.2]oct-5-en-2-yl ester;
Isobutyric acid (1S,2S,4S)-2-(2-{[3-(4,5-dimethoxy-7-methyl-1H-benzoimidazol-2-yl)-propyl]-methyl-amino}-ethyl)-5-phenyl-bicyclo[2.2.2]oct-5-en-2-yl ester;
Isobutyric acid (1S*,5S*,6S*)-6-(2-{[3-(7-methoxy-4-methyl-1H-benzoimidazol-2-yl)-propyl]-methyl-amino}-ethyl)-8-phenyl-bicyclo[3.2.2]non-8-en-6-yl ester;
Isobutyric acid (1R,2R,4R)-2-(2-{[3-(4,7-dimethoxy-1H-benzoimidazol-2-yl)-propyl]-methyl-amino}-ethyl)-5-phenyl-bicyclo[2.2.2]oct-5-en-2-yl ester;
Isobutyric acid (1S*,2S*,4S*)-2-(2-{methyl-[3-(4-trifluoromethoxy-1H-benzoimidazol-2-yl)-propyl]-amino}-ethyl)-5-phenyl-bicyclo[2.2.2]oct-5-en-2-yl ester;
Isobutyric acid (1S*,5S*,6S*)-6-(2-{[3-(4,7-dimethoxy-1H-benzoimidazol-2-yl)-propyl]-methyl-amino}-ethyl)-8-phenyl-bicyclo[3.2.2]non-8-en-6-yl ester;
Isobutyric acid (1S,2S,4S)-2-(2-{[3-(4,7-dimethoxy-1H-benzoimidazol-2-yl)-propyl]-methyl-amino}-ethyl)-5-phenyl-bicyclo[2.2.2]oct-5-en-2-yl ester;
Isobutyric acid (1S*,2S*,4S*)-2-(2-{methyl-[3-(4-methyl-5-phenyl-1H-imidazol-2-yl)-propyl]-amino}-ethyl)-5-phenyl-bicyclo[2.2.2]oct-5-en-2-yl ester;
Isobutyric acid (1S*,2S*,4S*)-2-[2-({3-[5-(2-methoxy-phenyl)-1H-imidazol-2-yl]-propyl}-methyl-amino)-ethyl]-5-phenyl-bicyclo[2.2.2]oct-5-en-2-yl ester;
Isobutyric acid (1R*,2R*,4R*,5R*)-2-(2-{[3-(1H-benzoimidazol-2-yl)-propyl]-methyl-amino}-ethyl)-5-phenyl-bicyclo[2.2.2]oct-2-yl ester;
Isobutyric acid (1R*,2R*,4R*,5S*)-2-(2-{[3-(1H-benzoimidazol-2-yl)-propyl]-methyl-amino}-ethyl)-5-phenyl-bicyclo[2.2.2]oct-2-yl ester;
Isobutyric acid (1S,4S,5R)-5-(2-{[3-(1H-benzoimidazol-2-yl)-propyl]-methyl-amino}-ethyl)-2-phenyl-2-aza-bicyclo[2.2.2]oct-5-yl ester;
Isobutyric acid (1R*,2R*,4R*)-2-(2-{[3-(1H-benzoimidazol-2-yl)-propyl]-methyl-amino}-ethyl)-bicyclo[2.2.2]oct-5-en-2-yl ester;
Isobutyric acid (1R*,2R*,4R*,5R*)-2-(2-{[3-(1H-benzoimidazol-2-yl)-propyl]-methyl-amino}-ethyl)-5-methoxy-5-phenyl-bicyclo[2.2.2]oct-2-yl ester;
Isobutyric acid (1R*,2S*,4R*,5S*)-2-(2-{[3-(1H-benzoimidazol-2-yl)-propyl]-methyl-amino}-ethyl)-5-methoxy-5-phenyl-bicyclo[2.2.2]oct-2-yl ester;
Isobutyric acid (1R*,2R*,4R*,5R*)-5-(2-{[3-(1H-benzoimidazol-2-yl)-propyl]-methyl-amino}-ethyl)-3'H-spiro(bicyclo[2.2.2]octane-2,1'-isobenzofuran)-5-yl ester;
Isobutyric acid (1R*,2S*,4R*,5R*)-5-(2-{[3-(1H-benzoimidazol-2-yl)-propyl]-methyl-amino}-ethyl)-3'H-spiro(bicyclo[2.2.2]octane-2,1'-isobenzofuran)-5-yl ester;

wherein the first 57 compounds of the above list constitute a particular sub-embodiment.

The relative configuration of stereoisomers is denoted as follows: for example,
(1R*,2R*,4R*)-2-(2-{[3-(1H-benzoimidazol-2-yl)-propyl]-methyl-amino}-ethyl)-5-methyl-6-phenyl-bicyclo[2.2.2]oct-5-en-2-ol denominates
(1R,2R,4R)-2-(2-{[3-(1H-benzoimidazol-2-yl)-propyl]-methyl-amino}-ethyl)-5-methyl-6-phenyl-bicyclo[2.2.2]oct-5-en-2-ol,
(1S,2S,4S)-2-(2-{[3-(1H-benzoimidazol-2-yl)-propyl]-methyl-amino}-ethyl)-5-methyl-6-phenyl-bicyclo[2.2.2]oct-5-en-2-ol,
or mixtures of these two enantiomers.

The compounds of formulae (I), (I$_P$), (I$_{E1}$) and/or (I$_{E2}$) and their pharmaceutically acceptable salts can be used as medicaments, e.g. in the form of pharmaceutical compositions for enteral or parenteral administration.

The production of the pharmaceutical compositions can be effected in a manner which will be familiar to any person skilled in the art (see for example Remington, *The Science and Practice of Pharmacy*, 21st Edition 2005, Part 5, "Pharmaceutical Manufacturing" [published by Lippincott Williams & Wilkins]) by bringing the described compounds of formula (I), or their pharmaceutically acceptable salts, optionally in combination with other therapeutically valuable substances, into a galenical administration form together with suitable, non-toxic, inert, therapeutically compatible solid or liquid carrier materials and, if desired, usual pharmaceutical adjuvants.

The compounds of formula (I), or a pharmaceutically acceptable salt thereof, are useful in the preparation of a medicament
for the treatment or prevention of chronic stable angina, hypertension, ischemia (renal and cardiac), cardiac arrhythmias including atrial fibrillation, cardiac hypertrophy, or congestive heart failure.

The compounds of formula (I), or a pharmaceutically acceptable salt thereof, are further also useful in the preparation of a medicament for the following disease groups alone or in any combination:
for the treatment of renal diseases, diabetes and its complications, hyperaldosteronism, epilepsy, neuropathic pain, or cancer in humans and other mammals;
for use as anti-fibrillatory agent, anti-asthmatic agent, anti-atherosclerotic agent, additive to cardioplegic solutions for pulmonary bypasses, adjunct to thrombolytic therapy, as antiaggregant agent, or as agent for the treatment of unstable angina;
for the treatment or prophylaxis of hypertension, especially portal hypertension, hypertension secondary to treatment with erythropoietin and low renin hypertension;
for use in hypoxic or ischemic diseases, or as anti ischemic agent for the treatment of e.g. cardiac, renal and cerebral ischemia and reperfusion (e.g. occurring after cardiopulmonary bypass surgery), coronary and cerebral vasospasm and the like, therapy for peripheral vascular diseases (e.g. Raynaud's disease, intermittent claudication, Takayashus disease), sickle cell disease including initiation and/or evolution of the pain crisis;
for the treatment or prophylaxis of disorders related to renal, glomerular and mesangial cell function, including acute and chronic renal failure, diabetic nephropathy, hypertension-induced nephropathy, glomerular injury, renal damage related to age or dialysis, nephrosclerosis, nephrotoxicity related to imaging and contrast agent and to cyclosporine, renal ischemia, primary vesicoureteral reflux, or glomerulosclerosis;

for use in therapy for myocardial infarction, treatment of cardiac hypertrophy, primary and secondary pulmonary hypertension, therapy for congestive heart failure including inhibition of fibrosis, inhibition of left ventricular dilatation, remodelling and dysfunction, or restenosis following angioplasty or stenting;

for the treatment of endotoxemia or endotoxin shock, or hemorrhagic shock;

for the treatment of sexual dysfunction in both men (erectile dysfunction e.g. due to diabetes mellitus, spinal cord injury, radical prostatectomy, psychogenic etiology and other causes) and women by improving blood flow to the genitalia, especially corpus cavernosum;

for the prevention and/or reduction of cancer or end-organ damage associated with cell proliferation;

for therapy of metabolic disorders or chronic inflammatory diseases, insulin-dependent and non insulin-dependent diabetes mellitus and their complications (e.g. neuropathy, retinopathy), hyperaldosteronism, bone remodelling, psoriasis, arthritis, rheumatoid arthritis, osteoarthritis sarcoidosis, or eczematous dermatitis;

for the treatment of hepatotoxicity and sudden death, early and advanced liver disease and injury including attendant complication (e.g. hepatotoxicity, fibrosis, cirrhosis), deleterious consequences of tumors such as hypertension resulting from hemangiopericytoma, spastic diseases of the urinary tract and/or bladder, hepatorenal syndrome, immunological diseases involving vasculitis such as lupus, systemic sclerosis, mixed cryoglobulinemia, fibrosis associated with renal dysfunction and hepatotoxicity;

for use in gastrointestinal diseases such as ulcerative colitis, Crohn's disease, gastric mucosal damage, ulcer inflammatory bowel disease and ischemic bowel disease, gall bladder or bile duct-based diseases such as cholangitis, pancreatitis, regulation of cell growth, begning prostatic hypertrophy, or transplantation, or for use as anti-diarrheal agent;

for the treatment of disorders involving bronchoconstriction or disorders of chronic or acute inflammation such as obstructive pulmonary disease and adult distress syndrome;

for the alleviation of pain including neuropathic pain, peripheral pain and pain associated with cancer such as pain associated with prostate cancer or bone-cancer;

for the treatment of central nervous system vascular disorders such as stroke, transient ischemic attacks, migraine and subarachnoid hemorrhage, central nervous system behavioural disorders, treatment of dementia including Alzheimer's dementia, senile dementia and vascular dementia, epilepsy, or sleep disorders; or for reduction of general morbidity and/or mortality as a result of above utilities.

The present invention also relates to a method for the prevention or treatment of a disease or disorder mentioned herein comprising administering to a subject a pharmaceutically active amount of a compound of formula (I).

Furthermore, the compounds of the formula (I) may also be used favourably in combination with one or more agents selected from lipid lowering agents such as statins, anticoagulants such as coumarins, antithrombotic agents such as clopidogrel, β-blockers, and other cardioprotective agents.

Besides, any preferences indicated for the compounds of formula (I) (whether for the compounds themselves, salts thereof, compositions containing the compounds or salts thereof, uses of the compounds or salts thereof, etc.) apply mutatis mutandis to compounds of formulae $(I_P)$, $(I_{E1})$, and/or $(I_{E2})$ and vice versa.

Preparation of Compounds of Formula (I):

A further aspect of the invention is a process for the preparation of compounds of formulae (I), $(I_{E1})$, and/or $(I_{E2})$ of the present invention. The compounds obtained may also be converted into pharmaceutically acceptable salts thereof in a manner known per se.

In general, all chemical transformations can be performed according to well-known standard methodologies as described in the literature or as described in the procedures as summarized in Schemes 1 to 8 below. If not indicated otherwise, the generic groups or integers W, $R^1$, $R^{1a}$, $R^2$, $R^{2a}$, $R^3$, $R^4$, $R^5$, $R^6$, $R^7$, $R^8$, $R^9$, $R^{10}$, $R^{11}$, $R^{12}$, A, B, p, m and n are as defined for formula (I). Other abbreviations used are defined in the experimental section. In some instances the generic groups W, $R^1$, $R^2$, $R^3$, $R^5$, $R^8$, $R^9$, $R^{10}$, or $R^{12}$ might be incompatible with the assembly illustrated in the schemes below and so will require the use of protecting groups (PG). The use of protecting groups is well known in the art (see for example "Protective Groups in Organic Synthesis", T. W. Greene, P. G. M. Wuts, Wiley-Interscience, 1999). For the purposes of this discussion, it will be assumed that such protecting groups as are necessary are in place.

Compounds of formula (I) are prepared following the procedures outlined in Scheme 1 below. The key intermediate K is reduced to the corresponding diol 1.1 using standard reducing reagents and conditions such as $LiAlH_4$ and solvents like $Et_2O$ or THF, preferably at temperatures between −20° C. to rt. The primary alcohol group in 1.1 is transformed into a leaving group $L^1$ of compound 1.2, wherein $L^1$ is OTs, OMs, OTf, Cl or Br, using well known methods such as Ts-Cl in presence of bases such as $NEt_3$, DMAP, and in an adequate solvent such as toluene. Treatment of 1.2 with the appropriate amine $R^4$—NHB—W in presence of a non-nuclear base such as DIPEA at temperatures between rt and 110° C. gives compounds of formula (I) wherein $R^3$ represents H.

Scheme 1:

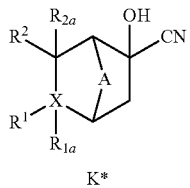

K*

$\downarrow$ n = 1

-continued

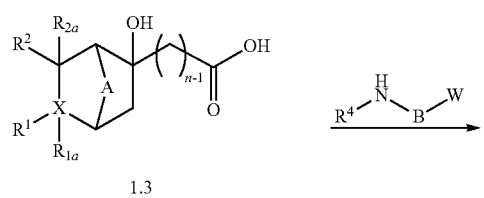 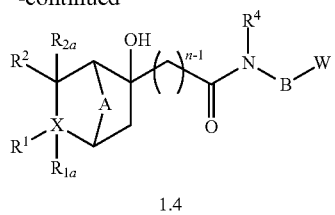

1.3    1.4

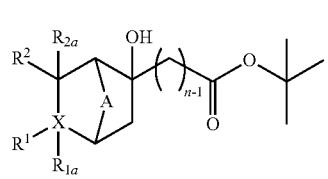

K

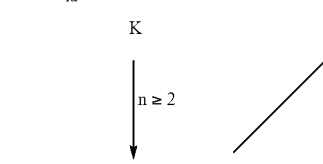 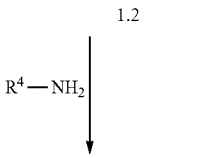 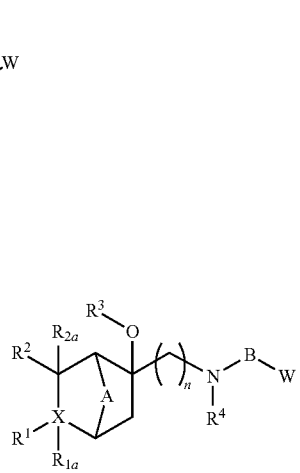

1.2    (I)

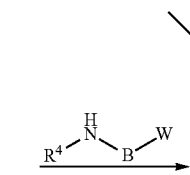

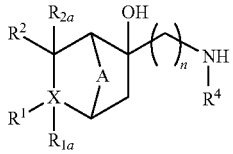 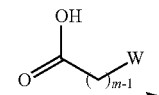 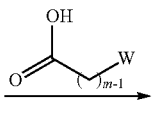 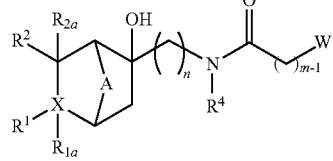

1.1    1.5    1.6

Alternatively, compounds of formula (I) wherein $R^3$ represents H can be prepared by saponification of the ester K using standard basic conditions such as LiOH or NaOH in solvents like ethanol, methanol, THF or water at rt, or standard acidic conditions such as aq. HCl or TFA in solvents like ethanol, methanol, THF, DCM, or water at rt to yield the acid derivatives 1.3 wherein $n \geq 2$. Starting from nitrile K* a hydrolysis under standard acidic conditions gives access to acid 1.3 wherein n=1. The acid 1.3 is then coupled with amine $R^4$—NH—B—W to give the amide derivatives 1.4 using standard coupling reagents such as EDC, HOBt or PyBOP in the presence of a base such as $NEt_3$ or DIPEA and in solvents such as THF, DCM or DMF, preferably at rt. The amide 1.4 is then reduced to give the desired compounds of formula (I) wherein $R^3$ represents H using standard reducing agents like $LiAlH_4$ or Red-Al in adequate solvents such as toluene at temperatures between 0° C. and rt.

In a variation the compounds of formula (I) wherein $R^3$ represents H can be prepared by reacting the activated compound 1.2 with the appropriate amine $R^4$—$NH_2$ in a solvent such as ethanol at slightly elevated temperatures (about 40° C.) to give the amino alcohol derivatives 1.5. Reductive amination of 1.5 using the appropriate aldehyde W—$(CH_2)_{m-1}$—CHO under standard conditions leads to compounds of formula (I) wherein $R^3$ represents H.

In another variation the compounds of formula (I) wherein $R^3$ represents H can be prepared by coupling of the amino alcohol derivatives 1.5 with the appropriate acid W—$(CH_2)_{m-1}$—COOH to yield amide derivatives 1.6 which are then further reduced to compounds of formula (I) wherein $R^3$ represents H using the same conditions as described before.

Alcohols of formula (I) wherein $R^3$ represents H can be acylated using standard reagents such as acid chlorides, acid anhydrides, chloroformates, isocyanates, or carbamoylchlorides, if necessary in presence of a Lewis acid such as $MgBr_2$, or in presence of a base such as $NEt_3$ in inert solvents such as DCM or THF at temperatures between 0° C. and 65° C. to give compounds of formula (I) wherein $R^3$ represents —$COR^{31}$.

The key intermediates K, wherein $R^2$ is H are prepared according to Scheme 2. Diketones 2.1 and mono protected ketones 2.2 can be prepared according to known procedures (Can. J. Chem. 1992, 70, 974-980, Can. J. Chem. 1968, 46, 3713-17, J. Org. Chem. 1978, 43, 4648-4650).

Alkylation of the ketone 2.2 with nucleophiles like Grignard reagents or lithiated reagents (prepared from the corresponding bromo compound with e.g. butyllithium using standard reaction conditions) such as phenylmagnesiumbromide, 3-lithiopyridine, 2-lithiobenzyl alcohol, or 2-lithiothiazole in adequate solvents like $Et_2O$ or THF at temperatures between −78° C. and rt yields the alcohols 2.3.

Hydrolysis of the ketal of alcohol derivative 2.3 and subsequent elimination of water using standard dehydration reagents and procedures such as TsOH in adequate solvents such as acetone preferably at rt leads to the ketone 2.4.

O-alkylation of alcohols 2.3 with alkylating reagents such as MeI using standard conditions yields ethers 2.8 wherein R* is $(C_{1-4})$alkyl. Ethers 2.8 can then be transformed into the ketone 2.4 under the same conditions as described above for alcohols 2.3.

Scheme 2

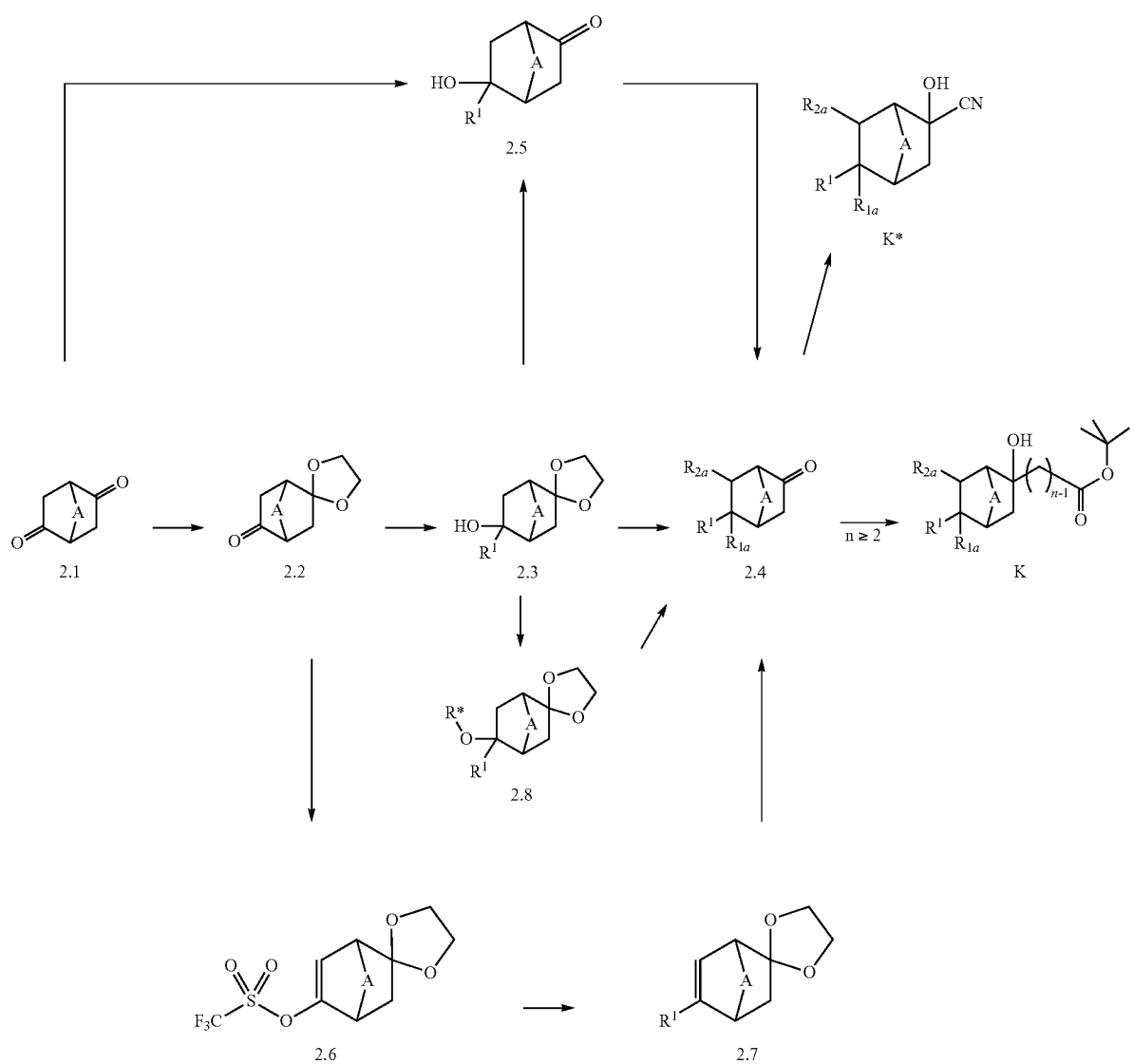

In a variation, compounds 2.4 wherein $R^1$ and $R^{1a}$ together form a 3H-benzofuran-2,2-diyl group can be formed from compounds 2.3, wherein $R^1$ represents 2-hydroxymethylphenyl, using acids like TFA in solvents like DCM at temperatures between 0° C. and rt.

Alternatively, this deprotection/elimination reaction can be performed in two steps. The ketal of alcohol derivative 2.3 is hydrolyzed as described above using protic conditions such as TsOH in solvents such as acetone at rt to yield the ketone derivative 2.5. The elimination of water can be performed using standard conditions such as Ms-Cl in presence of a base like $NEt_3$ and in adequate solvents like DCM at temperatures between 0° C. and rt or using the Burgess reagent in adequate solvents like THF at temperatures between 0° C. and rt to lead to ketone derivatives 2.4.

In another variation the diketone 2.1 can be alkylated directly to ketone derivative 2.5 by appropriate nucleophiles like Grignard reagents in standard solvents like $Et_2O$ or THF at temperatures about 0° C.

In a variation the ketone 2.2 is reacted with a strong electrophile e.g. trifluoromethanesulfonic acid anhydride in an inert solvent such as DCM at temperatures about 0° C. to rt to give 2.6. The enol derivative 2.6 is then treated with appropriate organo-boronic acids that are commercially available or well known in adequate solvents such as DME, in presence of a base such as aq. $Na_2CO_3$ and a suitable catalyst such as tetrakis-(triphenylphosphine)-palladium to yield the protected ketone derivative 2.7. Deprotection of 2.7 using standard hydrolysis conditions such as TsOH in adequate solvents such as acetone preferably at rt leads to the ketone derivative 2.4.

Ketone derivatives 2.4 are transformed to the desired key intermediates K by addition of nucleophiles such as Grignard reagents or lithiated alkyl groups such as lithiated tert.-butylacetate (prepared in situ using tert.-butyl bromoacetate, n-butyllithium and DIPA at temperatures of –50° C. in an adequate mixture of solvents such as toluene-THF or hexane-THF) at temperatures between –50° C. and rt.

The key intermediates K* can be formed via hydrocyanation of ketone 2.4 under standard conditions using e.g. KCN or TMSCN in appropriate solvents like MeCN or DCM at rt.

The key intermediates K, wherein $R^2$ is not H are prepared according to Scheme 3.

Scheme 3

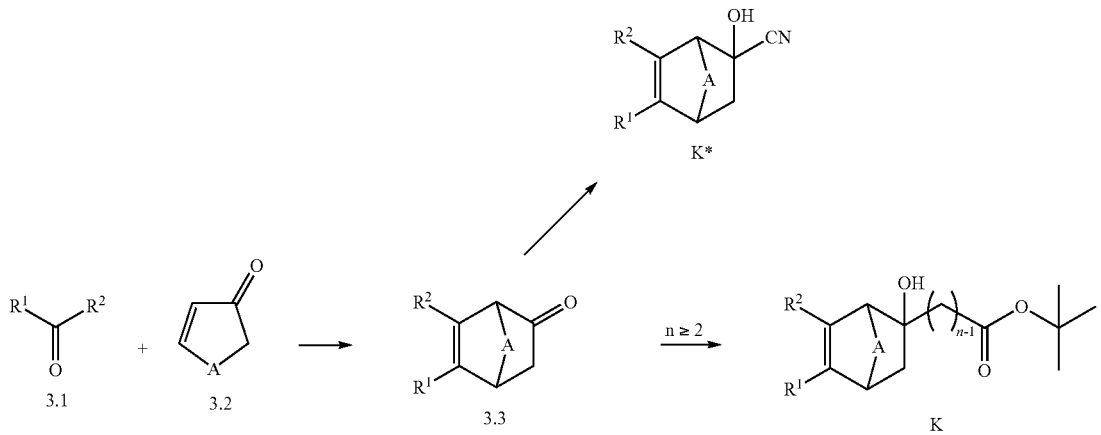

A mixture of the appropriate ketone 3.1, which is commercially available or well known and the commercially available enone 3.2 is reacted in appropriate solvents such as DCM in the presence of a dehydrating agent like phosphorous pentoxide and a strong electrophile such as trifluoromethanesulfonic acid at temperatures of about 0° C. as described by Jung, Michael E.; Tetrahedron Letters 2005, 46(30), 5057-5061, to give the bicyclic derivative 3.3. Alkylation of ketone derivatives 3.3 using analogous methods as described above for the alkylation of ketone derivatives 2.4 provides the key intermediates K. Hydrocyanation of ketone derivatives 3.3 using analogous methods as described above for ketones 2.4 yields key intermediates K*.

The key intermediates K, wherein X is N are prepared according to Scheme 4.

derivatives 4.3 using analogous methods as described above for the alkylation of ketone derivatives 2.4 provides the key intermediates K. Hydrocyanation of ketone derivatives 4.3 using analogous methods as described above for ketones 2.4 yields key intermediates K*.

The amino building blocks $R^4$—NH—B—W can be prepared according to the description below.

In the case where W represents a benzimidazole group the synthesis is outlined in Scheme 5. A suitably substituted dianiline derivative 5.1, which is commercially available or synthesized according to the methods given in the experimental part below, is coupled to an accordingly protected, commercially available N-alkylamino-alkanoic acid derivative using standard coupling reagents and conditions such as EDC/HOBt in presence of a base such as $NEt_3$, in solvents like THF at rt to give the aniline derivatives 5.2. Heating of 5.2, preferably under microwave conditions to about 150° C., Scheme 4

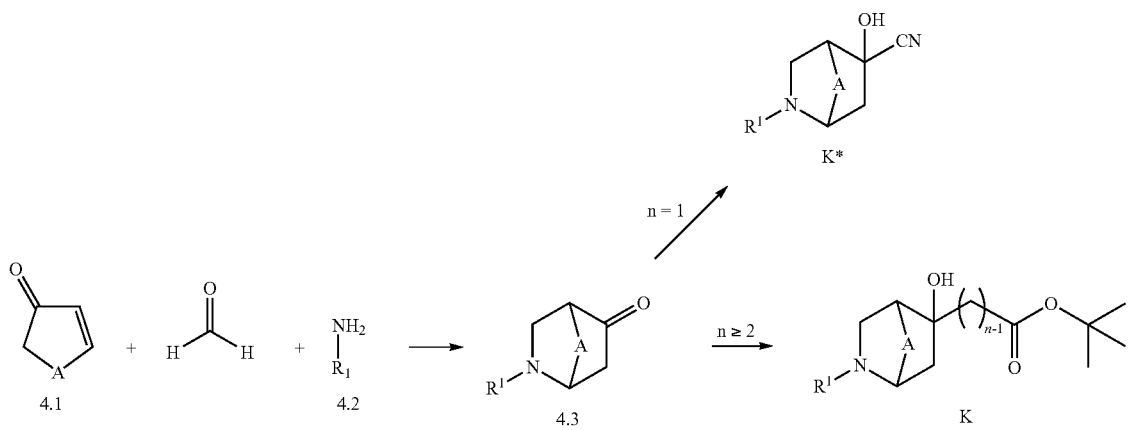

A mixture of the appropriate enone 4.1, which is commercially available or well known, formaldehyde and the commercially available amine 4.2 is reacted in appropriate solvents such as DMSO in the presence of a catalytic amount of (S)-proline at temperatures of about rt to 50° C. as described by Sunden, Henrik; Angew. Chem. Int. Ed. 2005, 44, 4877-4880, to give the bicyclic derivative 4.3. Alkylation of ketone neat or in appropriate solvents such as toluene or acetic acid leads to the protected aminoalkyl benzimidazole derivatives 5.3. Optionally, in case $R^5$ is alkyl, the substituent can be introduced using standard reactions such as alkylation with an appropriate alkyl halogenide in presence of a base like NaH or $K_2CO_3$ in a solvent like acetone, DMF or THF at temperatures of about 0° C. Deprotection using standard deprotection reagents and procedures known to the ones skilled in the art (hydrogen for PG=Cbz, TFA or HCl for PG=BOC) gives the desired aminoalkyl benzimidazole derivatives 5.4.

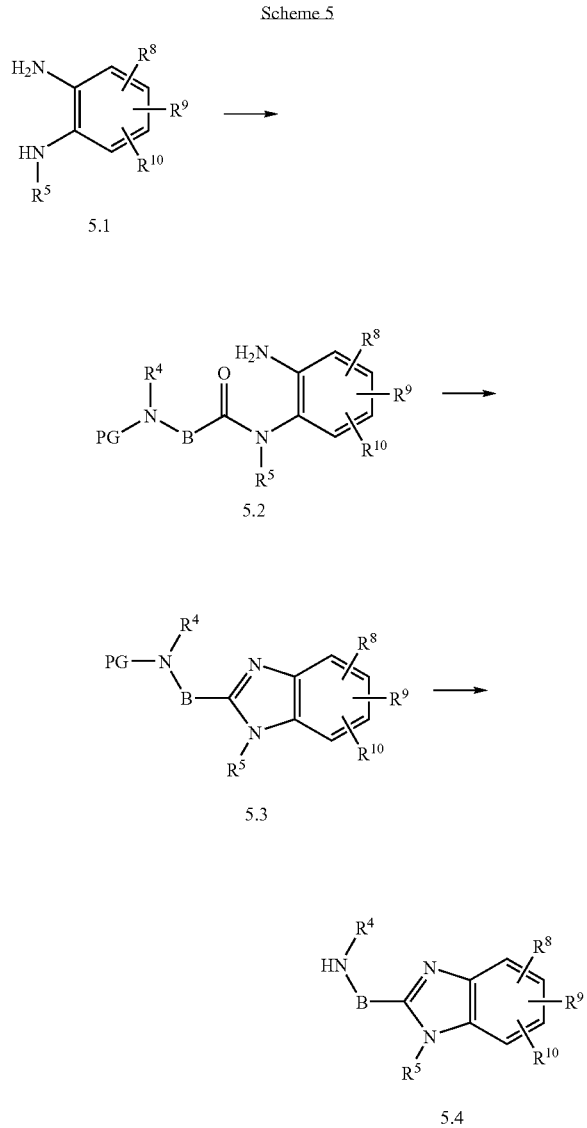

Scheme 5

In case W represents an aryl or heteroaryl group the required building blocks $R^4$—NH—B—W, CHO—$(CH_2)_{m-1}$—W and HOOC—$(CH_2)_{m-1}$—W are commercially available, or synthesized according to well known methods or along the methods described below.

Appropriate substituents on W being an aryl or heteroaryl group can be introduced by first protecting the amino group of $R^4$—NH—B—W with standard N-protecting groups such as BOC or Cbz before introducing the corresponding substituents applying standard chemistry described in the literature and known to those skilled in the art. Deprotection of the nitrogen as described above leads to the desired $R^4$—NH—B—W.

Further synthetic pathways to amino derivatives of formula $R^4$—NH—B—W are shown in Scheme 6 below. In Scheme 6, R represents alkyl, $L^2$ represents O-Tf, Cl or Br, and ring A represents W being an aryl or heteroaryl group.

In one variation the appropriate substituents on W being an aryl or heteroaryl group can be introduced by applying the same substituent modifications described above to the corresponding esters 6.1 of the compounds of formula HOOC—$(CH_2)_{m-1}$—W. Subsequent saponification of the ester, reaction of the resulting acid with $R^4$—$NH_2$ to give the corresponding amide followed by reduction using standard procedures gives the corresponding amines $R^4$—NH—$(CH_2)_m$—W. In another variation the appropriate substituents on W can be introduced by applying the same substituent modifications described above to aldehydes of formula CHO—$(CH_2)_{m-1}$—W. Subsequent reductive amination with $R^4$—$NH_2$ using standard procedures gives the corresponding amines $R^4$—NH—$(CH_2)_m$—W. Amines of formula $R^4$—$NH_2$ are commercially available.

In a variation the acid derivatives HOOC—$(CH_2)_2$—W, wherein m=3 and W represents an aryl or heteroaryl group, are prepared by the reaction of aryl- or heteroaryl derivatives 6.2 with esters of acrylic acid in presence of palladium catalysts, phosphine ligands (e.g. palladium acetate, trimethoxyphosphine) in presence of a base like DIPEA in solvents like DMF followed by hydrogenation in presence of a palladium catalyst and standard ester cleavage (TFA for tert.-butyl, LiOH in THF-water for methyl, ethyl) as shown in Scheme 6.

In case $R^4$ represents alkyl the substituent can be introduced by applying processes to compounds of formula $NH_2$—$(CH_2)_m$—W (in absence or presence of a protecting group on the nitrogen of the amino group) known to those skilled in the art such as alkylation with an alkyl halide in presence of a base or by reductive amination with an aldehyde, or treatment with a nitrile such as acetonitrile in presence of hydrogen and a suitable catalyst such as rhodium on carbon. Cleavage of the protecting group using standard conditions leads to the desired derivatives of formula $R^4$—NH—B—W.

In case m represents the integer 3 the compounds of formula $R^4$—NH—$(CH_2)_m$—W can alternatively be prepared from commercially available esters 6.3 and/or their parent acids or from aldehydes of formula 6.4. Esters 6.3 and/or their parent acids can be transformed to the aldehydes 6.4 using well known reaction techniques such as reduction to the alcohol using reagents such as $LiAlH_4$ in solvents such as THF and subsequent oxidation of the alcohol to the parent aldehyde of formula 6.4 using Swern- or Dess-Martin conditions. Olefination of the aldehyde derivatives 6.4 using Wittig reagents, which are commercially available or synthesized according to well-known methods (see eg. J. Med. Chem. 2003, 46, 399), under conditions well known in the art leads either directly or via subsequent amide formation to unsaturated amides 6.5 which can be reduced to the desired compounds of formula $R^4$—NH—$(CH_2)_m$—W, wherein m represents the integer 3, using for example a sequence of hydrogenation of the double bond in presence of a palladium catalyst followed by reduction of the amide using standard conditions described before.

Scheme 6

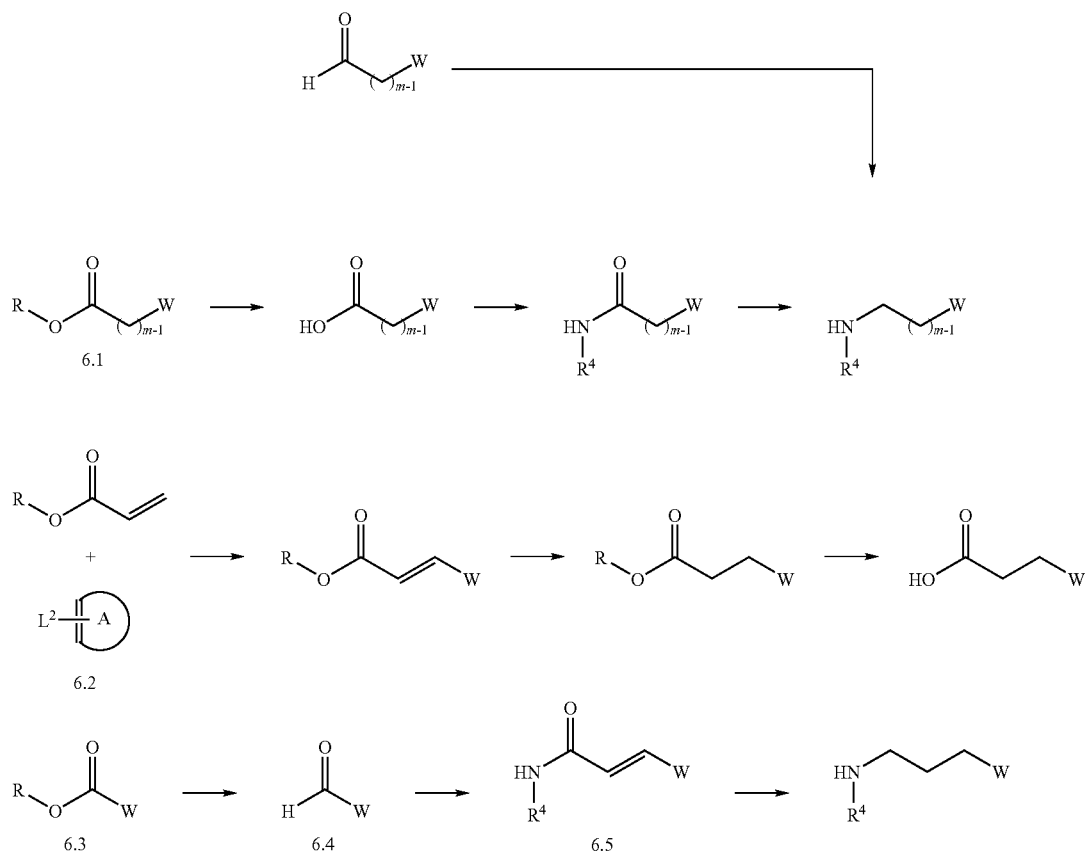

In case W represents an imidazole group various syntheses to prepare substituted imidazoles are known in the literature and those skilled in the art (Katritzky; Rees. *Comprehensive Heterocyclic Chemistry*. Vol. 5, p. 469-498, 1984; Grimmett, M. Ross. *Imidazole and Benzimidazole Synthesis*. Academic Press, 1997; T L Gilchrist, *Heterocyclic Chemistry*, The Bath Press 1985). One variation is outlined in Scheme 7. In Scheme 7 R represents an alkyl group and $R^a$ and $R^b$ independently represent ethyl or methyl, or together form an ethane-1,2-diyl, or propane-1,3-diyl linker.

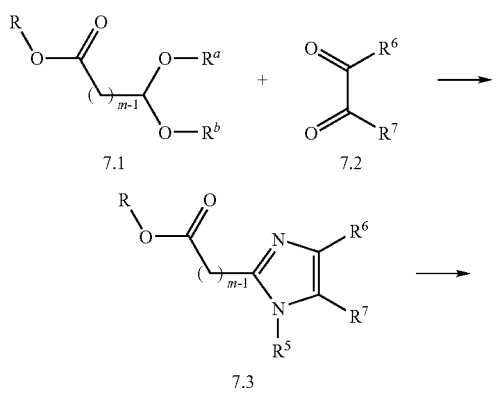

Scheme 7

-continued

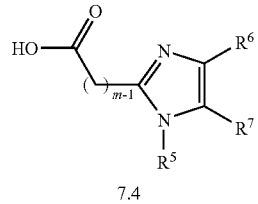

7.4

Reaction of a diketone 7.2 with an appropriately protected acetal-ester 7.1 in a protic solvent such as acetic acid and in presence of ammonium acetate at temperatures of about 100° C. for several hours yields the imidazole derivative 7.3 wherein $R^5$ is hydrogen. Diketones 7.2 and esters 7.1 are commercially available or well known in the art. In case $R^5$ is alkyl, the substituent can be introduced using standard reactions such as alkylation with an appropriate alkyl halogenide in presence of a base like sodium hydride or $K_2CO_3$ in solvents like acetone, DMF or THF at about 0° C. to give the corresponding imidazole derivative 7.3. Saponification of the ester group in 7.3 using methods described above leads to the desired imidazole building block 7.4.

Compounds of formula (I) wherein W represents —N($R^{11}$)—CO—$R^{12}$ are preferably synthesized using the building block CHO—$(CH_2)_{m-1}$—W. The required building blocks can be synthesized as outlined in Scheme 8 wherein $R^a$ and $R^b$ are as defined in Scheme 7 above. A commercially available alkylamine derivative 8.1 is coupled to the appropriate acid 8.2, which is commercially available, using standard amide coupling reagents and conditions such as EDC/HOBt in presence of a base such as NEt$_3$, in solvents like THF at rt to give the amide derivative 8.3. Hydrolysis of the acetal using standard acidic conditions such as TsOH in acetone at rt leads to the desired aldehyde 8.4.

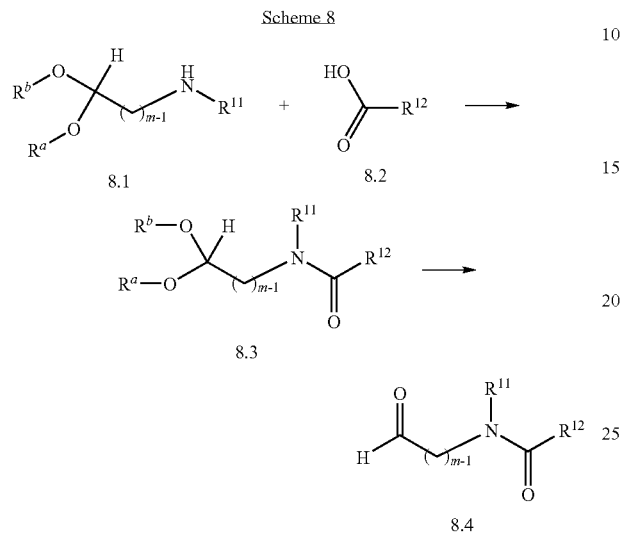

Scheme 8

Whenever the compounds of formula (I) are obtained in the form of mixtures of enantiomers, the enantiomers can be separated using methods known to one skilled in the art: e.g. by formation and separation of diastereomeric salts or by HPLC over a chiral stationary phase such as a Regis Whelk-O1(R,R) (10 μm) column, a Daicel ChiralCel OD-H (5-10 μm) column, or a Daicel ChiralPak IA (10 μm) or AD-H (5 μm) column. Typical conditions of chiral HPLC are an isocratic mixture of eluent A (EtOH, in presence or absence of an amine such as triethylamine, diethylamine) and eluent B (hexane), at a flow rate of 0.8 to 150 mL/min.

EXPERIMENTAL PART

The following examples illustrate the invention but do not at all limit the scope thereof.

All temperatures are stated in ° C. Compounds are characterized by $^1$H-NMR (400 MHz) or $^{13}$C-NMR (100 MHz) (Bruker; chemical shifts are given in ppm relative to the solvent used; multiplicities: s=singlet, d=doublet, t=triplet, q=quartet, p=pentuplet, hex=hexet, hept=heptet, m=multiplet, br=broad, coupling constants are given in Hz); by LC-MS (Finnigan Navigator with HP 1100 Binary Pump and DAD, column: 4.6×50 mm, Zorbax SB-AQ, 5 μm, 120 Å, gradient: 5-95% acetonitrile in water, 1 min, with 0.04% trifluoroacetic acid, flow: 4.5 mL/min), $t_R$ is given in min; by TLC (TLC-plates from Merck, Silica gel 60 F$_{254}$); or by melting point. Compounds are purified by preparative HPLC (column: X-terra RP18, 50×19 mm, 5 μm, gradient: 10-95% acetonitrile in water containing 0.5% of formic acid) or by column chromatography on silica gel. Racemates can be separated into their enantiomers by preparative HPLC (preferred conditions: Daicel, ChiralCel OD 20×250 mm, 10 μm, 4% ethanol in hexane, flow 10-20 mL/min).

| Abbreviations: (as used herein or in the description above) | |
|---|---|
| aq. | aqueous |
| Ac | acetyl |
| AcOH | acetic acid |
| anh. | anhydrous |
| BOC | tert.-butoxycarbonyl |
| BSA | bovine serum albumin |
| Bu | butyl |
| Cbz | benzyloxycarbonyl |
| CC | column chromatography on silica gel |
| Burgess reagent | (methoxycarbonylsulfamoyl)triethylammonium hydroxide |
| d | day(s) |
| DCM | dichloromethane |
| dil. | diluted |
| DIPA | diisopropylamine |
| DIPEA | diisopropyl-ethylamine, Hünig's base, ethyl-diisopropylamine |
| DMAP | dimethylaminopyridine |
| DME | dimethoxyethane |
| DMF | dimethylformamide |
| DMSO | dimethylsulfoxide |
| dppf | 1,1'-bis(diphenylphosphino-κP)ferrocene |
| EDC | N-(3-dimethylaminopropyl)-N'-ethylcarbodiimide |
| eq. | equivalent(s) |
| Et | ethyl |
| EtOAc | ethyl acetate |
| EtOH | ethanol |
| Et$_2$O | diethyl ether |
| h | hour(s) |
| HATU | (O-(7-azabenzotriazol-1-yl)-1,1,3,3-tetramethyl-uronium hexafluorphoshate |
| Hept | heptane |
| Hex | hexane |
| HOBt | 1-hydroxybenzotriazole |
| HPLC | high performance liquid chromatography |
| LC-MS | liquid chromatography-mass spectrometry |
| Me | methyl |
| MeCN | acetonitrile |
| MeOH | methanol |
| min | minute(s) |
| Ms | methanesulfonyl |
| NaOAc | sodium acetate |
| NEt$_3$ | triethylamine |
| OAc | O-acetyl, acetate |
| Pd/C | palladium on carbon |
| prep. | preparative |
| PyBOP | benzotriazole-1-yl-oxy-tris-pyrrolidino-phosphonium hexafluorophosphate |
| sat. | saturated |
| SEM | 2-(trimethylsilyl)ethoxymethyl |
| tert.- | tertiary (tert.-butyl = t-butyl = tertiary butyl) |
| Tf | trifluoromethanesulfonyl |
| TFA | trifluoroacetic acid |
| THF | tetrahydrofuran |
| TLC | thin layer chromatography |
| TMS | trimethylsilyl |
| Red-Al | sodium-bis(2-methoxyethoxy)aluminumhydride |
| Rh/C | rhodium on carbon |
| rt | room temperature |
| $t_R$ | retention time |
| Ts | para-toluenesulfonyl |
| TsOH | para-toluenesulfonic acid |

Preparation of Intermediates
General Procedures for the Preparation of Key Intermediates K:

Key intermediates K1A to K10B which are bicyclo[2.2.2]oct-5-en-2-yl or bicyclo[3.2.2]non-8-en-6-yl derivatives are obtained as a mixture between the major racemate having the relative configuration (R*,R*,R*) (i.e. the bridge —(CH$_2$)$_p$— of the cyclohexene moiety is cis to the group —OR$^3$ being hydroxy) and the minor racemate having the relative configuration (R*,S*,R*) or (R*,R*,S*), respectively (i.e. the bridge —(CH$_2$)$_p$—, wherein p represents 2 or 3, respectively, of the cyclohexene moiety is trans to the group —OR³ being hydroxy). The major and the minor racemates can be separated as described for key intermediate K1A in procedure A1.5. If not stated otherwise only the major racemate is isolated and used in the preparation of the examples below.

K1A: rac-(1R*,2R*,4R*)-(2-Hydroxy-5-phenyl-bicyclo[2.2.2]oct-5-en-2-yl)-acetic acid tert.-butyl ester K1A.1 (Procedure A1.1): rac-(1R*,4R*)-Bicyclo[2.2.2]octane-2,5-dione 25 mL of 2-(trimethylsilyloxy)-1,3-cyclohexadiene and 13 mL of α-acetoxyacrylonitrile were mixed and heated at 150° C. in a closed vessel for 22 h. The obtained dark orange viscous oil was dissolved in 200 mL of MeOH. After dropwise addition of a solution of 2.2 g of sodium methoxide in 150 mL of MeOH the reaction mixture was stirred for 3 h at rt, poured into ice/water and extracted with DCM. The organic phases were concentrated in vacuo and the crude residue was purified by CC with EtOAc-Hept (1:2) to yield 7.9 g of rac-(1R*,4R*)-bicyclo[2.2.2]octane-2,5-dione.
LC-MS: $t_R$=0.44 min.

K1A.2 (Procedure A1.2): rac-(1R*,4R*)-Spiro[bicyclo[2.2.2]octane-2,2'-[1,3]-dioxolan]-5-one To 4.0 g of rac-(1R*,4R*)-bicyclo[2.2.2]octane-2,5-dione (intermediate K1A.1), dissolved in 120 mL of toluene, 1.7 mL of ethylene glycol and 0.27 g of TsOH were added and the solution was heated under vigorous stirring to reflux for 3.5 h. The reaction mixture was cooled to rt, quenched with saturated aq. NaHCO₃, extracted with Et₂O, and the organic phase was evaporated. The crude product was purified by CC with Hex-EtOAc (7:3) to yield 2.41 g of rac-(1R*,4R*)-spiro[bicyclo[2.2.2]octane-2,2'-[1,3]dioxolan]-5-one as yellow oil.
LC-MS: $t_R$=0.64 min; [M+H+CH₃CN]⁺: 224.35.

K1A.3 (Procedure A1.3): Mixture of rac-(7R*,8R*,10R*) and rac-(7R*,8S*,10R*)-7,10-(1,2-Ethylen)-8-phenyl-1,4-dioxa-spiro[4.5]decan-8-ol To a solution of 2.41 g of rac-(1R*,4R*)-spiro[bicyclo[2.2.2]octane-2,2'-[1,3]dioxolan]-5-one (intermediate K1A.2) in 80 mL Et₂O, 14.5 mL phenylmagnesium bromide solution (1M in Et₂O) was added dropwise over 10 min. The reaction mixture was stirred for 4 h at rt. Then, the mixture was quenched carefully with ice, 8 mL 2N HCl were added and the phases were separated. The organic phase was evaporated and the crude product was purified by CC with Hept-EtOAC (7:3) to give 0.37 g of 7,10-(1,2-ethylen)-8-phenyl-1,4-dioxa-spiro[4.5]decan-8-ol as colorless oil. (Separation of the diastereomers by CC is possible but was only performed if stated.)
LC-MS: $t_R$=0.84 min; [M−H₂O+H]⁺: 243.34.

K1A.4 (Procedure A1.4): rac-(1R*,4R*)-5-Phenyl-bicyclo[2.2.2]oct-5-en-2-one

To a solution of 540 mg of 7,10-(1,2-ethylen)-8-phenyl-1,4-dioxa-spiro[4.5]decan-8-ol (intermediate K1A.3) in 20 mL acetone was added 200 mg of TsOH and then the mixture was stirred for 2 days at rt. The reaction mixture was quenched with sat. aq. NaHCO₃, extracted with EtOAC and the organic phase was evaporated. The crude product was purified by CC with Hept-EtOAC (7:3) to give 0.34 g of rac-(1R*,4R*)-5-phenyl-bicyclo[2.2.2]oct-5-en-2-one as colorless oil.
LC-MS: $t_R$=0.93 min; [M+H+CH₃CN]⁺: 240.11.

K1A.5 (Procedure A1.5): rac-(1R*,2R*,4R*)-(2-Hydroxy-5-phenyl-bicyclo[2.2.2]oct-5-en-2-yl)-acetic acid tert.-butyl ester and rac-(1R*,2S*,4R*)-(2-hydroxy-5-phenyl-bicyclo[2.2.2]oct-5-en-2-yl)-acetic acid tert.-butyl ester To a solution of 0.51 mL of DIPA in 0.5 mL THF 2.2 mL of n-butyllithium (1.6M in hexane) were added dropwise at −20° C. After 10 min, 0.5 mL of toluene were added and the solution was stirred for 30 min. The mixture was cooled to −50° C., 0.73 mL of tert.-butyl acetate were added and stirring was continued for 1 h at −50° C. Then 0.32 g of rac-(1R*,4R*)-5-phenyl-bicyclo[2.2.2]oct-5-en-2-one (intermediate K1A.4) dissolved in 1 mL of THF was added and the solution was stirred at −50 to −20° C. over 2.5 h. The reaction mixture was poured on ice/aq. HCl, the organic phase was separated, washed and evaporated. The crude reaction product was purified by CC with Hept-EtOAc (9:1) to yield 0.30 g of the major racemate, rac-(1R*,2R*,4R*)-2-hydroxy-5-phenyl-bicyclo[2.2.2]oct-5-en-2-yl)-acetic acid tert.-butyl ester, as white solid and 0.07 g of the minor racemate, rac-(1R*,2S*,4R*)-2-hydroxy-5-phenyl-bicyclo[2.2.2]oct-5-en-2-yl)-acetic acid tert.-butyl ester, as colorless oil.
LC-MS (major racemate): $t_R$=1.06 min; [M−(CH₃)₃—H₂O+H]⁺: 241.11.
LC-MS (minor racemate): $t_R$=1.05 min; [M+H]⁺: 315.18.

K1A.6: (1S,2S,4S)-(2-Hydroxy-5-phenyl-bicyclo[2.2.2]oct-5-en-2-yl)-acetic acid tert.-butyl ester and (1R,2R,4R)-(2-Hydroxy-5-phenyl-bicyclo[2.2.2]oct-5-en-2-yl)-acetic acid tert.-butyl ester rac-(1R*,2R*,4R*)-(2-Hydroxy-5-phenyl-bicyclo[2.2.2]oct-5-en-2-yl)-acetic acid tert.-butyl ester was separated into the respective enantiomers using prep. chiral HPLC (column: Daicel ChiralPak AD-H, 20×250 mm, 5 μm; Hex/EtOH 95:5, flow 16 mL/min)
Chiral analytic HPLC (Daicel ChiralPak AD-H, 4.6×250 mm, 5 μm; Hex/EtOH 95:5, flow 0.8 mL/min):
Enantiomer A: $t_R$=6.70 min.
Enantiomer B: $t_R$=7.93 min.

K1B: rac-(1R*,2R*,4R*)-(2-Hydroxy-5-(3-methoxyphenyl-bicyclo[2.2.2]oct-5-en-2-yl)-acetic acid tert.-butyl ester Synthesized in analogy to K1A from rac-(1R*,4R*)-bicyclo[2.2.2]octane-2,5-dione using a Grignard reagent freshly prepared from 3-bromoanisol and Mg in step A1.3.
LC-MS (major racemate): $t_R$=1.06 min; [M−(CH₃)₃—H₂O+H]⁺: 271.31.

K1C: rac-(1R*,2R*,4R*)-(5-(2,6-Dimethyl-phenyl)-2-hydroxy-bicyclo[2.2.2]oct-5-en-2-yl)-acetic acid tert.-butyl ester Synthesized in analogy to K1A from rac-(1R*,4R*)-bicyclo[2.2.2]octane-2,5-dione using 2,6-dimethyl-phenylmagnesiumbromide in step A1.3.
LC-MS (major racemate): $t_R$=1.12 min; [M−(CH₃)₃—H₂O+H]⁺: 269.42.

K1D: rac-(1R*,2R*,4R*)-(2-Hydroxy-5-thiophen-2-yl-bicyclo[2.2.2]oct-5-en-2-yl)-acetic acid tert.-butyl ester Synthesized in analogy to K1A from rac-(1R*,4R*)-bicyclo[2.2.2]octane-2,5-dione using thiophen-2-yl-magnesiumbromide in step A1.3.
LC-MS (major racemate): $t_R$=1.05 min; [M-(CH$_3$)$_3$—H$_2$O+H]$^+$: 247.32

K2A: rac-(1R*,2R*,4R*)-(2-Hydroxy-5-(4-methoxy-phenyl)-bicyclo[2.2.2]oct-5-en-2-yl)-acetic acid tert.-butyl ester

K2A.1 (Procedure A1.6): Mixture of rac-(1R*,4R*,5R*) and rac-(1R*,4R*,5S*)-(5-Hydroxy-5-(4-methoxy-phenyl))-bicyclo[2.2.2]octan-2-one To a solution of 2.11 g of rac-(1R*,4R*)-bicyclo[2.2.2]octane-2,5-dione (intermediate K1A.1) in 80 mL of Et$_2$O 33.6 mL of 4-methoxyphenylmagnesium bromide solution (0.5M in THF) was added successively at 0° and the mixture stirred for 85 min. at 0° C. The reaction mixture was quenched with ice-water, acidified with aq. HCl, and extracted with Et$_2$O. The organic phase was concentrated in vacuo to give 3.03 g of the title product as colorless oil, which was directly engaged in the next dehydration step without any characterization.

K2A.2 (Procedure A1.7): rac-(1R*,4R*)-5-(4-Methoxy-phenyl)-bicyclo[2.2.2]oct-5-en-2-one 3.03 g of crude 5-hydroxy-5-(4-methoxy-phenyl)-bicyclo[2.2.2]octan-2-one (intermediate K2A.1) was dissolved in 100 mL of acetone, 2.90 g of TsOH were added and the mixture was stirred at rt overnight. Then the reaction mixture was diluted with EtOAc, the organic phase washed with sat. aq. NaHCO$_3$ and evaporated. The crude material was purified by CC with Hep-EtOAc (20:1) to yield 2.36 g of rac-(1R*,4R*)-5-(4-methoxy-phenyl)-bicyclo[2.2.2]oct-5-en-2-one.
LC-MS: $t_R$=0.94 min; [M+H]$^+$=229.36.

K2A.3: rac-(1R*,2R*,4R*)-(2-Hydroxy-5-(4-methoxy-phenyl)-bicyclo[2.2.2]oct-5-en-2-yl)-acetic acid tert.-butyl ester Prepared from rac-(1R*,4R*)-5-(4-methoxy-phenyl)-bicyclo[2.2.2]oct-5-en-2-one (intermediate K2A. 2) using procedure A1.5.
LC-MS (major racemate): $t_R$=1.06 min; [M-(CH$_3$)$_3$—H$_2$O+H]$^+$: 271.39.

K2B: rac-(1R*,2R*,4R*)-(2-Hydroxy-5-(2-methoxy-phenyl)-bicyclo[2.2.2]oct-5-en-2-yl)-acetic acid tert.-butyl ester Prepared in analogy to intermediate K2A using 2-methoxyphenylmagnesium bromide in procedure A1.6.
LC-MS (major racemate): $t_R$=1.07 min; [M-H$_2$O+H]$^+$: 327.49

K2C: rac-(1R*,2R*,4R*)-(2-Hydroxy-5-(2-methyl-phenyl)-bicyclo[2.2.2]oct-5-en-2-yl)-acetic acid tert.-butyl ester Prepared in analogy to intermediate K2A using 4-methoxyphenylmagnesium bromide in procedure A1.6.
LC-MS (major racemate): $t_R$=1.09 min; [M-(CH$_3$)$_3$—H$_2$O+H]$^+$: 255.24.

K2D: rac-(1R*,2R*,4R*)-(2-Hydroxy-5-(3-methyl-phenyl)-bicyclo[2.2.2]oct-5-en-2-yl)-acetic acid tert.-butyl ester Prepared in analogy to intermediate K2A using 3-methylphenylmagnesium bromide in procedure A1.6.
LC-MS (major racemate): $t_R$=1.09 min; [M-H$_2$O+H]$^+$: 311.39.

K2E: rac-(1R*,2R*,4R*)-(2-Hydroxy-5-(4-methyl-phenyl)-bicyclo[2.2.2]oct-5-en-2-yl)-acetic acid tert.-butyl ester Prepared in analogy to intermediate K2A using 4-methylphenylmagnesium bromide in procedure A1.6.
LC-MS (major racemate): $t_R$=1.10 min; [M-H$_2$O+H]$^+$: 311.46

K2F: rac-(1R*,2R*,4R*)-(5-(3-Fluoro-phenyl)-2-hydroxy-bicyclo[2.2.2]oct-5-en-2-yl)-acetic acid tert.-butyl ester Prepared in analogy to intermediate K2A using 3-fluorophenylmagnesium bromide in procedure A1.6.
LC-MS (major racemate): $t_R$=1.09 min; [M+H]$^+$: 333.19.

K2G: rac-(1R*,2R*,4R*)-(5-(4-Fluoro-phenyl)-2-hydroxy-bicyclo[2.2.2]oct-5-en-2-yl)-acetic acid tert.-butyl ester Prepared in analogy to intermediate K2A using 4-fluorophenylmagnesium bromide in procedure A1.6.
LC-MS (major racemate): $t_R$=1.07 min; [M-H$_2$O+H]$^+$: 315.32.

K2H: rac-(1R*,5R*,6R*)-(6-Hydroxy-8-phenyl-bicyclo[3.2.2]non-8-en-6-yl)-acetic acid tert.-butyl ester Prepared from rac-(1R*,5R*)-bicyclo[3.2.2]nonane-6,8-dione (synthesized according to known procedures: Can. J. Chem. 1968, 46, 3713-3717) in analogy to intermediate K2A using phenylmagnesium bromide in procedure A1.6.
LC-MS (major racemate): $t_R$=1.11 min; [M-(CH$_3$)$_3$—H$_2$O+H]$^+$: 254.02.

K3A: rac-(1R*,2R*,4R*)-(2-Hydroxy-5-pyridin-3-yl-bicyclo[2.2.2]oct-5-en-2-yl)-acetic acid tert.-butyl ester

K3A.1 (Procedure A1.8): Mixture of rac-(7R*,8R*,10R*) and rac-(7R*,8S*,10R*)-7,10-(1,2-Ethylen)-8-pyridin-3-yl-1,4-dioxa-spiro[4.5]decan-8-ol To a solution of 3.56 mL n-BuLi (1.6M in hexanes) in 7 mL Et$_2$O was added dropwise a solution of 0.55 mL 3-bromopyridine in 7 mL Et$_2$O at -72° C. The obtained suspension was stirred for 30 min at the same temperature before 0.70 g of rac-(1R*,4R*)-spiro[bicyclo[2.2.2]octane-2,2'-[1,3]dioxolan]-5-one (intermediate KA1.2) in 6 mL Et$_2$O was added. The reaction mixture was stirred for 3 h at -60° C. and then poured into a mixture of sat. NH$_4$Cl solution/ice. The water phase was extracted with DCM, the combined organic phases were washed with sat. aq. NaHCO$_3$, dried over MgSO$_4$ and then concentrated in vacuo to give 1.1 g of crude 7,10-(1,2-ethylen)-8-pyridin-3-yl-1,4-dioxa-spiro[4.5]decan-8-ol as yellow oil.

LC-MS: $t_R$=0.52 min; [M+H]$^+$: 262.38.

K3A.2 (Procedure A1.9): Mixture of rac-(1R*,4R*,5R*) and rac-(1R*,4R*,5S*)-5-Hydroxy-5-pyridin-3-yl-bicyclo[2.2.2]octan-2-one To a solution of 0.99 g of 7,10-(1,2-ethylen)-8-pyridin-3-yl-1,4-dioxa-spiro[4.5]decan-8-ol (intermediate KA3.1) in 20 mL acetone was added 2.16 g of TsOH and the mixture was stirred overnight at rt. The reaction was quenched by the addition of sat. aq. NaHCO$_3$ solution. The pH was adjusted to 10 by using 1M NaOH. The mixture was extracted with EtOAc, the organic phase was washed with brine, dried over MgSO$_4$ and concentrated in vacuo to obtain 0.98 g of crude 5-hydroxy-5-pyridin-3-yl-bicyclo[2.2.2]octan-2-one as yellow oil.

LC-MS: $t_R$=0.37 min; [M+H]$^+$: 218.34.

K3A.3 (Procedure A1.10): rac-(1R*,4R*)-5-Pyridin-3-yl-bicyclo[2.2.2]oct-5-en-2-one To a solution of 0.5 g of crude 5-hydroxy-5-pyridin-3-yl-bicyclo[2.2.2]octan-2-one (intermediate K3A.2) in 20 mL DCM were added 84 mg DMAP and 1.6 mL NEt$_3$. The mixture was cooled to 0° C. before 0.53 mL of mesylchloride was added dropwise. The resulting suspension was stirred at 0° C. for 1 h and then overnight at rt. The reaction was quenched by the addition of sat. aq. NaHCO$_3$ solution. The water phase was extracted with EtOAc. The combined organic phases were washed with brine, dried over MgSO$_4$ and concentrated in vacuo. Purification by CC (EtOAc) yielded 0.27 g of rac-(1R*,4R*)-5-pyridin-3-yl-bicyclo[2.2.2]oct-5-en-2-one as yellow oil.

LC-MS: $t_R$=0.51 min; [M+H]$^+$: 200.30.

K3A.4: rac-(1R*,2R*,4R*)-(2-Hydroxy-5-pyridin-3-yl-bicyclo[2.2.2]oct-5-en-2-yl)-acetic acid tert.-butyl ester Prepared using procedure A1.5 from rac-(1R*,4R*)-5-pyridin-3-yl-bicyclo[2.2.2]oct-5-en-2-one (intermediate K3A.3).

LC-MS (major racemate): $t_R$=0.71 min; [M+H]$^+$: 316.50.

K4A: rac-(1R*,2R*,4R*)-(2-Hydroxy-5-thiazol-2-yl-bicyclo[2.2.2]oct-5-en-2-yl)-acetic acid tert.-butyl ester K4A.1: Mixture of rac-(7R*,8R*,10R*) and rac-(7R*,8S*,10R*)-7,10-(1,2-Ethylen)-8-thiazol-1,4-dioxa-spiro[4.5]decan-8-ol In analogy to procedure A1.8, 0.228 mL of thiazole were dissolved in anh. THF (7.4 mL) under argon and the mixture was cooled to −78° C. 1.85 mL of a n-BuLi solution (1.6 M in hexanes) was added dropwise for 10 min. The resulting pale orange reaction mixture was stirred for 1 h at −78° C. 450 mg of rac-(1R*,4R*)-spiro[bicyclo[2.2.2]octane-2,2'-[1,3]dioxolan]-5-one in THF (5 mL) was added dropwise at −78° C. and the reaction mixture was stirred for 5 h allowing the temperature to increase to rt. The reaction was quenched with sat. NH$_4$Cl and extracted with DCM. The organic phase was washed with water and brine, dried over anh. Na$_2$SO$_4$ and concentrated in vacuo to give 576 mg of 7,10-(1,2-ethylen)-8-thiazol-1,4-dioxa-spiro[4.5]decan-8-ol as a yellow oil.

LC-MS: $t_R$=0.69/0.71 min; [M+H]$^+$: 268.37.

K4A.2: Mixture of rac-(1R*,4R*,5R*) and rac-(1R*,4R*,5S*)-5-Hydroxy-5-thiazol-2-yl-bicyclo[2.2.2]octan-2-one Prepared from 7,10-(1,2-ethylen)-8-thiazol-1,4-dioxa-spiro[4.5]decan-8-ol in analogy to procedure A1.9.

LC-MS: $t_R$=0.62/0.63 min; [M+H]$^+$: 224.29.

K4A.3 (Procedure A1.11): rac-(1R*,4R*)-5-Thiazol-2-yl-bicyclo[2.2.2]oct-5-en-2-one 806 mg of 5-hydroxy-5-thiazol-2-yl-bicyclo[2.2.2]octan-2-one were dissolved in THF (7.2 mL) and 2.58 g of the Burgess'reagent was added portionwise at 0° C. The ice bath was removed and the reaction mixture was stirred at rt for 4 h, then quenched with cold water and extracted with DCM. The organic phase was washed with water and brine, dried over anh. Na$_2$SO$_4$, filtered and concentrated in vacuo. The crude material was purified by CC using EtOAc/heptane (1/2) as eluant to yield 412 mg of rac-(1R*,4R*)-5-thiazol-2-yl-bicyclo[2.2.2]oct-5-en-2-one as a yellowish oil.

LC-MS: $t_R$=0.77 min; [M+H]$^+$: 206.25.

K4A.4: rac-(1R*,2R*,4R*)-(2-Hydroxy-5-thiazol-2-yl-bicyclo[2.2.2]oct-5-en-2-yl)-acetic acid tert.-butyl ester Prepared from rac-(1R*,4R*)-5-thiazol-2-yl-bicyclo[2.2.2]oct-5-en-2-one (intermediate K4A.3) in analogy to procedure A1.5.

LC-MS (major racemate): $t_R$=0.93 min; [M+H]$^+$: 322.39.

K4B: rac-(1R*,2R*,4R*)-(2-Hydroxy-5-oxazol-2-yl-bicyclo[2.2.2]oct-5-en-2-yl)-acetic acid tert.-butyl ester K4B.1: Mixture of rac-(7R*,8R*,10R*) and rac-(7R*,8S*,10R*)-7,10-(1,2-Ethylen)-8-oxazol-1,4-dioxa-spiro[4.5]decan-8-ol In analogy to procedure A1.8, 264 mg of oxazole were dissolved in anh. THF (8.5 mL) under argon and 3.8 mL of a solution of BH$_3$-THF complex (1M in THF) were added at rt. The mixture was stirred for 3 h at rt and cooled to −78° C. 2.2 mL of a n-BuLi solution (1.6 M in hexanes) was added dropwise for 5 min. The resulting dark yellow reaction mixture was stirred for 1 h at −78° C. and 536 mg of rac-(1R*,4R*)-spiro[bicyclo[2.2.2]octane-2,2'-[1,3]dioxolan]-5-one in THF (6.6 mL) was added dropwise at −78° C. and the reaction mixture was stirred overnight allowing the temperature to increase to rt. The reaction was quenched with sat. NH$_4$Cl and extracted with DCM. The organic phase was dried over anh. Na$_2$SO$_4$ and concentrated in vacuo to give 698 mg of crude 7,10-(1,2-ethylen)-8-oxazol-1,4-dioxa-spiro[4.5]decan-8-ol as a yellowish oil.

LC-MS: $t_R$=0.64 min; [M+H]$^+$: 252.32.

K4B.2: rac-(1R*,2R*,4R*)-(2-Hydroxy-5-oxazol-2-yl-bicyclo[2.2.2]oct-5-en-2-yl)-acetic acid tert.-butyl ester Prepared in analogy to intermediate K3A using 7,10-(1,2-ethylen)-8-oxazol-1,4-dioxa-spiro[4.5]decan-8-ol in procedure A1.9.

LC-MS (major racemate): $t_R$=0.92 min; [M+H]$^+$: 306.40

K5A: rac-(1R*,2R*,4R*)-(2-Hydroxy-5-naphthalen-2-yl-bicyclo[2.2.2]oct-5-en-2-yl)-acetic acid tert.-butyl ester

K5A.1 (Procedure A1.12): rac-Trifluoro-methane-sulfonic acid (1R*,4R*)-5-oxo-bicyclo[2.2.2]oct-2-en-2-yl ester To a solution of 0.8 g of rac-(1R*,4R*)-spiro[bicyclo[2.2.2]octane-2,2'-[1,3]dioxolan]-5-one (A1.2) and 3.16 g of 2,5-di-tert.-butyl-4-methylpyridine in 25 mL of DCM, 1.1 mL of trifluoromethanesulfonic acid anhydride was added at 0° C. After stirring for 2 h at 0° C. and at rt overnight the reaction mixture was filtered and the solvent was evaporated to give rac-trifluoro-methanesulfonic acid (1R*,4R*)-5-oxo-bicyclo[2.2.2]oct-2-en-2-yl ester. The crude material was used without purification.

$^1$H-NMR (CDCl$_3$): 6.02 (dd, 1H); 3.93 (m, 4H); 2.79 (m, 2H); 1.98 (m, 2H); 1.81 (dd, 1H); 1.68 (m, 2H); 1.32 (m, 1H).

K5A.2 (Procedure A1.13): rac-(6R*,9R*)-6,9-(1,2-Ethylen)-8-(2-naphthyl)-1,4-dioxa-spiro[4.5]dec-7-ene To a solution of 0.42 g of crude rac-trifluoro-methane-sulfonic acid (1R*,4R*)-5-oxo-bicyclo[2.2.2]oct-2-en-2-yl ester in 6 mL DME were added 0.58 g of 2-naphthalene boronic acid and 0.75 mL of 2M aq. Na$_2$CO$_3$ and the mixture was flushed with N$_2$. Then, 0.15 g of tetrakis-(triphenylphosphin)-palladium was added and the mixture was heated in a closed vessel to 80° C. overnight. The black crude mixture was diluted with DCM, washed with water, dried over MgSO$_4$ and concentrated in vacuo. Purification by CC with Hept to Hept-EtOAc (7:3) yielded 0.095 g of rac-(6R*,9R*)-6,9-(1,2-ethylen)-8-(2-naphthyl)-1,4-dioxa-spiro[4.5]dec-7-ene as yellow oil.

LC-MS: $t_R$=1.06 min; [M+H]$^+$: 293.29.

K5A.2: rac-(1R*,4R*)-5-Naphthalen-2-yl-bicyclo[2.2.2]oct-5-en-2-one

Prepared from rac-(6R*,9R*)-6,9-(1,2-ethylen)-8-(2-naphthyl)-1,4-dioxa-spiro[4.5]dec-7-ene using procedure A1.4.

LC-MS: $t_R$=1.02 min; [M+H]$^+$: 249.40

K5A.3: rac-(1R*,2R*,4R*)-(2-Hydroxy-5-naphthalen-2-yl-bicyclo[2.2.2]oct-5-en-2-yl)-acetic acid tert.-butyl ester Prepared using procedure A1.5 from rac-(1R*,4R*)-5-naphthalen-2-yl-bicyclo[2.2.2]oct-5-en-2-one.

LC-MS (major racemate): $t_R$=1.12 min; [M-(CH$_3$)$_3$—H$_2$O+H]$^+$: 291.40

K6A: rac-(1R*,2R*,4R*)-(2-Hydroxy-6-methyl-5-propyl-bicyclo[2.2.2]oct-5-en-2-yl)-acetic acid tert.-butyl ester

K6A.1: rac-(1R*,4R*)-6-Methyl-5-propyl-bicyclo[2.2.2]oct-5-en-2-one

Prepared using the method described in Jung, Michael E.; Tetrahedron Letters 2005, 46(30), 5057-5061. To a suspension of 2.8 g of phosphorous pentoxide in 30 mL anh. DCM were added 6.1 mL of 2-hexanone followed by 14.4 mL of 2-cyclohexen-1-one at rt. The suspension was cooled to 0° C. with an ice bath before 13 mL of trifluoromethanesulfonic acid was carefully added. The reaction mixture was warmed to rt and then heated at 40° C. overnight. 27 mL of NEt$_3$ were dropwise added at 0° C., the mixture was stirred at rt for 10 min and then evaporated to dryness. Purification by CC with EtOAc-Hept (25:75) yielded 3.37 g of rac-(1R*,4R*)-6-methyl-5-propyl-bicyclo[2.2.2]oct-5-en-2-one as brown oil.

LC-MS: $t_R$=0.98 min; [M+H+CH$_3$CN]$^+$: 220.31

K6A.2: rac-(1R*,2R*,4R*)-(2-Hydroxy-6-methyl-5-propyl-bicyclo[2.2.2]oct-5-en-2-yl)-acetic acid tert.-butyl ester Prepared using procedure A1.5 from rac-(1R*,4R*)-6-methyl-5-propyl-bicyclo[2.2.2]oct-5-en-2-one.

LC-MS (major racemate): $t_R$=1.12 min; [M+H]$^+$: 295.38

K6B: rac-(1R*,2R*,4R*)-(2-Hydroxy-5-methyl-6-phenyl-bicyclo[2.2.2]oct-5-en-2-yl)-acetic acid tert.-butyl ester

K6B.1: rac-(1R*,4R*)-5-Methyl-6-phenyl-bicyclo[2.2.2]oct-5-en-2-one

To a suspension of 0.5 g of phosphorous pentoxide in 30 mL anh. DCM were added 1.3 mL of propiophenone followed by 2.9 mL of 2-cyclohexen-1-one at rt. The suspension was cooled to 0° C. with an ice bath before 2.6 mL of trifluoromethanesulfonic acid was carefully added. The reaction mixture was warmed to rt and then heated at 40° C. overnight. 5.4 mL of NEt$_3$ were dropwise added at 0° C., the mixture was stirred at rt for 10 min and then evaporated to dryness. Purification by CC with EtOAc-Hept (2:8) yielded 1.2 g of rac-(1R*,4R*)-5-methyl-6-phenyl-bicyclo[2.2.2]oct-5-en-2-one as yellow oil.

LC-MS: $t_R$=0.99 min; [M+H]$^+$: 213.09

K6B.2: rac-(1R*,2R*,4R*)-(2-Hydroxy-5-methyl-6-phenyl-bicyclo[2.2.2]oct-5-en-2-yl)-acetic acid tert.-butyl ester and rac-(1R*,2S*,4R*)-(2-Hydroxy-5-methyl-6-phenyl-bicyclo[2.2.2]oct-5-en-2-yl)-acetic acid tert.-butyl ester Prepared using procedure A1.5 from rac-(1R*,4R*)-5-methyl-6-phenyl-bicyclo[2.2.2]oct-5-en-2-one.

LC-MS (major racemate): $t_R$=1.11 min; [M+H]$^+$: 329.36
LC-MS (minor racemate): $t_R$=1.10 min; [M+H]$^+$: 329.34

K6C: rac-(1R*,3R*,4R*)-1,2,3,4,9,10-Hexahydro-3-hydroxy-1,4-ethanophenanthren-3-ylacetic acid tert.-butyl ester

K6C.1: rac-(1R*,4R*)-1,2,3,4,9,10-Hexahydro-3-oxo-1,4-ethanophenanthrene

To a suspension of 1.9 g of phosphorous pentoxide in 50 mL DCM$_{anh.}$ were added 4.5 mL of alpha tetralone followed by 9.9 mL of 2-cyclohexen-1-one at rt. The suspension was cooled to 0° C. with an ice bath before 9.0 mL of trifluoromethanesulfonic acid was carefully added. The reaction mixture was warmed to rt and then heated at 40° C. overnight. 18.5 mL of NEt$_3$ were dropwise added at 0° C., the mixture was stirred at rt for 10 min and then evaporated to dryness. Purification by CC with EtOAc-Hept (2:8) yielded 3.9 g of rac-(1R*,4R*)-1,2,3,4,9,10-hexahydro-3-oxo-1,4-ethanophenanthrene as yellow oil.

LC-MS: $t_R$=1.00 min; [M+H]$^+$: 225.10

K6C.2: rac-(1R*,3R*,4R*)-1,2,3,4,9,10-Hexahydro-3-hydroxy-1,4-ethanophenanthren-3-ylacetic acid tert.-butyl ester Prepared using procedure A1.5 from rac-(1R*,4R*)-1,2,3,4,9,10-hexahydro-3-oxo-1,4-ethanophenanthrene.
LC-MS (major racemate): $t_R$=1.12 min; [M+H]$^+$: 341.12

K7A: ((1S,4S)-(5RS)-5-Hydroxy-2-phenyl-2-aza-bicyclo[2.2.2]oct-5-yl)-acetic acid tert-butyl ester

K7A.1: (1S,4S)-2-Phenyl-2-aza-bicyclo[2.2.2]octan-5-one

Prepared using the method described in Sunden, Henrik, Angew. Chem. Int. Ed. 2005, 44, 4877-4880:

To a solution of 2.4 mL of formaldehyde (36.5% in water), 3.1 mL of aniline and 1.0 g of (S)-proline in 125 mL of DMSO was added 6.0 mL of 2-cyclohexen-1-one. The mixture was stirred for 72 h at rt, quenched with water and extracted with toluene. The organic phase was dried over anh. Na$_2$SO$_4$ and concentrated in vacuo. The crude product was purified by CC using EtOAc/heptane 1/5 to 1/3 to yield 1.1 g of (1S,4S)-2-phenyl-2-aza-bicyclo[2.2.2]octan-5-one a as yellow oil.
LC-MS: $t_R$=0.90 min; [M+H]$^+$: 202.32.

K7A.2: ((1S,4S)-(5RS)-5-Hydroxy-2-phenyl-2-aza-bicyclo[2.2.2]oct-5-yl)-acetic acid tert-butyl ester Prepared using procedure A1.5 from (1S,4S)-2-phenyl-2-aza-bicyclo[2.2.2]octan-5-one, except that the diastereoisomers were not separated.
LC-MS (both diastereoisomers): $t_R$=0.90/0.99 min; [M+H]$^+$: 318.48.

K8A: rac-((1R*,2R*,4R*)-2-Hydroxy-bicyclo[2.2.2]oct-5-en-2-yl)-acetic acid tert-butyl ester

K8A.1: rac-(1R*,4R*)-Bicyclo[2.2.2]oct-5-en-2-one

A mixture of 7.0 g of α-acetoxyacrylonitrile and 3.2 g of 1,3-cyclohexadiene was heated in a closed microwave tube at 90° C. for 24 h. The obtained brown oil was taken up in DCM and evaporated. The crude mixture was washed over a pad of Celite (2 cm) using 300 mL of Hept-EtOAc (9:1) and then concentrated in vacuo. The yellow oil was redissolved in 10 mL DMSO and 3.2 g of KOH, dissolved in 5 mL water, was carefully added. The resulting black mixture was stirred for 2 d at rt, diluted with water and extracted 3 times with Hept. The combined organic phases were washed 3 times with brine, dried over Na$_2$SO$_4$ and concentrated in vacuo to obtain 1.0 g of rac-(1R*,4R*)-bicyclo[2.2.2]oct-5-en-2-one as beige solid.
$^1$H-NMR (CDCl$_3$): 6.42 (m, 1H); 6.18 (m, 1H); 3.08 (m, 1H); 2.96 (m, 1H); 1.80-1.40 (m, 6H).

K8A.2: rac-((1R*,2R*,4R*)-2-Hydroxy-bicyclo[2.2.2]oct-5-en-2-yl)-acetic acid tert-butyl ester Prepared from rac-(1R*,4R*)-bicyclo[2.2.2]oct-5-en-2-one (intermediate K8A.1) using procedure A1.5.
$^1$H-NMR (DMSO) (major racemate): 6.16 (t, 2H); 4.44 (s, 1H); 2.41 (m, 1H); 2.15 (s, 2H); 2.05 (m, 1H); 1.49 (m, 3H); 1.36 (s, 9H); 1.30 (m, 1H); 1.11 (m, 1H); 0.89 (m, 1H).

K9A: rac-((1R*,2R*,4R*,5R*)-2-Hydroxy-5-methoxy-5-phenyl-bicyclo[2.2.2]oct-2-yl)-acetic acid tert-butyl ester

K9A.1 (Procedure A1.14): rac-(7R*,8R*,10R*)-8-Methoxy-7,10-(1,2-ethylen)-8-phenyl-1,4-dioxa-spiro[4.5]decane To a solution of 267 mg of rac-(7R*,8R*,10R*)-7,10-(1,2-ethylen)-8-phenyl-1,4-dioxa-spiro[4,5]decan-8-ol (intermediate K1A.3, minor isomer) in 8 mL THF were added 123 mg of NaH (60%) followed by 0.19 mL of MeI at 0° C. The ice bath was removed after 10 min and stirring was continued overnight at rt. The reaction mixture was quenched with water, extracted with EtOAc, dried over MgSO$_4$ and concentrated in vacuo to give 0.32 mg of rac-(7R*,8R*,10R*)-8-methoxy-7,10-(1,2-ethylen)-8-phenyl-1,4-dioxa-spiro[4.5]decane as yellow oil.
LC-MS: $t_R$=0.98 min; [M-MeOH+H]$^+$: 243.40

K9A.2: rac-(1R*,4R*,5R*)-5-Methoxy-5-phenyl-bicyclo[2.2.2]octan-2-one

Prepared from rac-(7R*,8R*,10R*)-8-methoxy-7,10-(1,2-ethylen)-8-phenyl-1,4-dioxa-spiro[4.5]decane (intermediate K9A.1) using procedure A1.4.
LC-MS: $t_R$=0.91 min; [M+H+CH$_3$CN]$^+$: 272.39

K9A.3: rac-((1R*,2R*,4R*,5R*)-2-Hydroxy-5-methoxy-5-phenyl-bicyclo[2.2.2]oct-2-yl)-acetic acid tert-butyl ester Prepared from rac-(7R*,8R*,10R*)-8-methoxy-7,10-(1,2-ethylen)-8-phenyl-1,4-dioxa-spiro[4.5]decane (intermediate K9A.2) using procedure A1.5.
LC-MS (major racemate): $t_R$=1.07 min; [M+H]$^+$: 347.54.

K9B: rac-((1R*,2R*,4R*,5S*)-2-Hydroxy-5-methoxy-5-phenyl-bicyclo[2.2.2]oct-2-yl)-acetic acid tert-butyl ester Prepared in analogy to intermediate K9A using rac-(7R*,8S*,10R*)-7,10-(1,2-ethylen)-8-phenyl-1,4-dioxa-spiro[4,5]decan-8-ol (intermediate K1A.3, major isomer) in procedure A1.14.
LC-MS (major racemate): $t_R$=1.06 min; [M-MeOH+H]$^+$: 315.45.

K9C: rac-((1R*,2S*,4R*,5S*)-2-Hydroxy-5-methoxy-5-phenyl-bicyclo[2.2.2]oct-2-yl)-acetic acid tert-butyl ester Prepared in analogy to intermediate K9A using rac-(7R*,8S*,10R*)-7,10-(1,2-ethylen)-8-phenyl-1,4-dioxa-spiro[4,5]decan-8-ol (intermediate K1A.3, major isomer) in procedure A1.14.
LC-MS (minor racemate): $t_R$=1.06 min; [M-MeOH—H2O+H]$^+$: 297.46.

K10A: rac-(1R*,2R*,4R*,5R*)-5-hydroxy-(3'H-spiro(bicyclo[2.2.2]octane-2,1'-isobenzofuran)-5-yl)-acetic acid tert-butyl ester

K10A.1: rac-(7R*,8R*,10R*)-7,10-(1,2-ethylen)-8-(2-hydroxymethyl-phenyl)-1,4-dioxa-spiro[4,5]decan-8-ol and rac-(7R*,8S*,10R*)-7,10-(1,2-ethylen)-8-(2-hydroxymethyl-phenyl)-1,4-dioxa-spiro[4,5]decan-8-ol To a solution of 7.20 g of 2-bromobenzyl alcohol in 75 mL THF anh. were added dropwise at −78° C. 36.3 mL of n-butyllithium (1.6M in hexane). After stirring for 30 min at the same temperature a solution of 2.30 g of rac-(1R*,4R*)-spiro [bicyclo[2.2.2]octane-2,2'-[1,2]dioxolan]-5-one (intermediate K1A.2) in 25 mL THF anh. was added and stirring was continued for 2.5 h in the cooling bath. The reaction mixture was quenched with sat. aq. NH$_4$Cl, extracted with EtOAc, dried over MgSO$_4$ and concentrated in vacuo. The crude product was purified by CC with Hept-EtOAc (1:1) to yield 0.66 g of the minor racemate, rac-(7R*,8R*,10R*)-7,10-(1, 2-ethylen)-8-(2-hydroxymethyl-phenyl)-1,4-dioxa-spiro[4, 5]decan-8-ol, as yellow oil and 1.74 g of the major racemate, rac-(7R*,8S*,10R*)-7,10-(1,2-ethylen)-8-(2-hydroxymethyl-phenyl)-1,4-dioxa-spiro[4,5]decan-8-ol, as yellow oil.

LC-MS (minor racemate): $t_R$=0.76 min; [M–H$_2$O+H]$^+$: 273.39.

LC-MS (major racemate): $t_R$=0.79 min; [M–H$_2$O+H]$^+$: 273.40.

K10A.2 (Procedure A1.15): rac-(1R*,2R*,4R*)-3'H-spiro(bicyclo[2.2.2]octan-2,1'-isobenzofuran)-5-one To a solution of 0.72 g of rac-(7R*,8R*,10R*)-7,10-(1,2-ethylen)-8-(2-hydroxymethyl-phenyl)-1,4-dioxa-spiro[4,5] decan-8-ol (intermediate K10A.1, minor racemate) in 7 mL DCM was added 1.0 mL of TFA at 0° C. The reaction mixture was stirred overnight at rt and then concentrated in vacuo. The crude product was purified by CC with Hept-EtOAc (9:1) to yield 0.30 g of rac-(1R*,2R*,4R*)-3'H-spiro(bicyclo[2.2.2] octan-2,1'-isobenzofuran)-5-one as white solid.

LC-MS: $t_R$=0.89 min; [M+CH$_3$CN+H]$^+$: 270.41.

K10A.3: rac-(1R*,2R*,4R*,5R*)-5-hydroxy-(3'H-spiro(bicyclo[2.2.2]octane-2,1'-isobenzofuran)-5-yl)-acetic acid tert-butyl ester Prepared from rac-(1R*,2R*,4R*)-3'H-spiro(bicyclo [2.2.2]octan-2,1'-isobenzofuran)-5-one (intermediate K10A.2) using procedure A1.5.

LC-MS: $t_R$=1.06 min; [M+H]$^+$: 345.66.

K10B: rac-(1R*,2S*,4R*,5R*)-5-hydroxy-(3'H-spiro(bicyclo[2.2.2]octane-2,1'-isobenzofuran)-5-yl)-acetic acid tert-butyl ester Prepared in analogy to intermediate K1M using rac-(7R*, 8S*,10R*)-7,10-(1,2-ethylen)-8-(2-hydroxymethyl-phenyl)-1,4-dioxa-spiro[4,5]decan-8-ol (intermediate K10A.1, major isomer) in procedure A1.15.

LC-MS: $t_R$=1.05 min; [M+H]$^+$: 345.54.

Preparation of Building Blocks

BB1. [3-(5,6-Dimethoxy-1H-benzoimidazol-2-yl)-propyl]-methyl-amine

BB1.1 [3-(2-Amino-4,5-dimethoxy-phenylcarbamoyl)-propyl]-methyl-carbamic acid benzyl ester To a solution of 0.95 g 4-(benzyloxycarbonyl-methyl-amino)-butyric acid in 20 mL THF were added 3.3 mL of DIPEA, 0.61 g of HOBt and 0.86 g EDC. After stirring for 5 min 1.0 g of 4,5-dimethoxy-benzene-1,2-diamine dihydrochloride was added and the mixture was stirred at rt overnight. Saturated aq. NaHCO$_3$ solution was added, the phases were separated and the organic phase was washed with brine. The combined organic phases were dried over MgSO$_4$, and concentrated in vacuo.

LC-MS: $t_R$=0.73 min; [M+H]$^+$: 402.56.

BB1.2 [3-(5,6-Dimethoxy-1H-benzoimidazol-2-yl)-propyl]-methyl-carbamic acid benzyl ester To a mixture of crude [3-(2-amino-4,5-dimethoxy-phenyl-carbamoyl)-propyl]-methyl-carbamic acid benzyl ester acid (obtained from 4-(methylamino)butyric acid and benzylchloroformate) in 6 mL toluene were added a few drops of DMF and 358 mg of TsOH and the reaction mixture was heated at 150° C. for 2 h in the microwave. Saturated aq. NaHCO$_3$ solution was added, the phases were separated and the organic phase was washed with brine. The combined organic phases were dried over MgSO$_4$, and concentrated in vacuo. Purification by CC EtOAc-MeOH (95:5) yielded 0.65 g of [3-(5, 6-dimethoxy-1H-benzoimidazol-2-yl)-propyl]-methyl-carbamic acid benzyl ester as brown oil.

LC-MS: $t_R$=0.74 min; [M+H]$^+$: 384.49.

BB1.3 [3-(5,6-Dimethoxy-1H-benzoimidazol-2-yl)-propyl]-methyl-amine

A solution of 0.65 g of [3-(5,6-dimethoxy-1H-benzoimidazol-2-yl)-propyl]-methyl-carbamic acid benzyl ester in 10 mL EtOH was evacuated 3 times with N$_2$ before 100 mg of 10 wt % Pd/C were added. The reaction mixture was then stirred under a H$_2$ atmosphere (balloon) at rt overnight. Filtration over a pad of celite and washing with 100 mL EtOH yielded after concentration in vacuo 377 mg of [3-(5,6-dimethoxy-1H-benzoimidazol-2-yl)-propyl]-methyl-amine as yellow oil.

LC-MS: $t_R$=0.48 min; [M+H]$^+$: 250.20.

Analogous to the procedure described for [3-(5,6-dimethoxy-1H-benzoimidazol-2-yl)-propyl]-methyl-amine the following benzimidazole analogues were synthesized:

BB2. [3-(7-Methoxy-4-methyl-1H-benzoimidazol-2-yl)-propyl]-methyl-amine

BB2.1 3-Methoxy-6-methyl-benzene-1,2-diamine

3-Methoxy-6-methyl-benzene-1,2-diamine was synthesized by suspending 3.3 g of 1-methoxy-4-methyl-2,3-dinitro-benzene (Can. J. Chem. 65, 1233-1240, 1987) in 100 mL EtOH, evacuating 3 times with N$_2$ and addition of 450 mg of 10 wt % Pd/C. The reaction mixture was stirred under a H$_2$ atmosphere (balloon) overnight. Filtration over a pad of celite and washing with 100 mL EtOH yielded after concentration in vacuo 2.2 g of 3-methoxy-6-methyl-benzene-1,2-diamine as brown oil.

LC-MS: $t_R$=0.45 min; [M+H]$^+$: 153.35.

BB2.2 [3-(7-Methoxy-4-methyl-1H-benzoimidazol-2-yl)-propyl]-methyl-amine

Prepared from 3-methoxy-6-methyl-benzene-1,2-diamine in analogy to the methods described for [3-(5,6-dimethoxy-1H-benzoimidazol-2-yl)-propyl]-methyl-amine.

LC-MS: $t_R$=0.52 min; [M+H]$^+$: 234.18.

BB3. {3-[4-(tert.-Butyl-dimethyl-silanyloxy)-1H-benzoimidazol-2-yl]-propyl}-methyl-amine BB3.1 3-(tert.-Butyl-dimethyl-silanyloxy)-benzene-1,2-diamine 3-(tert.-Butyl-dimethyl-silanyloxy)-benzene-1,2-diamine was synthesized by dissolving 4.86 g of 2,3-diamino-phenol in 80 mL DCM and addition of 6.5 g of TBDMSCl followed by 3.2 g of imidazole. After stirring overnight at rt water was added, the organic phase was separated, washed with sat. aq. NH$_4$Cl and dried over MgSO$_4$. Concentration in vacuo afforded 9.0 g of 3-(tert.-butyl-dimethyl-silanyloxy)-benzene-1,2-diamine as brown oil.

LC-MS: $t_R$=0.80 min; [M+H]$^+$: 239.33.

BB3.2 {3-[4-(tert.-Butyl-dimethyl-silanyloxy)-1H-benzoimidazol-2-yl]-propyl}-methyl-amine Prepared from 3-(tert.-butyl-dimethyl-silanyloxy)-benzene-1,2-diamine in analogy to the methods described for [3-(5,6-dimethoxy-1H-benzoimidazol-2-yl)-propyl]-methyl-amine.

LC-MS: $t_R$=0.70 min; [M+H]$^+$: 320.37.

BB4. [3-(4-Methoxy-1-methyl-1H-benzoimidazol-2-yl)-propyl]-methyl-amine

Prepared from 3-methoxy-N$^1$-methyl-benzene-1,2-diamine (J. Med. Chem. 1998, 41, 4062-4079) in analogy to the methods described for [3-(5,6-dimethoxy-1H-benzoimidazol-2-yl)-propyl]-methyl-amine.

LC-MS: $t_R$=0.42 min; [M+H]$^+$: 234.33.

BB5. [3-(4-Isopropoxy-1H-benzoimidazol-2-yl)-propyl]-methyl-amine

BB5.1 3-Isopropoxy-benzene-1,2-diamine

To a solution of 5 g of 2-amino-3-nitrophenol in 10 mL DMF were added 4.9 g of K$_2$CO$_3$ and 3.6 mL of 2-iodopropane. The reaction mixture was stirred at rt overnight and then concentrated in vacuo. The residue was taken up in sat. aq. NH$_4$Cl and extracted with EtOAc (3 times). The organic phases were combined, washed with water, brine, dried over MgSO4 and concentrated in vacuo. Purification by CC with EtOAc-Hept (2:8) afforded 5.2 g of 2-isopropoxy-6-nitro-phenylamine as orange oil.

LC-MS: $t_R$=0.95 min; [M+H]$^+$: 197.04.

A solution of 5.2 g of 2-isopropoxy-6-nitro-phenylamine in 100 mL EtOH was evacuated 3 times with N$_2$ before 600 mg of 10 wt % Pd/C were added. The reaction mixture was stirred under a H$_2$ atmosphere (balloon) for 6 h. Filtration over a pad of celite and washing with EtOH yielded after concentration in vacuo 4.2 g of 3-isopropoxy-benzene-1,2-diamine as black oil.

LC-MS: $t_R$=0.48 min; [M+H]$^+$: 167.05

BB5.2 [3-(4-Isopropoxy-1H-benzoimidazol-2-yl)-propyl]-methyl-amine

Prepared from 3-isopropoxy-benzene-1,2-diamine in analogy to the methods described for [3-(5,6-dimethoxy-1H-benzoimidazol-2-yl)-propyl]-methyl-amine.

LC-MS: $t_R$=0.54 min; [M+H]$^+$: 248.34.

BB6. [3-(4-Ethoxy-1H-benzoimidazol-2-yl)-propyl]-methyl-amine

BB6.1 3-Ethoxy-benzene-1,2-diamine

Prepared from iodoethan in analogy to 3-isopropoxy-benzene-1,2-diamine.

LC-MS: $t_R$=0.43 min; [M+H]$^+$: 153.26

BB6.2 [3-(4-Ethoxy-1H-benzoimidazol-2-yl)-propyl]-methyl-amine

Prepared from 3-ethoxy-benzene-1,2-diamine in analogy to the methods described for [3-(5,6-dimethoxy-1H-benzoimidazol-2-yl)-propyl]-methyl-amine.

LC-MS: $t_R$=0.51 min; [M+H]$^+$: 234.33.

BB7. 2-(3-Methylamino-propyl)-1H-benzoimidazole-4-carboxylic acid methyl ester Prepared from 2,3-diamino-benzoic acid methyl ester (J. Med. Chem. 2000, 43(22), 4084-4097) in analogy to the methods described for [3-(5,6-dimethoxy-1H-benzoimidazol-2-yl)-propyl]-methyl-amine.

LC-MS: $t_R$=0.49 min; [M+H]$^+$: 248.37.

BB8. 2-(3-Methylamino-propyl)-1H-benzoimidazole-5-carboxylic acid methyl ester Prepared from 3,4-diamino-benzoic acid methyl ester (Eur. J. Med. Chem. 2004, 39(3), 291-298) in analogy to the methods described for [3-(5,6-dimethoxy-1H-benzoimidazol-2-yl)-propyl]-methyl-amine.

LC-MS: $t_R$=0.49 min; [M+H]$^+$: 248.31.

BB9. [3-(4-Methoxy-1H-benzoimidazol-2-yl)-propyl]-methyl-amine

Prepared from 3-methoxy-benzene-1,2-diamine in analogy to the methods described for [3-(5,6-dimethoxy-1H-benzoimidazol-2-yl)-propyl]-methyl-amine.

LC-MS: $t_R$=0.46 min; [M+H]$^+$: 220.17.

BB10. [3-(6-Methoxy-1H-benzoimidazol-2-yl)-propyl]-methyl-amine

Prepared from 4-methoxy-benzene-1,2-diamine in analogy to the methods described for [3-(5,6-dimethoxy-1H-benzoimidazol-2-yl)-propyl]-methyl-amine.

LC-MS: $t_R$=0.45 min; [M+H]$^+$: 220.28.

BB11. [2-(7-Methoxy-1H-benzoimidazol-2-yl)-ethyl]-methyl-amine

BB11.1 [2-(2-Amino-3-methoxy-phenylcarbamoyl)-ethyl]-methyl-carbamic acid tert.-butyl ester To a solution of 1.35 g of tert.-butoxycarbonyl-methylamino-propanoic acid in 50 mL DCM were added 3.4 mL of DIPEA, 81 mg of DMAP, 1.0 g of HOBt, 1.5 g of EDC and 0.91 g of 3-methoxybenzene-1,2-diamine. The resulting mixture was stirred at rt for 3 h and then quenched with water. The organic phase was washed with sat. aq. NaHCO$_3$, dried over MgSO$_4$ and concentrated on vacuo to yield 2.9 g of [2-(2-amino-3-methoxy-phenylcarbamoyl)-ethyl]-methyl-carbamic acid tert.-butyl ester as brown oil.

LC-MS: $t_R$=0.72 min; [M+H]$^+$: 324.35.

BB11.2 [2-(7-Methoxy-1H-benzoimidazol-2-yl)-ethyl]-methyl-carbamic acid tert.-butyl ester A solution of 2.1 g of crude [2-(2-amino-3-methoxy-phenylcarbamoyl)-ethyl]-methyl-carbamic acid tert.-butyl ester in 10 mL acetic acid was heated at 65° C. for 2 h. The reaction mixture was concentrated and purified by CC with EtOAc to yield 1.5 g of [2-(7-methoxy-1H-benzoimidazol-2-yl)-ethyl]-methyl-carbamic acid tert.-butyl ester as orange foam.
LC-MS: $t_R$=0.70 min; $[M+H]^+$: 306.22

BB11.3 [2-(7-Methoxy-1H-benzoimidazol-2-yl)-ethyl]-methyl-amine

A solution of 1.5 g of [2-(7-methoxy-1H-benzoimidazol-2-yl)-ethyl]-methyl-carbamic acid tert.-butyl ester in 10 mL DCM was treated with 0.39 mL of TFA and stirred overnight at rt. The reaction mixture was concentrated in vacuo, redissolved in DCM and treated with diluted NaOH. After separation of the 2 phases the water phase was lyophilized to yield 380 mg of [2-(7-methoxy-1H-benzoimidazol-2-yl)-ethyl]-methyl-amine as beige solid.
LC-MS: $t_R$=0.43 min; $[M+H]^+$: 206.25.

BB12. [3-(5,6-Dichloro-1H-benzoimidazol-2-yl)-propyl]-methyl-amine

Prepared from 4,5-dichlorobenzene-1,2-diamine in analogy to the methods described for [3-(5,6-dimethoxy-1H-benzoimidazol-2-yl)-propyl]-methyl-amine.
LC-MS: $t_R$=0.64 min; $[M+H]^+$: 258.25.

BB13. 3-Pyridin-3-yl-propionaldehyde

Prepared as described in J. Med. Chem. 2004, 47(10), 2414-2417.

BB14. [3-(3,4-Dimethoxy-phenyl)-propyl]-methyl-amine

Prepared as described in Hengartner, Urs; Ramuz, Henri: EP 388739.

BB15. [3-(3,4-Diethoxy-phenyl)-propyl]-methyl-amine

BB15.1 3-(3,4-Diethoxy-phenyl)-propionic acid ethyl ester

To a solution of 1.9 g of 3-(3,4-dihydroxy-phenyl)-propionic acid ethyl ester in 3 mL DMF were added 2.5 g of $K_2CO_3$ and 1.5 mL of iodoethane. The reaction mixture was stirred overnight at rt. The solvent was removed in vacuo, the residue was diluted with sat. aq. $NH_4Cl$ and extracted with EtOAc (3×). The organic phases were combined and washed with water, brine, dried over $MgSO_4$ and concentrated in vacuo. Purification by CC with EtOAc-Hept (2:8) afforded 1.6 g of 3-(3,4-diethoxy-phenyl)-propionic acid ethyl ester as yellow oil.
LC-MS: $t_R$=0.98 min; $[M+H]^+$: 267.36.

BB15.2 3-(3,4-Diethoxy-phenyl)-propionic acid

To a solution of 0.94 g of 3-(3,4-diethoxy-phenyl)-propionic acid ethyl ester in 6 mL EtOH were added 0.59 g of $LiOH.H_2O$ dissolved in 3 mL $H_2O$ and 5 mL MeOH. The mixture was stirred at rt for 30 min. The reaction mixture was then concentrated in vacuo and the residue was partitioned between water and $Et_2O$. The aq. layer was separated and acidified with 1N HCl. The resulting white solid was filtrated and dried to yield 0.67 g of 3-(3,4-diethoxy-phenyl)-propionic acid as white solid.
LC-MS: $t_R$=0.82 min; $[M+H]^+$: 239.30.

BB15.3 3-(3,4-Diethoxy-phenyl)-N-methyl-propionamide

To a solution of 0.72 g of 3-(3,4-diethoxy-phenyl)-propionic acid in 10 mL THF were added 1.6 mL of DIPEA, 0.45 g of HOBt, 0.63 g of EDC and 10 mL of $MeNH_2$ (2M in THF). The reaction mixture was heated in a closed vessel overnight at 70° C. Further additions of $MeNH_2$ were done during the next 12 h. The mixture was then concentrated in vacuo, the residue was taken up in sat. aq. $NaHCO_3$ and washed with EtOAc (2×). The organic layers were combined, washed with brine, dried over $MgSO_4$ and concentrated in vacuo. Purification by CC with EtOAc yielded 0.16 g of 3-(3,4-diethoxy-phenyl)-N-methyl-propionamide as solid.
LC-MS: $t_R$=0.78 min; $[M+H]^+$: 252.32.

BB15.4 [3-(3,4-Diethoxy-phenyl)-propyl]-methyl-amine

To a solution of 0.26 g of 3-(3,4-diethoxy-phenyl)-N-methyl-propionamide in 5 mL THF was added 1.4 mL of a $LiAlH_4$ solution (2.3M in THF) at 0° C. The reaction mixture was stirred for 1 h at rt and for 2 h at 60° C. At rt, a 1M NaOH solution was added dropwise. The resulting mixture was filtrated over a pad of celite, washed with THF and the filtrate concentrated in vacuo. Purification by CC with EtOAc-MeOH (7:3) yielded 0.13 g of [3-(3,4-diethoxy-phenyl)-propyl]-methyl-amine as yellow oil.
LC-MS: $t_R$=0.66 min; $[M+H]^+$: 238.35.

BB16. [2-(3,4-Diethoxy-phenyl)-ethyl]-ethyl-amine

BB16.1 [2-(3,4-Diethoxy-phenyl)-ethyl]-carbamic acid tert.-butyl ester

To a solution of 7.5 g of [2-(3,4-dihydroxy-phenyl)-ethyl]-carbamic acid tert.-butyl ester (J. Am. Chem. Soc. 2004, 126(46), 15030-15031) in 20 mL DMF were added 8.1 g of $K_2CO_3$ and 4.7 mL of iodoethane. The reaction mixture was stirred overnight at rt and then concentrated in vacuo. The residue was taken up with sat. $NH_4Cl$ solution and extracted with EtOAc (3×). The organic phases were combined and washed with water, brine, dried over $MgSO_4$ and concentrated in vacuo. Purification by CC with EtOAc-Hept (2:8) yielded 6.8 g of [2-(3,4-diethoxy-phenyl)-ethyl]-carbamic acid tert.-butyl ester as yellow oil.
LC-MS: $t_R$=0.99 min; $[M+H]^+$: 310.27.

BB16.2 2-(3,4-Diethoxy-phenyl)-ethylamine

To a solution of 6.5 g of [2-(3,4-diethoxy-phenyl)-ethyl]-carbamic acid tert.-butyl ester in 20 mL DCM were added 5 mL of TFA at 0° C. The reaction mixture was stirred at rt for 30 min when another 5 mL of TFA were added. After stirring for further 2 h, 1M NaOH solution was dropwise added. The mixture was extracted twice with DCM, washed with water and brine. The organic phase was dried over $MgSO_4$ and concentrated in vacuo to yield 4.3 g of 2-(3,4-diethoxy-phenyl)-ethylamine as yellow oil.
LC-MS: $t_R$=0.57 min; $[M+H]^+$: 210.32.

BB16.3 [2-(3,4-Diethoxy-phenyl)-ethyl]-ethyl-amine

To a solution of 0.43 g of 2-(3,4-diethoxy-phenyl)-ethylamine in 3 mL MeOH were added 270 mg of 5 wt % Rh/C and 0.22 mL of MeCN. The reaction mixture was stirred under a $H_2$ atmosphere (balloon) for 3 days and then filtrated over a pad of celite and washed with 100 mL MeOH. Concentration in vacuo afforded 0.4 g of [2-(3,4-diethoxy-phenyl)-ethyl]-ethyl-amine as yellow oil.
LC-MS: $t_R$=0.64 min; [M+H]$^+$: 238.35.

BB17. 3-Methoxy-2-methoxymethyl-2-methyl-N-(3-oxo-propyl)-propionamide

BB 17.1 N-(3,3-Diethoxy-propyl)-3-methoxy-2-methoxymethyl-2-methyl-propionamide 5 g of 3-methoxy-2-methoxymethyl-2-methyl-propionic acid (prepared as in EP609058) were dissolved in 49 mL of DCM and 12 mL of THF. 11.4 mL of DIPEA, 5.84 g of HOBt, 7.07 g of EDCI and 5.45 g of 3,3-diethoxy-propylamine were added sequentially. The mixture was stirred for 23 h at rt, diluted with DCM and washed with sat. $NaHCO_3$. The organic phase was dried over anh. $Na_2SO_4$ and concentrated in vacuo. The resulting crude material was purified by CC using heptane/EtOAc from 3/1 to 0/1 as eluant to yield 7.25 g of N-(3,3-diethoxy-propyl)-3-methoxy-2-methoxymethyl-2-methyl-propionamide as a yellowish oil.
$^1$H-NMR (CDCl$_3$): 7.04 (s, 1H), 4.51 (t, 1H), 3.45-3.7 (m, 4H), 3.43 (s, 4H), 3.32 (s, 6H), 3.30 (dd, 2H), 1.79 (dd, 2H), 1.19 (t, 6H), 1.12 (s, 3H).

BB17.2 3-methoxy-2-methoxymethyl-2-methyl-N-(3-oxo-propyl)-propionamide

To a solution of 3 g of N-(3,3-diethoxy-propyl)-3-methoxy-2-methoxymethyl-2-methyl-propionamide in 71 mL of acetone was added 3.91 g of TsOH.H$_2$O. The mixture was stirred over night at rt, quenched with sat.-NaHCO$_3$ and extracted with DCM. The organic phase was washed with brine, dried over anh. Na$_2$SO$_4$ and concentrated in vacuo. The resulting crude material was purified by CC using heptane/EtOAc from 100/0 to 0/100 as eluant to yield 2.19 g of 3-methoxy-2-methoxymethyl-2-methyl-N-(3-oxo-propyl)-propionamide
LC-MS: $t_R$=0.52/0.67 min; [M+H]$^+$: 218.35.

BB18. 2-Methoxy-2-methyl-N-(3-oxo-propyl)-propionamide

Prepared from 2-methoxy-2-methyl-propionic acid (prepared as in J. Am. Chem. Soc. 1948, 70 1153-8) in analogy to the methods described for 3-methoxy-2-methoxymethyl-2-methyl-N-(3-oxo-propyl)-propionamide.
LC-MS: $t_R$=0.41 min; [M+H]$^+$: 174.39.

BB19. 2,2-Dimethyl-N-(3-oxo-propyl)-propionamide

Prepared from 2,2-dimethyl-propionyl chloride in absence of a coupling reagent in analogy to the methods described for 3-methoxy-2-methoxymethyl-2-methyl-N-(3-oxo-propyl)-propionamide.
$^1$H-NMR (CDCl$_3$): 9.81 (s, 1H), 6.18 (s, 1H), 3.52 (dd, 2H), 2.72 (t, 2H), 1.16 (s, 9H).

BB20. 3-[4,5-Diphenyl-1-(2-trimethylsilanyl-ethoxymethyl)-1H-imidazol-2-yl]-propionic acid

BB20.1. 3-[4,5-Diphenyl-1-(2-trimethylsilanyl-ethoxymethyl)-1H-imidazol-2-yl]-propionic acid A solution of 1 g of benzil, 1.01 g of methyl 4,4-dimethoxy-butyrate and 2.87 g of ammonium acetate in 23 mL of acetic acid was refluxed for 5 h. The mixture was poured into water, basified with a 25% aq. ammonium hydroxide solution and extracted with DCM. The organic phase was dried over anh. Na$_2$SO$_4$ and concentrated in vacuo. The resulting crude material was purified by CC using heptane/EtOAc from 85/15 to 0/100 as eluant to yield 633 mg of 3-(4,5-diphenyl-1H-imidazol-2-yl)-propionic acid methyl ester as a yellowish solid.
LC-MS: $t_R$=0.78 min; [M+H]$^+$: 307.31.

BB20.2 3-[4,5-Diphenyl-1-(2-trimethylsilanyl-ethoxymethyl)-1H-imidazol-2-yl]-propionic acid methyl ester 47 mg of sodium hydride were added portionwise to a solution of 300 mg of 3-(4,5-diphenyl-1H-imidazol-2-yl)-propionic acid methyl ester in 2 mL of anh. DMF at 0° C. The mixture was stirred for 1 h at 0° C. then 179 mg of SEM-Cl were added dropwise at 0° C. The reaction mixture was allowed to warm up to rt, stirred for 1 h then poured into water and extracted with Et$_2$O. The organic phase was washed with water/brine, dried over anh. Na$_2$SO$_4$ and concentrated in vacuo. The resulting crude material was purified by CC using heptane/EtOAc from 88/12 to 0/100 as eluant to yield 308 mg of 3-[4,5-diphenyl-1-(2-trimethylsilanyl-ethoxymethyl)-1H-imidazol-2-yl]-propionic acid methyl ester as a yellowish oil.
LC-MS: $t_R$=0.96 min; [M+H]$^+$: 437.41.

BB20.3 3-[4,5-Diphenyl-1-(2-trimethylsilanyl-ethoxymethyl)-1H-imidazol-2-yl]-propionic acid 150 mg of 3-[4,5-diphenyl-1-(2-trimethylsilanyl-ethoxymethyl)-1H-imidazol-2-yl]-propionic acid methyl ester were dissolved in 1 mL of ethanol and treated with 0.7 mL of a 1M aq. solution of sodium hydroxide. The mixture was partitioned between water and Et$_2$O. The aq. layer was separated, acidified with 25%-HCl and extracted with DCM. The organic phase was dried over anh. Na$_2$SO$_4$ and concentrated in vacuo to give 137 mg of 3-[4,5-diphenyl-1-(2-trimethylsilanyl-ethoxymethyl)-1H-imidazol-2-yl]-propionic acid the product as a white solid.
LC-MS: $t_R$=0.92 min; [M+H]$^+$: 423.47.

BB21. 3-Isoquinolin-4-yl-propionic acid

BB21.1 3-Isoquinolin-4-yl-acrylic acid tert.-butyl ester

To a mixture of 3 g of 4-bromoisoquinoline, 6.2 mL of acrylic acid tert.-butyl ester and 2.66 mL of DIPEA in 30 mL of DMF under argon was added 0.169 mL of P(OMe)$_3$ and 160 mg of Pd(OAc)$_2$. The reaction mixture was heated for 2 h at 120° C. and the DMF was evaporated under vacuo. The resulting residue was diluted with DCM and filtered over a pad of silica gel. The filtrate was washed with 10%-citric acid, water and brine. The organic phase was dried over anh. Na$_2$SO$_4$ and concentrated in vacuo. The resulting crude material was purified by CC using heptane/EtOAc from 94/6 to 50/50 as eluant to yield 2.7 g of 3-isoquinolin-4-yl-acrylic acid tert.-butyl ester as a yellow solid.
LC-MS: $t_R$=0.84 min; [M+H]$^+$: 256.29.

BB21.2 3-Isoquinolin-4-yl-propionic acid tert.-butyl ester

A solution of 1.58 g of 3-isoquinolin-4-yl-acrylic acid tert.-butyl ester in 12 mL of EtOAc was evacuated 3 times with N$_2$ before 200 mg of 10 wt % Pd/C were added. The reaction mixture was stirred under a H$_2$ atmosphere overnight at rt and filtered over a pad of celite. The cake was washed with EtOAc/MeOH and the filtrate was concentrated in vacuo to yield 1.54 g of 3-Isoquinolin-4-yl-propionic acid tert.-butyl ester as a yellow oil.

LC-MS: $t_R$=0.72 min; [M+H]$^+$: 258.31

BB21.3 3-Isoquinolin-4-yl-propionic acid

To a solution of 800 mg of 3-isoquinolin-4-yl-propionic acid tert.-butyl ester in 6.2 mL of DCM was added 6.2 mL of TFA. The reaction mixture was stirred for 2 h at rt and evaporated to dryness to yield 1.57 g of 3-isoquinolin-4-yl-propionic acid as the trifluoroacetic acid salt as a brown solid.

LC-MS: $t_R$=0.52 min; [M+H]$^+$: 202.24

BB22. 3-Quinolin-3-yl-propionic acid

Prepared as 3-quinolin-3-yl-propionic acid trifluoroacetic acid salt from 3-bromoquinoline in analogy to the methods described for 3-isoquinolin-4-yl-propionic acid using PdCl$_2$dPPf.CH$_2$Cl$_2$ and NaOAc in the Heck reaction.

LC-MS: $t_R$=0.53 min; [M+H]$^+$: 202.23.

BB23. 3-Quinolin-4-yl-propionic acid

Prepared as 3-quinolin-4-yl-propionic acid trifluoroacetic acid salt from 4-chloroquinoline in analogy to the methods described for 3-isoquinolin-4-yl-propionic acid using the conditions described in J. Org. Chem. 2003, 68(18), 7077-7084, in the Heck reaction.

LC-MS: $t_R$=0.52 min; [M+H]$^+$: 202.25.

BB24.
(3-Furo[2,3-b]pyridin-5-yl-propyl)-methyl-amine

BB24.1 Furo[2,3-b]pyridin-5-yl-methanol

To a solution of 1.9 g of furo[2,3-b]pyridine-5-carboxylic acid ethyl ester (GB 2289276) in 30 ml of THF was added dropwise 17.3 ml of a LiAlH$_4$ (2.3M THF) solution at −20° C. The reaction mixture was stirred for 3 h at −20° C. and then quenched by addition of 1M NaOH solution. The resulting mixture was filtrated over a pad of celite, washed with THF and the filtrate was concentrated in vacuo. Purification by CC using EtOAc yielded 0.5 g of furo[2,3-b]pyridin-5-yl-methanol as yellow oil.

LC-MS: $t_R$=0.57 min; [M+H]$^+$: 150.20.

BB24.2 Furo[2,3-b]pyridine-5-carbaldehyde

To a solution of 0.47 g of furo[2,3-b]pyridin-5-yl-methanol in 2 ml of DCM was added 10 ml of a Dess-Martins-Periodinane solution (15% in DCM). The reaction mixture was stirred overnight and then quenched with sat.-NaHCO$_3$ and extracted with DCM. The organic phase was washed with brine, dried over MgSO4 and concentrated in vacuo. The resulting crude material was purified by CC using heptane/EtOAc 30/70 as eluant to yield 0.38 g of furo[2,3-b]pyridine-5-carbaldehyde as white solid.

LC-MS: $t_R$=0.68 min; [M+H]$^+$: 148.02.

BB24.3
3-Furo[2,3-b]pyridin-5-yl-N-methyl-acrylamide

To a solution of 0.25 g of methylcarbamoylmethyl-triphenyl-phosphonium chloride (J. Med. Chem. 2003, 46, 399) in 1 ml of THF was added 0.88 ml of n-BuLi (1.6M) at −60° C. After stirring for 1 h at −60° C. a solution of 0.1 g of furo[2,3-b]pyridine-5-carbaldehyde in 1 ml of THF was added and the resulting reaction mixture was stirred for 5 h reaching slowly rt. The reaction mixture was poured over ice. The organic phase was washed with brine, dried over MgSO4 and concentrated in vacuo. Purification by CC using EtOAc as eluant yielded 0.13 g of 3-furo[2,3-b]pyridin-5-yl-N-methyl-acrylamide as a mixture of E/Z isomers.

LC-MS: $t_R$=0.71 min; [M+H]$^+$: 203.03.

BB24.4
3-Furo[2,3-b]pyridin-5-yl-N-methyl-propionamide

A solution of 1.69 g of 3-furo[2,3-b]pyridin-5-yl-N-methyl-acrylamide in 19 mL of EtOH was evacuated 3 times with N$_2$ before 350 mg of 10 wt % Pd/C were added. The reaction mixture was stirred under a H$_2$ atmosphere for 90 min at rt and filtered over a pad of celite. The cake was washed with EtOAc/MeOH and the filtrate was concentrated in vacuo. Purification by CC using EtOAc/MeOH 90/10 as eluant yielded 0.39 g of 3-furo[2,3-b]pyridin-5-yl-N-methyl-propionamide as white solid.

LC-MS: $t_R$=0.69 min; [M+H]$^+$: 205.48.

BB24.5
(3-Furo[2,3-b]pyridin-5-yl-propyl)-methyl-amine

To a solution of 0.36 g of 3-furo[2,3-b]pyridin-5-yl-N-methyl-propionamide in 10 ml of THF was added dropwise 2.3 ml of a LiAlH4 (2.3M THF) solution at 0° C. The reaction mixture was slowly heated to 60° C. over 1 h and stirred for another 2 h at 60° C. The reaction was quenched by addition of 1M NaOH solution. The resulting mixture was filtrated over a pad of celite, washed with THF and the filtrate was concentrated in vacuo to yield 0.35 g of (3-furo[2,3-b]pyridin-5-yl-propyl)-methyl-amine as brown oil.

LC-MS: $t_R$=0.56 min; [M+H]$^+$: 191.09.

BB25. Methyl-[3-(2-methyl-furo[2,3-b]pyridin-5-yl)-propyl]-amine

Prepared from 2-methoxymethyl-furo[2,3-b]pyridine-5-carboxylic acid ethyl ester in analogy to the methods described for (3-furo[2,3-b]pyridin-5-yl-propyl)methyl-amine.

LC-MS: $t_R$=0.68 min; [M+H]$^+$: 205.54.

BB26. Methyl-[3-(4-trifluoromethoxy-1H-benzoimidazol-2-yl)-propyl]-amine

BB26.1 3-Trifluoromethoxy-benzene-1,2-diamine

3-Trifluoromethoxy-benzene-1,2-diamine was synthesized by dissolving 0.79 g of 2-nitro-6-trifluoromethoxy-phenylamine (J. Med. Chem. 1999, 42, 15, 2828-2843) in 20 mL EtOH, evacuating 3 times with N$_2$ and adding 80 mg of 10 wt % Pd/C. The reaction mixture was stirred under a H$_2$ atmosphere (balloon) for 5 h. Filtration over a pad of celite and washing with EtOH and EtOAc yielded after concentration in vacuo 0.55 g of 3-trifluoromethoxy-benzene-1,2-diamine as brown oil.

LC-MS: $t_R$=0.68 min; [M+H]$^+$: 193.20.

BB26.2 Methyl-[3-(4-trifluoromethoxy-1H-benzoimidazol-2-yl)-propyl]-amine

Prepared from 3-trifluoromethoxy-benzene-1,2-diamine in analogy to the methods described for [3-(5,6-dimethoxy-1H-benzoimidazol-2-yl)-propyl]-methyl-amine.

LC-MS: $t_R$=0.62 min; [M+H]$^+$: 274.06.

BB27. [3-(4,7-Dimethoxy-1H-benzoimidazol-2-yl)-propyl]-methyl-amine

BB27.1 3,6-Dimethoxy-benzene-1,2-diamine 3,6-Dimethoxy-benzene-1,2-diamine was synthesized by dissolving 6.0 g of 1,4-dimethoxy-2,3-dinitro-benzene (Eur. J. Org. Chem. 2006, 2786-2794) in 220 mL EtOH, evacuating 3 times with $N_2$ and adding 600 mg of 10 wt % Pd/C. The reaction was stirred under a $H_2$ atmosphere (balloon). Another 300 mg of 10 wt % Pd/C were added after 2 days and the mixture was stirred for another 24 h. Filtration over a pad of celite and washing with EtOH and EtOAc yielded after concentration in vacuo 4.3 g of 3,6-dimethoxy-benzene-1,2-diamine as black solid.

LC-MS: $t_R$=0.48 min; $[M+H]^+$: 169.09.

BB27.2 [3-(4,7-Dimethoxy-1H-benzoimidazol-2-yl)-propyl]-methyl-amine

Prepared from 3,6-dimethoxy-benzene-1,2-diamine in analogy to the methods described for [3-(5,6-dimethoxy-1H-benzoimidazol-2-yl)-propyl]-methyl-amine.

LC-MS: $t_R$=0.57 min; $[M+H]^+$: 250.13.

BB28. [3-(4,5-Dimethoxy-7-methyl-1H-benzoimidazol-2-yl)-propyl]-methyl-amine

BB28.1 1,2-Dimethoxy-5-methyl-3,4-dinitro-benzene 1,2-Dimethoxy-5-methyl-3,4-dinitro-benzene was synthesized by adding 15.0 g of 3,4-dimethoxytoluene portionwise to a mixture of 60 mL fumic nitric acid and 300 mL water keeping the temperature<20° C. with the aid of an ice bath. The reaction was stirred for 1 h at 0° C., quenched by the addition of ice and stirred for another 1 h. The yellow solid was filtered off, washed with ice cold water and dried in vacuo to yield 9.2 g of 1,2-dimethoxy-5-methyl-3,4-dinitro-benzene as yellow solid.

$^1$H-NMR (CDCl$_3$): 6.88 (s, 1H); 4.01 (s, 3H); 3.98 (s, 3H); 2.52 (s, 3H).

BB28.2 3,4-Dimethoxy-6-methyl-benzene-1,2-diamine 3,4-Dimethoxy-6-methyl-benzene-1,2-diamine was synthesized by dissolving 11.5 g of 1,2-dimethoxy-5-methyl-3,4-dinitro-benzene in 300 mL EtOH, evacuating 3 times with $N_2$ and adding 1.0 g of 10 wt % Pd/C. The reaction was stirred under a $H_2$ atmosphere (balloon) for 2 days. Filtration over a pad of celite and washing with EtOH yielded after concentration in vacuo 8.8 g of 3,4-dimethoxy-6-methyl-benzene-1,2-diamine as brown oil.

LC-MS: $t_R$=0.55 min; $[M+H]^+$: 183.27.

BB28.3 [3-(4,5-Dimethoxy-7-methyl-1H-benzoimidazol-2-yl)-propyl]-methyl-amine Prepared from 3,4-dimethoxy-6-methyl-benzene-1,2-diamine in analogy to the methods described for [3-(5,6-dimethoxy-1H-benzoimidazol-2-yl)-propyl]-methyl-amine.

LC-MS: $t_R$=0.58 min; $[M+H]^+$: 264.14.

BB29. {3-[4-(2-Methoxy-ethoxy)-1H-benzoimidazol-2-yl]-propyl}-methyl-amine

BB29.1 3-(2-Methoxy-ethoxy)-benzene-1,2-diamine

Prepared from 1-bromo-2-methoxyethan and 2-amino-3-nitrophenol in analogy to 3-isopropoxy-benzene-1,2-diamine.

LC-MS: $t_R$=0.48 min; $[M+H]^+$: 183.12.

BB29.2 {3-[4-(2-Methoxy-ethoxy)-1H-benzoimidazol-2-yl]-propyl}-methyl-amine Prepared from 3-(2-methoxy-ethoxy)-benzene-1,2-diamine in analogy to the methods described for [3-(5,6-dimethoxy-1H-benzoimidazol-2-yl)-propyl]-methyl-amine.

LC-MS: $t_R$=0.56 min; $[M+H]^+$: 264.12.

BB30. [3-(4-Chloro-1H-benzoimidazol-2-yl)-propyl]-methyl-amine

Prepared from 3-chloro-benzene-1,2-diamine (J. Med. Chem. 1981, 24(1), 93-101) in analogy to the methods described for [3-(5,6-dimethoxy-1H-benzoimidazol-2-yl)-propyl]-methyl-amine.

LC-MS: $t_R$=0.52 min; $[M+H]^+$: 224.18.

BB31. N-[2-(3-Methylamino-propyl)-1H-benzoimidazol-4-yl]-acetamide

BB31.1 [3-(2-Amino-3-nitro-phenylcarbamoyl)-propyl]-methyl-carbamic acid tert-butyl ester To a solution of 9 g of 4-(tert-butoxycarbonyl-methyl-amino)-butyric acid (prepared from 4-(methylamino)butyric acid and BOC anhydride) in 159 mL DCM were added 14.2 mL of DIPEA, 8 g of HOBt and 9.1 g of EDC. After stirring for 5 min 6.1 g of 3-nitro-benzene-1,2-diamine were added and the mixture was stirred for 4 days at rt. Saturated aq. NaHCO$_3$ solution was added, the phases were separated and the organic phase washed with brine. The combined organic phases were dried over MgSO$_4$, and concentrated in vacuo. Purification by CC using EtOAc/heptane 1/4 to 3/1 yielded 5.2 g of [3-(2-Amino-3-nitro-phenylcarbamoyl)-propyl]methyl-carbamic acid tert-butyl ester as orange foam.

LC-MS: $t_R$=0.94 min; $[M+H]^+$: 352.48.

BB31.2 Methyl-[3-(4-nitro-1H-benzoimidazol-2-yl)-propyl]-carbamic acid tert-butyl ester A solution of 4.4 g of [3-(2-amino-3-nitro-phenylcarbamoyl)-propyl]methyl-carbamic acid tert-butyl ester in 36 mL of acetic acid was heated at 90° C. for 5 h and concentrated in vacuo. The residue was taken up in DCM, washed with sat. NaHCO$_3$ solution, dried over anh. Na$_2$SO$_4$ and concentrated in vacuo to yield 3.8 g of methyl-[3-(4-nitro-1H-benzoimidazol-2-yl)-propyl]-carbamic acid tert-butyl ester as dark yellow oil.

LC-MS: $t_R$=0.81 min; $[M+H]^+$: 335.15

BB31.3 [3-(4-Amino-1H-benzoimidazol-2-yl)-propyl]-methyl-carbamic acid tert-butyl ester A solution of 4.4 g of methyl-[3-(4-nitro-1H-benzoimidazol-2-yl)-propyl]-carbamic acid tert-butyl ester in 85 mL of EtOH was evacuated 3 times with N$_2$ before 347 mg of 10 wt % Pd/C were added. The reaction mixture was then stirred under a H₂ atmosphere (balloon) at rt for 6 h. Filtration over a pad of celite and washing with EtOH yielded after concentration in vacuo 3.79 g of [3-(4-amino-1H-benzoimidazol-2-yl)-propyl]-methyl-carbamic acid tert-butyl ester as dark green foam.
LC-MS: $t_R$=0.75 min; [M+H]⁺: 305.47.

BB31.4 [3-(4-Acetylamino-1H-benzoimidazol-2-yl)-propyl]-methyl-carbamic acid tert-butyl ester A solution of 3.66 g of [3-(4-amino-1H-benzoimidazol-2-yl)-propyl]-methyl-carbamic acid tert-butyl ester in 40 mL of acetic anhydride was refluxed for 2 h. The excess of acetic anhydride was evaporated off and the residue was treated with 16 mL of EtOH and 1M-NaOH until pH 10 then extracted with EtOAc. The organic phase was dried over anh. Na₂SO₄ and concentrated in vacuo. Purification by CC using EtOAc/MeOH 100/1 to 90/1 yielded 1.86 g of [3-(4-acetylamino-1H-benzoimidazol-2-yl)-propyl]-methyl-carbamic acid tert-butyl ester as yellow foam.
LC-MS: $t_R$=0.68 min; [M+H]⁺: 347.15.

BB31.5 N-[2-(3-Methylamino-propyl)-1H-benzoimidazol-4-yl]-acetamide hydrochloride salt A solution of 1.84 g of [3-(4-Acetylamino-1H-benzoimidazol-2-yl)-propyl]-methyl-carbamic acid tert-butyl ester in 2.6 mL of EtOAc was treated with 7.75 mL of 4M-HCl in dioxane for 5 h and concentrated in vacuo to yield 1.7 g of N-[2-(3-methylamino-propyl)-1H-benzoimidazol-4-yl]-acetamide hydrochloride salt as yellow solid.
LC-MS: $t_R$=0.30 min; [M+H]⁺: 247.12.

BB32. [3-(7-Chloro-4-methoxy-1H-benzoimidazol-2-yl)-propyl]-methyl-amine

BB32.1 N-(2-Chloro-5-methoxy-phenyl)-acetamide

To a solution of 10.59 g of 2-chloro-5-methoxyaniline in 50 mL of AcOH were added dropwise at 0° C. 6.8 mL of acetic anhydride. The reaction mixture was allowed to warm up to rt, stirred for 6 h and concentrated in vacuo. The crude product was purified by CC using EtOAc/heptane 1/3 to yield 13.0 g of N-(2-chloro-5-methoxy-phenyl)-acetamide as white solid.
LC-MS: $t_R$=0.77 min; [M+CH₃CN+H]⁺: 241.05.

BB32.2 6-Chloro-3-methoxy-2-nitro-phenylamine

To a suspension of 8.56 g of tetramethylammonium nitrate in 160 mL of DCM were added 10.4 mL of trifluoromethanesulfonic anhydride and the mixture was stirred for 2 h. 12.0 g of N-(2-chloro-5-methoxy-phenyl)-acetamide was added at −45° C. and the reaction mixture was further stirred for 1 h at −45° C. to −30° C., then allowed to warm up to rt and stirred overnight. The reaction mixture was washed with water, dried over anh. Na₂SO₄ and concentrated in vacuo. The crude product was purified by CC using EtOAc/heptane 1/3 to yield 6.25 g of a mixture of N-(6-chloro-3-methoxy-2-nitro-phenyl)-acetamide and N-(2-chloro-5-methoxy-4-nitro-phenyl)-acetamide as brownish solid.
LC-MS: $t_R$=0.78 min; [M+CH₃CN+H]⁺: 286.04.
A solution of 6.25 g of a mixture of N-(6-chloro-3-methoxy-2-nitro-phenyl)-acetamide and N-(2-chloro-5-methoxy-4-nitro-phenyl)-acetamide in 30 mL of 25%-HCl and 150 mL of 1M-HCl was refluxed for 2 h. The reaction mixture was basified with 2M-NaOH and extracted with EtOAc. The organic phase was dried over anh. Na₂SO₄ and concentrated in vacuo. The crude product was purified by CC using EtOAc/heptane 1/3 to yield 819 mg of 6-chloro-3-methoxy-2-nitro-phenylamine as dark yellow oil.
LC-MS: $t_R$=0.89 min; [M+CH₃CN+H]⁺: 243.57.

BB32.3 3-Chloro-6-methoxy-benzene-1,2-diamine

A solution of 819 mg of 6-chloro-3-methoxy-2-nitro-phenylamine in 26 mL of EtOH was evacuated 3 times with N₂ before 107 mg of 10 wt % Pd/C were added. The reaction mixture was then stirred under a H₂ atmosphere (balloon) at rt for 4 h. Filtration over a pad of celite and washing with EtOH yielded after concentration in vacuo 317 mg of 3-chloro-6-methoxy-benzene-1,2-diamine as yellow solid.
LC-MS: $t_R$=0.60 min; [M+CH₃CN+H]⁺: 214.20.

BB32.4 [3-(7-Chloro-4-methoxy-1H-benzoimidazol-2-yl)-propyl]-methyl-amine

Prepared from 3-chloro-6-methoxy-benzene-1,2-diamine in analogy to the methods described for [3-(5,6-dimethoxy-1H-benzoimidazol-2-yl)-propyl]-methyl-amine.
LC-MS: $t_R$=0.59 min; [M+H]⁺: 254.05

BB33. [3-(4,6-Dimethoxy-1H-benzoimidazol-2-yl)-propyl]-methyl-amine

BB33.1 N-(3,5-Dimethoxy-phenyl)-acetamide

Prepared from 4,5-dimethoxyaniline in analogy to the methods described for N-(2-chloro-5-methoxy-phenyl)-acetamide.
LC-MS: $t_R$=0.79 min; [M+H]⁺: 196.29.

BB33.2 N-(3,5-Dimethoxy-2-nitro-phenyl)-acetamide

Prepared from N-(3,5-dimethoxy-phenyl)-acetamide in analogy to the method described for N-(6-chloro-3-methoxy-2-nitro-phenyl)-acetamide.
LC-MS: $t_R$=0.83 min; [M+CH₃CN+H]⁺: 282.09.

BB33.3 3,5-Dimethoxy-2-nitro-phenylamine

A solution of 9.7 g of N-(3,5-dimethoxy-2-nitro-phenyl)-acetamide in 47 mL of 25%-HCl and 100 mL of 1M-HCl was refluxed for 1.5 h. The reaction mixture was basified with 2M-NaOH and extracted with EtOAc. The organic phase was dried over anh. Na₂SO₄ and concentrated in vacuo. The crude product was purified by CC using EtOAc/heptane 1/3 to yield 5.6 g of a mixture of 3-amino-5-methoxy-4-nitro-phenol and 3,5-dimethoxy-2-nitro-phenylamine as orange solid. To a solution of 5.33 g of the aforementioned mixture in 78 mL of THF were added 9.3 g of triphenylphosphine, 1.4 mL of MeOH and 5.7 mL of diethyl azodicarboxylate. The mixture was stirred for 4 h at rt then concentrated in vacuo. The residue was taken up in DCM, quenched with water at 0° C. The organic phase was dried over anh. Na₂SO₄ and concentrated in vacuo. The crude product was purified by CC using DCM to yield 4.21 g of 3,5-dimethoxy-2-nitro-phenylamine as orange solid.
LC-MS: $t_R$=0.86 min; [M+H]⁺: 199.22.

BB33.4 3,5-Dimethoxy-benzene-1,2-diamine

Prepared from 3,5-dimethoxy-2-nitro-phenylamine in analogy to the method described for 3-chloro-6-methoxy-benzene-1,2-diamine.
LC-MS: $t_R$=0.50 min; [M+H]⁺: 169.05.

BB33.5 [3-(4,6-Dimethoxy-1H-benzoimidazol-2-yl)-propyl]-methyl-amine

Prepared from 3,5-dimethoxy-benzene-1,2-diamine in analogy to the methods described for [3-(5,6-dimethoxy-1H-benzoimidazol-2-yl)-propyl]-methyl-amine.
LC-MS: $t_R$=0.52 min; [M+H]$^+$: 250.17.

BB34. [3-(4,6-Bis-trifluoromethyl-1H-benzoimidazol-2-yl)-propyl]-methyl-amine Prepared from 3,5-bis-trifluoromethyl-benzene-1,2-diamine in analogy to the methods described for [3-(5,6-dimethoxy-1H-benzoimidazol-2-yl)-propyl]-methyl-amine.
LC-MS: $t_R$=0.78 min; [M+H]$^+$: 326.09.

BB35. 3-[4-Methyl-5-phenyl-1-(2-trimethylsilanyl-ethoxymethyl)-1H-imidazol-2-yl]-propionic acid Prepared in analogy to the methods described for 3-[4,5-diphenyl-1-(2-trimethylsilanyl-ethoxymethyl)-1H-imidazol-2-yl]-propionic acid replacing benzil with 1-phenyl-propane-1,2-dione.
LC-MS: $t_R$=0.90 min; [M+H]$^+$: 361.14.

BB36. 3-[5-(2-Methoxy-phenyl)-1-(2-trimethylsilanyl-ethoxymethyl)-1H-imidazol-2-yl]-propionic acid Prepared in analogy to the methods described for 3-[4,5-diphenyl-1-(2-trimethylsilanyl-ethoxymethyl)-1H-imidazol-2-yl]-propionic acid replacing benzil with (2-methoxy-phenyl)-oxo-acetaldehyde.
LC-MS: $t_R$=0.91 min; [M+H]$^+$: 377.08.

PREPARATION OF EXAMPLES

Example 1 rac-(1R*,2R*,4R*)-2-(2-{[3-(1H-Benzoimidazol-2-yl)-propyl]-methyl-amino}-ethyl)-5-phenyl-bicyclo[2.2.2]oct-5-en-2-ol

1.1 (Procedure P1.1): rac-(1R*,2R*,4R*)-2-(2-Hydroxy-ethyl)-5-phenyl-bicyclo[2.2.2]oct-5-en-2-ol 295 mg of rac-(1R*,2R*,4R*)-(2-hydroxy-5-phenyl-bicyclo[2.2.2]oct-5-en-2-yl)-acetic acid tert.-butyl ester (intermediate K1A, major racemate) were dissolved in 6 mL THF and cooled to −15° C. To this solution were added dropwise 1.65 mL of a LiAlH$_4$ solution (2.3M in THF). After complete addition the reaction mixture was allowed to warm to 0° C. over 3 h. Under cooling 1M aq. NaOH was added dropwise. The mixture was diluted with THF, filtrated over a pad of celite, washed with THF, EtOAc. The filtrate was evaporated to dryness to give 0.25 g of rac-(1R*,2R*,4R*)-2-(2-hydroxy-ethyl)-5-phenyl-bicyclo[2.2.2]oct-5-en-2-ol as white solid.
LC-MS: $t_R$=0.85 min; [M−H$_2$O+H]$^+$: 227.10.

1.1A: (1S,2S,4S)-2-(2-Hydroxy-ethyl)-5-phenyl-bicyclo[2.2.2]oct-5-en-2-ol and (1R,2R,4R)-2-(2-Hydroxy-ethyl)-5-phenyl-bicyclo[2.2.2]oct-5-en-2-ol rac-(1R*,2R*,4R*)-2-(2-Hydroxy-ethyl)-5-phenyl-bicyclo[2.2.2]oct-5-en-2-ol was separated into the respective enantiomers using prep. chiral HPLC (column: ChiralCel OD 20×250 mm, 10 μm; Hex/EtOH 96:4).
Chiral analytic HPLC (ChiralCel OD 4.6×250 mm, 10 μM, Hex/EtOH 97:3, flow 0.8 mL/min):
Enantiomer A: $t_R$=18.1 min.
Enantiomer B: $t_R$=21.2 min.

1.2 (Procedure P1.2): rac-Toluene-4-sulfonic acid (1R*,2R*,4R*)-2-(2-hydroxy-5-phenyl-bicyclo[2.2.2]oct-5-en-2-yl)-ethyl ester A mixture of 227 mg of rac-(1R*,2R*,4R*)-2-(2-hydroxy-ethyl)-5-phenyl-bicyclo[2.2.2]oct-5-en-2-ol, 195 mg of Ts-Cl, 0.16 mL of NEt$_3$ and 11 mg of DMAP in 3 mL toluene was stirred overnight at rt. The reaction mixture was quenched with water, the organic phase was separated, washed with brine and evaporated. The residue was purified by CC with Hept-EtOAc (6:4) to yield 0.32 g of oily rac-toluene-4-sulfonic acid (1R*,2R*,4R*)-2-(2-hydroxy-5-phenyl-bicyclo[2.2.2]oct-5-en-2-yl)-ethyl ester as yellowish oil.
LC-MS: $t_R$=1.06 min; [M−H$_2$O+H]$^+$: 381.00.

1.3 (Procedure P1.3): rac-(1R*,2R*,4R*)-2-(2-{[3-(1H-Benzoimidazol-2-yl)-propyl]-methyl-amino}-ethyl)-5-phenyl-bicyclo[2.2.2]oct-5-en-2-ol A mixture of 115 mg of rac-toluene-4-sulfonic acid (1R*,2R*,4R*)-2-(2-hydroxy-5-phenyl-bicyclo[2.2.2]oct-5-en-2-yl)-ethyl ester and 55 mg of [3-(1H-benzoimidazol-2-yl)-propyl]-methyl-amine in 2 mL of DIPEA was heated to 110° C. for 30 min. The reaction mixture was cooled to rt, quenched with MeOH-water and extracted with EtOAc. The organic phase was separated, dried and evaporated and the residue was purified by CC with EtOAc-MeOH (3:1) to give 34 mg of rac-(1R*,2R*,4R*)-2-(2-{[3-(1H-benzoimidazol-2-yl)-propyl]-methyl-amino}-ethyl)-5-phenyl-bicyclo[2.2.2]oct-5-en-2-ol as beige foam.
LC-MS: $t_R$=0.70 min; [M+H]$^+$: 416.25.

Example 1A rac-Isobutyric acid (1R*,2R*,4R*)-2-(2-{[3-(1H-Benzoimidazol-2-yl)-propyl]-methyl-amino}-ethyl)-5-phenyl-bicyclo[2.2.2]oct-5-en-2-yl ester

1A.1 (Procedure P1.4): rac-Isobutyric acid (1R*,2R*,4R*)-2-(2-{[3-(1H-benzoimidazol-2-yl)-propyl]-methyl-amino}-ethyl)-5-phenyl-bicyclo[2.2.2]oct-5-en-2-yl ester To a solution of 150 mg of rac-(1R*,2R*,4R*)-2-(2-{[3-(1H-benzoimidazol-2-yl)-propyl]-methyl-amino}-ethyl)-5-phenyl-bicyclo[2.2.2]oct-5-en-2-ol and 0.176 mL of NEt$_3$ in 4 mL DCM 0.1 mL of isobutyrylchloride was added at 0° C. The yellow reaction mixture was stirred for 3 h at rt and then quenched with sat. aq. NaHCO$_3$. The product was extracted with DCM, the organic phase was evaporated to dryness. The residue was dissolved in EtOAc, silica gel and a few drops of MeOH were added and the mixture was stirred vigorously for 5 h. The mixture was filtered, the filtrate evaporated and the residue purified by CC with EtOAc-MeOH (3:1) to yield 86 mg of pure rac-isobutyric acid (1R*,2R*,4R*)-2-(2-{[3-(1H-benzoimidazol-2-yl)-propyl]-methyl-amino}-ethyl)-5-phenyl-bicyclo[2.2.2]oct-5-en-2-yl ester as colorless foam.
LC-MS: $t_R$=0.82 min; [M+H]$^+$: 486.50.

1A.2 (Procedure P1.5): rac-Isobutyric acid (1R*, 2R*,4R*)-2-(2-{[3-(1H-benzoimidazol-2-yl)-propyl]-methyl-amino}-ethyl)-5-phenyl-bicyclo[2.2.2] oct-5-en-2-yl ester dihydrochloride The above product may be transformed into the corresponding dihydrochloride salt using the following procedure.

86 mg of rac-isobutyric acid (1R*,2R*,4R*)-2-(2-{[3-(1H-benzoimidazol-2-yl)-propyl]-methyl-amino}-ethyl)-5-phenyl-bicyclo[2.2.2]oct-5-en-2-yl ester were dissolved in 2 mL EtOAc, the solution was cooled with an ice bath and 1 mL of 3M HCl in EtOAC was added. The reaction mixture was evaporated to dryness without heating to give the desired rac-isobutyric acid (1R*,2R*,4R*)-2-(2-{[3-(1H-benzoimidazol-2-yl)-propyl]-methyl-amino}-ethyl)-5-phenyl-bicyclo [2.2.2]oct-5-en-2-yl ester dihydrochloride.

Example 2 rac-(1R*,2R*,4R*)-2-(2-{[3-(1H-Benzoimidazol-2-yl)-propyl]-methyl-amino}-ethyl)-5-(3-methoxy-phenyl)-bicyclo[2.2.2]oct-5-en-2-ol Prepared according to procedures P1.1 to P1.3 in Example 1 using rac-(1R*,2R*,4R*)-(2-hydroxy-5-(3-methoxyphenyl)-bicyclo[2.2.2]oct-5-en-2-yl)acetic acid tert.-butyl ester.
LC-MS: $t_R$=0.70 min; [M+H]$^+$: 446.34

Example 2A rac-Isobutyric acid (1R*,2R*,4R*)-2-(2-{[3-(1H-benzoimidazol-2-yl)-propyl]-methyl-amino}-ethyl)-5-(3-methoxy-phenyl)-bicyclo[2.2.2]oct-5-en-2-yl ester Prepared according to procedure P1.4 in Example 1A using rac-(1R*,2R*,4R*)-2-(2-{[3-(1H-benzoimidazol-2-yl)-propyl]-methyl-amino}-ethyl)-5-(3-methoxy-phenyl)-bicyclo [2.2.2]oct-5-en-2-ol.
LC-MS: $t_R$=0.82 min; [M+H]$^+$: 516.39

Example 3 rac-(1R*,2R*,4R*)-2-(2-{[3-(1H-Benzoimidazol-2-yl)-propyl]-methyl-amino}-ethyl)-5-(2,6-dimethyl-phenyl)-bicyclo[2.2.2]oct-5-en-2-ol Prepared according to procedures P1.1 to P1.3 in Example 1 using rac-(1R*,2R*,4R*)-(5-(2,6-dimethyl-phenyl)-2-hydroxy-bicyclo[2.2.2]oct-5-en-2-yl)-acetic acid tert.-butyl ester.
LC-MS: $t_R$=0.74 min; [M+H]$^+$: 444.47.

Example 3A rac-Isobutyric acid (1R*,2R*,4R*)-2-(2-{[3-(1H-benzoimidazol-2-yl)-propyl]-methyl-amino}-ethyl)-5-(2,6-dimethyl-phenyl)-bicyclo[2.2.2]oct-5-en-2-yl ester Prepared according to procedure P1.4 in Example 1A using rac-(1R*,2R*,4R*)-2-(2-{[3-(1H-benzoimidazol-2-yl)-propyl]-methyl-amino}-ethyl)-5-(2,6-dimethyl-phenyl)-bicyclo [2.2.2]oct-5-en-2-ol.
LC-MS: $t_R$=0.85 min; [M+H]$^+$: 514.58.

Example 4 rac-(1R*,2R*,4R*)-2-(2-{[3-(1H-Benzoimidazol-2-yl)-propyl]-methyl-amino}-ethyl)-5-(2-methyl-phenyl)-bicyclo[2.2.2]oct-5-en-2-ol Prepared according to procedures P1.1 to P1.3 in Example 1 using rac-(1R*,2R*,4R*)-(2-hydroxy-5-(2-methyl-phenyl)-bicyclo[2.2.2]oct-5-en-2-yl)-acetic acid tert.-butyl ester.
LC-MS: $t_R$=0.71 min; [M+H]$^+$: 430.46.

Example 4A rac-Isobutyric acid (1R*,2R*,4R*)-2-(2-{[3-(1H-benzoimidazol-2-yl)-propyl]-methyl-amino}-ethyl)-5-(2-methyl-phenyl)-bicyclo[2.2.2]oct-5-en-2-yl ester Prepared according to procedure P1.4 in Example 1A using rac-(1R*,2R*,4R*)-2-(2-{[3-(1H-benzoimidazol-2-yl)-propyl]-methyl-amino}-ethyl)-5-(2-methyl-phenyl)-bicyclo [2.2.2]oct-5-en-2-ol.
LC-MS: $t_R$=0.84 min; [M+H]$^+$: 500.50.

Example 5 rac-(1R*,2R*,4R*)-2-(2-{[3-(1H-Benzoimidazol-2-yl)-propyl]-methyl-amino}-ethyl)-5-(3-methyl-phenyl)-bicyclo[2.2.2]oct-5-en-2-ol Prepared according to procedures P1.1 to P1.3 in Example 1 using rac-(1R*,2R*,4R*)-(2-hydroxy-5-(3-methyl-phenyl)-bicyclo[2.2.2]oct-5-en-2-yl)-acetic acid tert.-butyl ester.
LC-MS: $t_R$=0.75 min; [M+H]$^+$: 430.55.

Example 5A rac-Isobutyric acid (1R*,2R*,4R*)-2-(2-{[3-(1H-benzoimidazol-2-yl)-propyl]-methyl-amino}-ethyl)-5-(3-methyl-phenyl)-bicyclo[2.2.2]oct-5-en-2-yl ester Prepared according to procedure P1.4 in Example 1A using rac-(1R*,2R*,4R*)-2-(2-{[3-(1H-benzoimidazol-2-yl)-propyl]-methyl-amino}-ethyl)-5-(3-methyl-phenyl)-bicyclo [2.2.2]oct-5-en-2-ol.
LC-MS: $t_R$=0.83 min; [M+H]$^+$: 500.71.

Example 6 rac-(1R*,2R*,4R*)-2-(2-{[3-(1H-Benzoimidazol-2-yl)-propyl]-methyl-amino}-ethyl)-5-(4-methyl-phenyl)-bicyclo[2.2.2]oct-5-en-2-ol Prepared according to procedures P1.1 to P1.3 in Example 1 using rac-(1R*,2R*,4R*)-(2-hydroxy-5-(4-methyl-phenyl)-bicyclo[2.2.2]oct-5-en-2-yl)-acetic acid tert.-butyl ester.
LC-MS: $t_R$=0.74 min; [M+H]$^+$: 430.62.

Example 6A rac-Isobutyric acid (1R*,2R*,4R*)-2-(2-{[3-(1H-benzoimidazol-2-yl)-propyl]-methyl-amino}-ethyl)-5-(4-methyl-phenyl)-bicyclo[2.2.2]oct-5-en-2-yl ester Prepared according to procedure P1.4 in Example 1A using rac-(1R*,2R*,4R*)-2-(2-{[3-(1H-benzoimidazol-2-yl)-propyl]-methyl-amino}-ethyl)-5-(4-methyl-phenyl)-bicyclo[2.2.2]oct-5-en-2-ol.
LC-MS: $t_R$=0.84 min; [M+H]$^+$: 500.53.

Example 7 rac-(1R*,2R*,4R*)-2-(2-{[3-(1H-Benzoimidazol-2-yl)-propyl]-methyl-amino}-ethyl)-5-(3-fluoro-phenyl)-bicyclo[2.2.2]oct-5-en-2-ol Prepared according to procedures P1.1 to P1.3 in Example 1 using rac-(1R*,2R*,4R*)-(2-hydroxy-5-(3-fluoro-phenyl)-bicyclo[2.2.2]oct-5-en-2-yl)-acetic acid tert.-butyl ester.
LC-MS: $t_R$=0.73 min; [M+H]$^+$: 434.20.

Example 7A rac-Isobutyric acid (1R*,2R*,4R*)-2-(2-{[3-(1H-benzoimidazol-2-yl)-propyl]-methyl-amino}-ethyl)-5-(3-fluoro-phenyl)-bicyclo[2.2.2]oct-5-en-2-yl ester Prepared according to procedure P1.4 in Example 1A using rac-(1R*,2R*,4R*)-2-(2-{[3-(1H-benzoimidazol-2-yl)-propyl]-methyl-amino}-ethyl)-5-(3-fluoro-phenyl)-bicyclo[2.2.2]oct-5-en-2-ol.
LC-MS: $t_R$=0.81 min; [M+H]$^+$: 504.50.

Example 8 rac-(1R*,2R*,4R*)-2-(2-{[3-(1H-Benzoimidazol-2-yl)-propyl]-methyl-amino}-ethyl)-5-(4-fluoro-phenyl)-bicyclo[2.2.2]oct-5-en-2-ol Prepared according to procedures P1.1 to P1.3 in Example 1 using rac-(1R*,2R*,4R*)-(2-hydroxy-5-(4-fluoro-phenyl)-bicyclo[2.2.2]oct-5-en-2-yl)-acetic acid tert.-butyl ester.
LC-MS: $t_R$=0.72 min; [M+H]$^+$: 434.54.

Example 8A rac-Isobutyric acid (1R*,2R*,4R*)-2-(2-{[3-(1H-benzoimidazol-2-yl)-propyl]-methyl-amino}-ethyl)-5-(4-fluoro-phenyl)-bicyclo[2.2.2]oct-5-en-2-yl ester Prepared according to procedure P1.4 in Example 1A using rac-(1R*,2R*,4R*)-2-(2-{[3-(1H-benzoimidazol-2-yl)-propyl]-methyl-amino}-ethyl)-5-(4-fluoro-phenyl)-bicyclo[2.2.2]oct-5-en-2-ol.
LC-MS: $t_R$=0.81 min; [M+H]$^+$: 504.68.

Example 9 rac-(1R*,2R*,4R*)-2-(2-{[3-(1H-Benzoimidazol-2-yl)-propyl]-methyl-amino}-ethyl)-5-pyridin-3-yl-bicyclo[2.2.2]oct-5-en-2-ol Prepared according to procedures P1.1 to P1.3 in Example 1 using rac-(1R*,2R*,4R*)-(2-hydroxy-5-pyridin-3-yl-bicyclo[2.2.2]oct-5-en-2-yl)-acetic acid tert.-butyl ester.
LC-MS: $t_R$=0.52 min; [M+H]$^+$: 417.60.

Example 9A rac-Isobutyric acid (1R*,2R*,4R*)-2-(2-{[3-(1H-benzoimidazol-2-yl)-propyl]-methyl-amino}-ethyl)-5-pyridin-3-yl-bicyclo[2.2.2]oct-5-en-2-yl ester Prepared according to procedure P1.4 in Example 1A using rac-(1R*,2R*,4R*)-2-(2-{[3-(1H-benzoimidazol-2-yl)-propyl]-methyl-amino}-ethyl)-5-pyridin-3-yl-bicyclo[2.2.2]oct-5-en-2-ol.
LC-MS: $t_R$=0.65 min; [M+H]$^+$: 487.25.

Example 10 rac-(1R*,2R*,4R*)-2-(2-{[3-(1H-Benzoimidazol-2-yl)-propyl]-methyl-amino}-ethyl)-5-naphthalen-2-yl-bicyclo[2.2.2]oct-5-en-2-ol Prepared according to procedures P1.1 to P1.3 in Example 1 using rac-(1R*,2R*,4R*)-(2-hydroxy-5-naphthalen-2-yl-bicyclo[2.2.2]oct-5-en-2-yl)-acetic acid tert.-butyl ester.
LC-MS: $t_R$=0.77 min; [M+H]$^+$: 466.59.

Example 10A rac-Isobutyric acid (1R*,2R*,4R*)-2-(2-{[3-(1H-benzoimidazol-2-yl)-propyl]-methyl-amino}-ethyl)-5-naphthalen-2-yl-bicyclo[2.2.2]oct-5-en-2-yl ester Prepared according to procedure P1.4 in Example 1A using rac-(1R*,2R*,4R*)-2-(2-{[3-(1H-benzoimidazol-2-yl)-propyl]-methyl-amino}-ethyl)-5-naphthalen-2-yl-bicyclo[2.2.2]oct-5-en-2-ol.
LC-MS: $t_R$=0.87 min; [M+H]$^+$: 536.49.

Example 11

(1R,2R,4R)-2-(2-{[3-(1H-Benzoimidazol-2-yl)-propyl]-methyl-amino}-ethyl)-5-phenyl-bicyclo[2.2.2]oct-5-en-2-ol or (1S,2S,4S)-2-(2-{[3-(1H-benzoimidazol-2-yl)-propyl]-methyl-amino}-ethyl)-5-phenyl-bicyclo[2.2.2]oct-5-en-2-ol Prepared according to procedures P1.1 to P1.3 in Example 1 using enantiomer A of rac-(1R*,2R*,4R*)-2-(2-hydroxy-ethyl)-5-phenyl-bicyclo[2.2.2]oct-5-en-2-ol (see example 1.1A).
LC-MS: $t_R$=0.71 min; [M+H]$^+$: 416.54.

Example 11A

Isobutyric acid (1R,2R,4R)-2-(2-{[3-(1H-benzoimidazol-2-yl)-propyl]-methyl-amino}-ethyl)-5-phenyl-bicyclo[2.2.2]oct-5-en-2-yl ester or isobutyric acid (1S,2S,4S)-2-(2-{[3-(1H-benzoimidazol-2-yl)-propyl]-methyl-amino}-ethyl)-5-phenyl-bicyclo[2.2.2]oct-5-en-2-yl ester Prepared according to procedure P1.4 in Example 1A using the above 2-(2-{[3-(1H-benzoimidazol-2-yl)-propyl]-methyl-amino}-ethyl)-5-phenyl-bicyclo[2.2.2]oct-5-en-2-ol (compound of example 11).
LC-MS: $t_R$=0.82 min; [M+H]$^+$: 486.70.

Example 12

(1R,2R,4R)-2-(2-{[3-(1H-Benzoimidazol-2-yl)-propyl]-methyl-amino}-ethyl)-5-phenyl-bicyclo[2.2.2]oct-5-en-2-ol or (1S,2S,4S)-2-(2-{[3-(1H-benzoimidazol-2-yl)-propyl]-methyl-amino}-ethyl)-5-phenyl-bicyclo[2.2.2]oct-5-en-2-ol Prepared according to procedures P1.1 to P1.3 in Example 1 using enantiomer B of rac-(1R*,2R*,4R*)-2-(2-hydroxy-ethyl)-5-phenyl-bicyclo[2.2.2]oct-5-en-2-ol (see example 1.1A).
LC-MS: $t_R$=0.71 min; [M+H]$^+$: 416.61.

Example 12A

Isobutyric acid (1R,2R,4R)-2-(2-{[3-(1H-benzoimidazol-2-yl)-propyl]-methyl-amino}-ethyl)-5-phenyl-bicyclo[2.2.2]oct-5-en-2-yl ester or isobutyric acid (1S,2S,4S)-2-(2-{[3-(1H-benzoimidazol-2-yl)-propyl]-methyl-amino}-ethyl)-5-phenyl-bicyclo[2.2.2]oct-5-en-2-yl ester Prepared according to procedure P1.4 in Example 1A using the above 2-(2-{[3-(1H-benzoimidazol-2-yl)-propyl]-methyl-amino}-ethyl)-5-phenyl-bicyclo[2.2.2]oct-5-en-2-ol (compound of example 12).
LC-MS: $t_R$=0.82 min; [M+H]$^+$: 486.70.

Example 13 rac-(1R*,2R*,4R*)-2-(2-{[2-(1H-Benzoimidazol-2-yl)-ethyl]-methyl-amino}-ethyl)-5-phenyl-bicyclo[2.2.2]oct-5-en-2-ol Prepared according to procedures P1.1 to P1.3 in Example 1 using [2-(1H-benzoimidazol-2-yl)-ethyl]-methyl-amine in step P1.3.
LC-MS: $t_R$=0.72 min; [M+H]$^+$: 402.58.

Example 13A rac-Isobutyric acid (1R*,2R*,4R*)-2-(2-{[2-(1H-benzoimidazol-2-yl)-ethyl]-methyl-amino}-ethyl)-5-phenyl-bicyclo[2.2.2]oct-5-en-2-yl ester Prepared according to procedure P1.4 in Example 1A using rac-(1R*,2R*,4R*)-2-(2-{[2-(1H-benzoimidazol-2-yl)-ethyl]-methyl-amino}-ethyl)-5-phenyl-bicyclo[2.2.2]oct-5-en-2-ol.
LC-MS: $t_R$=0.85 min; [M+H]$^+$: 472.63.

Example 14 rac-(1R*,2R*,4R*)-2-{2-[(1H-Benzoimidazol-2-ylmethyl)-methyl-amino]-ethyl}-5-phenyl-bicyclo[2.2.2]oct-5-en-2-ol Prepared according to procedures P1.1 to P1.3 in Example 1 using (1H-benzoimidazol-2-ylmethyl)-methyl-amine in step P1.3.
LC-MS: $t_R$=0.80 min; [M+H]$^+$: 388.51.

Example 14A rac-Isobutyric acid (1R*,2R*,4R*)-2-{2-[(1H-benzoimidazol-2-ylmethyl)-methyl-amino]-ethyl}-5-phenyl-bicyclo[2.2.2]oct-5-en-2-yl ester Prepared according to procedure P1.4 in Example 1A using rac-(1R*,2R*,4R*)-2-{2-[(1H-benzoimidazol-2-ylmethyl)-methyl-amino]-ethyl}-5-phenyl-bicyclo[2.2.2]oct-5-en-2-ol.
LC-MS: $t_R$=0.93 min; [M+H]$^+$: 458.61.

Example 15 rac-(1R*,2R*,4R*)-2-{2-[Methyl-(3-phenyl-propyl)-amino]-ethyl}-5-phenyl-bicyclo[2.2.2]oct-5-en-2-ol Prepared according to procedures P1.1 to P1.3 in Example 1 using methyl-(3-phenyl-propyl)-amine in step P1.3.
LC-MS: $t_R$=0.88 min; [M+H]$^+$: 376.55.

Example 15A rac-Isobutyric acid (1R*,2R*,4R*)-2-{2-[methyl-(3-phenyl-propyl)-amino]-ethyl}-5-phenyl-bicyclo[2.2.2]oct-5-en-2-yl ester Prepared according to procedure P1.4 in Example 1A using rac-(1R*,2R*,4R*)-2-{2-[methyl-(3-phenyl-propyl)-amino]-ethyl}-5-phenyl-bicyclo[2.2.2]oct-5-en-2-ol.
LC-MS: $t_R$=1.00 min; [M+H]$^+$: 446.59.

Example 16 rac-(1R*,2R*,4R*)-2-(2-{[3-(1H-Benzoimidazol-2-yl)-propyl]-methyl-amino}-ethyl)-6-methyl-5-propyl-bicyclo[2.2.2]oct-5-en-2-ol Prepared according to procedures P1.1 to P1.3 in Example 1 using rac-(1R*,2R*,4R*)-(2-hydroxy-6-methyl-5-propyl-bicyclo[2.2.2]oct-5-en-2-yl)-acetic acid tert.-butyl ester.
LC-MS: $t_R$=0.73 min; [M+H]$^+$: 396.23.

Example 16A rac-Isobutyric acid (1R*,2R*,4R*)-2-(2-{[3-(1H-benzoimidazol-2-yl)-propyl]-methyl-amino}-ethyl)-6-methyl-5-propyl-bicyclo[2.2.2]oct-5-en-2-yl ester Prepared according to procedure P3.3 in Example 43A below using rac-(1R*,2R*,4R*)-2-(2-{[3-(1H-benzoimidazol-2-yl)-propyl]-methyl-amino}-ethyl)-6-methyl-5-propyl-bicyclo[2.2.2]oct-5-en-2-ol.
LC-MS: $t_R$=0.84 min; [M+H]$^+$: 466.32.

Example 17 rac-(1R*,2R*,4R*)-2-(2-{[3-(1H-Benzoimidazol-2-yl)-propyl]-methyl-amino}-ethyl)-5-methyl-6-phenyl-bicyclo[2.2.2]oct-5-en-2-ol Prepared according to procedures P1.1 to P1.3 in Example 1 using rac-(1R*,2R*,4R*)-(2-hydroxy-5-methyl-6-phenyl-bicyclo[2.2.2]oct-5-en-2-yl)acetic acid tert.-butyl ester.
LC-MS: $t_R$=0.72 min; [M+H]$^+$: 430.56.

Example 17A rac-Isobutyric acid (1R*,2R*,4R*)-2-(2-{[3-(1H-benzoimidazol-2-yl)-propyl]-methyl-amino}-ethyl)-5-methyl-6-phenyl-bicyclo[2.2.2]oct-5-en-2-yl ester Prepared according to procedure P1.4 in Example 1A using rac-(1R*,2R*,4R*)-2-(2-{[3-(1H-benzoimidazol-2-yl)-propyl]-methyl-amino}-ethyl)-5-methyl-6-phenyl-bicyclo[2.2.2]oct-5-en-2-ol.
LC-MS: $t_R$=0.83 min; [M+H]$^+$: 500.31.

Example 17B rac-(1R*,2S*,4R*)-2-(2-{[3-(1H-Benzoimidazol-2-yl)-propyl]-methyl-amino}-ethyl)-5-methyl-6-phenyl-bicyclo[2.2.2]oct-5-en-2-ol Prepared according to procedures P1.1 to P1.3 in Example 1 using the minor racemate rac-(1R*,2S*,4R*)-(2-hydroxy-5-methyl-6-phenyl-bicyclo[2.2.2]oct-5-en-2-yl)-acetic acid tert.-butyl ester.
LC-MS: $t_R$=0.73 min; [M+H]$^+$: 430.56

Example 17C rac-Isobutyric acid (1R*,2S*,4R*)-2-(2-{[3-(1H-benzoimidazol-2-yl)-propyl]-methyl-amino}-ethyl)-5-methyl-6-phenyl-bicyclo[2.2.2]oct-5-en-2-yl ester Prepared according to procedure P1.4 in Example 1A using rac-(1R*,2S*,4R*)-2-(2-{[3-(1H-benzoimidazol-2-yl)-propyl]-methyl-amino}-ethyl)-5-methyl-6-phenyl-bicyclo[2.2.2]oct-5-en-2-ol.
LC-MS: $t_R$=0.82 min; [M+H]$^+$: 500.32.

Example 18 rac-(1R*,3R*,4R*)-1,2,3,4,9,10-Hexahydro-3-hydroxy-3-{N-methyl-N-(3-benzimidazol-2-ylpropyl)aminoethyl}-1,4-ethanophenanthrene Prepared according to procedures P1.1 to P1.3 in Example 1 using rac-(1R*,3R*,4R*)-1,2,3,4,9,10-hexahydro-3-hydroxy-1,4-ethanophenanthren-3-ylacetic acid tert.-butyl ester.
LC-MS: $t_R$=0.73 min; [M+H]$^+$: 440.23.

Example 18A rac-Isobutyric acid (1R*,3R*,4R*)-1,2,3,4,9,10-hexahydro-3-hydroxy-3-{N-methyl-N-(3-benzimidazol-2-ylpropyl)aminoethyl}-1,4-ethanophenanthrene ester Prepared according to procedure P1.4 in Example 1A using rac-(1R*,3R*,4R*)-1,2,3,4,9,10-hexahydro-3-hydroxy-3-{N-methyl-N-(3-benzimidazol-2-ylpropyl)aminoethyl}-1,4-ethanophenanthrene.
LC-MS: $t_R$=0.84 min; [M+H]$^+$: 512.43.

Example 19 rac-2-(3-{[2-((1R*,2R*,4R*)-2-Hydroxy-5-phenyl-bicyclo[2.2.2]oct-5-en-2-yl)-ethyl]-methyl-amino}-propyl)-1H-benzoimidazole-4-carboxylic acid methyl ester Prepared according to procedures P1.1 to P1.3 in Example 1 using 2-(3-methylamino-propyl)-1H-benzoimidazole-4-carboxylic acid methyl ester in step P1.3.
LC-MS: $t_R$=0.77 min; [M+H]$^+$: 474.22.

Example 19A rac-2-(3-{[2-((1R*,2R*,4R*)-2-Isobutyryloxy-5-phenyl-bicyclo[2.2.2]oct-5-en-2-yl)-ethyl]-methyl-amino}-propyl)-1H-benzoimidazole-4-carboxylic acid methyl ester Prepared according to procedure P1.4 in Example 1A using rac-2-(3-{[2-((1R*,2R*,4R*)-2-hydroxy-5-phenyl-bicyclo[2.2.2]oct-5-en-2-yl)-ethyl]-methyl-amino}-propyl)-1H-benzoimidazole-4-carboxylic acid methyl ester.
LC-MS: $t_R$=0.95 min; [M+H]$^+$: 543.95.

Example 20 rac-2-(3-{[2-((1R*,2R*,4R*)-2-Hydroxy-5-phenyl-bicyclo[2.2.2]oct-5-en-2-yl)-ethyl]-methyl-amino}-propyl)-1H-benzoimidazole-5-carboxylic acid methyl ester Prepared according to procedures P1.1 to P1.3 in Example 1 using 2-(3-methylamino-propyl)-1H-benzoimidazole-5-carboxylic acid methyl ester in step P1.3.
LC-MS: $t_R$=0.79 min; [M+H]$^+$: 474.34.

Example 20A rac-2-(3-{[2-((1R*,2R*,4R*)-2-Isobutyryloxy-5-phenyl-bicyclo[2.2.2]oct-5-en-2-yl)-ethyl]-methyl-amino}-propyl)-1H-benzoimidazole-5-carboxylic acid methyl ester Prepared according to procedure P1.4 in Example 1A using rac-2-(3-{[2-((1R*,2R*,4R*)-2-Hydroxy-5-phenyl-bicyclo[2.2.2]oct-5-en-2-yl)-ethyl]-methyl-amino}-propyl)-1H-benzoimidazole-5-carboxylic acid methyl ester.
LC-MS: $t_R$=0.93 min; [M+H]$^+$: 543.35.

Example 21 rac-(1R*,2R*,4R*)-2-(2-{[3-(1H-Benzoimidazol-2-yl)-propyl]-methyl-amino}-ethyl)-5-thiophen-2-yl-bicyclo[2.2.2]oct-5-en-2-ol

21.1 (Procedure P2.1): rac-(1R*,2R*,4R*)-(2-Hydroxy-5-thiophen-2-yl-bicyclo[2.2.2]oct-5-en-2-yl)-acetic acid 276 mg of rac-(1R*,2R*,4R*)-(2-hydroxy-5-thiophen-2-yl-bicyclo[2.2.2]oct-5-en-2-yl)-acetic acid tert.-butyl ester were dissolved in EtOH (1.7 mL) and treated with LiOH.H$_2$O (181 mg), H$_2$O (0.55 mL) and MeOH (1.65 mL). The reaction mixture was stirred at rt for 4 days and concentrated in vacuo.

The resulting aq. residue was partitioned between water and Et$_2$O. The aq. layer was separated, acidified with 25%-HCl, and extracted with DCM. The organic phase was dried over anh. Na$_2$SO$_4$ and concentrated to give 205 mg of rac-(1R*,2R*,4R*)-(2-hydroxy-5-thiophen-2-yl-bicyclo[2.2.2]oct-5-en-2-yl)-acetic acid as a white solid.

LC-MS: $t_R$=0.85 min; [M−H$_2$O+H]$^+$: 247.30.

21.2 (Procedure P2.2): rac-(1R*,2R*,4R*)-N-[3-(1H-Benzoimidazol-2-yl)-propyl]-2-(2-hydroxy-5-thiophen-2-yl-bicyclo[2.2.2]oct-5-en-2-yl)-N-methyl-acetamide 100 mg of rac-(1R*,2R*,4R*)-(2-hydroxy-5-thiophen-2-yl-bicyclo[2.2.2]oct-5-en-2-yl)-acetic acid were dissolved in THF (0.15 mL)/DCM (0.6 mL). 0.194 mL of DIPEA, 77 mg of HOBt and 109 mg of EDC were added sequentially at rt. The reaction mixture was stirred for 10 min then 86 mg of [3-(1H-benzoimidazol-2-yl)-propyl]-methyl-amine were added on at rt. The reaction mixture was stirred on at rt then diluted with DCM and washed with sat.-NaHCO$_3$ and brine. The organic phase was dried over anh. Na$_2$SO$_4$, filtered and concentrated in vacuo. The resulting crude material was purified by CC using EtOAc/MeOH/NEt$_3$ as eluant from 98/2/1 to 70/30/1 to yield 82 mg of rac-(1R*,2R*,4R*)-N-[3-(1H-benzoimidazol-2-yl)-propyl]-2-(2-hydroxy-5-thiophen-2-yl-bicyclo[2.2.2]oct-5-en-2-yl)-N-methyl-acetamide as a colorless oil.

LC-MS: $t_R$=0.82 min; [M+H]$^+$: 436.52.

21.3 (Procedure P2.3): rac-(1R*,2R*,4R*)-2-(2-{[3-(1H-Benzoimidazol-2-yl)-propyl]-methyl-amino}-ethyl)-5-thiophen-2-yl-bicyclo[2.2.2]oct-5-en-2-ol 0.196 mL of a Red-Al solution (65% in toluene) was added dropwise at 0° C. to a solution of 70 mg of rac-(1R*,2R*,4R*)-N-[3-(1H-benzoimidazol-2-yl)-propyl]-2-(2-hydroxy-5-thiophen-2-yl-bicyclo[2.2.2]oct-5-en-2-yl)-N-methyl-acetamide in toluene (0.8 mL). The reaction mixture was stirred for 30 min at 0° C. then the temperature was allowed to increase to rt for 3.5 h. The mixture was carefully poured onto a mixture of 1M-NaOH (6.1 mL) and ice. The mixture was stirred for 5 min until rt and extracted with toluene. The aq. phase was extracted with toluene. The combined toluene phase was washed with 1M-NaOH and brine, dried over anh. Na$_2$SO$_4$ and concentrated in vacuo to yield 54 mg of rac-(1R*,2R*,4R*)-2-(2-{[3-(1H-benzoimidazol-2-yl)-propyl]-methyl-amino}-ethyl)-5-thiophen-2-yl-bicyclo[2.2.2]oct-5-en-2-ol as a colorless solid.

LC-MS: $t_R$=0.71 min; [M+H]$^+$: 422.56.

Example 21A rac-Isobutyric acid (1R*,2R*,4R*)-2-(2-{[3-(1H-benzoimidazol-2-yl)-propyl]-methyl-amino}-ethyl)-5-thiophen-2-yl-bicyclo[2.2.2]oct-5-en-2-yl ester Prepared according to procedure P1.4 in Example 1A using rac-(1R*,2R*,4R*)-2-(2-{[3-(1H-benzoimidazol-2-yl)-propyl]-methyl-amino}-ethyl)-5-thiophen-2-yl-bicyclo[2.2.2]oct-5-en-2-ol.

LC-MS: $t_R$=0.80 min; [M+H]$^+$: 492.62.

Example 22 rac-(1R*,2R*,4R*)-2-(2-{[3-(1H-Benzoimidazol-2-yl)-propyl]-methyl-amino}-ethyl)-5-(4-methoxy-phenyl)-2-yl-bicyclo[2.2.2]oct-5-en-2-ol Prepared according to procedures P2.1 to P2.3 in Example 21 using rac-(1R*,2R*,4R*)-(2-hydroxy-5-(4-methoxy-phenyl)-bicyclo[2.2.2]oct-5-en-2-yl)-acetic acid tert.-butyl ester.

LC-MS: $t_R$=0.72 min; [M+H]$^+$: 446.58.

Example 22A rac-Isobutyric acid (1R*,2R*,4R*)-2-(2-{[3-(1H-benzoimidazol-2-yl)-propyl]-methyl-amino}-ethyl)-5-(4-methoxy-phenyl)-bicyclo[2.2.2]oct-5-en-2-yl ester Prepared according to procedure P1.4 in Example 1A using rac-(1R*,2R*,4R*)-2-(2-{[3-(1H-benzoimidazol-2-yl)-propyl]-methyl-amino}-ethyl)-5-(4-methoxy-phenyl)-2-yl-bicyclo[2.2.2]oct-5-en-2-ol.

LC-MS: $t_R$=1.08 min; [M+H]$^+$: 516.29.

Example 23 rac-(1R*,2R*,4R*)-2-(2-{[3-(1H-Benzoimidazol-2-yl)-propyl]-methyl-amino}-ethyl)-5-(2-methoxy-phenyl)-2-yl-bicyclo[2.2.2]oct-5-en-2-ol Prepared according to procedures P2.1 to P2.3 in Example 21 using rac-(1R*,2R*,4R*)-(2-hydroxy-5-(2-methoxy-phenyl)-bicyclo[2.2.2]oct-5-en-2-yl)-acetic acid tert.-butyl ester.

LC-MS: $t_R$=0.73 min; [M+H]$^+$: 446.56.

Example 23A rac-Isobutyric acid (1R*,2R*,4R*)-2-(2-{[3-(1H-benzoimidazol-2-yl)-propyl]-methyl-amino}-ethyl)-5-(2-methoxy-phenyl)-bicyclo[2.2.2]oct-5-en-2-yl ester Prepared according to procedure P1.4 in Example 1A using rac-(1R*,2R*,4R*)-2-(2-{[3-(1H-benzoimidazol-2-yl)-propyl]-methyl-amino}-ethyl)-5-(2-methoxy-phenyl)-2-yl-bicyclo[2.2.2]oct-5-en-2-ol.

LC-MS: $t_R$=0.83 min; [M+H]$^+$: 516.54.

Example 24 rac-(1R*,2R*,4R*)-2-(2-{[3-(1H-Benzoimidazol-2-yl)-propyl]-methyl-amino}-ethyl)-5-thiazol-2-yl-bicyclo[2.2.2]oct-5-en-2-ol Prepared according to procedures P2.1 to P2.3 in Example 21 using rac-(1R*,2R*,4R*)-(2-hydroxy-5-thiazol-2-yl-bicyclo[2.2.2]oct-5-en-2-yl)-acetic acid tert.-butyl ester.

LC-MS: $t_R$=0.62 min; [M+H]$^+$: 423.55.

Example 24A rac-Isobutyric acid (1R*,2R*,4R*)-2-(2-{[3-(1H-benzoimidazol-2-yl)-propyl]-methyl-amino}-ethyl)-5-thiazol-2-yl-bicyclo[2.2.2]oct-5-en-2-yl ester Prepared according to procedure P1.4 in Example 1A using rac-(1R*,2R*,4R*)-2-(2-{[3-(1H-benzoimidazol-2-yl)-propyl]-methyl-amino}-ethyl)-5-thiazol-2-yl-bicyclo[2.2.2]oct-5-en-2-ol.
LC-MS: $t_R$=0.74 min; [M+H]$^+$: 493.63.

Example 25 rac-(1R*,2R*,4R*)-2-(2-{[3-(1H-Benzoimidazol-2-yl)-propyl]-methyl-amino}-ethyl)-5-oxazol-2-yl-bicyclo[2.2.2]oct-5-en-2-ol Prepared according to procedures P2.1 to P2.3 in Example 21 using rac-(1R*,2R*,4R*)-(2-hydroxy-5-oxazol-2-yl-bicyclo[2.2.2]oct-5-en-2-yl)acetic acid tert.-butyl ester.
LC-MS: $t_R$=0.62 min; [M+H]$^+$: 407.23.

Example 25A rac-Isobutyric acid (1R*,2R*,4R*)-2-(2-{[3-(1H-benzoimidazol-2-yl)-propyl]-methyl-amino}-ethyl)-5-oxazol-2-yl-bicyclo[2.2.2]oct-5-en-2-yl ester Prepared (as dihydrochloride salt) according to procedure P1.4 in Example 1A using rac-(1R*,2R*,4R*)-2-(2-{[3-(1H-benzoimidazol-2-yl)-propyl]-methyl-amino}-ethyl)-5-oxazol-2-yl-bicyclo[2.2.2]oct-5-en-2-ol.
LC-MS: $t_R$=0.73 min; [M+H]$^+$: 477.45.

Example 26 rac-(1R*,2R*,4R*)-2-(2-{[3-(4-Methoxy-1H-benzoimidazol-2-yl)-propyl]-methyl-amino}-ethyl)-5-phenyl-bicyclo[2.2.2]oct-5-en-2-ol 26.1 rac-(1R*,2R*,4R*)-(2-Hydroxy-5-phenyl-bicyclo[2.2.2]oct-5-en-2-yl)-acetic acid To a solution of 4.0 g of rac-(1R*,2R*,4R*)-(2-hydroxy-5-phenyl-bicyclo[2.2.2]oct-5-en-2-yl)-acetic acid tert.-butyl ester dissolved in 25 mL EtOH were added 2.1 g of LiOH.H$_2$O, 8 mL H$_2$O and 22 mL MeOH. The reaction mixture was stirred at rt for 3 days and then concentrated. The residue was partitioned between water and Et$_2$O. The aq. layer was separated and acidified with 1N HCl resulting in the formation of a white solid. The solid was filtrated, washed with 5 mL dil. HCl and dried in vacuo to obtain 3.19 g of rac-(1R*,2R*,4R*)-(2-hydroxy-5-phenyl-bicyclo[2.2.2]oct-5-en-2-yl)-acetic acid as white solid.
LC-MS: $t_R$=0.86 min; [M–H$_2$O+H]$^+$: 241.28.

26.1 rac-(1R*,2R*,4R*)-2-(2-{[3-(4-Methoxy-1H-benzoimidazol-2-yl)-propyl]-methyl-amino}-ethyl)-5-phenyl-bicyclo[2.2.2]oct-5-en-2-ol Prepared according to procedures P2.2 to P2.3 in Example 21 using rac-(1R*,2R*,4R*)-(2-hydroxy-5-phenyl-bicyclo[2.2.2]oct-5-en-2-yl)-acetic acid and [3-(4-methoxy-1H-benzoimidazol-2-yl)-propyl]methyl-amine.
LC-MS: $t_R$=0.73 min; [M+H]$^+$: 446.47.

Example 26A rac-Isobutyric acid (1R*,2R*,4R*)-2-(2-{[3-(4-methoxy-1H-benzoimidazol-2-yl)-propyl]-methyl-amino}-ethyl)-5-phenyl-bicyclo[2.2.2]oct-5-en-2-yl ester Prepared according to procedure P1.4 in Example 1A using rac-(1R*,2R*,4R*)-2-(2-{[3-(4-methoxy-1H-benzoimidazol-2-yl)-propyl]-methyl-amino}-ethyl)-5-phenyl-bicyclo[2.2.2]oct-5-en-2-ol.
LC-MS: $t_R$=0.83 min; [M+H]$^+$: 516.36.

Example 26B rac-Cyclobutanecarboxylic acid (1R*,2R*,4R*)-2-(2-{[3-(4-methoxy-1H-benzoimidazol-2-yl)-propyl]-methyl-amino}-ethyl)-5-phenyl-bicyclo[2.2.2]oct-5-en-2-yl ester Prepared according to procedure P1.4 in Example 1A using rac-(1R*,2R*,4R*)-2-(2-{[3-(4-methoxy-1H-benzoimidazol-2-yl)-propyl]-methyl-amino}-ethyl)-5-phenyl-bicyclo[2.2.2]oct-5-en-2-ol and cyclobutancarbonyl chloride.
LC-MS: $t_R$=0.84 min; [M+H]$^+$: 528.64.

Example 26C rac-3,3,3-Trifluoro-propionic acid (1R*,2R*,4R*)-2-(2-{[3-(4-methoxy-1H-benzoimidazol-2-yl)-propyl]-methyl-amino}-ethyl)-5-phenyl-bicyclo[2.2.2]oct-5-en-2-yl ester Prepared according to procedure P1.4 in Example 1A using rac-(1R*,2R*,4R*)-2-(2-{[3-(4-methoxy-1H-benzoimidazol-2-yl)-propyl]-methyl-amino}-ethyl)-5-phenyl-bicyclo[2.2.2]oct-5-en-2-ol and 3,3,3-trifluoropropionyl chloride.
LC-MS: $t_R$=0.84 min; [M+H]$^+$: 556.31.

Example 26D rac-2,2-Dimethyl propionic acid (1R*,2R*,4R*)-2-(2-{[3-(4-methoxy-1H-benzoimidazol-2-yl)-propyl]-methyl-amino}-ethyl)-5-phenyl-bicyclo[2.2.2]oct-5-en-2-yl ester To a solution of 150 mg of rac-(1R*,2R*,4R*)-2-(2-{[3-(4-methoxy-1H-benzoimidazol-2-yl)-propyl]-methyl-amino}-ethyl)-5-phenyl-bicyclo[2.2.2]oct-5-en-2-ol in 2 mL DCM and 2 mL THF were added 0.21 mL of NEt$_3$ and 41 mg of DMAP. The reaction mixture was cooled to 0° C., 0.17 mL of pivaloyl chloride were added and it was then stirred at 65° C. for 24 h. During the next 4 days further 0.52 mL of NEt$_3$ and 0.41 mL of pivaloyl chloride were added in small aliquots. The reaction was quenched with sat. aq. NaHCO$_3$, extracted with DCM, dried and concentrated in vacuo. Purification by CC using DCM-MeOH (10:1) yielded 40 mg of rac-2,2-dimethyl propionic acid (1R*,2R*,4R*)-2-(2-{[3-(4-methoxy-1H-benzoimidazol-2-yl)-propyl]-methyl-amino}-ethyl)-5-phenyl-bicyclo[2.2.2]oct-5-en-2-yl ester as brownish foam.
LC-MS: $t_R$=0.90 min; [M+H]$^+$: 530.12.

Example 26E rac-Isopropyl-carbamic acid (1R*,2R*,4R*)-2-(2-{[3-(4-methoxy-1H-benzoimidazol-2-yl)-propyl]-methyl-amino}-ethyl)-5-phenyl-bicyclo[2.2.2]oct-5-en-2-yl ester To a solution of 91 mg of rac-(1R*,2R*,4R*)-2-(2-{[3-(4-methoxy-1H-benzoimidazol-2-yl)-propyl]-methyl-amino}-ethyl)-5-phenyl-bicyclo[2.2.2]oct-5-en-2-ol in 2 mL of anh. THF were added 57 mg of NaH at −10° C. The suspension was stirred for 45 min allowing the temperature to reach 0° C. 171 mg of 1,1'-carbonyldiimidazole were added at −10° C. and the mixture stirred for 30 min at rt. 0.178 mL of isopropyl amine was added at 0° C. and the reaction mixture stirred overnight at rt. After quenching with sat. NaHCO$_3$ and extracting with DCM, the organic phase was dried over anh. Na$_2$SO$_4$ and concentrated in vacuo. The crude product was purified by prep. TLC using chloroform/MeOH/NEt$_3$ 70/30/1 to yield 45 mg of rac-isopropyl-carbamic acid (1R*,2R*,4R*)-2-(2-{[3-(4-methoxy-1H-benzoimidazol-2-yl)-propyl]-methyl-amino}-ethyl)-5-phenyl-bicyclo[2.2.2]oct-5-en-2-yl ester as yellowish oil.

LC-MS: $t_R$=0.84 min; [M+H]$^+$: 531.11.

Example 26F rac-2-Methoxy-2-methyl-propionic acid (1R*,2R*,4R*)-2-(2-{[3-(4-methoxy-1H-benzoimidazol-2-yl)-propyl]-methyl-amino}-ethyl)-5-phenyl-bicyclo[2.2.2]oct-5-en-2-yl ester To a solution of 295 mg of rac-(1R*,2R*,4R*)-2-(2-{[3-(4-methoxy-1H-benzoimidazol-2-yl)-propyl]-methyl-amino}-ethyl)-5-phenyl-bicyclo[2.2.2]oct-5-en-2-ol in 6.6 mL of DCM was added 1.4 mL of NEt$_3$, 81 mg of DMAP and 0.8 mL of 2-methoxy-2-methyl propanoyl chloride (prepared as in JOC, 1976, 41, 19, 3182-3187) at 0° C. The reaction mixture was allowed to warm up to rt and stirred for 5 min at rt before 0.3 mL of anh. THF was added. The reaction mixture was stirred overnight at 50° C., extracted with DCM and washed with sat. NaHCO$_3$. The organic phase was dried over anh. Na$_2$SO$_4$ and concentrated in vacuo. The crude product was purified by CC using DCM/MeOH/DIPEA 95/5/1 to yield 214 mg of rac-2-methoxy-2-methyl-propionic acid (1R*,2R*,4R*)-2-(2-{[3-(4-methoxy-1H-benzoimidazol-2-yl)-propyl]-methyl-amino}-ethyl)-5-phenyl-bicyclo[2.2.2]oct-5-en-2-yl ester as white foam.

LC-MS: $t_R$=0.86 min; [M+H]$^+$: 546.16.

Example 26G rac-Carbonic acid isopropyl ester (1R*,2R*,4R*)-2-(2-{[3-(4-methoxy-1H-benzoimidazol-2-yl)-propyl]-methyl-amino}-ethyl)-5-phenyl-bicyclo[2.2.2]oct-5-en-2-yl ester To a solution of 221 mg of rac-(1R*,2R*,4R*)-2-(2-{[3-(4-methoxy-1H-benzoimidazol-2-yl)-propyl]-methyl-amino}-ethyl)-5-phenyl-bicyclo[2.2.2]oct-5-en-2-ol in 5 mL of toluene was added at 0° C. 1.0 mL of NEt$_3$, 61 mg of DMAP and 5 mL of isopropyl chlorofomate. The mixture was stirred for 30 min at rt then for 30 min at 50° C. After cooling down to rt, the mixture was extracted with EtOAc and washed with sat. NaHCO3. The organic phase was dried over anh. Na$_2$SO$_4$ and concentrated in vacuo. The crude was dissolved in 1 mL of anh. THF and treated with 0.6 mL of TBAF (1M in THF) at rt. The mixture was stirred for 2 h at 50° C. and 0.6 mL of TBAF (1M in THF) was added at rt. The reaction mixture was further stirred for 4 h at 50° C. and concentrated in vacuo. The residue was taken up in DCM and washed with water. The organic phase was dried over anh. Na$_2$SO$_4$ and concentrated in vacuo. The crude product was purified by CC using EtOAc/MeOH from 98/2 to 80/20 to yield 140 mg of rac-carbonic acid isopropyl ester (1R*,2R*,4R*)-2-(2-{[3-(4-methoxy-1H-benzoimidazol-2-yl)-propyl]-methyl-amino}-ethyl)-5-phenyl-bicyclo[2.2.2]oct-5-en-2-yl ester as yellow oil.

LC-MS: $t_R$=0.88 min; [M+H]$^+$: 532.03.

Example 27 rac-(1R*,2R*,4R*)-2-(2-{[3-(5,6-Dichloro-1H-benzoimidazol-2-yl)-propyl]-methyl-amino}-ethyl)-5-phenyl-bicyclo[2.2.2]oct-5-en-2-ol Prepared according to procedures P2.2 to P2.3 in Example 21 using rac-(1R*,2R*,4R*)-(2-hydroxy-5-phenyl-bicyclo[2.2.2]oct-5-en-2-yl)-acetic acid and [3-(5,6-dichloro-1H-benzoimidazol-2-yl)-propyl]-methyl-amine.

LC-MS: $t_R$=0.83 min; [M+H]$^+$: 484.50.

Example 27A rac-Isobutyric acid (1R*,2R*,4R*)-2-(2-{[3-(5,6-dichloro-1H-benzoimidazol-2-yl)-propyl]-methyl-amino}-ethyl)-5-phenyl-bicyclo[2.2.2]oct-5-en-2-yl ester Prepared according to procedure P1.4 in Example 1A using rac-(1R*,2R*,4R*)-2-(2-{[3-(5,6-dichloro-1H-benzoimidazol-2-yl)-propyl]-methyl-amino}-ethyl)-5-phenyl-bicyclo[2.2.2]oct-5-en-2-ol.

LC-MS: $t_R$=0.96 min; [M+H]$^+$: 554.59.

Example 27B rac-Cyclopropanecarboxylic acid (1R*,2R*,4R*)-2-(2-{[3-(5,6-dichloro-1H-benzoimidazol-2-yl)-propyl]-methyl-amino}-ethyl)-5-phenyl-bicyclo[2.2.2]oct-5-en-2-yl ester Prepared according to procedure P1.4 in Example 1A using rac-(1R*,2R*,4R*)-2-(2-{[3-(5,6-dichloro-1H-benzoimidazol-2-yl)-propyl]-methyl-amino}-ethyl)-5-phenyl-bicyclo[2.2.2]oct-5-en-2-ol and cyclopropancarbonyl chloride.

LC-MS: $t_R$=0.95 min; [M+H]$^+$: 552.61.

Example 28 rac-(1R*,2R*,4R*)-2-(2-{[3-(5,6-Dimethoxy-1H-benzoimidazol-2-yl)-propyl]-methyl-amino}-ethyl)-5-phenyl-bicyclo[2.2.2]oct-5-en-2-ol Prepared according to procedures P2.2 to P2.3 in Example 21 using rac-(1R*,2R*,4R*)-(2-hydroxy-5-phenyl-bicyclo[2.2.2]oct-5-en-2-yl)-acetic acid and [3-(5,6-dimethoxy-1H-benzoimidazol-2-yl)-propyl]-methyl-amine.

LC-MS: $t_R$=0.71 min; [M+H]$^+$: 476.36.

Example 28A rac-Isobutyric acid (1R*,2R*,4R*)-2-(2-{[3-(5,6-dimethoxy-1H-benzoimidazol-2-yl)-propyl]-methyl-amino}-ethyl)-5-phenyl-bicyclo[2.2.2]oct-5-en-2-yl ester Prepared according to procedure P1.4 in Example 1A using rac-(1R*,2R*,4R*)-2-(2-{[3-(5,6-dimethoxy-1H-benzoimidazol-2-yl)-propyl]-methyl-amino}-ethyl)-5-phenyl-bicyclo[2.2.2]oct-5-en-2-ol.

LC-MS: $t_R$=0.81 min; [M+H]$^+$: 546.39.

Example 29 rac-(1R*,2R*,4R*)-2-(2-{[3-(5-Methoxy-1H-benzoimidazol-2-yl)-propyl]-methyl-amino}-ethyl)-5-phenyl-bicyclo[2.2.2]oct-5-en-2-ol Prepared according to procedures P2.2 to P2.3 in Example 21 using rac-(1R*,2R*,4R*)-(2-hydroxy-5-phenyl-bicyclo[2.2.2]oct-5-en-2-yl)-acetic acid and [3-(5-methoxy-1H-benzoimidazol-2-yl)-propyl]-methyl-amine.

LC-MS: $t_R$=0.72 min; [M+H]$^+$: 446.59.

Example 29A rac-Isobutyric acid (1R*,2R*,4R*)-2-(2-{[3-(5-methoxy-1H-benzoimidazol-2-yl)-propyl]-methyl-amino}-ethyl)-5-phenyl-bicyclo[2.2.2]oct-5-en-2-yl ester Prepared according to procedure P1.4 in Example 1A using rac-(1R*,2R*,4R*)-2-(2-{[3-(5-methoxy-1H-benzoimidazol-2-yl)-propyl]-methyl-amino}-ethyl)-5-phenyl-bicyclo[2.2.2]oct-5-en-2-ol.

LC-MS: $t_R$=0.82 min; [M+H]$^+$: 516.91.

Example 30 rac-(1R*,2R*,4R*)-2-(2-{[3-(7-Methoxy-4-methyl-1H-benzoimidazol-2-yl)-propyl]-methyl-amino}-ethyl)-5-phenyl-bicyclo[2.2.2]oct-5-en-2-ol Prepared according to procedures P2.2 to P2.3 in Example 21 using rac-(1R*,2R*,4R*)-(2-hydroxy-5-phenyl-bicyclo[2.2.2]oct-5-en-2-yl)-acetic acid and [3-(7-methoxy-4-methyl-1H-benzoimidazol-2-yl)-propyl]-methyl-amine.

LC-MS: $t_R$=0.74 min; [M+H]$^+$: 460.39.

Example 30A rac-Isobutyric acid (1R*,2R*,4R*)-2-(2-{[3-(7-methoxy-4-methyl-1H-benzoimidazol-2-yl)-propyl]-methyl-amino}-ethyl)-5-phenyl-bicyclo[2.2.2]oct-5-en-2-yl ester Prepared according to procedure P1.4 in Example 1A using rac-(1R*,2R*,4R*)-2-(2-{[3-(7-methoxy-4-methyl-1H-benzoimidazol-2-yl)-propyl]-methyl-amino}-ethyl)-5-phenyl-bicyclo[2.2.2]oct-5-en-2-ol.

LC-MS: $t_R$=0.85 min; [M+H]$^+$: 530.40.

Example 31 rac-(1R*,2R*,4R*)-2-(2-{[3-(7-Ethoxy-1H-benzoimidazol-2-yl)-propyl]-methyl-amino}-ethyl)-5-phenyl-bicyclo[2.2.2]oct-5-en-2-ol Prepared according to procedures P2.2 to P2.3 in Example 21 using rac-(1R*,2R*,4R*)-(2-hydroxy-5-phenyl-bicyclo[2.2.2]oct-5-en-2-yl)acetic acid and [3-(7-ethoxy-1H-benzoimidazol-2-yl)-propyl]-methyl-amine.

LC-MS: $t_R$=0.74 min; [M+H]$^+$: 460.49

Example 31A rac-Isobutyric acid (1R*,2R*,4R*)-2-(2-{[3-(7-ethoxy-1H-benzoimidazol-2-yl)-propyl]-methyl-amino}-ethyl)-5-phenyl-bicyclo[2.2.2]oct-5-en-2-yl ester Prepared according to procedure P1.4 in Example 1A using rac-(1R*,2R*,4R*)-2-(2-{[3-(7-ethoxy-1H-benzoimidazol-2-yl)-propyl]-methyl-amino}-ethyl)-5-phenyl-bicyclo[2.2.2]oct-5-en-2-ol.

LC-MS: $t_R$=0.85 min; [M+H]$^+$: 530.37.

Example 32 rac-(1R*,2R*,4R*)-2-(2-{[2-(7-Methoxy-1H-benzoimidazol-2-yl)-ethyl]-methyl-amino}-ethyl)-5-phenyl-bicyclo[2.2.2]oct-5-en-2-ol Prepared according to procedures P2.2 to P2.3 in Example 21 using rac-(1R*,2R*,4R*)-(2-hydroxy-5-phenyl-bicyclo[2.2.2]oct-5-en-2-yl)acetic acid and [2-(7-methoxy-1H-benzoimidazol-2-yl)-ethyl]-methyl-amine.

LC-MS: $t_R$=0.75 min; [M+H]$^+$: 432.44.

Example 32A rac-Isobutyric acid (1R*,2R*,4R*)-2-(2-{[2-(7-methoxy-1H-benzoimidazol-2-yl)-ethyl]-methyl-amino}-ethyl)-5-phenyl-bicyclo[2.2.2]oct-5-en-2-yl ester Prepared according to procedure P1.4 in Example 1A using rac-(1R*,2R*,4R*)-2-(2-{[2-(7-methoxy-1H-benzoimidazol-2-yl)-ethyl]-methyl-amino}-ethyl)-5-phenyl-bicyclo[2.2.2]oct-5-en-2-ol.

LC-MS: $t_R$=0.86 min; [M+H]$^+$: 502.57.

Example 33 rac-(1R*,2R*,4R*)-2-(2-{[3-(7-Isopropoxy-1H-benzoimidazol-2-yl)-propyl]-methyl-amino}-ethyl)-5-phenyl-bicyclo[2.2.2]oct-5-en-2-ol Prepared according to procedures P2.2 to P2.3 in Example 21 using rac-(1R*,2R*,4R*)-(2-hydroxy-5-phenyl-bicyclo[2.2.2]oct-5-en-2-yl)-acetic acid and [3-(7-isopropoxy-1H-benzoimidazol-2-yl)-propyl]-methyl-amine.

LC-MS: $t_R$=0.77 min; [M+H]$^+$: 474.54.

Example 33A rac-Isobutyric acid (1R*,2R*,4R*)-2-(2-{[3-(7-isopropoxy-1H-benzoimidazol-2-yl)-propyl]-methyl-amino}-ethyl)-5-phenyl-bicyclo[2.2.2]oct-5-en-2-yl ester Prepared according to procedure P1.4 in Example 1A using rac-(1R*,2R*,4R*)-2-(2-{[3-(7-isopropoxy-1H-benzoimidazol-2-yl)-propyl]-methyl-amino}-ethyl)-5-phenyl-bicyclo[2.2.2]oct-5-en-2-ol.
LC-MS: $t_R$=0.86 min; [M+H]$^+$: 544.63.

Example 34 rac-(1R*,2R*,4R*)-2-(3-{[2-(2-Hydroxy-5-phenyl-bicyclo[2.2.2]oct-5-en-2-yl)-ethyl]-methyl-amino}-propyl)-3H-benzoimidazol-4-ol Prepared according to procedures P2.2 to P2.3 in Example 21 using rac-(1R*,2R*,4R*)-(2-hydroxy-5-phenyl-bicyclo[2.2.2]oct-5-en-2-yl)-acetic acid and 2-(3-methylamino-propyl)-3H-benzoimidazol-4-ol.
LC-MS: $t_R$=0.70 min; [M+H]$^+$: 432.44.

Example 34A rac-Isobutyric acid (1R*,2R*,4R*)-2-(2-{[3-(7-isobutyryloxy-1H-benzoimidazol-2-yl)-propyl]-methyl-amino}-ethyl)-5-phenyl-bicyclo[2.2.2]oct-5-en-2-yl ester Prepared according to procedure P1.4 in Example 1A using rac-(1R*,2R*,4R*)-2-(3-{[2-(2-hydroxy-5-phenyl-bicyclo[2.2.2]oct-5-en-2-yl)-ethyl]-methyl-amino}-propyl)-3H-benzoimidazol-4-ol and 5 eq. of isobutyryl chloride.
LC-MS: $t_R$=0.91 min; [M+H]$^+$: 572.51.

Example 35A rac-Isobutyric acid (1R*,2R*,4R*)-2-(2-{[3-(7-hydroxy-1H-benzoimidazol-2-yl)-propyl]-methyl-amino}-ethyl)-5-phenyl-bicyclo[2.2.2]oct-5-en-2-yl ester 35A.1: rac-Isobutyric acid (1R*,2R*,4R*)-2-[2-({3-[7-(tert.-butyl-dimethyl-silanyloxy)-1H-benzoimidazol-2-yl]-propyl}-methyl-amino)-ethyl]-5-phenyl-bicyclo[2.2.2]oct-5-en-2-yl ester Prepared according to procedures P2.1 to P2.3 in Example 21 and procedure P1.4 in Example 1A using {3-[4-(tert.-butyl-dimethyl-silanyloxy)-1H-benzoimidazol-2-yl]-propyl}-methyl-amine.

35A.2: rac-Isobutyric acid (1R*,2R*,4R*)-2-(2-{[3-(7-hydroxy-1H-benzoimidazol-2-yl)-propyl]-methyl-amino}-ethyl)-5-phenyl-bicyclo[2.2.2]oct-5-en-2-yl ester To a solution of 287 mg of rac-isobutyric acid (1R*,2R*,4R*)-2-[2-({3-[7-(tert.-butyl-dimethyl-silanyloxy)-1H-benzoimidazol-2-yl]-propyl}-methyl-amino)-ethyl]-5-phenyl-bicyclo[2.2.2]oct-5-en-2-yl ester in 6 mL THF were added 73 mg of NEt$_3$ trihydrofluoride. After stirring for 45 min the reaction was quenched by addition of sat. aq. NaHCO$_3$. The mixture was extracted with EtOAc and the organic phase was dried over MgSO$_4$. Concentration in vacuo and purification by CC with EtOAc-MeOH (2:1) yielded 131 mg of rac-isobutyric acid (1R*,2R*,4R*)-2-(2-{[3-(7-hydroxy-1H-benzoimidazol-2-yl)-propyl]-methyl-amino}-ethyl)-5-phenyl-bicyclo[2.2.2]oct-5-en-2-yl ester as yellow oil.
LC-MS: $t_R$=0.80 min; [M+H]$^+$: 502.39.

Example 36 rac-(1R*,5R*,6R*)-6-(2-{[3-(4-Methoxy-1H-benzoimidazol-2-yl)-propyl]-methyl-amino}-ethyl)-8-phenyl-bicyclo[3.2.2]non-8-en-6-ol Prepared according to procedures P2.1 to P2.3 in Example 21 using rac-(1R*,5R*,6R*)-(6-hydroxy-8-phenyl-bicyclo[3.2.2]non-8-en-6-yl)-acetic acid tert.-butyl ester in step P2.1 and [3-(4-methoxy-1H-benzoimidazol-2-yl)-propyl]-methyl-amine in step P2.2.
LC-MS: $t_R$=0.76 min; [M+H]$^+$: 460.29.

Example 36A rac-Isobutyric acid (1R*,5R*,6R*)-6-(2-{[3-(4-methoxy-1H-benzoimidazol-2-yl)-propyl]-methyl-amino}-ethyl)-8-phenyl-bicyclo[3.2.2]non-8-en-6-yl ester Prepared according to procedure P1.4 in Example 1A using rac-(1R*,5R*,6R*)-6-(2-{[3-(4-methoxy-1H-benzoimidazol-2-yl)-propyl]-methyl-amino}-ethyl)-8-phenyl-bicyclo[3.2.2]non-8-en-6-ol.
LC-MS: $t_R$=0.90 min; [M+H]$^+$: 530.32.

Example 36B rac-3,3,3-Trifluoro-propionic acid (1R*,5R*,6R*)-6-(2-{[3-(4-methoxy-1H-benzoimidazol-2-yl)-propyl]-methyl-amino}-ethyl)-8-phenyl-bicyclo[3.2.2]non-8-en-6-yl ester Prepared according to procedure P1.4 in Example 1A using 3,3,3-trifluoropropionyl chloride and rac-(1R*,5R*,6R*)-6-(2-{[3-(4-methoxy-1H-benzoimidazol-2-yl)-propyl]-methyl-amino}-ethyl)-8-phenyl-bicyclo[3.2.2]non-8-en-6-ol.
LC-MS: $t_R$=0.91 min; [M+H]$^+$: 570.29.

Example 37 rac-(1R*,2R*,4R*)-2-(2-{[3-(4-Methoxy-1-methyl-1H-benzoimidazol-2-yl)-propyl]-methyl-amino}-ethyl)-5-phenyl-bicyclo[2.2.2]oct-5-en-2-ol Prepared according to procedures P2.2 to P2.3 in Example 21 using rac-(1R*,2R*,4R*)-(2-hydroxy-5-phenyl-bicyclo[2.2.2]oct-5-en-2-yl)-acetic acid and [3-(4-methoxy-1-methyl-1H-benzoimidazol-2-yl)-propyl]-methyl-amine.
LC-MS: $t_R$=0.74 min; [M+H]$^+$: 460.46.

Example 37A rac-Isobutyric acid (1R*,2R*,4R*)-2-(2-{[3-(4-methoxy-1-methyl-1H-benzoimidazol-2-yl)-propyl]-methyl-amino}-ethyl)-5-phenyl-bicyclo[2.2.2]oct-5-en-2-yl ester Prepared according to procedure P1.4 in Example 1A using rac-(1R*,2R*,4R*)-2-(2-{[3-(4-methoxy-1-methyl-1H-benzoimidazol-2-yl)-propyl]-methyl-amino}-ethyl)-5-phenyl-bicyclo[2.2.2]oct-5-en-2-ol.
LC-MS: $t_R$=0.87 min; [M+H]$^+$: 530.52.

Example 38 rac-(1R*,2R*,4R*)-2-(2-{[2-(3,4-Diethoxy-phenyl)-ethyl]-ethyl-amino}-ethyl)-5-phenyl-bicyclo[2.2.2]oct-5-en-2-ol Prepared according to procedures P2.2 to P2.3 in Example 21 using rac-(1R*,2R*,4R*)-(2-hydroxy-5-phenyl-bicyclo[2.2.2]oct-5-en-2-yl)-acetic acid and [2-(3,4-diethoxy-phenyl)-ethyl]-ethyl-amine.
LC-MS: $t_R$=0.88 min; [M+H]$^+$: 464.51.

Example 38A rac-Isobutyric acid (1R*,2R*,4R*)-2-(2-{[2-(3,4-diethoxy-phenyl)-ethyl]-ethyl-amino}-ethyl)-5-phenyl-bicyclo[2.2.2]oct-5-en-2-yl ester Prepared according to procedure P1.4 in Example 1A using rac-(1R*,2R*,4R*)-2-(2-{[2-(3,4-diethoxy-phenyl)-ethyl]-ethyl-amino}-ethyl)-5-phenyl-bicyclo[2.2.2]oct-5-en-2-ol.
LC-MS: $t_R$=1.01 min; [M+H]$^+$: 534.55.

Example 39 rac-(1R*,2R*,4R*)-2-(2-{[3-(3,4-Dimethoxy-phenyl)-propyl]-methyl-amino}-ethyl)-5-phenyl-bicyclo[2.2.2]oct-5-en-2-ol Prepared according to procedures P2.2 to P2.3 in Example 21 using rac-(1R*,2R*,4R*)-(2-hydroxy-5-phenyl-bicyclo[2.2.2]oct-5-en-2-yl)acetic acid and [3-(3,4-dimethoxy-phenyl)-propyl]-methyl-amine.
LC-MS: $t_R$=0.91 min; [M+H]$^+$: 436.48.

Example 39A rac-Isobutyric acid (1R*,2R*,4R*)-2-(2-{[3-(3,4-dimethoxy-phenyl)-propyl]-methyl-amino}-ethyl)-5-phenyl-bicyclo[2.2.2]oct-5-en-2-yl ester Prepared according to procedure P1.4 in Example 1A using rac-(1R*,2R*,4R*)-2-(2-{[3-(3,4-dimethoxy-phenyl)-propyl]-methyl-amino}-ethyl)-5-phenyl-bicyclo[2.2.2]oct-5-en-2-ol.
LC-MS: $t_R$=0.97 min; [M+H]$^+$: 506.25.

Example 40 rac-(1R*,2R*,4R*)-2-(2-{[3-(3,4-Diethoxy-phenyl)-propyl]-methyl-amino}-ethyl)-5-phenyl-bicyclo[2.2.2]oct-5-en-2-ol Prepared according to procedures P2.2 to P2.3 in Example 21 using rac-(1R*,2R*,4R*)-(2-hydroxy-5-phenyl-bicyclo[2.2.2]oct-5-en-2-yl)-acetic acid and [3-(3,4-diethoxy-phenyl)-propyl]-methyl-amine.
LC-MS: $t_R$=0.92 min; [M+H]$^+$: 464.33.

Example 40A rac-Isobutyric acid (1R*,2R*,4R*)-2-(2-{[3-(3,4-diethoxy-phenyl)-propyl]-methyl-amino}-ethyl)-5-phenyl-bicyclo[2.2.2]oct-5-en-2-yl ester Prepared according to procedure P1.4 in Example 1A using rac-(1R*,2R*,4R*)-2-(2-{[3-(3,4-diethoxy-phenyl)-propyl]-methyl-amino}-ethyl)-5-phenyl-bicyclo[2.2.2]oct-5-en-2-ol.
LC-MS: $t_R$=1.02 min; [M+H]$^+$: 534.29.

Example 41 rac-(1R*,2R*,4R*)-2-{2-[(3-Furo[2,3-b]pyridin-5-yl-propyl)-methyl-amino]-ethyl}-5-phenyl-bicyclo[2.2.2]oct-5-en-2-ol Prepared according to procedures P2.2 to P2.3 in Example 21 using rac-(1R*,2R*,4R*)-(2-hydroxy-5-phenyl-bicyclo[2.2.2]oct-5-en-2-yl)-acetic acid and (3-furo[2,3-b]pyridin-5-yl-propyl)-methyl-amine.
LC-MS: $t_R$=0.88 min; [M+H]$^+$: 416.31.

Example 41A rac-Isobutyric acid (1R*,2R*,4R*)-2-{2-[(3-furo[2,3-b]pyridin-5-yl-propyl)-methyl-amino]-ethyl}-5-phenyl-bicyclo[2.2.2]oct-5-en-2-yl ester Prepared according to procedure P1.4 in Example 1A using rac-(1R*,2R*,4R*)-2-{2-[(3-furo[2,3-b]pyridin-5-yl-propyl)-methyl-amino]-ethyl}-5-phenyl-bicyclo[2.2.2]oct-5-en-2-ol.
LC-MS: $t_R$=1.00 min; [M+H]$^+$: 487.26.

Example 42 rac-(1R*,2R*,4R*)-2-(2-{Methyl-[3-(2-methyl-furo[2,3-b]pyridin-5-yl)-propyl]-amino}-ethyl)-5-phenyl-bicyclo[2.2.2]oct-5-en-2-ol Prepared according to procedures P2.2 to P2.3 in Example 21 using rac-(1R*,2R*,4R*)-(2-hydroxy-5-phenyl-bicyclo[2.2.2]oct-5-en-2-yl)acetic acid and methyl-[3-(2-methyl-furo[2,3-b]pyridin-5-yl)-propyl]-amine.
LC-MS: $t_R$=0.90 min; [M+H]$^+$: 431.35.

Example 42A rac-Isobutyric acid (1R*,2R*,4R*)-2-(2-{methyl-[3-(2-methyl-furo[2,3-b]pyridin-5-yl)-propyl]-amino}-ethyl)-5-phenyl-bicyclo[2.2.2]oct-5-en-2-yl ester Prepared according to procedure P1.4 in Example 1A using rac-(1R*,2R*,4R*)-2-(2-{methyl-[3-(2-methyl-furo[2,3-b]pyridin-5-yl)-propyl]-amino}-ethyl)-5-phenyl-bicyclo[2.2.2]oct-5-en-2-ol.
LC-MS: $t_R$=1.02 min; [M+H]$^+$: 501.27.

Example 43 rac-N-(3-{[2-((1R*,2R*,4R*)-2-Hydroxy-5-phenyl-bicyclo[2.2.2]oct-5-en-2-yl)-ethyl]-methyl-amino}-propyl)-3-methoxy-2-methoxymethyl-2-methyl-propionamide 43.1 (Procedure P3.1): rac-(1R*,2R*,4R*)-2-(2-Methylamino-ethyl)-5-phenyl-bicyclo[2.2.2]oct-5-en-2-ol 4.28 g of rac-toluene-4-sulfonic acid (1R*,2R*,4R*)-2-(2-hydroxy-5-phenyl-bicyclo[2.2.2]oct-5-en-2-yl)-ethyl ester (see Example 1, procedures P1.1 and P1.2) were dissolved in a 8 M solution of MeNH$_2$ in EtOH (54 mL). The mixture was stirred overnight at 40° C., diluted with DCM and washed with sat.-NaHCO$_3$. The organic phase was dried over anh.

Na$_2$SO$_4$ and concentrated to give 2.73 g of rac-(1R*,2R*,4R*)-2-(2-methylamino-ethyl)-5-phenyl-bicyclo[2.2.2]oct-5-en-2-ol as a white solid.

LC-MS: $t_R$=0.72 min; [M+H]$^+$: 258.35.

43.2 (Procedure P3.2): rac-N-(3-{[2-((1R*,2R*,4R*)-2-Hydroxy-5-phenyl-bicyclo[2.2.2]oct-5-en-2-yl)-ethyl]-methyl-amino}-propyl)-3-methoxy-2-methoxymethyl-2-methyl-propionamide 50 mg of rac-(1R*,2R*,4R*)-2-(2-methylamino-ethyl)-5-phenyl-bicyclo[2.2.2]oct-5-en-2-ol were dissolved in DCM/AcOH. 46 mg of 3-methoxy-2-methoxymethyl-2-methyl-N-(3-oxo-propyl)-propionamide and 50 mg of sodium cyanoborohydride were added. The reaction mixture was stirred for 3 days at room temperature, quenched with sat.-NaHCO$_3$ and extracted with DCM. The organic phase was washed with brine, dried over anh. Na$_2$SO$_4$ and concentrated in vacuo. The resulting crude material was purified by CC using EtOAc/MeOH/NEt$_3$ 90/10/1 as eluant to yield 49 mg of rac-N-(3-{[2-((1R*,2R*,4R*)-2-hydroxy-5-phenyl-bicyclo[2.2.2]oct-5-en-2-yl)-ethyl]-methyl-amino}-propyl)-3-methoxy-2-methoxymethyl-2-methyl-propionamide as a yellow oil.

LC-MS: $t_R$=0.80 min; [M+H]$^+$: 459.63.

Example 43A rac-Isobutyric acid (1R*,2R*,4R*)-2-(2-{[3-(3-methoxy-2-methoxymethyl-2-methyl-propionylamino)-propyl]-methyl-amino}-ethyl)-5-phenyl-bicyclo[2.2.2]oct-5-en-2-yl ester 43A.1 (Procedure P3.3): rac-Isobutyric acid (1R*,2R*,4R*)-2-(2-{[3-(3-methoxy-2-methoxymethyl-2-methyl-propionylamino)-propyl]-methyl-amino}-ethyl)-5-phenyl-bicyclo[2.2.2]oct-5-en-2-yl ester 44 mg of rac-N-(3-{[2-((1R*,2R*,4R*)-2-hydroxy-5-phenyl-bicyclo[2.2.2]oct-5-en-2-yl)-ethyl]-methyl-amino}-propyl)-3-methoxy-2-methoxymethyl-2-methyl-propionamide were dissolved in anh. DCM. 50 mg of magnesium bromide ethyl etherate and 77 mg of isobutyric anhydride were added. The reaction mixture was stirred for 5 h at room temperature, quenched with sat.-NaHCO$_3$ and extracted with DCM. The organic phase was washed with sat.-NaHCO$_3$, dried over anh. Na$_2$SO$_4$ and concentrated in vacuo. The resulting crude material was purified by CC using EtOAc/MeOH/NEt$_3$ 98/2/1 as eluant to yield 22 mg of rac-isobutyric acid (1R*,2R*,4R*)-2-(2-{[3-(3-methoxy-2-methoxymethyl-2-methyl-propionylamino)-propyl]-methyl-amino}-ethyl)-5-phenyl-bicyclo[2.2.2]oct-5-en-2-yl ester as a yellowish oil.

LC-MS: $t_R$=0.94 min; [M+H]$^+$: 529.74.

43A.2: rac-Isobutyric acid (1R*,2R*,4R*)-2-(2-{[3-(3-methoxy-2-methoxymethyl-2-methyl-propionylamino)-propyl]-methyl-amino}-ethyl)-5-phenyl-bicyclo[2.2.2]oct-5-en-2-yl ester dihydrochloride The above product may be transformed into the corresponding dihydrochloride salt using procedure P1.5 in Example 1A.

Example 44 rac-N-(3-{[2-((1R*,2R*,4R*)-2-Hydroxy-5-phenyl-bicyclo[2.2.2]oct-5-en-2-yl)-ethyl]-methyl-amino}-propyl)-2-methoxy-2-methyl-propionamide Prepared according to procedures P3.1 and P3.2 in Example 43 using 2-methoxy-2-methyl-N-(3-oxo-propyl)-propionamide.

LC-MS: $t_R$=0.79 min; [M+H]$^+$: 415.65.

Example 44A rac-Isobutyric acid (1R*,2R*,4R*)-2-(2-{[3-(2-methoxy-2-methyl-propionylamino)-propyl]-methyl-amino}-ethyl)-5-phenyl-bicyclo[2.2.2]oct-5-en-2-yl ester Prepared according to procedure P3.3 in Example 43A using rac-N-(3-{[2-((1R*,2R*,4R*)-2-hydroxy-5-phenyl-bicyclo[2.2.2]oct-5-en-2-yl)-ethyl]-methyl-amino}-propyl)-2-methoxy-2-methyl-propionamide.

LC-MS: $t_R$=0.91 min; [M+H]$^+$: 485.54.

Example 45 rac-N-(3-{[2-((1R*,2R*,4R*)-2-Hydroxy-5-phenyl-bicyclo[2.2.2]oct-5-en-2-yl)-ethyl]-methyl-amino}-propyl)-2,2-dimethyl-propionamide Prepared according to procedures P3.1 and P3.2 in Example 43 using 2,2-dimethyl-N-(3-oxo-propyl)-propionamide.

LC-MS: $t_R$=0.81 min; [M+H]$^+$: 399.63.

Example 45A rac-Isobutyric acid (1R*,2R*,4R*)-2-(2-{[3-(2,2-dimethyl-propionylamino)-propyl]-methyl-amino}-ethyl)-5-phenyl-bicyclo[2.2.2]oct-5-en-2-yl ester Prepared according to procedure P3.3 in Example 43A using rac-N-(3-{[2-((1R*,2R*,4R*)-2-hydroxy-5-phenyl-bicyclo[2.2.2]oct-5-en-2-yl)-ethyl]methyl-amino}-propyl)-2,2-dimethyl-propionamide.

LC-MS: $t_R$=0.96 min; [M+H]$^+$: 469.64.

Example 46 rac-(1R*,2R*,4R*)-2-{2-[Methyl-(3-pyridin-3-yl-propyl)-amino]-ethyl}-5-phenyl-bicyclo[2.2.2]oct-5-en-2-ol Prepared according to procedures P3.1 and P3.2 in Example 43 using 3-pyridin-3-yl-propionaldehyde.

LC-MS: $t_R$=0.67 min; [M+H]$^+$: 377.52.

Example 46A rac-Isobutyric acid (1R*,2R*,4R*)-2-{2-[methyl-(3-pyridin-3-yl-propyl)-amino]-ethyl}-5-phenyl-bicyclo[2.2.2]oct-5-en-2-yl ester Prepared according to procedure P.1.4 in Example 1A using rac-(1R*,2R*,4R*)-2-{2-[methyl-(3-pyridin-3-yl-propyl)-amino]-ethyl}-5-phenyl-bicyclo[2.2.2]oct-5-en-2-ol.

LC-MS: $t_R$=0.79 min; [M+H]$^+$: 447.38.

Example 47A rac-Isobutyric acid (1R*,2R*,4R*)-2-(2-{[3-(4,5-diphenyl-1H-imidazol-2-yl)-propyl]-methyl-amino}-ethyl)-5-phenyl-bicyclo[2.2.2]oct-5-en-2-yl ester

47A.1 (Procedure P4.1): rac-3-[4,5-Diphenyl-1-(2-trimethylsilanyl-ethoxymethyl)-1H-imidazol-2-yl]-N-[2-((1R*,2R*,4R*)-2-hydroxy-5-phenyl-bicyclo[2.2.2]oct-5-en-2-yl)-ethyl]-N-methyl-propionamide 145 mg of 3-[4,5-diphenyl-1-(2-trimethylsilanyl-ethoxymethyl)-1H-imidazol-2-yl]-propionic acid were dissolved in THF (0.13 mL)/DCM (0.5 mL). 0.160 mL of DIPEA, 50 mg of HOBt and 71 mg of EDC were added sequentially at rt. The reaction mixture was stirred for 5 min then 80 mg of rac-(1R*,2R*,4R*)-2-(2-methylamino-ethyl)-5-phenyl-bicyclo[2.2.2]oct-5-en-2-ol were added at rt. The reaction mixture was stirred on at rt then diluted with DCM and washed with sat.-NaHCO$_3$ and brine. The organic phase was dried over anh. Na$_2$SO$_4$, filtered and concentrated in vacuo. The resulting crude material was purified by CC using EtOAc/MeOH/NEt$_3$ as eluant from 100/0/1 to 95/5/1 to yield 189 mg of rac-3-[4,5-diphenyl-1-(2-trimethylsilanyl-ethoxymethyl)-1H-imidazol-2-yl]-N-[2-((1R*,2R*,4R*)-2-hydroxy-5-phenyl-bicyclo[2.2.2]oct-5-en-2-yl)-ethyl]-N-methyl-propionamide as a yellow oil.
LC-MS: $t_R$=1.04 min; [M+H]$^+$: 662.51.

47A.2 (Procedure P4.2): rac-(1R*,2R*,4R*)-2-[2-({3-[4,5-Diphenyl-1-(2-trimethylsilanyl-ethoxymethyl)-1H-imidazol-2-yl]-propyl}-methyl-amino)-ethyl]-5-phenyl-bicyclo[2.2.2]oct-5-en-2-ol 0.241 mL of a Red-Al solution (65% in toluene) was added dropwise at 0° C. to a solution of 131 mg of rac-3-[4,5-diphenyl-1-(2-trimethylsilanyl-ethoxymethyl)-1H-imidazol-2-yl]-N-[2-((1R*,2R*,4R*)-2-hydroxy-5-phenyl-bicyclo[2.2.2]oct-5-en-2-yl)-ethyl]-N-methyl-propionamide in toluene (0.23 mL). The reaction mixture was stirred for 30 min at 0° C. and for 2 h at room temperature. The mixture was carefully poured onto a mixture of 1M-NaOH (1.75 mL) and ice. The mixture was stirred for 5 min until rt and extracted with toluene. The aq. phase was extracted with toluene. The combined toluene phases were washed with 1M-NaOH and brine, dried over anh. Na$_2$SO$_4$ and concentrated in vacuo. The resulting crude material was purified by CC using EtOAc/MeOH/NEt$_3$ as eluant from 100/0/1 to 95/5/1 to yield 125 mg of rac-(1R*,2R*,4R*)-2-[2-({3-[4,5-diphenyl-1-(2-trimethylsilanyl-ethoxymethyl)-1H-imidazol-2-yl]-propyl}-methyl-amino)-ethyl]-5-phenyl-bicyclo[2.2.2]oct-5-en-2-ol as a colorless oil.
LC-MS: $t_R$=0.95 min; [M+H]$^+$: 648.48.

47A.3 (Procedure P4.3) rac-Isobutyric acid (1R*,2R*,4R*)-2-[2-({3-[4,5-diphenyl-1-(2-trimethylsilanyl-ethoxymethyl)-1H-imidazol-2-yl]-propyl}-methyl-amino)-ethyl]-5-phenyl-bicyclo[2.2.2]oct-5-en-2-yl ester Prepared according to procedure P.1.4 in Example 1A using rac-(1R*,2R*,4R*)-2-[2-({3-[4,5-diphenyl-1-(2-trimethylsilanyl-ethoxymethyl)-1H-imidazol-2-yl]-propyl}-methyl-amino)-ethyl]-5-phenyl-bicyclo[2.2.2]oct-5-en-2-ol
LC-MS: $t_R$=1.05 min; [M+H]$^+$: 718.64.

47A.4 (Procedure P4.4) rac-Isobutyric acid (1R*,2R*,4R*)-2-(2-{[3-(4,5-diphenyl-1H-imidazol-2-yl)-propyl]-methyl-amino}-ethyl)-5-phenyl-bicyclo[2.2.2]oct-5-en-2-yl ester To a solution of 30 mg of rac-isobutyric acid (1R*,2R*,4R*)-2-[2-({3-[4,5-diphenyl-1-(2-trimethylsilanyl-ethoxymethyl)-1H-imidazol-2-yl]-propyl}-methyl-amino)-ethyl]-5-phenyl-bicyclo[2.2.2]oct-5-en-2-yl ester in 0.5 mL of anh. THF was added dropwise 0.2 mL of a 1M solution of TBAF in THF. The reaction mixture was refluxed for 6 h, diluted with DCM and washed with sat.-NaHCO$_3$. The organic phase was dried over anh. Na$_2$SO$_4$ and concentrated in vacuo. The resulting crude material was purified by CC using EtOAc/MeOH/NEt$_3$ from 100/0/1 to 90/10/1 as eluant to yield 14 mg of rac-isobutyric acid (1R*,2R*,4R*)-2-(2-{[3-(4,5-diphenyl-1H-imidazol-2-yl)-propyl]-methyl-amino}-ethyl)-5-phenyl-bicyclo[2.2.2]oct-5-en-2-yl ester as a yellowish solid.
LC-MS: $t_R$=0.90 min; [M+H]$^+$: 588.54.

47A.5 rac-Isobutyric acid (1R*,2R*,4R*)-2-(2-{[3-(4,5-diphenyl-1H-imidazol-2-yl)-propyl]-methyl-amino}-ethyl)-5-phenyl-bicyclo[2.2.2]oct-5-en-2-yl ester dihydrochloride The above product may be transformed into the corresponding dihydrochloride salt using procedure P1.5 in Example 1A.

Example 48 rac-(1R*,2R*,4R*)-2-{2-[(3-Isoquinolin-4-yl-propyl)-methyl-amino]-ethyl}-5-phenyl-bicyclo[2.2.2]oct-5-en-2-ol Prepared according to procedures P4.1 and P4.2 in Example 47 using 3-isoquinolin-4-yl-propionic acid trifluoroacetic acid salt and a larger excess of DIPEA in step P4.1 and replacing Red-Al by LiAlH$_4$ in step P4.2.
LC-MS: $t_R$=0.73 min; [M+H]$^+$: 427.18.

Example 48A rac-Isobutyric acid (1R*,2R*,4R*)-2-{2-[(3-isoquinolin-4-yl-propyl)-methyl-amino]-ethyl}-5-phenyl-bicyclo[2.2.2]oct-5-en-2-yl ester Prepared according to procedure P.1.4 in Example 1A using rac-(1R*,2R*,4R*)-2-{2-[(3-isoquinolin-4-yl-propyl)-methyl-amino]-ethyl}-5-phenyl-bicyclo[2.2.2]oct-5-en-2-ol.
LC-MS: $t_R$=0.87 min; [M+H]$^+$: 497.24.

Example 49 rac-(1R*,2R*,4R*)-2-{2-[Methyl-(3-quinolin-3-yl-propyl)-amino]-ethyl}-5-phenyl-bicyclo[2.2.2]oct-5-en-2-ol Prepared according to procedures P4.1 and P4.2 in Example 47 using 3-quinolin-3-yl-propionic acid trifluoroacetic acid salt and a larger excess of DIPEA in step P4.1.
LC-MS: $t_R$=0.79 min; [M+H]$^+$: 427.28.

Example 49A rac-Isobutyric acid (1R*,2R*,4R*)-2-{2-[methyl-(3-quinolin-3-yl-propyl)-amino]-ethyl}-5-phenyl-bicyclo[2.2.2]oct-5-en-2-yl ester Prepared according to procedure P.1.4 in Example 1A using rac-(1R*,2R*,4R*)-2-{2-[methyl-(3-quinolin-3-yl-propyl)-amino]-ethyl}-5-phenyl-bicyclo[2.2.2]oct-5-en-2-ol.
LC-MS: $t_R$=0.91 min; [M+H]$^+$: 497.21.

Example 50 rac-(1R*,2R*,4R*)-2-{2-[Methyl-(3-quinolin-4-yl-propyl)-amino]-ethyl}-5-phenyl-bicyclo[2.2.2]oct-5-en-2-ol Prepared according to procedures P4.1 and P4.2 in Example 47 using 3-quinolin-4-yl-propionic acid trifluoroacetic acid salt and a larger excess of DIPEA in step P4.1.
LC-MS: $t_R$=0.76 min; [M+H]$^+$: 427.33.

Example 50A rac-Isobutyric acid (1R*,2R*,4R*)-2-{2-[methyl-(3-quinolin-4-yl-propyl)-amino]-ethyl}-5-phenyl-bicyclo[2.2.2]oct-5-en-2-yl ester Prepared according to procedure P.1.4 in Example 1A using rac-(1R*,2R*,4R*)-2-{2-[methyl-(3-quinolin-4-yl-propyl)-amino]-ethyl}-5-phenyl-bicyclo[2.2.2]oct-5-en-2-ol.
LC-MS: $t_R$=0.87 min; [M+H]$^+$: 497.32.

Example 51 rac-N-(3-{[2-((1R*,2R*,4R*)-2-Hydroxy-5-phenyl-bicyclo[2.2.2]oct-5-en-2-yl)-ethyl]-methyl-amino}-propyl)-3-methoxy-2-methoxymethyl-2,N-dimethyl-propionamide

51.1 (Procedure P5.1): rac-(2-{[2-((1R*,2R*,4R*)-2-Hydroxy-5-phenyl-bicyclo[2.2.2]oct-5-en-2-yl)-ethyl]-methyl-carbamoyl}-ethyl)-carbamic acid tert.-butyl ester To a solution of 159 mg of BOC-beta-alanine in 4 mL DCM were added 0.36 mL DIPEA and 113 mg of HOBt. After stirring for 15 min, 300 mg of rac-(1R*,2R*,4R*)-2-(2-methylamino-ethyl)-5-phenyl-bicyclo[2.2.2]oct-5-en-2-ol in 4 mL DCM were added followed by 161 mg of EDCI. The resulting suspension was stirred for 2 h at rt, then quenched with water. The water phase was reextracted with DCM, the combined organic phases were washed with sat. aq. NaHCO$_3$, dried and concentrated in vacuo. The residue was purified by preparative TLC with EtOAc to give 168 mg of rac-(2-{[2-((1R*,2R*,4R*)-2-hydroxy-5-phenyl-bicyclo[2.2.2]oct-5-en-2-yl)-ethyl]-methyl-carbamoyl}-ethyl)-carbamic acid tert.-butyl ester as white foam.
LC-MS: $t_R$=0.98 min; [M+H]$^+$: 429.17.

51.2 (Procedure P5.2): rac-(1R*,2R*,4R*)-2-{2-[Methyl-(3-methylamino-propyl)-amino]-ethyl}-5-phenyl-bicyclo[2.2.2]oct-5-en-2-ol To a cold solution of 88 mg of rac-(2-{[2-((1R*,2R*,4R*)-2-hydroxy-5-phenyl-bicyclo[2.2.2]oct-5-en-2-yl)-ethyl]-methyl-carbamoyl}-ethyl)-carbamic acid tert.-butyl ester in 5 mL THF was added dropwise 0.5 mL Red-Al, 65% toluenel. The ice bath was removed and the reaction mixture was heated to 60° C. for 1.5 h. The reaction was cooled with an ice bath and quenched by careful addition of 1M NaOH. After stirring for 10 min, the 2 phases were separated and the organic phase was concentrated in vacuo to obtain 80 mg of crude rac-(1R*,2R*,4R*)-2-{2-[methyl-(3-methylamino-propyl)-amino]-ethyl}-5-phenyl-bicyclo[2.2.2]oct-5-en-2-ol as yellow oil.
LC-MS: $t_R$=0.67 min; [M+H]$^+$: 329.22

51.3 (Procedure P5.3): rac-N-(3-{[2-((1R*,2R*,4R*)-2-Hydroxy-5-phenyl-bicyclo[2.2.2]oct-5-en-2-yl)-ethyl]-methyl-amino}-propyl)-3-methoxy-2-methoxymethyl-2, N-dimethyl-propionamide To a solution of 65 mg 3-methoxy-2-methoxymethyl-2-methyl-propionic acid in 0.5 mL DCM was added 0.14 mL DIPEA followed by 133 mg HATU. The resulting mixture was stirred at rt for 20 min before 88 mg of rac-(1R*,2R*,4R*)-2-{2-[methyl-(3-methylamino-propyl)-amino]-ethyl}-5-phenyl-bicyclo[2.2.2]oct-5-en-2-ol, dissolved in 1 mL DCM was added. After stirring overnight the reaction was quenched with water. The water phase was extracted with DCM, the combined organic phases were washed with brine, dried and concentrated in vacuo. The residue was purified by CC with EtOAc-MeOH (3:1) to obtain 115 mg of rac-N-(3-{[2-((1R*,2R*,4R*)-2-hydroxy-5-phenyl-bicyclo[2.2.2]oct-5-en-2-yl)-ethyl]-methyl-amino}-propyl)-3-methoxy-2-methoxymethyl-2,N-dimethyl-propionamide as colorless oil.
LC-MS: $t_R$=0.85 min; [M+H]$^+$: 473.35.

Example 51A rac-Isobutyric acid (1R*,2R*,4R*)-2-[2-({3-[(3-methoxy-2-methoxymethyl-2-methyl-propionyl)-methyl-amino]-propyl}-methyl-amino)-ethyl]-5-phenyl-bicyclo[2.2.2]oct-5-en-2-yl ester Prepared according to procedure P.1.4 in Example 1A using rac-N-(3-{[2-((1R*,2R*,4R*)-2-hydroxy-5-phenyl-bicyclo[2.2.2]oct-5-en-2-yl)-ethyl]-methyl-amino}-propyl)-3-methoxy-2-methoxymethyl-2,N-dimethyl-propionamide.
LC-MS: $t_R$=0.97 min; [M+H]$^+$: 543.67.

Example 52 rac-N-(3-{[2-((1R*,2R*,4R*)-2-hydroxy-6-methyl-5-propyl-bicyclo[2.2.2]oct-5-en-2-yl)-ethyl]-methyl-amino}-propyl)-3-methoxy-2-methoxymethyl-2,N-dimethyl-propionamide Prepared according to procedures P1.1, P1.2, P3.1, and P5.1 to P5.3 using rac-(1R*,2R*,4R*)-(2-hydroxy-6-methyl-5-propyl-bicyclo[2.2.2]oct-5-en-2-yl)-acetic acid tert.-butyl ester in step P1.1.
LC-MS: $t_R$=0.86 min; [M+H]$^+$: 453.71.

Example 52A rac-Isobutyric acid (1R*,2R*,4R*)-2-[2-({3-[(3-methoxy-2-methoxymethyl-2-methyl-propionyl)-methyl-amino]-propyl}-methyl-amino)-ethyl]-6-methyl-5-propyl-bicyclo[2.2.2]oct-5-en-2-yl ester Prepared according to procedure P.1.4 in Example 1A using rac-N-(3-{[2-((1R*,2R*,4R*)-2-hydroxy-6-methyl-5- propyl-bicyclo[2.2.2]oct-5-en-2-yl)-ethyl]-methyl-amino}-propyl)-3-methoxy-2-methoxymethyl-2,N-dimethyl-propionamide.

LC-MS: $t_R$=1.00 min; [M+H]$^+$: 523.66.

Example 53 rac-N-(3-{[2-((1R*,2R*,4R*)-2-hydroxy-5-methyl-6-phenyl-bicyclo[2.2.2]oct-5-en-2-yl)-ethyl]-methyl-amino}-propyl)-3-methoxy-2-methoxymethyl-2,N-dimethyl-propionamide Prepared according to procedures P1.1, P1.2, P3.1, and P5.1 to P5.3 using rac-(1R*,2R*,4R*)-(2-hydroxy-5-methyl-6-phenyl-bicyclo[2.2.2]oct-5-en-2-yl)-acetic acid tert.-butyl ester in step P1.1.

LC-MS: $t_R$=0.87 min; [M+H]$^+$: 487.31.

Example 53A rac-Isobutyric acid (1R*,2R*,4R*)-2-[2-({3-[(3-methoxy-2-methoxymethyl-2-methyl-propionyl)-methyl-amino]-propyl}-methyl-amino)-ethyl]-5-methyl-6-phenyl-bicyclo[2.2.2]oct-5-en-2-yl ester Prepared according to procedure P.1.4 in Example 1A using rac-N-(3-{[2-((1R*,2R*,4R*)-2-hydroxy-6-methyl-5-propyl-bicyclo[2.2.2]oct-5-en-2-yl)-ethyl]-methyl-amino}-propyl)-3-methoxy-2-methoxymethyl-2,N-dimethyl-propionamide.

LC-MS: $t_R$=0.97 min; [M+H]$^+$: 557.68.

Example 53B rac-(1R*,2S*,4R*)-N-(3-{[2-(2-hydroxy-5-methyl-6-phenyl-bicyclo[2.2.2]oct-5-en-2-yl)-ethyl]-methyl-amino}-propyl)-3-methoxy-2-methoxymethyl-2,N-dimethyl-propionamide Prepared according to procedures P1.1, P1.2, P3.1, and P5.1 to P5.3 using the minor racemate rac-(1R*,2S*,4R*)-(2-hydroxy-5-methyl-6-phenyl-bicyclo[2.2.2]oct-5-en-2-yl)-acetic acid tert.-butyl ester in step P1.1.

LC-MS: $t_R$=0.87 min; [M+H]$^+$: 487.75.

Example 53C rac-Isobutyric acid (1R*,2S*,4R*)-2-[2-({3-[(3-methoxy-2-methoxymethyl-2-methyl-propionyl)-methyl-amino]-propyl}-methyl-amino)-ethyl]-5-methyl-6-phenyl-bicyclo[2.2.2]oct-5-en-2-yl ester Prepared according to procedure P.1.4 in Example 1A using rac-(1R*,2S*,4R*)-N-(3-{[2-(2-hydroxy-5-methyl-6-phenyl-bicyclo[2.2.2]oct-5-en-2-yl)-ethyl]-methyl-amino}-propyl)-3-methoxy-2-methoxymethyl-2,N-dimethyl-propionamide.

LC-MS: $t_R$=0.99 min; [M+H]$^+$: 557.35.

Example 54

(1R,2R,4R)-2-(2-{[3-(4-Methoxy-1H-benzoimidazol-2-yl)-propyl]-methyl-amino}-ethyl)-5-phenyl-bicyclo[2.2.2]oct-5-en-2-ol or (1S,2S,4S)-2-(2-{[3-(4-methoxy-1H-benzoimidazol-2-yl)-propyl]-methyl-amino}-ethyl)-5-phenyl-bicyclo[2.2.2]oct-5-en-2-ol Prepared according to procedures P1.2 to P1.3 in Example 1 using enantiomer A of rac-(1R*,2R*,4R*)-2-(2-hydroxy-ethyl)-5-phenyl-bicyclo[2.2.2]oct-5-en-2-ol (see example 1.1A in step P1.2) and [3-(4-methoxy-1H-benzoimidazol-2-yl)-propyl]-methyl-amine in step P1.3.

LC-MS: $t_R$=0.78 min; [M+H]$^+$: 446.14.

Example 54A

Isobutyric acid (1R,2R,4R)-2-(2-{[3-(4-methoxy-1H-benzoimidazol-2-yl)-propyl]-methyl-amino}-ethyl)-5-phenyl-bicyclo[2.2.2]oct-5-en-2-yl ester or isobutyric acid (1S,2S,4S)-2-(2-{[3-(4-methoxy-1H-benzoimidazol-2-yl)-propyl]-methyl-amino}-ethyl)-5-phenyl-bicyclo[2.2.2]oct-5-en-2-yl ester Prepared according to procedure P1.4 in Example 1A using the above 2-(2-{[3-(4-methoxy-1H-benzoimidazol-2-yl)-propyl]-methyl-amino}-ethyl)-5-phenyl-bicyclo[2.2.2]oct-5-en-2-ol (compound of example 54).

LC-MS: $t_R$=0.83 min; [M+H]$^+$: 516.27.

Example 55

(1R,2R,4R)-2-(2-{[3-(4-Methoxy-1H-benzoimidazol-2-yl)-propyl]-methyl-amino}-ethyl)-5-phenyl-bicyclo[2.2.2]oct-5-en-2-ol or (1S,2S,4S)-2-(2-{[3-(4-methoxy-1H-benzoimidazol-2-yl)-propyl]-methyl-amino}-ethyl)-5-phenyl-bicyclo[2.2.2]oct-5-en-2-ol Prepared according to procedures P1.2 to P1.3 in Example 1 using enantiomer B of rac-(1R*,2R*,4R*)-2-(2-hydroxy-ethyl)-5-phenyl-bicyclo[2.2.2]oct-5-en-2-ol (see example 1.1A in step P1.2) and [3-(4-methoxy-1H-benzoimidazol-2-yl)-propyl]-methyl-amine in step P1.3.

LC-MS: $t_R$=0.78 min; [M+H]$^+$: 446.17.

Example 55A

Isobutyric acid (1R,2R,4R)-2-(2-{[3-(4-methoxy-1H-benzoimidazol-2-yl)-propyl]-methyl-amino}-ethyl)-5-phenyl-bicyclo[2.2.2]oct-5-en-2-yl ester or isobutyric acid (1S,2S,4S)-2-(2-{[3-(4-methoxy-1H-benzoimidazol-2-yl)-propyl]-methyl-amino}-ethyl)-5-phenyl-bicyclo[2.2.2]oct-5-en-2-yl ester Prepared according to procedure P1.4 in Example 1A using the above 2-(2-{[3-(4-methoxy-1H-benzoimidazol-2-yl)-propyl]-methyl-amino}-ethyl)-5-phenyl-bicyclo[2.2.2]oct-5-en-2-ol (compound of example 55).

LC-MS: $t_R$=0.83 min; [M+H]$^+$: 516.28.

Example 56 rac-N-[2-(3-{[2-((1R*,2R*,4R*)-2-Hydroxy-5-phenyl-bicyclo[2.2.2]oct-5-en-2-yl)-ethyl]-methyl-amino}-propyl)-1H-benzoimidazol-4-yl]-acetamide Prepared according to procedures P1.1 to P1.3 in Example 1 using N-[2-(3-methylamino-propyl)-1H-benzoimidazol-4-yl]-acetamide as hydrochloride salt in step P1.3.

LC-MS: $t_R$=0.75 min; [M+H]$^+$: 473.21.

Example 56A rac-Isobutyric acid (1R*,2R*,4R*)-2-(2-{[3-(4-acetylamino-1H-benzoimidazol-2-yl)-propyl]-methyl-amino}-ethyl)-5-phenyl-bicyclo[2.2.2]oct-5-en-2-yl ester Prepared according to procedure P1.4 in Example 1A using rac-N-[2-(3-{[2-((1R*,2R*,4R*)-2-hydroxy-5-phenyl-bicyclo[2.2.2]oct-5-en-2-yl)-ethyl]-methyl-amino}-propyl)-1H-benzoimidazol-4-yl]-acetamide.

LC-MS: $t_R$=0.80 min; [M+H]$^+$: 543.27.

Example 57 rac-(1R*,2R*,4R*)-2-(2-{[3-(4-Chloro-1H-benzoimidazol-2-yl)-propyl]-methyl-amino}-ethyl)-5-phenyl-bicyclo[2.2.2]oct-5-en-2-ol Prepared according to procedures P2.2 to P2.3 in Example 21 using rac-(1R*,2R*,4R*)-(2-hydroxy-5-phenyl-bicyclo[2.2.2]oct-5-en-2-yl)-acetic acid and [3-(4-chloro-1H-benzoimidazol-2-yl)-propyl]methyl-amine.

LC-MS: $t_R$=0.79 min; [M+H]$^+$: 450.21.

Example 57A rac-Isobutyric acid (1R*,2R*,4R*)-2-(2-{[3-(4-chloro-1H-benzoimidazol-2-yl)-propyl]-methyl-amino}-ethyl)-5-phenyl-bicyclo[2.2.2]oct-5-en-2-yl ester Prepared according to procedure P1.4 in Example 1A using. rac-(1R*,2R*,4R*)-2-(2-{[3-(4-Chloro-1H-benzoimidazol-2-yl)-propyl]-methyl-amino}-ethyl)-5-phenyl-bicyclo[2.2.2]oct-5-en-2-ol.

LC-MS: $t_R$=0.98 min; [M+H]$^+$: 520.13.

Example 58 rac-(1R*,2R*,4R*)-2-(2-{[3-(7-Chloro-4-methoxy-1H-benzoimidazol-2-yl)-propyl]-methyl-amino}-ethyl)-5-phenyl-bicyclo[2.2.2]oct-5-en-2-ol Prepared according to procedures P2.2 to P2.3 in Example 21 using rac-(1R*,2R*,4R*)-(2-hydroxy-5-phenyl-bicyclo[2.2.2]oct-5-en-2-yl)-acetic acid and [3-(7-chloro-4-methoxy-1H-benzoimidazol-2-yl)-propyl]-methyl-amine.

LC-MS: $t_R$=0.86 min; [M+H]$^+$: 479.89.

Example 58A rac-Isobutyric acid (1R*,2R*,4R*)-2-(2-{[3-(7-chloro-4-methoxy-1H-benzoimidazol-2-yl)-propyl]-methyl-amino}-ethyl)-5-phenyl-bicyclo[2.2.2]oct-5-en-2-yl ester Prepared according to procedure P1.4 in Example 1A using rac-(1R*,2R*,4R*)-2-(2-{[3-(7-chloro-4-methoxy-1H-benzoimidazol-2-yl)-propyl]-methyl-amino}-ethyl)-5-phenyl-bicyclo[2.2.2]oct-5-en-2-ol.

LC-MS: $t_R$=1.00 min; [M+H]$^+$: 550.03

Example 59 rac-(1R*,2R*,4R*)-2-(2-{[3-(4,6-Dimethoxy-1H-benzoimidazol-2-yl)-propyl]-methyl-amino}-ethyl)-5-phenyl-bicyclo[2.2.2]oct-5-en-2-ol Prepared according to procedures P2.2 to P2.3 in Example 21 using rac-(1R*,2R*,4R*)-(2-hydroxy-5-phenyl-bicyclo[2.2.2]oct-5-en-2-yl)-acetic acid and [3-(4,6-dimethoxy-1H-benzoimidazol-2-yl)-propyl]-methyl-amine.

LC-MS: $t_R$=0.79 min; [M+H]$^+$: 476.19.

Example 59A rac-Isobutyric acid (1R*,2R*,4R*)-2-(2-{[3-(4,6-dimethoxy-1H-benzoimidazol-2-yl)-propyl]-methyl-amino}-ethyl)-5-phenyl-bicyclo[2.2.2]oct-5-en-2-yl ester Prepared according to procedure P1.4 in Example 1A using rac-(1R*,2R*,4R*)-2-(2-{[3-(4,6-dimethoxy-1H-benzoimidazol-2-yl)-propyl]-methyl-amino}-ethyl)-5-phenyl-bicyclo[2.2.2]oct-5-en-2-ol.

LC-MS: $t_R$=0.88 min; [M+H]$^+$: 546.24.

Example 60

(1R,2R,4R)-2-(2-{[3-(4,6-Dimethoxy-1H-benzoimidazol-2-yl)-propyl]-methyl-amino}-ethyl)-5-phenyl-bicyclo[2.2.2]oct-5-en-2-ol or (1S,2S,4S)-2-(2-{[3-(4,6-dimethoxy-1H-benzoimidazol-2-yl)-propyl]-methyl-amino}-ethyl)-5-phenyl-bicyclo[2.2.2]oct-5-en-2-ol 60.1: (1R,2R,4R)-(2-Hydroxy-5-phenyl-bicyclo[2.2.2]oct-5-en-2-yl)-acetic acid or (1S,2S,4S)-(2-hydroxy-5-phenyl-bicyclo[2.2.2]oct-5-en-2-yl)-acetic acid Prepared according to procedure P2.1 in Example 21 using enantiomer A of rac-(1R*,2R*,4R*)-(2-hydroxy-5-phenyl-bicyclo[2.2.2]oct-5-en-2-yl)-acetic acid tert.-butyl ester (see K1A.6)

LC-MS: $t_R$=0.91 min; [M–H$_2$O+H]$^+$: 241.05.

60.2: (1R,2R,4R)-2-(2-{[3-(4,6-Dimethoxy-1H-benzoimidazol-2-yl)-propyl]-methyl-amino}-ethyl)-5-phenyl-bicyclo[2.2.2]oct-5-en-2-ol or (1S,2S,4S)-2-(2-{[3-(4,6-dimethoxy-1H-benzoimidazol-2-yl)-propyl]-methyl-amino}-ethyl)-5-phenyl-bicyclo[2.2.2]oct-5-en-2-ol Prepared according to procedures P2.2 to P2.3 in Example 21 using the above (2-hydroxy-5-phenyl-bicyclo[2.2.2]oct-5-en-2-yl)-acetic acid and [3-(4,6-dimethoxy-1H-benzoimidazol-2-yl)-propyl]-methyl-amine.

LC-MS: $t_R$=0.79 min; [M+H]$^+$: 476.09.

Example 60A

Isobutyric acid (1R,2R,4R)-2-(2-{[3-(4,6-dimethoxy-1H-benzoimidazol-2-yl)-propyl]-methyl-amino}-ethyl)-5-phenyl-bicyclo[2.2.2]oct-5-en-2-yl ester or Isobutyric acid (1S,2S,4S)-2-(2-{[3-(4,6-dimethoxy-1H-benzoimidazol-2-yl)-propyl]-methyl-amino}-ethyl)-5-phenyl-bicyclo[2.2.2]oct-5-en-2-yl ester Prepared according to procedure P1.4 in Example 1A using the above 2-(2-{[3-(4,6-dimethoxy-1H-benzoimidazol-2-yl)-propyl]-methyl-amino}-ethyl)-5-phenyl-bicyclo[2.2.2]oct-5-en-2-ol (compound of example 60).
LC-MS: $t_R$=0.88 min; [M+H]$^+$: 546.11.

Example 61 rac-(1R*,2R*,4R*)-2-(2-{[3-(4,7-Dimethoxy-1H-benzoimidazol-2-yl)-propyl]-methyl-amino}-ethyl)-5-phenyl-bicyclo[2.2.2]oct-5-en-2-ol Prepared according to procedures P2.2 to P2.3 in Example 21 using rac-(1R*,2R*,4R*)-(2-hydroxy-5-phenyl-bicyclo[2.2.2]oct-5-en-2-yl)-acetic acid and [3-(4,7-dimethoxy-1H-benzoimidazol-2-yl)-propyl]methyl-amine.
LC-MS: $t_R$=0.79 min; [M+H]$^+$: 476.13.

Example 61A rac-Isobutyric acid (1R*,2R*,4R*)-2-(2-{[3-(4,7-dimethoxy-1H-benzoimidazol-2-yl)-propyl]-methyl-amino}-ethyl)-5-phenyl-bicyclo[2.2.2]oct-5-en-2-yl ester Prepared according to procedure P1.4 in Example 1A using rac-(1R*,2R*,4R*)-2-(2-{[3-(4,7-dimethoxy-1H-benzoimidazol-2-yl)-propyl]-methyl-amino}-ethyl)-5-phenyl-bicyclo[2.2.2]oct-5-en-2-ol.
LC-MS: $t_R$=0.90 min; [M+H]$^+$: 546.23.

Example 62 rac-(1R*,2R*,4R*)-2-(2-{[3-(4,6-Bis-trifluoromethyl-1H-benzoimidazol-2-yl)-propyl]-methyl-amino}-ethyl)-5-phenyl-bicyclo[2.2.2]oct-5-en-2-ol Prepared according to procedures P2.2 to P2.3 in Example 21 using rac-(1R*,2R*,4R*)-(2-hydroxy-5-phenyl-bicyclo[2.2.2]oct-5-en-2-yl)-acetic acid and [3-(4,6-bis-trifluoromethyl-1H-benzoimidazol-2-yl)-propyl]-methyl-amine.
LC-MS: $t_R$=0.97 min; [M+H]$^+$: 551.94.

Example 62A rac-Isobutyric acid (1R*,2R*,4R*)-2-(2-{[3-(4,6-bis-trifluoromethyl-1H-benzoimidazol-2-yl)-propyl]-methyl-amino}-ethyl)-5-phenyl-bicyclo[2.2.2]oct-5-en-2-yl ester Prepared according to procedure P1.4 in Example 1A using rac-(1R*,2R*,4R*)-2-(2-{[3-(4,6-bis-trifluoromethyl-1H-benzoimidazol-2-yl)-propyl]-methyl-amino}-ethyl)-5-phenyl-bicyclo[2.2.2]oct-5-en-2-ol.
LC-MS: $t_R$=1.07 min; [M+H]$^+$: 622.01

Example 63 rac-(1R*,2R*,4R*)-2-[2-({3-[4-(2-Methoxy-ethoxy)-1H-benzoimidazol-2-yl]-propyl}-methyl-amino)-ethyl]-5-phenyl-bicyclo[2.2.2]oct-5-en-2-ol Prepared according to procedures P2.2 to P2.3 in Example 21 using rac-(1R*,2R*,4R*)-(2-hydroxy-5-phenyl-bicyclo[2.2.2]oct-5-en-2-yl)-acetic acid and {3-[4-(2-methoxy-ethoxy)-1H-benzoimidazol-2-yl]-propyl}-methyl-amine.
LC-MS: $t_R$=0.78 min; [M+H]$^+$: 490.18.

Example 63A rac-Isobutyric acid (1R*,2R*,4R*)-2-[2-({3-[4-(2-methoxy-ethoxy)-1H-benzoimidazol-2-yl]-propyl}-methyl-amino)-ethyl]-5-phenyl-bicyclo[2.2.2]oct-5-en-2-yl ester Prepared according to procedure P1.4 in Example 1A using rac-(1R*,2R*,4R*)-2-[2-({3-[4-(2-methoxy-ethoxy)-1H-benzoimidazol-2-yl]-propyl}-methyl-amino)-ethyl]-5-phenyl-bicyclo[2.2.2]oct-5-en-2-ol.
LC-MS: $t_R$=0.89 min; [M+H]$^+$: 560.07.

Example 64 rac-(1R*,2R*,4R*)-2-(2-{[3-(4,5-Dimethoxy-7-methyl-1H-benzoimidazol-2-yl)-propyl]-methyl-amino}-ethyl)-5-phenyl-bicyclo[2.2.2]oct-5-en-2-ol Prepared according to procedures P2.2 to P2.3 in Example 21 using rac-(1R*,2R*,4R*)-(2-hydroxy-5-phenyl-bicyclo[2.2.2]oct-5-en-2-yl)acetic acid and [3-(4,5-dimethoxy-7-methyl-1H-benzoimidazol-2-yl)-propyl]-methyl-amine.
LC-MS: $t_R$=0.79 min; [M+H]$^+$: 490.09.

Example 64A rac-Isobutyric acid (1R*,2R*,4R*)-2-(2-{[3-(4,5-dimethoxy-7-methyl-1H-benzoimidazol-2-yl)-propyl]-methyl-amino}-ethyl)-5-phenyl-bicyclo[2.2.2]oct-5-en-2-yl ester Prepared according to procedure P1.4 in Example 1A using rac-(1R*,2R*,4R*)-2-(2-{[3-(4,5-dimethoxy-7-methyl-1H-benzoimidazol-2-yl)-propyl]-methyl-amino}-ethyl)-5-phenyl-bicyclo[2.2.2]oct-5-en-2-ol.
LC-MS: $t_R$=0.88 min; [M+H]$^+$: 560.03.

Example 65

(1R,2R,4R)-2-(2-{[3-(4,5-Dimethoxy-7-methyl-1H-benzoimidazol-2-yl)-propyl]-methyl-amino}-ethyl)-5-phenyl-bicyclo[2.2.2]oct-5-en-2-ol or (1S,2S,4S)-2-(2-{[3-(4,5-dimethoxy-7-methyl-1H-benzoimidazol-2-yl)-propyl]-methyl-amino}-ethyl)-5-phenyl-bicyclo[2.2.2]oct-5-en-2-ol Prepared according to procedures P2.2 to P2.3 in Example 21 using enantiomer A of rac-(1R*,2R*,4R*)-(2-hydroxy-5-phenyl-bicyclo[2.2.2]oct-5-en-2-yl)-acetic acid (see example 60.1) and [3-(4,5-dimethoxy-7-methyl-1H-benzoimidazol-2-yl)-propyl]-methyl-amine.
LC-MS: $t_R$=0.78 min; [M+H]$^+$: 490.10.

Example 65A

Isobutyric acid (1R,2R,4R)-2-(2-{[3-(4,5-dimethoxy-7-methyl-1H-benzoimidazol-2-yl)-propyl]-methyl-amino}-ethyl)-5-phenyl-bicyclo[2.2.2]oct-5-en-2-yl ester or isobutyric acid (1S,2S,4S)-2-(2-{[3-(4,5-dimethoxy-7-methyl-1H-benzoimidazol-2-yl)-propyl]-methyl-amino}-ethyl)-5-phenyl-bicyclo[2.2.2]oct-5-en-2-yl ester Prepared according to procedure P1.4 in Example 1A using the above 2-(2-{[3-(4,5-dimethoxy-7-methyl-1H-benzoimidazol-2-yl)-propyl]-methyl-amino}-ethyl)-5-phenyl-bicyclo[2.2.2]oct-5-en-2-ol (compound of example 65).
LC-MS: $t_R$=0.88 min; [M+H]$^+$: 560.09.

Example 66 rac-(1R*,5R*,6R*)-6-(2-{[3-(7-Methoxy-4-methyl-1H-benzoimidazol-2-yl)-propyl]-methyl-amino}-ethyl)-8-phenyl-bicyclo[3.2.2]non-8-en-6-ol Prepared according to procedures P2.1 to P2.3 in Example 21 using rac-(1R*,5R*,6R*)-6-hydroxy-8-phenyl-bicyclo[3.2.2]non-8-en-6-yl)-acetic acid tert.-butyl ester in step P2.1 and [3-(7-methoxy-4-methyl-1H-benzoimidazol-2-yl)-propyl]-methyl-amine in step P2.2.
LC-MS: $t_R$=0.80 min; [M+H]$^+$: 474.14.

Example 66A rac-Isobutyric acid (1R*,5R*,6R*)-6-(2-{[3-(7-methoxy-4-methyl-1H-benzoimidazol-2-yl)-propyl]-methyl-amino}-ethyl)-8-phenyl-bicyclo[3.2.2]non-8-en-6-yl ester Prepared according to procedure P1.4 in Example 1A using rac-(1R*,5R*,6R*)-6-(2-{[3-(7-methoxy-4-methyl-1H-benzoimidazol-2-yl)-propyl]-methyl-amino}-ethyl)-8-phenyl-bicyclo[3.2.2]non-8-en-6-ol.
LC-MS: $t_R$=0.89 min; [M+H]$^+$: 544.45.

Example 67

(1R,2R,4R)-2-(2-{[3-(4,7-Dimethoxy-1H-benzoimidazol-2-yl)-propyl]-methyl-amino}-ethyl)-5-phenyl-bicyclo[2.2.2]oct-5-en-2-ol or (1S,2S,4S)-2-(2-{[3-(4,7-dimethoxy-1H-benzoimidazol-2-yl)-propyl]-methyl-amino}-ethyl)-5-phenyl-bicyclo[2.2.2]oct-5-en-2-ol 67.1: (1R,2R,4R)-(2-Hydroxy-5-phenyl-bicyclo[2.2.2]oct-5-en-2-yl)-acetic acid or (1S,2S,4S)-(2-hydroxy-5-phenyl-bicyclo[2.2.2]oct-5-en-2-yl)-acetic acid Prepared according to procedure P2.1 in Example 21 using enantiomer B of rac-(1R*,2R*,4R*)-(2-hydroxy-5-phenyl-bicyclo[2.2.2]oct-5-en-2-yl)-acetic acid tert.-butyl ester (see K1A.6).
LC-MS: $t_R$=0.91 min; [M−H$_2$O+H]$^+$: 241.10.

67.2: (1R,2R,4R)-2-(2-{[3-(4,7-Dimethoxy-1H-benzoimidazol-2-yl)-propyl]-methyl-amino}-ethyl)-5-phenyl-bicyclo[2.2.2]oct-5-en-2-ol or (1S,2S,4S)-2-(2-{[3-(4,7-dimethoxy-1H-benzoimidazol-2-yl)-propyl]-methyl-amino}-ethyl)-5-phenyl-bicyclo[2.2.2]oct-5-en-2-ol Prepared according to procedures P2.2 to P2.3 in Example 21 using the above (2-hydroxy-5-phenyl-bicyclo[2.2.2]oct-5-en-2-yl)-acetic acid and [3-(4,7-dimethoxy-1H-benzoimidazol-2-yl)-propyl]-methyl-amine.
LC-MS: $t_R$=0.78 min; [M+H]$^+$: 476.09.

Example 67A

Isobutyric acid (1R,2R,4R)-2-(2-{[3-(4,7-dimethoxy-1H-benzoimidazol-2-yl)-propyl]-methyl-amino}-ethyl)-5-phenyl-bicyclo[2.2.2]oct-5-en-2-yl ester or Isobutyric acid (1S,2S,4S)-2-(2-{[3-(4,7-dimethoxy-1H-benzoimidazol-2-yl)-propyl]-methyl-amino}-ethyl)-5-phenyl-bicyclo[2.2.2]oct-5-en-2-yl ester Prepared according to procedure P1.4 in Example 1A using the above 2-(2-{[3-(4,7-dimethoxy-1H-benzoimidazol-2-yl)-propyl]-methyl-amino}-ethyl)-5-phenyl-bicyclo[2.2.2]oct-5-en-2-ol (compound of example 67).
LC-MS: $t_R$=0.89 min; [M+H]$^+$: 546.19.

Example 68 rac-(1R*,2R*,4R*)-2-(2-{Methyl-[3-(4-trifluoromethoxy-1H-benzoimidazol-2-yl)-propyl]-amino}-ethyl)-5-phenyl-bicyclo[2.2.2]oct-5-en-2-ol Prepared according to procedures P2.2 to P2.3 in Example 21 using rac-(1R*,2R*,4R*)-2-hydroxy-5-phenyl-bicyclo[2.2.2]oct-5-en-2-yl)-acetic acid and methyl-[3-(4-trifluoromethoxy-1H-benzoimidazol-2-yl)-propyl]-amine.
LC-MS: $t_R$=0.88 min; [M+H]$^+$: 500.02.

Example 68A rac-Isobutyric acid (1R*,2R*,4R*)-2-(2-{methyl-[3-(4-trifluoromethoxy-1H-benzoimidazol-2-yl)-propyl]-amino}-ethyl)-5-phenyl-bicyclo[2.2.2]oct-5-en-2-yl ester Prepared according to procedure P1.4 in Example 1A using rac-(1R*,2R*,4R*)-2-(2-{methyl-[3-(4-trifluoromethoxy-1H-benzoimidazol-2-yl)-propyl]-amino}-ethyl)-5-phenyl-bicyclo[2.2.2]oct-5-en-2-ol
LC-MS: $t_R$=1.01 min; [M+H]$^+$: 569.97.

Example 69 rac-(1R*,5R*,6R*)-6-(2-{[3-(4,7-Dimethoxy-1H-benzoimidazol-2-yl)-propyl]-methyl-amino}-ethyl)-8-phenyl-bicyclo[3.2.2]non-8-en-6-ol Prepared according to procedures P2.1 to P2.3 in Example 21 using rac-(1R*,5R*,6R*)-6-hydroxy-8-phenyl-bicyclo[3.2.2]non-8-en-6-yl)-acetic acid tert.-butyl ester in step P2.1 and [3-(4,7-dimethoxy-1H-benzoimidazol-2-yl)-propyl]-methyl-amine in step P2.2.
LC-MS: $t_R$=0.80 min; [M+H]$^+$: 490.06.

Example 69A rac-Isobutyric acid (1R*,5R*,6R*)-6-(2-{[3-(4,7-dimethoxy-1H-benzoimidazol-2-yl)-propyl]-methyl-amino}-ethyl)-8-phenyl-bicyclo[3.2.2]non-8-en-6-yl ester Prepared according to procedure P1.4 in Example 1A using rac-(1R*,5R*,6R*)-6-(2-{[3-(4,7-dimethoxy-1H-benzoimidazol-2-yl)-propyl]-methyl-amino}-ethyl)-8-phenyl-bicyclo[3.2.2]non-8-en-6-ol.
LC-MS: $t_R$=0.91 min; [M+H]$^+$: 560.05.

Example 70

(1R,2R,4R)-2-(2-{[3-(4,7-Dimethoxy-1H-benzoimidazol-2-yl)-propyl]-methyl-amino}-ethyl)-5-phenyl-bicyclo[2.2.2]oct-5-en-2-ol or (1S,2S,4S)-2-(2-{[3-(4,7-dimethoxy-1H-benzoimidazol-2-yl)-propyl]-methyl-amino}-ethyl)-5-phenyl-bicyclo[2.2.2]oct-5-en-2-ol Prepared according to procedures P2.2 to P2.3 in Example 21 using enantiomer A of rac-(1R*,2R*,4R*)-(2-hydroxy-5-phenyl-bicyclo[2.2.2]oct-5-en-2-yl)-acetic acid (see example 60.1) and [3-(4,7-dimethoxy-1H-benzoimidazol-2-yl)-propyl]-methyl-amine.
LC-MS: $t_R$=0.79 min; [M+H]$^+$: 476.09.

Example 70A

Isobutyric acid (1R,2R,4R)-2-(2-{[3-(4,7-dimethoxy-1H-benzoimidazol-2-yl)-propyl]-methyl-amino}-ethyl)-5-phenyl-bicyclo[2.2.2]oct-5-en-2-yl ester or isobutyric acid (1S,2S,4S)-2-(2-{[3-(4,7-dimethoxy-1H-benzoimidazol-2-yl)-propyl]-methyl-amino}-ethyl)-5-phenyl-bicyclo[2.2.2]oct-5-en-2-yl ester Prepared according to procedure P1.4 in Example 1A using the above 2-(2-{[3-(4,7-dimethoxy-1H-benzoimidazol-2-yl)-propyl]-methyl-amino}-ethyl)-5-phenyl-bicyclo[2.2.2]oct-5-en-2-ol (compound of example 70).
LC-MS: $t_R$=0.89 min; [M+H]$^+$: 546.11.

Example 71A rac-Isobutyric acid (1R*,2R*,4R*)-2-(2-{methyl-[3-(4-methyl-5-phenyl-1H-imidazol-2-yl)-propyl]-amino}-ethyl)-5-phenyl-bicyclo[2.2.2]oct-5-en-2-yl ester Prepared according to procedures P4.1 to P4.4 in Example 47A using 3-[4-methyl-5-phenyl-1-(2-trimethylsilanyl-ethoxymethyl)-1H-imidazol-2-yl]-propionic acid.
LC-MS: $t_R$=0.88 min; [M+H]$^+$: 526.13.

Example 72A rac-Isobutyric acid (1R*,2R*,4R*)-2-[2-({3-[5-(2-methoxy-phenyl)-1H-imidazol-2-yl]-propyl}-methyl-amino)-ethyl]-5-phenyl-bicyclo[2.2.2]oct-5-en-2-yl ester Prepared according to procedures P4.1 to P4.4 in Example 47A using 3-[5-(2-methoxy-phenyl)-1-(2-trimethylsilanyl-ethoxymethyl)-1H-imidazol-2-yl]-propionic acid.
LC-MS: $t_R$=0.87 min; [M+H]$^+$: 542.05.

Example 73A rac-Isobutyric acid (1R*,2R*,4R*,5S*)-2-(2-{[3-(1H-benzoimidazol-2-yl)-propyl]-methyl-amino}-ethyl)-5-phenyl-bicyclo[2.2.2]oct-2-yl ester and rac-isobutyric acid (1R*,2R*,4R*,5R*)-2-(2-{[3-(1H-benzoimidazol-2-yl)-propyl]-methyl-amino}-ethyl)-5-phenyl-bicyclo[2.2.2]oct-2-yl ester To a solution of 22 mg of rac-isobutyric acid (1R*,2R*,4R*)-2-(2-{[3-(1H-benzoimidazol-2-yl)-propyl]-methyl-amino}-ethyl)-5-phenyl-bicyclo[2.2.2]oct-5-en-2-yl ester dissolved in 0.6 mL EtOH (evacuated 3 times with $N_2$) were added 10 mg of 10 wt % Pd/C. The reaction mixture was stirred under a $H_2$ atmosphere (balloon) for 1 h, filtered over a pad of celite and the cake was washed with EtOH and concentrated in vacuo to provide crude isobutyric acid (1R*,2R*,4R*)-(5RS)-2-(2-{[3-(1H-benzoimidazol-2-yl)-propyl]-methyl-amino}-ethyl)-5-phenyl-bicyclo[2.2.2]oct-2-yl ester as mixture of 2 diastereoisomeric racemates. Purification by CC using EtOAc/MeOH 2/1 yielded 5 mg of racemate A and 6 mg of racemate B, both as colorless oils.
LC-MS: $t_R$=0.83 min; [M+H]$^+$: 488.35. (racemate A)
LC-MS: $t_R$=0.83 min; [M+H]$^+$: 488.36. (racemate B)

Example 74

(1S,4S,5R)-5-(2-{[3-(1H-Benzoimidazol-2-yl)-propyl]-methyl-amino}-ethyl)-2-phenyl-2-aza-bicyclo[2.2.2]octan-5-ol 74.1: N-[3-(1H-Benzoimidazol-2-yl)-propyl]-2-((1S,4S,5R)-5-hydroxy-2-phenyl-2-aza-bicyclo[2.2.2]oct-5-yl)-N-methyl-acetamide Prepared according to procedures P2.1 to P2.2 in Example 21 using ((1S,4S)-(5RS)-5-hydroxy-2-phenyl-2-aza-bicyclo[2.2.2]oct-5-yl)-acetic acid tert-butyl ester.
LC-MS (major diastereoisomer): $t_R$=0.76 min; [M+H]$^+$: 433.60.
LC-MS (minor diastereoisomer): $t_R$=0.68 min; [M+H]$^+$: 433.59.

74.2: (1S,4S,5R)-5-(2-{[3-(1H-Benzoimidazol-2-yl)-propyl]-methyl-amino}-ethyl)-2-phenyl-2-aza-bicyclo[2.2.2]octan-5-ol Prepared according to procedure P2.3 in Example 21 using N-[3-(1H-benzoimidazol-2-yl)-propyl]-2-((1S,4S,5R)-5-hydroxy-2-phenyl-2-aza-bicyclo[2.2.2]oct-5-yl)-N-methyl-acetamide (major diastereoisomer).
LC-MS: $t_R$=0.67 min; [M+H]$^+$: 419.62.

Example 74A

Isobutyric acid (1S,4S,5R)-5-(2-{[3-(1H-benzoimidazol-2-yl)-propyl]-methyl-amino}-ethyl)-2-phenyl-2-aza-bicyclo[2.2.2]oct-5-yl ester Prepared according to procedure P1.4 in Example 1A using (1S,4S,5R)-5-(2-{[3-(1H-benzoimidazol-2-yl)-propyl]-methyl-amino}-ethyl)-2-phenyl-2-aza-bicyclo[2.2.2]octan-5-ol.
LC-MS: $t_R$=0.80 min; [M+H]$^+$: 489.67.

Example 75 rac-(1R*,2R*,4R*)-2-(2-{[3-(1H-Benzoimidazol-2-yl)-propyl]-methyl-amino}-ethyl)-bicyclo[2.2.2]oct-5-en-2-ol Prepared according to procedures P1.1 to P1.3 in Example 1 using rac-((1R*,2R*,4R*)-2-hydroxy-bicyclo[2.2.2]oct-5-en-2-yl)acetic acid tert-butyl ester.

LC-MS: $t_R$=0.60 min; [M+H]$^+$: 340.41

Example 75A rac-Isobutyric acid (1R*,2R*,4R*)-2-(2-{[3-(1H-benzoimidazol-2-yl)-propyl]-methyl-amino}-ethyl)-bicyclo[2.2.2]oct-5-en-2-yl ester Prepared according to procedure P1.4 in Example 1A using rac-(1R*,2R*,4R*)-2-(2-{[3-(1H-benzoimidazol-2-yl)-propyl]-methyl-amino}-ethyl)-bicyclo[2.2.2]oct-5-en-2-ol.

LC-MS: $t_R$=0.72 min; [M+H]$^+$: 410.37

Example 76 rac-(1R*,2R*,4R*,5R*)-2-(2-{[3-(1H-Benzoimidazol-2-yl)-propyl]-methyl-amino}-ethyl)-5-methoxy-5-phenyl-bicyclo[2.2.2]octan-2-ol Prepared according to procedures P1.1 to P1.3 in Example 1 using rac-((1R*,2R*,4R*,5R*)-2-hydroxy-5-methoxy-5-phenyl-bicyclo[2.2.2]oct-2-yl)-acetic acid tert-butyl ester (intermediate K9A) and [3-(1H-benzoimidazol-2-yl)-propyl]-methyl-amine in step P1.3.

LC-MS: $t_R$=0.68 min; [M+H]$^+$: 448.59

Example 76A rac-Isobutyric acid (1R*,2R*,4R*,5R*)-2-(2-{[3-(1H-benzoimidazol-2-yl)-propyl]-methyl-amino}-ethyl)-5-methoxy-5-phenyl-bicyclo[2.2.2]oct-2-yl ester Prepared according to procedure P1.4 in Example 1A using rac-(1R*,2R*,4R*,5R*)-2-(2-{[3-(1H-benzoimidazol-2-yl)-propyl]-methyl-amino}-ethyl)-5-methoxy-5-phenyl-bicyclo[2.2.2]octan-2-ol.

LC-MS: $t_R$=0.77 min; [M+H]$^+$: 518.65

Example 77 rac-(1R*,2S*,4R*,5S*)-2-(2-{[3-(1H-Benzoimidazol-2-yl)-propyl]-methyl-amino}-ethyl)-5-methoxy-5-phenyl-bicyclo[2.2.2]octan-2-ol Prepared according to procedures P1.1 to P1.3 in Example 1 using rac-((1R*,2S*,4R*,5S*)-2-hydroxy-5-methoxy-5-phenyl-bicyclo[2.2.2]oct-2-yl)-acetic acid tert-butyl ester (intermediate K9C) and [3-(1H-benzoimidazol-2-yl)-propyl]-methyl-amine in step P1.3.

LC-MS: $t_R$=0.70 min; [M+H]$^+$: 448.59

Example 77A rac-Isobutyric acid (1R*,2S*,4R*,5S*)-2-(2-{[3-(1H-benzoimidazol-2-yl)-propyl]-methyl-amino}-ethyl)-5-methoxy-5-phenyl-bicyclo[2.2.2]oct-2-yl ester Prepared according to procedure P1.4 in Example 1A using rac-(1R*,2S*,4R*,5S*)-2-(2-{[3-(1H-benzoimidazol-2-yl)-propyl]-methyl-amino}-ethyl)-5-methoxy-5-phenyl-bicyclo[2.2.2]octan-2-ol.

LC-MS: $t_R$=0.80 min; [M+H]$^+$: 518.68

Example 78 rac-(1R*,2R*,4R*,5S*)-2-(2-{[3-(1H-Benzoimidazol-2-yl)-propyl]-methyl-amino}-ethyl)-5-methoxy-5-phenyl-bicyclo[2.2.2]octan-2-ol Prepared according to procedures P1.1 to P1.3 in Example 1 using rac-((1R*,2R*,4R*,5S*)-2-hydroxy-5-methoxy-5-phenyl-bicyclo[2.2.2]oct-2-yl)-acetic acid tert-butyl ester (intermediate K9B) and [3-(1H-benzoimidazol-2-yl)-propyl]-methyl-amine in step P1.3.

LC-MS: $t_R$=0.72 min; [M+H]$^+$: 448.56

Example 79 rac-(1R*,2R*,4R*,5R*)-5-(2-{[3-(1H-Benzoimidazol-2-yl)-propyl]-methyl-amino}-ethyl)-3'H-spiro(bicyclo[2.2.2]octane-2,1'-isobenzofuran)-5-ol Prepared according to procedures P1.1 to P1.3 in Example 1 using rac-(1R*,2R*,4R*,5R*)-5-hydroxy-(3'H-spiro(bicyclo[2.2.2]octane-2,1'-isobenzofuran)-5-yl)-acetic acid tert-butyl ester (intermediate K10A) and [3-(1H-benzoimidazol-2-yl)-propyl]-methyl-amine in step P1.3.

LC-MS: $t_R$=0.68 min; [M+H]$^+$: 446.55

Example 79A rac-Isobutyric acid (1R*,2R*,4R*,5R*)-5-(2-{[3-(1H-benzoimidazol-2-yl)-propyl]-methyl-amino}-ethyl)-3'H-spiro(bicyclo[2.2.2]octane-2,1'-isobenzofuran)-5-yl ester Prepared according to procedure P1.4 in Example 1A using rac-(1R*,2R*,4R*,5R*)-5-(2-{[3-(1H-benzoimidazol-2-yl)-propyl]-methyl-amino}-ethyl)-3'H-spiro(bicyclo[2.2.2]octane-2,1'-isobenzofuran)-5-ol.

LC-MS: $t_R$=0.77 min; [M+H]$^+$: 516.61

Example 80 rac-(1R*,2S*,4R*,5R*)-5-(2-{[3-(1H-Benzoimidazol-2-yl)-propyl]-methyl-amino}-ethyl)-3'H-spiro(bicyclo[2.2.2]octane-2,1'-isobenzofuran)-5-ol Prepared according to procedures P1.1 to P1.3 in Example 1 using rac-(1R*,2S*,4R*,5R*)-5-hydroxy-(3'H-spiro(bicyclo[2.2.2]octane-2,1'-isobenzofuran)-5-yl)-acetic acid tert-butyl ester (intermediate K10B) and [3-(1H-benzoimidazol-2-yl)-propyl]-methyl-amine in step P1.3.

LC-MS: $t_R$=0.69 min; [M+H]$^+$: 446.55

Example 80A rac-Isobutyric acid (1R*,2S*,4R*,5R*)-5-(2-{[3-(1H-benzoimidazol-2-yl)-propyl]-methyl-amino}-ethyl)-3'H-spiro(bicyclo[2.2.2]octane-2,1'-isobenzofuran)-5-yl ester Prepared according to procedure P1.4 in Example 1A using rac-(1R*,2S*,4R*,5R*)-5-(2-{[3-(1H-benzoimidazol-2-yl)-propyl]-methyl-amino}-ethyl)-3'H-spiro(bicyclo[2.2.2]octane-2,1'-isobenzofuran)-5-ol.

LC-MS: $t_R$=0.80 min; [M+H]$^+$: 516.62

Biological Tests

In Vitro Assay L Channel

The L channel antagonistic activity ($IC_{50}$ values) of the compounds of formula (I) is determined in accordance with the following experimental method.

Human embryonic kidney (HEK293) cells expressing the human $Ca_v1.2$ channel in addition to the auxiliary subunits β-2a and α2δ-1, are grown in culture medium (DMEM containing 10% heat-inactivated fetal calf serum (FCS), 100 U/ml penicillin, 100 μg/ml streptomycin, 100 μg/ml G418, 40 μg/ml zeocin and 100 μg/ml hygromycin). The cells are seeded at 20.000 cells/well into 384-well black clear bottom sterile plates (poly-L-lysine-coated, Becton Dickinson). The seeded plates are incubated overnight at 37° C. in 5% $CO_2$. The KCl solution is prepared as 80 mM stock solution in assay buffer (HBSS containing 0.1% BSA, 20 mM HEPES, 0.375 g/l $NaHCO_3$, adjusted to pH 7.4 with NaOH) for use in the assay at a final concentration of 20 mM. Antagonists are prepared as 10 mM stock solutions in DMSO, then diluted in 384 w plates first in DMSO, then in assay buffer to obtain 3× stocks. On the day of the assay, 25 μl of staining buffer (HBSS containing 20 mM HEPES, 0.375 g/l $NaHCO_3$, and 3 μM of the fluorescent calcium indicator fluo-4 AM (1 mM stock solution in DMSO, containing 10% pluronic) is added to each well of the seeded plate. The 384-well cell-plates are incubated for 60 min at 37° C. in 5% $CO_2$ followed by washing with 2×50 μl per well using assay buffer leaving 50 μl/well of this buffer for equilibration at room temperature (30-60 min). Within the Fluorescent Imaging Plate Reader (FLIPR, Molecular Devices), antagonists are added to the plate in a volume of 25 μl/well, incubated for 3 min and finally 25 μl/well of KCl solution is added for cellular depolarization. Fluorescence is measured for each well at 2 second intervals for 8 minutes, and the area under the curve of each fluorescence peak is compared to the area of the fluorescence peak induced by 20 mM KCl with vehicle in place of antagonist. For each antagonist, the $IC_{50}$ value (the concentration (in nM) of compound needed to inhibit 50% of the KCl-induced fluorescence response) up to 10 μM is determined.

Compounds of examples 25, 75, and 10A have been tested >10 μM in this assay. Compounds of examples 45, 48, 52, 53, 54, 55, 56, 57, 58, 59, 60, 61, 62, 63, 64, 65, 66, 67, 68, 69, 70, 53B, 60A, and 65A have not been tested in this assay. $IC_{50}$ values of the remaining 140 example compounds are in the range of 156 to 9777 nM with an average of 1273 nM.

In Vitro Assay T Channel:

The T channel antagonistic activity ($IC_{50}$ values) of the compounds of formula (I) is determined in accordance with the following experimental method and data are shown in Table 1.

Human embryonic kidney (HEK293) cells expressing the human $Ca_v3.1$ $Ca_v3.2$ or $Ca_v3.3$ channel, respectively, are grown in culture medium (DMEM containing 10% heat-inactivated fetal calf serum (FCS), 100 U/ml penicillin, 100 μg/ml streptomycin and 1 mg/ml G418). The cells are seeded at 20.000 cells/well into 384-well black clear bottom sterile plates (poly-L-lysine-coated, Becton Dickinson). The seeded plates are incubated overnight at 37° C. in 5% $CO_2$. The $Ca^{2+}$ solution is prepared as 100 mM stock solution in 100 mM tetraethylammoniumchloride (TEA-chloride), 50 mM HEPES, 2.5 mM $CaCl_2$, 5 mM KCl, 1 mM $MgCl_2$, adjusted to pH 7.2 with TEA-hydroxide, for use in the assay at a final concentration of 10 mM. Antagonists are prepared as 10 mM stock solutions in DMSO, then diluted in 384 w plates first in DMSO, then in 100 mM TEA-chloride, 50 mM HEPES, 2.5 mM $CaCl_2$, 5 mM KCl, 1 mM $MgCl_2$, adjusted to pH 7.2 with TEA-hydroxide, to obtain 9× stocks. On the day of the assay, 25 μl of staining buffer (HBSS containing 20 mM HEPES, 0.375 g/l $NaHCO_3$ and 3 μM of the fluorescent calcium indicator fluo-4 AM (1 mM stock solution in DMSO, containing 10% pluronic) is added to each well of the seeded plate. The 384-well cell-plates are incubated for 60 min at 37° C. in 5% $CO_2$ followed by washing with 2×50 μl per well using HBSS containing 0.1% BSA, 20 mM HEPES, 0.375 g/l $NaHCO_3$, leaving 50 Owen of this buffer for equilibration at room temperature (30-60 min). Within the Fluorescent Imaging Plate Reader (FLIPR, Molecular Devices), antagonists are added to the plate in a volume of 6.25 μl/well, incubated for 3 min, and finally 6.25 Owen of $Ca^{2+}$ solution is added. Fluorescence is measured for each well at 2 second intervals for 8 minutes, and the area under the curve of each fluorescence peak is compared to the area of the fluorescence peak induced by 10 mM $Ca^{2+}$ with vehicle in place of antagonist. For each antagonist, the $IC_{50}$ value (the concentration (in nM) of compound needed to inhibit 50% of the $Ca^{2+}$-induced fluorescence response) up to 10 μM is determined.

TABLE 1

| Compound | $IC_{50}$ | Compound | $IC_{50}$ | Compound | $IC_{50}$ | Compound | $IC_{50}$ |
|---|---|---|---|---|---|---|---|
| 1 | 2295 | 2 | 5982 | 3 | 6632 | 4 | 3607.8 |
| 5 | 8415 | 6 | 4854.5 | 7 | 4401.5 | 8 | 1792 |
| 9 | >10000 | 10 | 5867.5 | 11 | >10000 | 12 | >10000 |
| 13 | 2728 | 14 | 8951.5 | 15 | >10000 | 16 | 5689.5 |
| 17 | 1255 | 18 | 1337 | 19 | 1570 | 20 | >10000 |
| 21 | 3470 | 22 | >10000 | 23 | 3309.5 | 24 | >10000 |
| 25 | >10000 | 26 | >10000 | 27 | >10000 | 28 | 2531 |
| 29 | >10000 | 30 | 1784.5 | 31 | 2575.5 | 32 | 1481.5 |
| 33 | 2993 | 34 | 2563 | 36 | 1334 | 37 | 6650.5 |
| 38 | 6698 | 39 | >10000 | 40 | 3326.5 | 41 | >10000 |
| 42 | >10000 | 43 | >10000 | 44 | >10000 | 45 | NA |
| 46 | >10000 | 48 | NA | 49 | >10000 | 50 | >10000 |
| 51 | >10000 | 52 | NA | 53 | NA | 54 | NA |
| 55 | NA | 56 | NA | 57 | NA | 58 | NA |
| 59 | NA | 60 | NA | 61 | NA | 62 | NA |
| 63 | NA | 64 | NA | 65 | NA | 66 | NA |

TABLE 1-continued

| Compound | IC$_{50}$ | Compound | IC$_{50}$ | Compound | IC$_{50}$ | Compound | IC$_{50}$ |
|---|---|---|---|---|---|---|---|
| 67 | NA | 68 | NA | 69 | NA | 70 | NA |
| 74 | 6074 | 75 | >10000 | 76 | >10000 | 77 | 9099 |
| 78 | >10000 | 79 | 2917 | 80 | 3710 | 1A | 4938 |
| 2A | 2308 | 3A | 4601 | 4A | 4222 | 5A | 3454 |
| 6A | 6831 | 7A | 3141.5 | 8A | 1626 | 9A | 2337 |
| 10A | >10000 | 11A | 4651 | 12A | 4234 | 13A | 4339 |
| 14A | 3178 | 15A | 8631.5 | 16A | 2391 | 17A | 1371 |
| 17B | 751 | 17C | 550.5 | 18A | 2054 | 19A | 1705 |
| 20A | 4566 | 21A | 2420 | 22A | 6932 | 23A | 4009 |
| 24A | 2750 | 25A | 1591 | 26A | 2091 | 26B | >10000 |
| 26C | 4638.3 | 26D | 1047 | 26E | 1112 | 26F | 951 |
| 26G | 935 | 27A | 6738 | 27B | 4734.5 | 28A | 3456 |
| 29A | 4506 | 30A | 1246.5 | 31A | 2604 | 32A | 3392 |
| 33A | 1656 | 34A | 4335 | 35A | 1335 | 36A | 1005.5 |
| 36B | 2446 | 37A | 935 | 38A | 2511.5 | 39A | 7493 |
| 40A | 8928.5 | 41A | 8262 | 42A | >10000 | 43A | 2709 |
| 44A | >10000 | 45A | 1704.5 | 46A | 2558.5 | 47A | 8030 |
| 48A | >10000 | 49A | 8504 | 50A | >10000 | 51A | 4429 |
| 52A | 4208 | 53A | 688 | 53B | NA | 53C | 906 |
| 54A | 1143 | 55A | 1067 | 56A | 2525 | 57A | 1985 |
| 58A | 762 | 59A | 952 | 60A | NA | 61A | 571 |
| 62A | 469 | 63A | 1441 | 64A | 914 | 65A | NA |
| 66A | 680 | 67A | 778 | 68A | 839 | 69A | 727 |
| 70A | 793 | 71A | 1454 | 72A | 2290 | 73A | 1750 |
| 73A | 2004 | 74A | 8601 | 75A | 1781 | 76A | 2124 |
| 77A | 2629 | 79A | 9474 | 80A | 4176 | | |

NA = not available/not tested

Effect on Isolated Hearts According to the Langendorff Method (Lgdff)

The compounds were tested for their potential to reduce blood pressure and their effect on the contractility of the heart muscle. EC$_{50}$ values on isolated mouse hearts were determined according to Literature (Doring H J., The isolated perfused heart according to Langendorff technique—function—application, Physiol. Bohemoslov. 1990, 39(6), 481-504; Kligfield P, Horner H, Brachfeld N., A model of graded ischemia in the isolated perfused rat heart, J. Appl. Physiol. 1976 June, 40(6), 1004-8).

51 example compounds have been measured using the procedure described above for the Langendorff experiment. The measured EC$_{50}$ values were in the range of 4 to 669 nM with an average of 37 nM. Results for selected compounds are given in table 2.

TABLE 2

| Compound of Example | Lgdff EC$_{50}$ [nM] |
|---|---|
| 2A | 15 |
| 10A | 13 |
| 17A | 12 |
| 21A | 10 |
| 26C | 4 |
| 46A | 9 |
| 61A | 5 |

The invention claimed is:

1. A compound of formula (I)

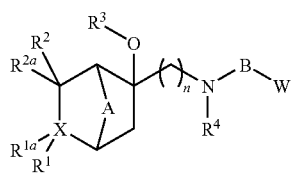

Formula (I)

wherein
X represents a carbon atom, and $R^{1a}$ and $R^{2a}$ together form a bond; or
X represents a carbon atom, $R^{1a}$ represents hydrogen or $(C_{1-4})$alkoxy, and $R^{2a}$ represents hydrogen;
$R^1$ and $R^2$, if not indicated otherwise, independently represent hydrogen; $(C_{1-5})$alkyl; aryl, which is unsubstituted, or independently mono-, di-, or tri-substituted wherein the substituents are independently selected from the group consisting of $(C_{1-4})$alkyl, $(C_{1-4})$alkoxy, halogen, trifluoromethyl, trifluoromethoxy, cyano, and $(C_{3-6})$cycloalkyl; or
heteroaryl, which is unsubstituted, or independently mono-, di-, or tri-substituted wherein the substituents are independently selected from the group consisting of $(C_{1-4})$alkyl, $(C_{1-4})$alkoxy, halogen, cyano, trifluoromethyl, and trifluoromethoxy; with the proviso that in the case $R^2$ represents aryl or heteroaryl, $R^1$ may not represent aryl or heteroaryl, wherein the aryl and heteroaryl independently are unsubstituted or substituted as defined before;
$R^3$ represents hydrogen, or —CO—$R^{31}$;
$R^{31}$ represents $(C_{1-5})$alkyl, $(C_{1-3})$fluoroalkyl, $(C_{3-6})$cycloalkyl, $(C_{3-6})$cycloalkyl-$(C_{1-3})$alkyl, $(C_{1-5})$alkoxy, $(C_{1-2})$alkoxy-$(C_{1-3})$alkyl, or $R^{32}R^{33}N$—;
$R^{32}$ represents $(C_{1-5})$alkyl;
$R^{33}$ represents hydrogen, or $(C_{1-5})$alkyl;
n represents the integer 1, 2, 3, or 4;
B represents a group —$(CH_2)_m$—, wherein m represents the integer 1, 2, 3, 4, or 5; or B together with $R^4$ and the nitrogen atom to which B and $R^4$ are attached forms a 4- to 6-membered saturated ring;
A represents a linear $(C_{1-3})$alkan-diyl chain, wherein said linear $(C_{1-3})$alkan-diyl chain is optionally substituted with one or more methyl;
$R^4$ represents hydrogen; $(C_{1-5})$alkyl; $(C_{1-2})$alkoxy-$(C_{1-3})$alkyl; $(C_{1-3})$fluoroalkyl;
$(C_{3-6})$cycloalkyl; $(C_{3-6})$cycloalkyl-$(C_{1-3})$alkyl; or $R^4$ together with B and the nitrogen atom to which $R^4$ and B are attached forms a 4- to 6-membered saturated ring;

W represents aryl, which is unsubstituted, mono-, di-, or tri-substituted, wherein the substituents are independently selected from the group consisting of $(C_{1-4})$alkyl, $(C_{1-4})$alkoxy, halogen, trifluoromethyl, trifluoromethoxy, cyano, and $(C_{3-6})$cycloalkyl;

or W represents heteroaryl, which is unsubstituted, mono-, di-, or tri-substituted, wherein the substituents are independently selected from the group consisting of $(C_{1-4})$alkyl, $(C_{1-4})$alkoxy, halogen, cyano, trifluoromethyl, and trifluoromethoxy;

or W represents a group selected from:

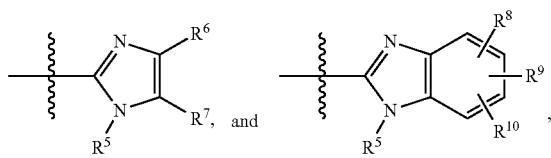

wherein $R^5$ represents hydrogen, or $(C_{1-5})$alkyl;

$R^6$ and $R^7$ independently represent hydrogen; $(C_{1-5})$alkyl; or phenyl, which is independently unsubstituted, mono-, or di-substituted, wherein each substituent is independently selected from the group consisting of $(C_{1-4})$alkyl, $(C_{1-4})$alkoxy, halogen and trifluoromethyl;

$R^8$, $R^9$ and $R^{10}$ independently represent hydrogen, halogen, $(C_{1-5})$alkyl, hydroxy, $(C_{1-5})$alkoxy, —O—CO—$(C_{1-5})$alkyl, $(C_{1-3})$fluoroalkyl, $(C_{1-3})$fluoroalkoxy, —COOH, —CO—$(C_{1-5})$alkoxy, $(C_{1-2})$alkoxy-$(C_{1-4})$alkoxy, or —NH—CO—$(C_{1-5})$alkyl;

in a free or a salt form.

2. The compound according to claim 1, wherein the configuration of the bridged cyclohexane, or cyclohexene moiety is such that the $R^3$—O— substituent and the bridge A of the cyclohexane or cyclohexene moiety are in cis relation; in a free or a salt form.

3. The compound according to claim 1, wherein X represents a carbon atom; $R^{1a}$ and $R^{2a}$ together form a bond; $R^1$ represents aryl, which is unsubstituted, mono-, di-, or tri-substituted wherein the substituents are independently selected from the group consisting of $(C_{1-4})$alkyl, $(C_{1-4})$alkoxy, halogen and trifluoromethyl; or $R^1$ represents unsubstituted heteroaryl; and $R^2$ represents hydrogen or $(C_{1-5})$alkyl;

in a free or a salt form.

4. The compound according to claim 1, wherein A represents —$(CH_2)_p$—, wherein p represents the integer 2 or 3;

in a free or a salt form.

5. The compound according to claim 1, wherein $R^3$ represents —CO—$R^{31}$; and $R^{31}$ represents $(C_{1-5})$alkyl, $(C_{1-3})$fluoroalkyl, or $(C_{3-6})$cycloalkyl;

in a free or a salt form.

6. The compound according to claim 1, wherein B represents a group —$(CH_2)_m$—, and m represents the integer 1 to 3;

in a free or a salt form.

7. The compound according to claim 1, wherein n represents the integer 2;

in a free or a salt form.

8. The compound according to claim 1, wherein $R^4$ represents (C1-5)alkyl;

in a free or a salt form.

9. The compound according to claim 1, wherein W represents

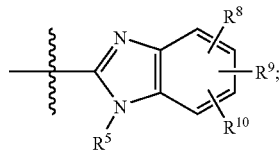

in a free or a salt form.

10. The compound according to claim 9, wherein W represents

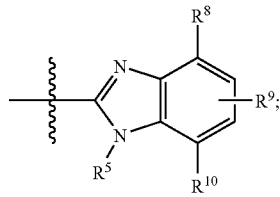

wherein $R^8$ and $R^{10}$ are independently $(C_{1-5})$alkoxy, and $R^5$ and $R^9$ represent hydrogen;

in a free or a salt form.

11. The compound according to claim 1, selected from the group consisting of (1S,2S,4S)-2-(2-{[3-(1H-Benzoimidazol-2-yl)-propyl]-methyl-amino}-ethyl)-5-phenyl-bicyclo[2.2.2]oct-5-en-2-ol;

(1R,2R,4R)-2-(2-{[3-(1H-Benzoimidazol-2-yl)-propyl]-methyl-amino}-ethyl)-5-phenyl-bicyclo[2.2.2]oct-5-en-2-ol;

(1S,2S,4S)-2-(2-{[3-(1H-Benzoimidazol-2-yl)-propyl]-methyl-amino}-ethyl)-5-(3-methoxy-phenyl)-bicyclo[2.2.2]oct-5-en-2-ol;

(1R,2R,4R)-2-(2-{[3-(1H-Benzoimidazol-2-yl)-propyl]-methyl-amino}-ethyl)-5-(3-methoxy-phenyl)-bicyclo[2.2.2]oct-5-en-2-ol;

(1S,2S,4S)-2-(2-{[3-(1H-Benzoimidazol-2-yl)-propyl]-methyl-amino}-ethyl)-5-(2,6-dimethyl-phenyl)-bicyclo[2.2.2]oct-5-en-2-ol;

(1R,2R,4R)-2-(2-{[3-(1H-Benzoimidazol-2-yl)-propyl]-methyl-amino}-ethyl)-5-(2,6-dimethyl-phenyl)-bicyclo[2.2.2]oct-5-en-2-ol;

(1S,2S,4S)-2-(2-{[3-(1H-Benzoimidazol-2-yl)-propyl]-methyl-amino}-ethyl)-5-o-tolyl-bicyclo[2.2.2]oct-5-en-2-ol;

(1R,2R,4R)-2-(2-{[3-(1H-Benzoimidazol-2-yl)-propyl]-methyl-amino}-ethyl)-5-o-tolyl-bicyclo[2.2.2]oct-5-en-2-ol;

(1S,2S,4S)-2-(2-{[3-(1H-Benzoimidazol-2-yl)-propyl] methyl-amino}-ethyl)-5-m-tolyl-bicyclo[2.2.2]oct-5-en-2-ol;

(1R,2R,4R)-2-(2-{[3-(1H-Benzoimidazol-2-yl)-propyl]-methyl-amino}-ethyl)-5-m-tolyl-bicyclo[2.2.2]oct-5-en-2-ol;

(1S,2S,4S)-2-(2-{[3-(1H-Benzoimidazol-2-yl)-propyl]-methyl-amino}-ethyl)-5-p-tolyl-bicyclo[2.2.2]oct-5-en-2-ol;

(1R,2R,4R)-2-(2-{[3-(1H-Benzoimidazol-2-yl)-propyl]-methyl-amino}-ethyl)-5-p-tolyl-bicyclo[2.2.2]oct-5-en-2-ol;

(1S,2S,4S)-2-(2-{[3-(1H-Benzoimidazol-2-yl)-propyl]-methyl-amino}-ethyl)-5-(3-fluoro-phenyl)-bicyclo[2.2.2]oct-5-en-2-ol;
(1R,2R,4R)-2-(2-{[3-(1H-Benzoimidazol-2-yl)-propyl]-methyl-amino}-ethyl)-5-(3-fluoro-phenyl)-bicyclo[2.2.2]oct-5-en-2-ol;
(1S,2S,4S)-2-(2-{[3-(1H-Benzoimidazol-2-yl)-propyl]-methyl-amino}-ethyl)-5-(4-fluoro-phenyl)-bicyclo[2.2.2]oct-5-en-2-ol;
(1R,2R,4R)-2-(2-{[3-(1H-Benzoimidazol-2-yl)-propyl]-methyl-amino}-ethyl)-5-(4-fluoro-phenyl)-bicyclo[2.2.2]oct-5-en-2-ol;
(1S,2S,4S)-2-(2-{[3-(1H-Benzoimidazol-2-yl)-propyl]-methyl-amino}-ethyl)-5-pyridin-3-yl-bicyclo[2.2.2]oct-5-en-2-ol;
(1R,2R,4R)-2-(2-{[3-(1H-Benzoimidazol-2-yl)-propyl]-methyl-amino}-ethyl)-5-pyridin-3-yl-bicyclo[2.2.2]oct-5-en-2-ol;
(1S,2S,4S)-2-(2-{[3-(1H-Benzoimidazol-2-yl)-propyl]-methyl-amino}-ethyl)-5-naphthalen-2-yl-bicyclo[2.2.2]oct-5-en-2-ol;
(1R,2R,4R)-2-(2-{[3-(1H-Benzoimidazol-2-yl)-propyl]-methyl-amino}-ethyl)-5-naphthalen-2-yl-bicyclo[2.2.2]oct-5-en-2-ol;
(1S,2S,4S)-2-(2-{[2-(1H-Benzoimidazol-2-yl)-ethyl]-methyl-amino}-ethyl)-5-phenyl-bicyclo[2.2.2]oct-5-en-2-ol;
(1R,2R,4R)-2-(2-{[2-(1H-Benzoimidazol-2-yl)-ethyl]-methyl-amino}-ethyl)-5-phenyl-bicyclo[2.2.2]oct-5-en-2-ol;
(1S,2S,4S)-2-{2-[(1H-Benzoimidazol-2-ylmethyl)-methyl-amino]-ethyl}-5-phenyl-bicyclo[2.2.2]oct-5-en-2-ol;
(1R,2R,4R)-2-{2-[(1H-Benzoimidazol-2-ylmethyl)-methyl-amino]-ethyl}-5-phenyl-bicyclo[2.2.2]oct-5-en-2-ol;
(1S,2S,4S)-2-{2-[Methyl-(3-phenyl-propyl)-amino]-ethyl}-5-phenyl-bicyclo[2.2.2]oct-5-en-2-ol;
(1R,2R,4R)-2-{2-[Methyl-(3-phenyl-propyl)-amino]-ethyl}-5-phenyl-bicyclo[2.2.2]oct-5-en-2-ol;
(1S,2S,4S)-2-(2-{[3-(1H-Benzoimidazol-2-yl)-propyl]methyl-amino}-ethyl)-6-methyl-5-propyl-bicyclo[2.2.2]oct-5-en-2-ol;
(1R,2R,4R)-2-(2-{[3-(1H-Benzoimidazol-2-yl)-propyl]-methyl-amino}-ethyl)-6-methyl-5-propyl-bicyclo[2.2.2]oct-5-en-2-ol;
(1S,2S,4S)-2-(2-{[3-(1H-Benzoimidazol-2-yl)-propyl]-methyl-amino}-ethyl)-5-methyl-6-phenyl-bicyclo[2.2.2]oct-5-en-2-ol;
(1R,2R,4R)-2-(2-{[3-(1H-Benzoimidazol-2-yl)-propyl]-methyl-amino}-ethyl)-5-methyl-6-phenyl-bicyclo[2.2.2]oct-5-en-2-ol;
2-(3-{[2-((1S,2S,4S)-2-Hydroxy-5-phenyl-bicyclo[2.2.2]oct-5-en-2-yl)-ethyl]-methyl-amino}-propyl)-1H-benzoimidazole-4-carboxylic acid methyl ester;
2-(3-{[2-((1R,2R,4R)-2-Hydroxy-5-phenyl-bicyclo[2.2.2]oct-5-en-2-yl)-ethyl]-methyl-amino}-propyl)-1H-benzoimidazole-4-carboxylic acid methyl ester;
2-(3-{[2-((1S,2S,4S)-2-Hydroxy-5-phenyl-bicyclo[2.2.2]oct-5-en-2-yl)-ethyl]-methyl-amino}-propyl)-1H-benzoimidazole-5-carboxylic acid methyl ester;
2-(3-{[2-((1R,2R,4R)-2-Hydroxy-5-phenyl-bicyclo[2.2.2]oct-5-en-2-yl)-ethyl]-methyl-amino}-propyl)-1H-benzoimidazole-5-carboxylic acid methyl ester;
(1S,2S,4S)-2-(2-{[3-(1H-Benzoimidazol-2-yl)-propyl]-methyl-amino}-ethyl)-5-thiophen-2-yl-bicyclo[2.2.2]oct-5-en-2-ol;
(1R,2R,4R)-2-(2-{[3-(1H-Benzoimidazol-2-yl)-propyl]-methyl-amino}-ethyl)-5-thiophen-2-yl-bicyclo[2.2.2]oct-5-en-2-ol;
(1S,2S,4S)-2-(2-{[3-(1H-Benzoimidazol-2-yl)-propyl]-methyl-amino}-ethyl)-5-(4-methoxy-phenyl)-bicyclo[2.2.2]oct-5-en-2-ol;
(1R,2R,4R)-2-(2-{[3-(1H-Benzoimidazol-2-yl)-propyl]-methyl-amino}-ethyl)-5-(4-methoxy-phenyl)-bicyclo[2.2.2]oct-5-en-2-ol;
(1S,2S,4S)-2-(2-{[3-(1H-Benzoimidazol-2-yl)-propyl]-methyl-amino}-ethyl)-5-(2-methoxy-phenyl)-bicyclo[2.2.2]oct-5-en-2-ol;
(1R,2R,4R)-2-(2-{[3-(1H-Benzoimidazol-2-yl)-propyl]-methyl-amino}-ethyl)-5-(2-methoxy-phenyl)-bicyclo[2.2.2]oct-5-en-2-ol;
(1S,2S,4S)-2-(2-{[3-(1H-Benzoimidazol-2-yl)-propyl]-methyl-amino}-ethyl)-5-thiazol-2-yl-bicyclo[2.2.2]oct-5-en-2-ol;
(1R,2R,4R)-2-(2-{[3-(1H-Benzoimidazol-2-yl)-propyl]-methyl-amino}-ethyl)-5-thiazol-2-yl-bicyclo[2.2.2]oct-5-en-2-ol;
(1S,2S,4S)-2-(2-{[3-(1H-Benzoimidazol-2-yl)-propyl]-methyl-amino}-ethyl)-5-oxazol-2-yl-bicyclo[2.2.2]oct-5-en-2-ol;
(1R,2R,4R)-2-(2-{[3-(1H-Benzoimidazol-2-yl)-propyl]-methyl-amino}-ethyl)-5-oxazol-2-yl-bicyclo[2.2.2]oct-5-en-2-ol;
(1S,2S,4S)-2-(2-{[3-(4-Methoxy-1H-benzoimidazol-2-yl)-propyl]-methyl-amino}-ethyl)-5-phenyl-bicyclo[2.2.2]oct-5-en-2-ol;
(1R,2R,4R)-2-(2-{[3-(4-Methoxy-1H-benzoimidazol-2-yl)-propyl]-methyl-amino}-ethyl)-5-phenyl-bicyclo[2.2.2]oct-5-en-2-ol;
(1S,2S,4S)-2-(2-{[3-(5,6-Dichloro-1H-benzoimidazol-2-yl)-propyl]-methyl-amino}-ethyl)-5-phenyl-bicyclo[2.2.2]oct-5-en-2-ol;
(1R,2R,4R)-2-(2-{[3-(5,6-Dichloro-1H-benzoimidazol-2-yl)-propyl]-methyl-amino}-ethyl)-5-phenyl-bicyclo[2.2.2]oct-5-en-2-ol;
(1S,2S,4S)-2-(2-{[3-(5,6-Dimethoxy-1H-benzoimidazol-2-yl)-propyl]-methyl-amino}-ethyl)-5-phenyl-bicyclo[2.2.2]oct-5-en-2-ol;
(1R,2R,4R)-2-(2-{[3-(5,6-Dimethoxy-1H-benzoimidazol-2-yl)-propyl]-methyl-amino}-ethyl)-5-phenyl-bicyclo[2.2.2]oct-5-en-2-ol;
(1S,2S,4S)-2-(2-{[3-(5-Methoxy-1H-benzoimidazol-2-yl)-propyl]-methyl-amino}-ethyl)-5-phenyl-bicyclo[2.2.2]oct-5-en-2-ol;
(1R,2R,4R)-2-(2-{[3-(5-Methoxy-1H-benzoimidazol-2-yl)-propyl]-methyl-amino}-ethyl)-5-phenyl-bicyclo[2.2.2]oct-5-en-2-ol;
(1S,2S,4S)-2-(2-{[3-(7-Methoxy-4-methyl-1H-benzoimidazol-2-yl)-propyl]-methyl-amino}-ethyl)-5-phenyl-bicyclo[2.2.2]oct-5-en-2-ol;
(1R,2R,4R)-2-(2-{[3-(7-Methoxy-4-methyl-1H-benzoimidazol-2-yl)-propyl]methyl-amino}-ethyl)-5-phenyl-bicyclo[2.2.2]oct-5-en-2-ol;
(1S,2S,4S)-2-(2-{[3-(7-Ethoxy-1H-benzoimidazol-2-yl)-propyl]-methyl-amino}-ethyl)-5-phenyl-bicyclo[2.2.2]oct-5-en-2-ol;
(1R,2R,4R)-2-(2-{[3-(7-Ethoxy-1H-benzoimidazol-2-yl)-propyl]-methyl-amino}-ethyl)-5-phenyl-bicyclo[2.2.2]oct-5-en-2-ol;
(1S,2S,4S)-2-(2-{[2-(4-Methoxy-1H-benzoimidazol-2-yl)-ethyl]-methyl-amino}-ethyl)-5-phenyl-bicyclo[2.2.2]oct-5-en-2-ol;

(1R,2R,4R)-2-(2-{[2-(4-Methoxy-1H-benzoimidazol-2-yl)-ethyl]-methyl-amino}-ethyl)-5-phenyl-bicyclo[2.2.2]oct-5-en-2-ol;
(1S,2S,4S)-2-(2-{[3-(7-Isopropoxy-1H-benzoimidazol-2-yl)-propyl]-methyl-amino}-ethyl)-5-phenyl-bicyclo[2.2.2]oct-5-en-2-ol;
(1R,2R,4R)-2-(2-{[3-(7-Isopropoxy-1H-benzoimidazol-2-yl)-propyl]-methyl-amino}-ethyl)-5-phenyl-bicyclo[2.2.2]oct-5-en-2-ol;
2-(3-{[2-((1S,2S,4S)-2-Hydroxy-5-phenyl-bicyclo[2.2.2]oct-5-en-2-yl)-ethyl]-methyl-amino}-propyl)-3H-benzoimidazol-4-ol;
2-(3-{[2-((1R,2R,4R)-2-Hydroxy-5-phenyl-bicyclo[2.2.2]oct-5-en-2-yl)-ethyl]-methyl-amino}-propyl)-3H-benzoimidazol-4-ol;
(1S,5S,6S)-6-(2-{[3-(7-Methoxy-1H-benzoimidazol-2-yl)-propyl]-methyl-amino}-ethyl)-8-phenyl-bicyclo[3.2.2]non-8-en-6-ol;
(1R,5R,6R)-6-(2-{[3-(7-Methoxy-1H-benzoimidazol-2-yl)-propyl]-methyl-amino}-ethyl)-8-phenyl-bicyclo[3.2.2]non-8-en-6-ol;
(1S,2S,4S)-2-(2-{[3-(4-Methoxy-1-methyl-1H-benzoimidazol-2-yl)-propyl]-methyl-amino}-ethyl)-5-phenyl-bicyclo[2.2.2]oct-5-en-2-ol;
(1R,2R,4R)-2-(2-{[3-(4-Methoxy-1-methyl-1H-benzoimidazol-2-yl)-propyl]-methyl-amino}-ethyl)-5-phenyl-bicyclo[2.2.2]oct-5-en-2-ol;
(1S,2S,4S)-2-(2-{[2-(3,4-Diethoxy-phenyl)-ethyl]-ethyl-amino}-ethyl)-5-phenyl-bicyclo[2.2.2]oct-5-en-2-ol;
(1R,2R,4R)-2-(2-{[2-(3,4-Diethoxy-phenyl)-ethyl]-ethyl-amino}-ethyl)-5-phenyl-bicyclo[2.2.2]oct-5-en-2-ol;
(1S,2S,4S)-2-(2-{[3-(3,4-Dimethoxy-phenyl)-propyl]-methyl-amino}-ethyl)-5-phenyl-bicyclo[2.2.2]oct-5-en-2-ol;
(1R,2R,4R)-2-(2-{[3-(3,4-Dimethoxy-phenyl)-propyl]-methyl-amino}-ethyl)-5-phenyl-bicyclo[2.2.2]oct-5-en-2-ol;
(1S,2S,4S)-2-(2-{[3-(3,4-Diethoxy-phenyl)-propyl]-methyl-amino}-ethyl)-5-phenyl-bicyclo[2.2.2]oct-5-en-2-ol;
(1R,2R,4R)-2-(2-{[3-(3,4-Diethoxy-phenyl)-propyl]-methyl-amino}-ethyl)-5-phenyl-bicyclo[2.2.2]oct-5-en-2-ol;
(1S,2S,4S)-2-{2-[(3-Furo[2,3-b]pyridin-5-yl-propyl)-methyl-amino]-ethyl}-5-phenyl-bicyclo[2.2.2]oct-5-en-2-ol;
(1R,2R,4R)-2-{2-[(3-Furo[2,3-b]pyridin-5-yl-propyl)-methyl-amino]-ethyl}-5-phenyl-bicyclo[2.2.2]oct-5-en-2-ol;
(1S,2S,4S)-2-(2-{Methyl-[3-(2-methyl-furo[2,3-b]pyridin-5-yl)-propyl]-amino}-ethyl)-5-phenyl-bicyclo[2.2.2]oct-5-en-2-ol;
(1R,2R,4R)-2-(2-{Methyl-[3-(2-methyl-furo[2,3-b]pyridin-5-yl)-propyl]-amino}-ethyl)-5-phenyl-bicyclo[2.2.2]oct-5-en-2-ol;
(1S,2S,4S)-2-{2-[Methyl-(3-pyridin-3-yl-propyl)-amino]-ethyl}-5-phenyl-bicyclo[2.2.2]oct-5-en-2-ol;
(1R,2R,4R)-2-{2-[Methyl-(3-pyridin-3-yl-propyl)-amino]-ethyl}-5-phenyl-bicyclo[2.2.2]oct-5-en-2-ol;
(1S,2S,4S)-2-{2-[(3-Isoquinolin-4-yl-propyl)-methyl-amino]-ethyl}-5-phenyl-bicyclo[2.2.2]oct-5-en-2-ol;
(1R,2R,4R)-2-{2-[(3-Isoquinolin-4-yl-propyl)-methyl-amino]-ethyl}-5-phenyl-bicyclo[2.2.2]oct-5-en-2-ol;
(1S,2S,4S)-2-{2-[Methyl-(3-quinolin-3-yl-propyl)-amino]-ethyl}-5-phenyl-bicyclo[2.2.2]oct-5-en-2-ol;
(1R,2R,4R)-2-{2-[Methyl-(3-quinolin-3-yl-propyl)-amino]-ethyl}-5-phenyl-bicyclo[2.2.2]oct-5-en-2-ol;
(1S,2S,4S)-2-{2-[Methyl-(3-quinolin-4-yl-propyl)-amino]-ethyl}-5-phenyl-bicyclo[2.2.2]oct-5-en-2-ol;
(1R,2R,4R)-2-{2-[Methyl-(3-quinolin-4-yl-propyl)-amino]-ethyl}-5-phenyl-bicyclo[2.2.2]oct-5-en-2-ol;
(1S,2R,4S)-2-(2-{[3-(1H-Benzoimidazol-2-yl)-propyl]-methyl-amino}-ethyl)-5-methyl-6-phenyl-bicyclo[2.2.2]oct-5-en-2-ol;
(1S,2S,4R)-2-(2-{[3-(1H-Benzoimidazol-2-yl)-propyl]-methyl-amino}-ethyl)-5-methyl-6-phenyl-bicyclo[2.2.2]oct-5-en-2-ol;
N-[2-(3-{[2-((1S,2S,4S)-2-Hydroxy-5-phenyl-bicyclo[2.2.2]oct-5-en-2-yl)-ethyl]-methyl-amino}-propyl)-1H-benzoimidazol-4-yl]-acetamide;
N-[2-(3-{[2-((1R,2R,4R)-2-Hydroxy-5-phenyl-bicyclo[2.2.2]oct-5-en-2-yl)-ethyl]-methyl-amino}-propyl)-1H-benzoimidazol-4-yl]-acetamide;
(1S,2S,4S)-2-(2-{[3-(4-Chloro-1H-benzoimidazol-2-yl)-propyl]-methyl-amino}-ethyl)-5-phenyl-bicyclo[2.2.2]oct-5-en-2-ol;
(1R,2R,4R)-2-(2-{[3-(4-Chloro-1H-benzoimidazol-2-yl)-propyl]-methyl-amino}-ethyl)-5-phenyl-bicyclo[2.2.2]oct-5-en-2-ol;
(1S,2S,4S)-2-(2-{[3-(7-Chloro-4-methoxy-1H-benzoimidazol-2-yl)-propyl]-methyl-amino}-ethyl)-5-phenyl-bicyclo[2.2.2]oct-5-en-2-ol;
(1R,2R,4R)-2-(2-{[3-(7-Chloro-4-methoxy-1H-benzoimidazol-2-yl)-propyl]-methyl-amino}-ethyl)-5-phenyl-bicyclo[2.2.2]oct-5-en-2-ol;
(1S,2S,4S)-2-(2-{[3-(4,6-Dimethoxy-1H-benzoimidazol-2-yl)-propyl]-methyl-amino}-ethyl)-5-phenyl-bicyclo[2.2.2]oct-5-en-2-ol;
(1R,2R,4R)-2-(2-{[3-(4,6-Dimethoxy-1H-benzoimidazol-2-yl)-propyl]-methyl-amino}-ethyl)-5-phenyl-bicyclo[2.2.2]oct-5-en-2-ol;
(1S,2S,4S)-2-(2-{[3-(4,7-Dimethoxy-1H-benzoimidazol-2-yl)-propyl]-methyl-amino}-ethyl)-5-phenyl-bicyclo[2.2.2]oct-5-en-2-ol;
(1R,2R,4R)-2-(2-{[3-(4,7-Dimethoxy-1H-benzoimidazol-2-yl)-propyl]-methyl-amino}-ethyl)-5-phenyl-bicyclo[2.2.2]oct-5-en-2-ol;
(1S,2S,4S)-2-(2-{[3-(4,6-Bis-trifluoromethyl-1H-benzoimidazol-2-yl)-propyl]-methyl-amino}-ethyl)-5-phenyl-bicyclo[2.2.2]oct-5-en-2-ol;
(1R,2R,4R)-2-(2-{[3-(4,6-Bis-trifluoromethyl-1H-benzoimidazol-2-yl)-propyl]-methyl-amino}-ethyl)-5-phenyl-bicyclo[2.2.2]oct-5-en-2-ol;
(1S,2S,4S)-2-[2-({3-[4-(2-Methoxy-ethoxy)-1H-benzoimidazol-2-yl]-propyl}-methyl-amino)-ethyl]-5-phenyl-bicyclo[2.2.2]oct-5-en-2-ol;
(1R,2R,4R)-2-[2-({3-[4-(2-Methoxy-ethoxy)-1H-benzoimidazol-2-yl]-propyl}-methyl-amino)-ethyl]-5-phenyl-bicyclo[2.2.2]oct-5-en-2-ol;
(1S,2S,4S)-2-(2-{[3-(4,5-Dimethoxy-7-methyl-1H-benzoimidazol-2-yl)-propyl]-methyl-amino}-ethyl)-5-phenyl-bicyclo[2.2.2]oct-5-en-2-ol;
(1R,2R,4R)-2-(2-{[3-(4,5-Dimethoxy-7-methyl-1H-benzoimidazol-2-yl)-propyl]-methyl-amino}-ethyl)-5-phenyl-bicyclo[2.2.2]oct-5-en-2-ol;
(1S,5S,6S)-6-(2-{[3-(7-Methoxy-4-methyl-1H-benzoimidazol-2-yl)-propyl]-methyl-amino}-ethyl)-8-phenyl-bicyclo[3.2.2]non-8-en-6-ol;
(1R,5R,6R)-6-(2-{[3-(7-Methoxy-4-methyl-1H-benzoimidazol-2-yl)-propyl]-methyl-amino}-ethyl)-8-phenyl-bicyclo[3.2.2]non-8-en-6-ol;
(1S,2S,4S)-2-(2-{Methyl-[3-(4-trifluoromethoxy-1H-benzoimidazol-2-yl)-propyl]-amino}-ethyl)-5-phenyl-bicyclo[2.2.2]oct-5-en-2-ol;

(1R,2R,4R)-2-(2-{Methyl-[3-(4-trifluoromethoxy-1H-benzoimidazol-2-yl)-propyl]-amino}-ethyl)-5-phenyl-bicyclo[2.2.2]oct-5-en-2-ol;
(1S,5S,6S)-6-(2-{[3-(4,7-Dimethoxy-1H-benzoimidazol-2-yl)-propyl]-methyl-amino}-ethyl)-8-phenyl-bicyclo[3.2.2]non-8-en-6-ol;
(1R,5R,6R)-6-(2-{[3-(4,7-Dimethoxy-1H-benzoimidazol-2-yl)-propyl]-methyl-amino}-ethyl)-8-phenyl-bicyclo[3.2.2]non-8-en-6-ol;
(1R,2R,4R)-2-(2-{[3-(1H-Benzoimidazol-2-yl)-propyl]-methyl-amino}-ethyl)-bicyclo[2.2.2]oct-5-en-2-ol;
(1S,2S,4S)-2-(2-{[3-(1H-Benzoimidazol-2-yl)-propyl]-methyl-amino}-ethyl)-bicyclo[2.2.2]oct-5-en-2-ol;
(1R,2R,4R,5R)-2-(2-{[3-(1H-Benzoimidazol-2-yl)-propyl]-methyl-amino}-ethyl)-5-methoxy-5-phenyl-bicyclo[2.2.2]octan-2-ol;
(1S,2S,4S,5S)-2-(2-{[3-(1H-Benzoimidazol-2-yl)-propyl]-methyl-amino}-ethyl)-5-methoxy-5-phenyl-bicyclo[2.2.2]octan-2-ol;
(1S,2S,4R,5S)-2-(2-{[341H-Benzoimidazol-2-yl)-propyl]-methyl-amino}-ethyl)-5-methoxy-5-phenyl-bicyclo[2.2.2]octan-2-ol;
(1R,2R,4S,5R)-2-(2-{[3-(1H-Benzoimidazol-2-yl)-propyl]-methyl-amino}-ethyl)-5-methoxy-5-phenyl-bicyclo[2.2.2]octan-2-ol;
(1R,2R,4R,5S)-2-(2-{[3-(1H-Benzoimidazol-2-yl)-propyl]-methyl-amino}-ethyl)-5-methoxy-5-phenyl-bicyclo[2.2.2]octan-2-ol;
(1S,2S,4S,5R)-2-(2-{[3-(1H-Benzoimidazol-2-yl)-propyl]-methyl-amino}-ethyl)-5-methoxy-5-phenyl-bicyclo[2.2.2]octan-2-ol;
Isobutyric acid (1S,2S,4S)-2-(2-{[3-(1H-benzoimidazol-2-yl)-propyl]-methyl-amino}-ethyl)-5-phenyl-bicyclo[2.2.2]oct-5-en-2-yl ester;
Isobutyric acid (1R,2R,4R)-2-(2-{[3-(1H-benzoimidazol-2-yl)-propyl]-methyl-amino}-ethyl)-5-phenyl-bicyclo[2.2.2]oct-5-en-2-yl ester;
Isobutyric acid (1S,2S,4S)-2-(2-{[3-(1H-benzoimidazol-2-yl)-propyl]-methyl-amino}-ethyl)-5-(3-methoxyphenyl)-bicyclo[2.2.2]oct-5-en-2-yl ester;
Isobutyric acid (1R,2R,4R)-2-(2-{[3-(1H-benzoimidazol-2-yl)-propyl]-methyl-amino}-ethyl)-5-(3-methoxyphenyl)-bicyclo[2.2.2]oct-5-en-2-yl ester;
Isobutyric acid (1S,2S,4S)-2-(2-{[3-(1H-benzoimidazol-2-yl)-propyl]-methyl-amino}-ethyl)-5-(2,6-dimethylphenyl)-bicyclo[2.2.2]oct-5-en-2-yl ester;
Isobutyric acid (1R,2R,4R)-2-(2-{[3-(1H-benzoimidazol-2-yl)-propyl]-methyl-amino}-ethyl)-5-(2,6-dimethylphenyl)-bicyclo[2.2.2]oct-5-en-2-yl ester;
Isobutyric acid (1S,2S,4S)-2-(2-{[3-(1H-benzoimidazol-2-yl)-propyl]-methyl-amino}-ethyl)-5-o-tolyl-bicyclo[2.2.2]oct-5-en-2-yl ester;
Isobutyric acid (1R,2R,4R)-2-(2-{[3-(1H-benzoimidazol-2-yl)-propyl]-methyl-amino}-ethyl)-5-o-tolyl-bicyclo[2.2.2]oct-5-en-2-yl ester;
Isobutyric acid (1S,2S,4S)-2-(2-{[3-(1H-benzoimidazol-2-yl)-propyl]-methyl-amino}-ethyl)-5-m-tolyl-bicyclo[2.2.2]oct-5-en-2-yl ester;
Isobutyric acid (1R,2R,4R)-2-(2-{[3-(1H-benzoimidazol-2-yl)-propyl]-methyl-amino}-ethyl)-5-m-tolyl-bicyclo[2.2.2]oct-5-en-2-yl ester;
Isobutyric acid (1S,2S,4S)-2-(2-{[3-(1H-benzoimidazol-2-yl)-propyl]-methyl-amino}-ethyl)-5-p-tolyl-bicyclo[2.2.2]oct-5-en-2-yl ester;
Isobutyric acid (1R,2R,4R)-2-(2-{[3-(1H-benzoimidazol-2-yl)-propyl]methyl-amino}-ethyl)-5-p-tolyl-bicyclo[2.2.2]oct-5-en-2-yl ester;
Isobutyric acid (1S,2S,4S)-2-(2-{[3-(1H-benzoimidazol-2-yl)-propyl]-methyl-amino}-ethyl)-5-(3-fluoro-phenyl)-bicyclo[2.2.2]oct-5-en-2-yl ester;
Isobutyric acid (1R,2R,4R)-2-(2-{[3-(1H-benzoimidazol-2-yl)-propyl]-methyl-amino}-ethyl)-5-(3-fluoro-phenyl)-bicyclo[2.2.2]oct-5-en-2-yl ester;
Isobutyric acid (1S,2S,4S)-2-(2-{[3-(1H-benzoimidazol-2-yl)-propyl]-methyl-amino}-ethyl)-5-(4-fluoro-phenyl)-bicyclo[2.2.2]oct-5-en-2-yl ester;
Isobutyric acid (1R,2R,4R)-2-(2-{[3-(1H-benzoimidazol-2-yl)-propyl]-methyl-amino}-ethyl)-5-(4-fluoro-phenyl)-bicyclo[2.2.2]oct-5-en-2-yl ester;
Isobutyric acid (1S,2S,4S)-2-(2-{[3-(1H-benzoimidazol-2-yl)-propyl]-methyl-amino}-ethyl)-5-pyridin-3-yl-bicyclo[2.2.2]oct-5-en-2-yl ester;
Isobutyric acid (1R,2R,4R)-2-(2-{[3-(1H-benzoimidazol-2-yl)-propyl]-methyl-amino}-ethyl)-5-pyridin-3-yl-bicyclo[2.2.2]oct-5-en-2-yl ester;
Isobutyric acid (1S,2S,4S)-2-(2-{[3-(1H-benzoimidazol-2-yl)-propyl]-methyl-amino}-ethyl)-5-naphthalen-2-yl-bicyclo[2.2.2]oct-5-en-2-yl ester;
Isobutyric acid (1R,2R,4R)-2-(2-{[3-(1H-benzoimidazol-2-yl)-propyl]-methyl-amino}-ethyl)-5-naphthalen-2-yl-bicyclo[2.2.2]oct-5-en-2-yl ester;
Isobutyric acid (1S,2S,4S)-2-(2-{[2-(1H-benzoimidazol-2-yl)-ethyl]-methyl-amino}-ethyl)-5-phenyl-bicyclo[2.2.2]oct-5-en-2-yl ester;
Isobutyric acid (1R,2R,4R)-2-(2-{[2-(1H-benzoimidazol-2-yl)-ethyl]-methyl-amino}-ethyl)-5-phenyl-bicyclo[2.2.2]oct-5-en-2-yl ester;
Isobutyric acid (1S,2S,4S)-2-{2-[(1H-benzoimidazol-2-ylmethyl)-methyl-amino]-ethyl}-5-phenyl-bicyclo[2.2.2]oct-5-en-2-yl ester;
Isobutyric acid (1R,2R,4R)-2-{2-[(1H-benzoimidazol-2-ylmethyl)-methyl-amino]-ethyl}-5-phenyl-bicyclo[2.2.2]oct-5-en-2-yl ester;
Isobutyric acid (1S,2S,4S)-2-{2-[methyl-(3-phenyl-propyl)-amino]-ethyl}-5-phenyl-bicyclo[2.2.2]oct-5-en-2-yl ester;
Isobutyric acid (1R,2R,4R)-2-{2-[methyl-(3-phenyl-propyl)-amino]-ethyl}-5-phenyl-bicyclo[2.2.2]oct-5-en-2-yl ester;
Isobutyric acid (1S,2S,4S)-2-(2-{[3-(1H-benzoimidazol-2-yl)-propyl]-methyl-amino}-ethyl)-6-methyl-5-propyl-bicyclo[2.2.2]oct-5-en-2-yl ester;
Isobutyric acid (1R,2R,4R)-2-(2-{[3-(1H-benzoimidazol-2-yl)-propyl]-methyl-amino}-ethyl)-6-methyl-5-propyl-bicyclo[2.2.2]oct-5-en-2-yl ester;
Isobutyric acid (1S,2S,4S)-2-(2-{[3-(1H-benzoimidazol-2-yl)-propyl]-methyl-amino}-ethyl)-5-methyl-6-phenyl-bicyclo[2.2.2]oct-5-en-2-yl ester;
Isobutyric acid (1R,2R,4R)-2-(2-{[3-(1H-benzoimidazol-2-yl)-propyl]-methyl-amino}-ethyl)-5-methyl-6-phenyl-bicyclo[2.2.2]oct-5-en-2-yl ester;
Isobutyric acid (1S,2R,4S)-2-(2-{[3-(1H-benzoimidazol-2-yl)-propyl]-methyl-amino}-ethyl)-5-methyl-6-phenyl-bicyclo[2.2.2]oct-5-en-2-yl ester;
Isobutyric acid (1R,2S,4R)-2-(2-{[3-(1H-benzoimidazol-2-yl)-propyl]-methyl-amino}-ethyl)-5-methyl-6-phenyl-bicyclo[2.2.2]oct-5-en-2-yl ester;
2-(3-{[2-((1S,2S,4S)-2-Isobutyryloxy-5-phenyl-bicyclo[2.2.2]oct-5-en-2-yl)-ethyl]-methyl-amino}-propyl)-1H-benzoimidazole-4-carboxylic acid methyl ester;
2-(3-{[2-((1R,2R,4R)-2-Isobutyryloxy-5-phenyl-bicyclo[2.2.2]oct-5-en-2-yl)-ethyl]-methyl-amino}-propyl)-1H-benzoimidazole-4-carboxylic acid methyl ester;

2-(3-{[2-((1S,2S,4S)-2-Isobutyryloxy-5-phenyl-bicyclo [2.2.2]oct-5-en-2-yl)-ethyl]-methyl-amino}-propyl)-1H-benzoimidazole-5-carboxylic acid methyl ester;

2-(3-{[2-((1R,2R,4R)-2-Isobutyryloxy-5-phenyl-bicyclo [2.2.2]oct-5-en-2-yl)-ethyl]-methyl-amino}-propyl)-1H-benzoimidazole-5-carboxylic acid methyl ester;

Isobutyric acid (1S,2S,4S)-2-(2-{[3-(1H-benzoimidazol-2-yl)-propyl]-methyl-amino}-ethyl)-5-thiophen-2-yl-bicyclo[2.2.2]oct-5-en-2-yl ester;

Isobutyric acid (1R,2R,4R)-2-(2-{[3-(1H-benzoimidazol-2-yl)-propyl]-methyl-amino}-ethyl)-5-thiophen-2-yl-bicyclo[2.2.2]oct-5-en-2-yl ester;

Isobutyric acid (1S,2S,4S)-2-(2-{[3-(1H-benzoimidazol-2-yl)-propyl]-methyl-amino}-ethyl)-5-(4-methoxy-phenyl)-bicyclo[2.2.2]oct-5-en-2-yl ester;

Isobutyric acid (1R,2R,4R)-2-(2-{[3-(1H-benzoimidazol-2-yl)-propyl]-methyl-amino}-ethyl)-5-(4-methoxy-phenyl)-bicyclo[2.2.2]oct-5-en-2-yl ester;

Isobutyric acid (1S,2S,4S)-2-(2-{[3-(1H-benzoimidazol-2-yl)-propyl]-methyl-amino}-ethyl)-5-(2-methoxy-phenyl)-bicyclo[2.2.2]oct-5-en-2-yl ester;

Isobutyric acid (1R,2R,4R)-2-(2-{[3-(1H-benzoimidazol-2-yl)-propyl]-methyl-amino}-ethyl)-5-(2-methoxy-phenyl)-bicyclo[2.2.2]oct-5-en-2-yl ester;

Isobutyric acid (1S,2S,4S)-2-(2-{[3-(1H-benzoimidazol-2-yl)-propyl]-methyl-amino}-ethyl)-5-thiazol-2-yl-bicyclo[2.2.2]oct-5-en-2-yl ester;

Isobutyric acid (1R,2R,4R)-2-(2-{[3-(1H-benzoimidazol-2-yl)-propyl]-methyl-amino}-ethyl)-5-thiazol-2-yl-bicyclo[2.2.2]oct-5-en-2-yl ester;

Isobutyric acid (1S,2S,4S)-2-(2-{[3-(1H-benzoimidazol-2-yl)-propyl]-methyl-amino}-ethyl)-5-oxazol-2-yl-bicyclo[2.2.2]oct-5-en-2-yl ester;

Isobutyric acid (1R,2R,4R)-2-(2-{[341H-benzoimidazol-2-yl)-propyl]-methyl-amino}-ethyl)-5-oxazol-2-yl-bicyclo[2.2.2]oct-5-en-2-yl ester;

Isobutyric acid (1S,2S,4S)-2-(2-{[3-(4-methoxy-1H-benzoimidazol-2-yl)-propyl]-methyl-amino}-ethyl)-5-phenyl-bicyclo[2.2.2]oct-5-en-2-yl ester;

Isobutyric acid (1R,2R,4R)-2-(2-{[3-(4-methoxy-1H-benzoimidazol-2-yl)-propyl]-methyl-amino}-ethyl)-5-phenyl-bicyclo[2.2.2]oct-5-en-2-yl ester;

Cyclobutanecarboxylic acid (1S,2S,4S)-2-(2-{[3-(4-methoxy-1H-benzoimidazol-2-yl)-propyl]-methyl-amino}-ethyl)-5-phenyl-bicyclo[2.2.2]oct-5-en-2-yl ester;

Cyclobutanecarboxylic acid (1R,2R,4R)-2-(2-{[3-(4-methoxy-1H-benzoimidazol-2-yl)-propyl]-methyl-amino}-ethyl)-5-phenyl-bicyclo[2.2.2]oct-5-en-2-yl ester;

3,3,3-Trifluoro-propionic acid (1S,2S,4S)-2-(2-{[3-(4-methoxy-1H-benzoimidazol-2-yl)-propyl]-methyl-amino}-ethyl)-5-phenyl-bicyclo[2.2.2]oct-5-en-2-yl ester;

3,3,3-Trifluoro-propionic acid (1R,2R,4R)-2-(2-{[3-(4-methoxy-1H-benzoimidazol-2-yl)-propyl]-methyl-amino}-ethyl)-5-phenyl-bicyclo[2.2.2]oct-5-en-2-yl ester;

Isobutyric acid (1S,2S,4S)-2-(2-{[3-(5,6-dichloro-1H-benzoimidazol-2-yl)-propyl]-methyl-amino}-ethyl)-5-phenyl-bicyclo[2.2.2]oct-5-en-2-yl ester;

Isobutyric acid (1R,2R,4R)-2-(2-{[3-(5,6-dichloro-1H-benzoimidazol-2-yl)-propyl]-methyl-amino}-ethyl)-5-phenyl-bicyclo[2.2.2]oct-5-en-2-yl ester;

Cyclopropanecarboxylic acid (1S,2S,4S)-2-(2-{[3-(5,6-dichloro-1H-benzoimidazol-2-yl)-propyl]-methyl-amino}-ethyl)-5-phenyl-bicyclo[2.2.2]oct-5-en-2-yl ester;

Cyclopropanecarboxylic acid (1R,2R,4R)-2-(2-{[3-(5,6-dichloro-1H-benzoimidazol-2-yl)-propyl]-methyl-amino}-ethyl)-5-phenyl-bicyclo[2.2.2]oct-5-en-2-yl ester;

Isobutyric acid (1S,2S,4S)-2-(2-{[3-(5,6-dimethoxy-1H-benzoimidazol-2-yl)-propyl]-methyl-amino}-ethyl)-5-phenyl-bicyclo[2.2.2]oct-5-en-2-yl ester;

Isobutyric acid (1R,2R,4R)-2-(2-{[3-(5,6-dimethoxy-1H-benzoimidazol-2-yl)-propyl]-methyl-amino}-ethyl)-5-phenyl-bicyclo[2.2.2]oct-5-en-2-yl ester;

Isobutyric acid (1S,2S,4S)-2-(2-{[3-(5-methoxy-1H-benzoimidazol-2-yl)-propyl]-methyl-amino}-ethyl)-5-phenyl-bicyclo[2.2.2]oct-5-en-2-yl ester;

Isobutyric acid (1R,2R,4R)-2-(2-{[3-(5-methoxy-1H-benzoimidazol-2-yl)-propyl]-methyl-amino}-ethyl)-5-phenyl-bicyclo[2.2.2]oct-5-en-2-yl ester;

Isobutyric acid (1S,2S,4S)-2-(2-{[3-(7-methoxy-4-methyl-1H-benzoimidazol-2-yl)-propyl]-methyl-amino}-ethyl)-5-phenyl-bicyclo[2.2.2]oct-5-en-2-yl ester;

Isobutyric acid (1R,2R,4R)-2-(2-{[3-(7-methoxy-4-methyl-1H-benzoimidazol-2-yl)-propyl]-methyl-amino}-ethyl)-5-phenyl-bicyclo[2.2.2]oct-5-en-2-yl ester;

Isobutyric acid (1S,2S,4S)-2-(2-{[3-(7-ethoxy-1H-benzoimidazol-2-yl)-propyl]-methyl-amino}-ethyl)-5-phenyl-bicyclo[2.2.2]oct-5-en-2-yl ester;

Isobutyric acid (1R,2R,4R)-2-(2-{[3-(7-ethoxy-1H-benzoimidazol-2-yl)-propyl]-methyl-amino}-ethyl)-5-phenyl-bicyclo[2.2.2]oct-5-en-2-yl ester;

Isobutyric acid (1S,2S,4S)-2-(2-{[2-(7-methoxy-1H-benzoimidazol-2-yl)-ethyl]-methyl-amino}-ethyl)-5-phenyl-bicyclo[2.2.2]oct-5-en-2-yl ester;

Isobutyric acid (1R,2R,4R)-2-(2-{[2-(7-methoxy-1H-benzoimidazol-2-yl)-ethyl]-methyl-amino}-ethyl)-5-phenyl-bicyclo[2.2.2]oct-5-en-2-yl ester;

Isobutyric acid (1S,2S,4S)-2-(2-{[3-(7-isopropoxy-1H-benzoimidazol-2-yl)-propyl]-methyl-amino}-ethyl)-5-phenyl-bicyclo[2.2.2]oct-5-en-2-yl ester;

Isobutyric acid (1R,2R,4R)-2-(2-{[3-(7-isopropoxy-1H-benzoimidazol-2-yl)-propyl]-methyl-amino}-ethyl)-5-phenyl-bicyclo[2.2.2]oct-5-en-2-yl ester;

Isobutyric acid (1S,2S,4S)-2-(2-{[3-(7-isobutyryloxy-1H-benzoimidazol-2-yl)-propyl]-methyl-amino}-ethyl)-5-phenyl-bicyclo[2.2.2]oct-5-en-2-yl ester;

Isobutyric acid (1R,2R,4R)-2-(2-{[3-(7-isobutyryloxy-1H-benzoimidazol-2-yl)-propyl]-methyl-amino}-ethyl)-5-phenyl-bicyclo[2.2.2]oct-5-en-2-yl ester;

Isobutyric acid (1S,2S,4S)-2-(2-{[3-(7-hydroxy-1H-benzoimidazol-2-yl)-propyl]-methyl-amino}-ethyl)-5-phenyl-bicyclo[2.2.2]oct-5-en-2-yl ester;

Isobutyric acid (1R,2R,4R)-2-(2-{[3-(7-hydroxy-1H-benzoimidazol-2-yl)-propyl]-methyl-amino}-ethyl)-5-phenyl-bicyclo[2.2.2]oct-5-en-2-yl ester;

Isobutyric acid (1S,5S,6S)-6-(2-{[3-(7-methoxy-1H-benzoimidazol-2-yl)-propyl]-methyl-amino}-ethyl)-8-phenyl-bicyclo[3.2.2]non-8-en-6-yl ester;

Isobutyric acid (1R,5R,6R)-6-(2-{[3-(7-methoxy-1H-benzoimidazol-2-yl)-propyl]-methyl-amino}-ethyl)-8-phenyl-bicyclo[3.2.2]non-8-en-6-yl ester;

3,3,3-Trifluoro-propionic acid (1S,5S,6S)-6-(2-{[3-(4-methoxy-1H-benzoimidazol-2-yl)-propyl]-methyl-amino}-ethyl)-8-phenyl-bicyclo[3.2.2]non-8-en-6-yl ester;

3,3,3-Trifluoro-propionic acid (1R,5R,6R)-6-(2-{[3-(4-methoxy-1H-benzoimidazol-2-yl)-propyl]-methyl-amino}-ethyl)-8-phenyl-bicyclo[3.2.2]non-8-en-6-yl ester;
Isobutyric acid (1S,2S,4S)-2-(2-{[3-(4-methoxy-1-methyl-1H-benzoimidazol-2-yl)-propyl]-methyl-amino}-ethyl)-5-phenyl-bicyclo[2.2.2]oct-5-en-2-yl ester;
Isobutyric acid (1R,2R,4R)-2-(2-{[3-(4-methoxy-1-methyl-1H-benzoimidazol-2-yl)-propyl]-methyl-amino}-ethyl)-5-phenyl-bicyclo[2.2.2]oct-5-en-2-yl ester;
Isobutyric acid (1S,2S,4S)-2-(2-{[2-(3,4-diethoxy-phenyl)-ethyl]-ethyl-amino}-ethyl)-5-phenyl-bicyclo[2.2.2]oct-5-en-2-yl ester;
Isobutyric acid (1R,2R,4R)-2-(2-{[2-(3,4-diethoxy-phenyl)-ethyl]ethyl-amino}-ethyl)-5-phenyl-bicyclo[2.2.2]oct-5-en-2-yl ester;
Isobutyric acid (1S,2S,4S)-2-(2-{[3-(3,4-dimethoxy-phenyl)-propyl]-methyl-amino}-ethyl)-5-phenyl-bicyclo[2.2.2]oct-5-en-2-yl ester;
Isobutyric acid (1R,2R,4R)-2-(2-{[3-(3,4-dimethoxy-phenyl)-propyl]-methyl-amino}-ethyl)-5-phenyl-bicyclo[2.2.2]oct-5-en-2-yl ester;
Isobutyric acid (1S,2S,4S)-2-(2-{[3-(3,4-diethoxy-phenyl)-propyl]-methyl-amino}-ethyl)-5-phenyl-bicyclo[2.2.2]oct-5-en-2-yl ester;
Isobutyric acid (1R,2R,4R)-2-(2-{[3-(3,4-diethoxy-phenyl)-propyl]-methyl-amino}-ethyl)-5-phenyl-bicyclo[2.2.2]oct-5-en-2-yl ester;
Isobutyric acid (1S,2S,4S)-2-{2-[(3-furo[2,3-b]pyridin-5-yl-propyl)-methyl-amino]-ethyl}-5-phenyl-bicyclo[2.2.2]oct-5-en-2-yl ester;
Isobutyric acid (1R,2R,4R)-2-{2-[(3-furo[2,3-b]pyridin-5-yl-propyl)-methyl-amino]-ethyl}-5-phenyl-bicyclo[2.2.2]oct-5-en-2-yl ester;
Isobutyric acid (1S,2S,4S)-2-(2-{methyl-[3-(2-methyl-furo[2,3-b]pyridin-5-yl)-propyl]-amino}-ethyl)-5-phenyl-bicyclo[2.2.2]oct-5-en-2-yl ester;
Isobutyric acid (1R,2R,4R)-2-(2-{methyl-[3-(2-methyl-furo[2,3-b]pyridin-5-yl)-propyl]-amino}-ethyl)-5-phenyl-bicyclo[2.2.2]oct-5-en-2-yl ester;
Isobutyric acid (1S,2S,4S)-2-{2-[methyl-(3-pyridin-3-yl-propyl)-amino]-ethyl}-5-phenyl-bicyclo[2.2.2]oct-5-en-2-yl ester;
Isobutyric acid (1R,2R,4R)-2-{2-[methyl-(3-pyridin-3-yl-propyl)-amino]-ethyl}-5-phenyl-bicyclo[2.2.2]oct-5-en-2-yl ester;
Isobutyric acid (1S,2S,4S)-2-(2-{[3-(4,5-diphenyl-1H-imidazol-2-yl)-propyl]-methyl-amino}-ethyl)-5-phenyl-bicyclo[2.2.2]oct-5-en-2-yl ester;
Isobutyric acid (1R,2R,4R)-2-(2-{[3-(4,5-diphenyl-1H-imidazol-2-yl)-propyl]-methyl-amino}-ethyl)-5-phenyl-bicyclo[2.2.2]oct-5-en-2-yl ester;
Isobutyric acid (1S,2S,4S)-2-{2-[(3-isoquinolin-4-yl-propyl)-methyl-amino]-ethyl}-5-phenyl-bicyclo[2.2.2]oct-5-en-2-yl ester;
Isobutyric acid (1R,2R,4R)-2-{2-[(3-isoquinolin-4-yl-propyl)-methyl-amino]-ethyl}-5-phenyl-bicyclo[2.2.2]oct-5-en-2-yl ester;
Isobutyric acid (1S,2S,4S)-2-{2-[methyl-(3-quinolin-3-yl-propyl)-amino]-ethyl}-5-phenyl-bicyclo[2.2.2]oct-5-en-2-yl ester;
Isobutyric acid (1R,2R,4R)-2-{2-[methyl-(3-quinolin-3-yl-propyl)-amino]-ethyl}-5-phenyl-bicyclo[2.2.2]oct-5-en-2-yl ester;
Isobutyric acid (1S,2S,4S)-2-{2-[methyl-(3-quinolin-4-yl-propyl)-amino]-ethyl}-5-phenyl-bicyclo[2.2.2]oct-5-en-2-yl ester;
Isobutyric acid (1R,2R,4R)-2-{2-[methyl-(3-quinolin-4-yl-propyl)-amino]-ethyl}-5-phenyl-bicyclo[2.2.2]oct-5-en-2-yl ester;
2,2-Dimethyl-propionic acid (1S,2S,4S)-2-(2-{[3-(4-methoxy-1H-benzoimidazol-2-yl)-propyl]-methyl-amino}-ethyl)-5-phenyl-bicyclo[2.2.2]oct-5-en-2-yl ester;
2,2-Dimethyl-propionic acid (1R,2R,4R)-2-(2-{[3-(4-methoxy-1H-benzoimidazol-2-yl)-propyl]-methyl-amino}-ethyl)-5-phenyl-bicyclo[2.2.2]oct-5-en-2-yl ester;
Isopropyl-carbamic acid (1S,2S,4S)-2-(2-{[3-(4-methoxy-1H-benzoimidazol-2-yl)-propyl]-methyl-amino}-ethyl)-5-phenyl-bicyclo[2.2.2]oct-5-en-2-yl ester;
Isopropyl-carbamic acid (1R,2R,4R)-2-(2-{[3-(4-methoxy-1H-benzoimidazol-2-yl)-propyl]-methyl-amino}-ethyl)-5-phenyl-bicyclo[2.2.2]oct-5-en-2-yl ester;
2-Methoxy-2-methyl-propionic acid (1S,2S,4S)-2-(2-{[3-(4-methoxy-1H-benzoimidazol-2-yl)-propyl]-methyl-amino}-ethyl)-5-phenyl-bicyclo[2.2.2]oct-5-en-2-yl ester;
2-Methoxy-2-methyl-propionic acid (1R,2R,4R)-2-(2-{[3-(4-methoxy-1H-benzoimidazol-2-yl)-propyl]-methyl-amino}-ethyl)-5-phenyl-bicyclo[2.2.2]oct-5-en-2-yl ester;
Carbonic acid isopropyl ester (1S,2S,4S)-2-(2-{[3-(4-methoxy-1H-benzoimidazol-2-yl)-propyl]-methyl-amino}-ethyl)-5-phenyl-bicyclo[2.2.2]oct-5-en-2-yl ester;
Carbonic acid isopropyl ester (1R,2R,4R)-2-(2-{[3-(4-methoxy-1H-benzoimidazol-2-yl)-propyl]-methyl-amino}-ethyl)-5-phenyl-bicyclo[2.2.2]oct-5-en-2-yl ester;
Isobutyric acid (1S,2S,4S)-2-(2-{[3-(4-acetylamino-1H-benzoimidazol-2-yl)-propyl]-methyl-amino}-ethyl)-5-phenyl-bicyclo[2.2.2]oct-5-en-2-yl ester;
Isobutyric acid (1R,2R,4R)-2-(2-{[3-(4-acetylamino-1H-benzoimidazol-2-yl)-propyl]-methyl-amino}-ethyl)-5-phenyl-bicyclo[2.2.2]oct-5-en-2-yl ester;
Isobutyric acid (1S,2S,4S)-2-(2-{[3-(4-chloro-1H-benzoimidazol-2-yl)-propyl]-methyl-amino}-ethyl)-5-phenyl-bicyclo[2.2.2]oct-5-en-2-yl ester;
Isobutyric acid (1R,2R,4R)-2-(2-{[3-(4-chloro-1H-benzoimidazol-2-yl)-propyl]-methyl-amino}-ethyl)-5-phenyl-bicyclo[2.2.2]oct-5-en-2-yl ester;
Isobutyric acid (1S,2S,4S)-2-(2-{[3-(7-chloro-4-methoxy-1H-benzoimidazol-2-yl)-propyl]-methyl-amino}-ethyl)-5-phenyl-bicyclo[2.2.2]oct-5-en-2-yl ester;
Isobutyric acid (1R,2R,4R)-2-(2-{[3-(7-chloro-4-methoxy-1H-benzoimidazol-2-yl)-propyl]-methyl-amino}-ethyl)-5-phenyl-bicyclo[2.2.2]oct-5-en-2-yl ester;
Isobutyric acid (1S,2S,4S)-2-(2-{[3-(4,6-dimethoxy-1H-benzoimidazol-2-yl)-propyl]-methyl-amino}-ethyl)-5-phenyl-bicyclo[2.2.2]oct-5-en-2-yl ester;
Isobutyric acid (1R,2R,4R)-2-(2-{[3-(4,6-dimethoxy-1H-benzoimidazol-2-yl)-propyl]-methyl-amino}-ethyl)-5-phenyl-bicyclo[2.2.2]oct-5-en-2-yl ester;
Isobutyric acid (1S,2S,4S)-2-(2-{[3-(4,7-dimethoxy-1H-benzoimidazol-2-yl)-propyl]-methyl-amino}-ethyl)-5-phenyl-bicyclo[2.2.2]oct-5-en-2-yl ester;
Isobutyric acid (1R,2R,4R)-2-(2-{[3-(4,7-dimethoxy-1H-benzoimidazol-2-yl)-propyl]-methyl-amino}-ethyl)-5-phenyl-bicyclo[2.2.2]oct-5-en-2-yl ester;
Isobutyric acid (1S,2S,4S)-2-(2-{[3-(4,6-bis-trifluoromethyl-1H-benzoimidazol-2-yl)-propyl]-methyl-amino}-ethyl)-5-phenyl-bicyclo[2.2.2]oct-5-en-2-yl ester;

Isobutyric acid (1R,2R,4R)-2-(2-{[3-(4,6-bis-trifluorom-ethyl-1H-benzoimidazol-2-yl)-propyl]-methyl-amino}-ethyl)-5-phenyl-bicyclo[2.2.2]oct-5-en-2-yl ester;
Isobutyric acid (1S,2S,4S)-2-[2-({3-[4-(2-methoxy-ethoxy)-1H-benzoimidazol-2-yl]-propyl}-methyl-amino)-ethyl]-5-phenyl-bicyclo[2.2.2]oct-5-en-2-yl ester;
Isobutyric acid (1R,2R,4R)-2-[2-({3-[4-(2-methoxy-ethoxy)-1H-benzoimidazol-2-yl]-propyl}-methyl-amino)-ethyl]-5-phenyl-bicyclo[2.2.2]oct-5-en-2-yl ester;
Isobutyric acid (1S,2S,4S)-2-(2-{[3-(4,5-dimethoxy-7-methyl-1H-benzoimidazol-2-yl)-propyl]-methyl-amino}-ethyl)-5-phenyl-bicyclo[2.2.2]oct-5-en-2-yl ester;
Isobutyric acid (1R,2R,4R)-2-(2-{[3-(4,5-dimethoxy-7-methyl-1H-benzoimidazol-2-yl)-propyl]-methyl-amino}-ethyl)-5-phenyl-bicyclo[2.2.2]oct-5-en-2-yl ester;
Isobutyric acid (1S,5S,6S)-6-(2-{[3-(7-methoxy-4-methyl-1H-benzoimidazol-2-yl)-propyl]-methyl-amino}-ethyl)-8-phenyl-bicyclo[3.2.2]non-8-en-6-yl ester;
Isobutyric acid (1R,5R,6R)-6-(2-{[3-(7-methoxy-4-methyl-1H-benzoimidazol-2-yl)-propyl]-methyl-amino}-ethyl)-8-phenyl-bicyclo[3.2.2]non-8-en-6-yl ester;
Isobutyric acid (1S,2S,4S)-2-(2-{methyl-[3-(4-trifluoromethoxy-1H-benzoimidazol-2-yl)-propyl]-amino}-ethyl)-5-phenyl-bicyclo[2.2.2]oct-5-en-2-yl ester;
Isobutyric acid (1R,2R,4R)-2-(2-{methyl-[3-(4-trifluoromethoxy-1H-benzoimidazol-2-yl)-propyl]-amino}-ethyl)-5-phenyl-bicyclo[2.2.2]oct-5-en-2-yl ester;
Isobutyric acid (1S,5S,6S)-6-(2-{[3-(4,7-dimethoxy-1H-benzoimidazol-2-yl)-propyl]-methyl-amino}-ethyl)-8-phenyl-bicyclo[3.2.2]non-8-en-6-yl ester;
Isobutyric acid (1R,5R,6R)-6-(2-{[3-(4,7-dimethoxy-1H-benzoimidazol-2-yl)-propyl]-methyl-amino}-ethyl)-8-phenyl-bicyclo[3.2.2]non-8-en-6-yl ester;
Isobutyric acid (1S,2S,4S)-2-(2-{methyl-[3-(4-methyl-5-phenyl-1H-imidazol-2-yl)-propyl]-amino}-ethyl)-5-phenyl-bicyclo[2.2.2]oct-5-en-2-yl ester;
Isobutyric acid (1R,2R,4R)-2-(2-{methyl-[3-(4-methyl-5-phenyl-1H-imidazol-2-yl)-propyl]-amino}-ethyl)-5-phenyl-bicyclo[2.2.2]oct-5-en-2-yl ester;
Isobutyric acid (1S,2S,4S)-2-[2-({3-[5-(2-methoxy-phenyl)-1H-imidazol-2-yl]-propyl}-methyl-amino)-ethyl]-5-phenyl-bicyclo[2.2.2]oct-5-en-2-yl ester;
Isobutyric acid (1R,2R,4R)-2-[2-({3-[5-(2-methoxy-phenyl)-1H-imidazol-2-yl]-propyl}-methyl-amino)-ethyl]-5-phenyl-bicyclo[2.2.2]oct-5-en-2-yl ester;
Isobutyric acid (1R,2R,4R,5R)-2-(2-{[3-(1H-benzoimidazol-2-yl)-propyl]-methyl-amino}-ethyl)-5-phenyl-bicyclo[2.2.2]oct-2-yl ester;
Isobutyric acid (1S,2S,4S,5R)-2-(2-{[3-(1H-benzoimidazol-2-yl)-propyl]-methyl-amino}-ethyl)-5-phenyl-bicyclo[2.2.2]oct-2-yl ester;
Isobutyric acid (1R,2R,4R,5S)-2-(2-{[3-(1H-benzoimidazol-2-yl)-propyl]-methyl-amino}-ethyl)-5-phenyl-bicyclo[2.2.2]oct-2-yl ester;
Isobutyric acid (1S,2S,4S,5S)-2-(2-{[3-(1H-benzoimidazol-2-yl)-propyl]-methyl-amino}-ethyl)-5-phenyl-bicyclo[2.2.2]oct-2-yl ester;
Isobutyric acid (1R,2R,4R)-2-(2-{[3-(1H-benzoimidazol-2-yl)-propyl]-methyl-amino}-ethyl)-bicyclo[2.2.2]oct-5-en-2-yl ester;
Isobutyric acid (1S,2S,4S)-2-(2-{[3-(1H-benzoimidazol-2-yl)-propyl]-methyl-amino}-ethyl)-bicyclo[2.2.2]oct-5-en-2-yl ester;
Isobutyric acid (1R,2R,4R,5R)-2-(2-{[3-(1H-benzoimidazol-2-yl)-propyl]-methyl-amino}-ethyl)-5-methoxy-5-phenyl-bicyclo[2.2.2]oct-2-yl ester;
Isobutyric acid (1S,2S,4S,5S)-2-(2-{[3-(1H-benzoimidazol-2-yl)-propyl]-methyl-amino}-ethyl)-5-methoxy-5-phenyl-bicyclo[2.2.2]oct-2-yl ester;
Isobutyric acid (1R,2S,4R,5S)-2-(2-{[3-(1H-benzoimidazol-2-yl)-propyl]-methyl-amino}-ethyl)-5-methoxy-5-phenyl-bicyclo[2.2.2]oct-2-yl ester; and
Isobutyric acid (1S,2R,4S,5R)-2-(2-{[3-(1H-benzoimidazol-2-yl)-propyl]-methyl-amino}-ethyl)-5-methoxy-5-phenyl-bicyclo[2.2.2]oct-2-yl ester;
in a free or a salt form.

12. The compound according to claim 1, wherein
X represents a carbon atom; $R^{1a}$ and $R^{2a}$ together form a bond; $R^1$ represents unsubstituted aryl;
$R^2$ represents hydrogen; and
A represents —(CH$_2$)$_p$—, wherein p represents the integer 2 or 3;
wherein the configuration of the bridged cyclohexene moiety is such that the $R^3$—O— substituent and the bridge A of the cyclohexene moiety are in cis relation;
$R^3$ represents —CO—$R^{31}$; and $R^{31}$ represents (C$_{1-5}$)alkyl;
B represents a group —(CH$_2$)$_m$—, and m represents the integer 3;
n represents the integer 2;
$R^4$ represents (C$_{1-5}$)alkyl; and
W represents

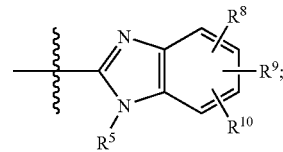

wherein
$R^5$ represents hydrogen; and
$R^8$, $R^9$ and $R^{10}$ independently represent hydrogen, halogen, (C$_{1-5}$)alkyl, (C$_{1-5}$)alkoxy, (C$_{1-3}$)fluoroalkyl, or (C$_{1-3}$)fluoroalkoxy,
in a free or a salt form.

13. The compound according to claim 12, wherein
W represents

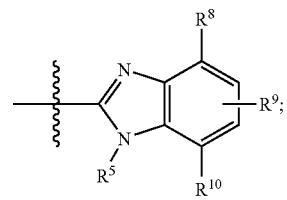

wherein $R^8$ and $R^{10}$ are independently (C$_{1-5}$)alkoxy, and $R^5$ and $R^9$ represent hydrogen;
in a free or a salt form.

14. The compound according to claim 1, wherein the compound is selected from the group consisting of:
Isobutyric acid (1R,2R,4R)-2-(2-{[3-(4,7-dimethoxy-1H-benzoimidazol-2-yl)-propyl]-methyl-amino}-ethyl)-5-phenyl-bicyclo[2.2.2]oct-5-en-2-yl ester;

Isobutyric acid (1S,2S,4S)-2-(2-{[3-(4,7-dimethoxy-1H-benzoimidazol-2-yl)-propyl]-methyl-amino}-ethyl)-5-phenyl-bicyclo[2.2.2]oct-5-en-2-yl ester;

Isobutyric acid (1R,5R,6R)-6-(2-{[3-(4,7-dimethoxy-1H-benzoimidazol-2-yl)-propyl]-methyl-amino}-ethyl)-8-phenyl-bicyclo[3.2.2]non-8-en-6-yl ester; and Isobutyric acid (1S,5S,6S)-6-(2-{[3-(4,7-dimethoxy-1H-benzoimidazol-2-yl)-propyl]-methyl-amino}-ethyl)-8-phenyl-bicyclo[3.2.2]non-8-en-6-yl ester;

in a free or a salt form.

15. The compound according to claim 1, wherein the compound is isobutyric acid
(1R,2R,4R)-2-(2-{[3-(4,7-dimethoxy-1H-benzoimidazol-2-yl)-propyl]-methyl-amino}-ethyl)-5-phenyl-bicyclo[2.2.2]oct-5-en-2-yl ester;
in a free or a salt form.

16. The compound according to claim 1, wherein the compound is isobutyric acid
(1S,2S,4S)-2-(2-{[3-(4,7-dimethoxy-1H-benzoimidazol-2-yl)-propyl]-methyl-amino}-ethyl)-5-phenyl-bicyclo[2.2.2]oct-5-en-2-yl ester;
in a free or a salt form.

17. A pharmaceutical composition comprising the compound according to claim 1 in a free or pharmaceutically acceptable salt form, and at least one therapeutically inert excipient.

18. The pharmaceutical composition according to claim 17, wherein the compound is a compound of formula (I)

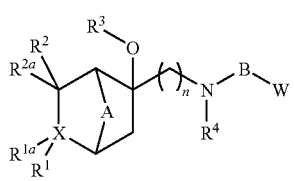

Formula (I)

Wherein

X represents a carbon atom; $R^{1a}$ and $R^{2a}$ together form a bond; $R^1$ represents unsubstituted aryl; $R^2$ represents hydrogen; and A represents —$(CH_2)_p$—, wherein p represents the integer 2 or 3;

wherein the configuration of the bridged cyclohexene moiety is such that the $R^3$—O— substituent and the bridge A of the cyclohexene moiety are in cis relation;

$R^3$ represents —CO—$R^{31}$; and $R^{31}$ represents $(C_{1-5})$alkyl;

B represents a group —$(CH_2)_m$—, and m represents the integer 3;

n represents the integer 2;

$R^4$ represents $(C_{1-5})$alkyl; and

W represents

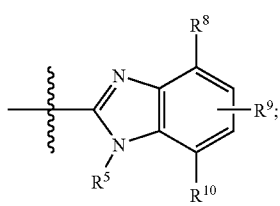

wherein $R^9$ and $R^{19}$ are independently $(C_{1-5})$alkoxy, and $R^5$ and $R^9$ represent hydrogen;

in a free or pharmaceutically acceptable salt form.

19. The pharmaceutical composition according to claim 17, wherein the compound is isobutyric acid (1R,2R,4R)-2-(2-{[3-(4,7-dimethoxy-1H-benzoimidazol-2-yl)-propyl]-methyl-amino}-ethyl)-5-phenyl-bicyclo[2.2.2]oct-5-en-2-yl ester in a free or pharmaceutically acceptable salt form.

20. The pharmaceutical composition according to claim 17, wherein the compound is isobutyric acid (1S,2S,4S)-2-(2-{[3-(4,7-dimethoxy-1H-benzoimidazol-2-yl)-propyl]-methyl-amino}-ethyl)-5-phenyl-bicyclo[2.2.2]oct-5-en-2-yl ester in a free or pharmaceutically acceptable salt form.

21. A method for the treatment of a disease or disorder selected from the group consisting of chronic stable angina and hypertension
comprising administering to a subject a pharmaceutically active amount of a compound according to claim 1, in a free or pharmaceutically acceptable salt form.

22. The method according to claim 21, wherein the disease or disorder is hypertension.

23. The method according to claim 21, wherein said compound is selected from the group consisting of:

(1S,2S,4S)-2-(2-{[3-(1H-Benzoimidazol-2-yl)-propyl]-methyl-amino}-ethyl)-5-phenyl-bicyclo[2.2.2]oct-5-en-2-ol;

(1R,2R,4R)-2-(2-{[3-(1H-Benzoimidazol-2-yl)-propyl]-methyl-amino}-ethyl)-5-phenyl-bicyclo[2.2.2]oct-5-en-2-ol;

(1S,2S,4S)-2-(2-{[3-(1H-Benzoimidazol-2-yl)-propyl]-methyl-amino}-ethyl)-5-(3-methoxy-phenyl)-bicyclo[2.2.2]oct-5-en-2-ol;

(1R,2R,4R)-2-(2-{[3-(1H-Benzoimidazol-2-yl)-propyl]-methyl-amino}-ethyl)-5-(3-methoxy-phenyl)-bicyclo[2.2.2]oct-5-en-2-ol;

(1S,2S,4S)-2-(2-{[3-(1H-Benzoimidazol-2-yl)-propyl]-methyl-amino}-ethyl)-5-(2,6-dimethyl-phenyl)-bicyclo[2.2.2]oct-5-en-2-ol;

(1R,2R,4R)-2-(2-{[3-(1H-Benzoimidazol-2-yl)-propyl]-methyl-amino}-ethyl)-5-(2,6-dimethyl-phenyl)-bicyclo[2.2.2]oct-5-en-2-ol;

(1S,2S,4S)-2-(2-{[3-(1H-Benzoimidazol-2-yl)-propyl]-methyl-amino}-ethyl)-5-o-tolyl-bicyclo[2.2.2]oct-5-en-2-ol;

(1R,2R,4R)-2-(2-{[3-(1H-Benzoimidazol-2-yl)-propyl]-methyl-amino}-ethyl)-5-o-tolyl-bicyclo[2.2.2]oct-5-en-2-ol;

(1S,2S,4S)-2-(2-{[3-(1H-Benzoimidazol-2-yl)-propyl]-methyl-amino}-ethyl)-5-m-tolyl-bicyclo[2.2.2]oct-5-en-2-ol;

(1R,2R,4R)-2-(2-{[3-(1H-Benzoimidazol-2-yl)-propyl]-methyl-amino}-ethyl)-5-m-tolyl-bicyclo[2.2.2]oct-5-en-2-ol;

(1S,2S,4S)-2-(2-{[3-(1H-Benzoimidazol-2-yl)-propyl]-methyl-amino}-ethyl)-5-o-tolyl-bicyclo[2.2.2]oct-5-en-2-ol;

(1R,2R,4R)-2-(2-{[3-(1H-Benzoimidazol-2-yl)-propyl]-methyl-amino}-ethyl)-5-O-tolyl-bicyclo[2.2.2]oct-5-en-2-ol;

(1S,2S,4S)-2-(2-{[3-(1H-Benzoimidazol-2-yl)-propyl]-methyl-amino}-ethyl)-5-(3-fluoro-phenyl)-bicyclo[2.2.2]oct-5-en-2-ol;

(1R,2R,4R)-2-(2-{[3-(1H-Benzoimidazol-2-yl)-propyl]-methyl-amino}-ethyl)-5-(3-fluoro-phenyl)-bicyclo[2.2.2]oct-5-en-2-ol;

(1S,2S,4S)-2-(2-{[3-(1H-Benzoimidazol-2-yl)-propyl]-methyl-amino}-ethyl)-5-(4-fluoro-phenyl)-bicyclo[2.2.2]oct-5-en-2-ol;

(1R,2R,4R)-2-(2-{[3-(1H-Benzoimidazol-2-yl)-propyl]-methyl-amino}-ethyl)-5-(4-fluoro-phenyl)-bicyclo[2.2.2]oct-5-en-2-ol;
(1S,2S,4S)-2-(2-{[3-(1H-Benzoimidazol-2-yl)-propyl]-methyl-amino}-ethyl)-5-pyridin-3-yl-bicyclo[2.2.2]oct-5-en-2-ol;
(1R,2R,4R)-2-(2-{[3-(1H-Benzoimidazol-2-yl)-propyl]-methyl-amino}-ethyl)-5-pyridin-3-yl-bicyclo[2.2.2]oct-5-en-2-ol;
(1S,2S,4S)-2-(2-{[3-(1H-Benzoimidazol-2-yl)-propyl]-methyl-amino}-ethyl)-5-naphthalen-2-yl-bicyclo[2.2.2]oct-5-en-2-ol;
(1R,2R,4R)-2-(2-{[3-(1H-Benzoimidazol-2-yl)-propyl]-methyl-amino}-ethyl)-5-naphthalen-2-yl-bicyclo[2.2.2]oct-5-en-2-ol;
(1S,2S,4S)-2-(2-{[2-(1H-Benzoimidazol-2-yl)-ethyl]-methyl-amino}-ethyl)-5-phenyl-bicyclo[2.2.2]oct-5-en-2-ol;
(1R,2R,4R)-2-(2-{[2-(1H-Benzoimidazol-2-yl)-ethyl]-methyl-amino}-ethyl)-5-phenyl-bicyclo[2.2.2]oct-5-en-2-ol;
(1S,2S,4S)-2-{2-[(1H-Benzoimidazol-2-ylmethyl)-methyl-amino]-ethyl}-5-phenyl-bicyclo[2.2.2]oct-5-en-2-ol;
(1R,2R,4R)-2-{2-[(1H-Benzoimidazol-2-ylmethyl)-methyl-amino]-ethyl}-5-phenyl-bicyclo[2.2.2]oct-5-en-2-ol;
(1S,2S,4S)-2-{2-[Methyl-(3-phenyl-propyl)-amino]-ethyl}-5-phenyl-bicyclo[2.2.2]oct-5-en-2-ol;
(1R,2R,4R)-2-{2-[Methyl-(3-phenyl-propyl)-amino]-ethyl}-5-phenyl-bicyclo[2.2.2]oct-5-en-2-ol;
(1S,2S,4S)-2-(2-{[3-(1H-Benzoimidazol-2-yl)-propyl]-methyl-amino}-ethyl)-6-methyl-5-propyl-bicyclo[2.2.2]oct-5-en-2-ol;
(1R,2R,4R)-2-(2-{[3-(1H-Benzoimidazol-2-yl)-propyl]-methyl-amino}-ethyl)-6-methyl-5-propyl-bicyclo[2.2.2]oct-5-en-2-ol;
(1S,2S,4S)-2-(2-{[3-(1H-Benzoimidazol-2-yl)-propyl]-methyl-amino}-ethyl)-5-methyl-6-phenyl-bicyclo[2.2.2]oct-5-en-2-ol;
(1S,2R,4R)-2-(2-{[3-(1H-Benzoimidazol-2-yl)-propyl]-methyl-amino}-ethyl)-5-methyl-6-phenyl-bicyclo[2.2.2]oct-5-en-2-ol;
2-(3-{[2-((1S,2S,4S)-2-Hydroxy-5-phenyl-bicyclo[2.2.2]oct-5-en-2-yl)-ethyl]-methyl-amino}-propyl)-1H-benzoimidazole-4-carboxylic acid methyl ester;
2-(3-{[2-((1R,2R,4R)-2-Hydroxy-5-phenyl-bicyclo[2.2.2]oct-5-en-2-yl)-ethyl]-methyl-amino}-propyl)-1H-benzoimidazole-4-carboxylic acid methyl ester;
2-(3-{[2-((1S,2S,4S)-2-Hydroxy-5-phenyl-bicyclo[2.2.2]oct-5-en-2-yl)-ethyl]-methyl-amino}-propyl)-1H-benzoimidazole-5-carboxylic acid methyl ester;
2-(3-{[2-((1R,2R,4R)-2-Hydroxy-5-phenyl-bicyclo[2.2.2]oct-5-en-2-yl)-ethyl]-methyl-amino}-propyl)-1H-benzoimidazole-5-carboxylic acid methyl ester;
(1S,2S,4S)-2-(2-{[3-(1H-Benzoimidazol-2-yl)-propyl]-methyl-amino}-ethyl)-5-thiophen-2-yl-bicyclo[2.2.2]oct-5-en-2-ol;
(1R,2R,4R)-2-(2-{[3-(1H-Benzoimidazol-2-yl)-propyl]-methyl-amino}-ethyl)-5-thiophen-2-yl-bicyclo[2.2.2]oct-5-en-2-ol;
(1S,2S,4S)-2-(2-{[3-(1H-Benzoimidazol-2-yl)-propyl]-methyl-amino}-ethyl)-5-(4-methoxy-phenyl)-bicyclo[2.2.2]oct-5-en-2-ol;
(1R,2R,4R)-2-(2-{[3-(1H-Benzoimidazol-2-yl)-propyl]-methyl-amino}-ethyl)-5-(4-methoxy-phenyl)-bicyclo[2.2.2]oct-5-en-2-ol;
(1S,2S,4S)-2-(2-{[3-(1H-Benzoimidazol-2-yl)-propyl]-methyl-amino}-ethyl)-5-(2-methoxy-phenyl)-bicyclo[2.2.2]oct-5-en-2-ol;
(1R,2R,4R)-2-(2-{[3-(1H-Benzoimidazol-2-yl)-propyl]-methyl-amino}-ethyl)-5-(2-methoxy-phenyl)-bicyclo[2.2.2]oct-5-en-2-ol;
(1S,2S,4S)-2-(2-{[3-(1H-Benzoimidazol-2-yl)-propyl]-methyl-amino}-ethyl)-5-thiazol-2-yl-bicyclo[2.2.2]oct-5-en-2-ol;
(1R,2R,4R)-2-(2-{[3-(1H-Benzoimidazol-2-yl)-propyl]-methyl-amino}-ethyl)-5-thiazol-2-yl-bicyclo[2.2.2]oct-5-en-2-ol;
(1S,2S,4S)-2-(2-{[3-(1H-Benzoimidazol-2-yl)-propyl]-methyl-amino}-ethyl)-5-oxazol-2-yl-bicyclo[2.2.2]oct-5-en-2-ol;
(1R,2R,4R)-2-(2-{[3-(1H-Benzoimidazol-2-yl)-propyl]-methyl-amino}-ethyl)-5-oxazol-2-yl-bicyclo[2.2.2]oct-5-en-2-ol;
(1S,2S,4S)-2-(2-{[3-(4-Methoxy-1H-benzoimidazol-2-yl)-propyl]-methyl-amino}-ethyl)-5-phenyl-bicyclo[2.2.2]oct-5-en-2-ol;
(1R,2R,4R)-2-(2-{[3-(4-Methoxy-1H-benzoimidazol-2-yl)-propyl]-methyl-amino}-ethyl)-5-phenyl-bicyclo[2.2.2]oct-5-en-2-ol;
(1S,2S,4S)-2-(2-{[3-(5,6-Dichloro-1H-benzoimidazol-2-yl)-propyl]-methyl-amino}-ethyl)-5-phenyl-bicyclo[2.2.2]oct-5-en-2-ol;
(1R,2R,4R)-2-(2-{[3-(5,6-Dichloro-1H-benzoimidazol-2-yl)-propyl]-methyl-amino}-ethyl)-5-phenyl-bicyclo[2.2.2]oct-5-en-2-ol;
(1S,2S,4S)-2-(2-{[3-(5,6-Dimethoxy-1H-benzoimidazol-2-yl)-propyl]-methyl-amino}-ethyl)-5-phenyl-bicyclo[2.2.2]oct-5-en-2-ol;
(1R,2R,4R)-2-(2-{[3-(5,6-Dimethoxy-1H-benzoimidazol-2-yl)-propyl]-methyl-amino}-ethyl)-5-phenyl-bicyclo[2.2.2]oct-5-en-2-ol;
(1S,2S,4S)-2-(2-{[3-(5-Methoxy-1H-benzoimidazol-2-yl)-propyl]-methyl-amino}-ethyl)-5-phenyl-bicyclo[2.2.2]oct-5-en-2-ol;
(1R,2R,4R)-2-(2-{[3-(5-Methoxy-1H-benzoimidazol-2-yl)-propyl]-methyl-amino}-ethyl)-5-phenyl-bicyclo[2.2.2]oct-5-en-2-ol;
(1S,2S,4S)-2-(2-{[3-(7-Methoxy-4-methyl-1H-benzoimidazol-2-yl)-propyl]-methyl-amino}-ethyl)-5-phenyl-bicyclo[2.2.2]oct-5-en-2-ol;
(1R,2R,4R)-2-(2-{[3-(7-Methoxy-4-methyl-1H-benzoimidazol-2-yl)-propyl]-methyl-amino}-ethyl)-5-phenyl-bicyclo[2.2.2]oct-5-en-2-ol;
(1S,2S,4S)-2-(2-{[3-(7-Ethoxy-1H-benzoimidazol-2-yl)-propyl]-methyl-amino}-ethyl)-5-phenyl-bicyclo[2.2.2]oct-5-en-2-ol;
(1R,2R,4R)-2-(2-{[3-(7-Ethoxy-1H-benzoimidazol-2-yl)-propyl]-methyl-amino}-ethyl)-5-phenyl-bicyclo[2.2.2]oct-5-en-2-ol;
(1S,2S,4S)-2-(2-{[2-(4-Methoxy-1H-benzoimidazol-2-yl)-ethyl]-methyl-amino}-ethyl)-5-phenyl-bicyclo[2.2.2]oct-5-en-2-ol;
(1R,2R,4R)-2-(2-{[2-(4-Methoxy-1H-benzoimidazol-2-yl)-ethyl]-methyl-amino}-ethyl)-5-phenyl-bicyclo[2.2.2]oct-5-en-2-ol;
(1S,2S,4S)-2-(2-{[3-(7-Isopropoxy-1H-benzoimidazol-2-yl)-propyl]-methyl-amino}-ethyl)-5-phenyl-bicyclo[2.2.2]oct-5-en-2-ol;
(1R,2R,4R)-2-(2-{[3-(7-Isopropoxy-1H-benzoimidazol-2-yl)-propyl]-methyl-amino}-ethyl)-5-phenyl-bicyclo[2.2.2]oct-5-en-2-ol;

2-(3-{[2-((1S,2S,4S)-2-Hydroxy-5-phenyl-bicyclo[2.2.2]oct-5-en-2-yl)-ethyl]-methyl-amino}-propyl)-3H-benzoimidazol-4-ol;

2-(3-{[2-((1R,2R,4R)-2-Hydroxy-5-phenyl-bicyclo[2.2.2]oct-5-en-2-yl)-ethyl]-methyl-amino}-propyl)-3H-benzoimidazol-4-ol;

(1S,5S,6S)-6-(2-{[3-(7-Methoxy-1H-benzoimidazol-2-yl)-propyl]-methyl-amino}-ethyl)-8-phenyl-bicyclo[3.2.2]non-8-en-6-ol;

(1R,5R,6R)-6-(2-{[3-(7-Methoxy-1H-benzoimidazol-2-yl)-propyl]-methyl-amino}-ethyl)-8-phenyl-bicyclo[3.2.2]non-8-en-6-ol;

(1S,2S,4S)-2-(2-{[3-(4-Methoxy-1-methyl-1H-benzoimidazol-2-yl)-propyl]-methyl-amino}-ethyl)-5-phenyl-bicyclo[2.2.2]oct-5-en-2-ol;

(1R,2R,4R)-2-(2-{[3-(4-Methoxy-1-methyl-1H-benzoimidazol-2-yl)-propyl]-methyl-amino}-ethyl)-5-phenyl-bicyclo[2.2.2]oct-5-en-2-ol;

(1S,2S,4S)-2-(2-{[2-(3,4-Diethoxy-phenyl)-ethyl]-ethyl-amino}-ethyl)-5-phenyl-bicyclo[2.2.2]oct-5-en-2-ol;

(1R,2R,4R)-2-(2-{[2-(3,4-Diethoxy-phenyl)-ethyl]-ethyl-amino}-ethyl)-5-phenyl-bicyclo[2.2.2]oct-5-en-2-ol;

(1S,2S,4S)-2-(2-{[3-(3,4-Dimethoxy-phenyl)-propyl]-methyl-amino}-ethyl)-5-phenyl-bicyclo[2.2.2]oct-5-en-2-ol;

(1R,2R,4R)-2-(2-{[3-(3,4-Dimethoxy-phenyl)-propyl]-methyl-amino}-ethyl)-5-phenyl-bicyclo[2.2.2]oct-5-en-2-ol;

(1S,2S,4S)-2-(2-{[3-(3,4-Diethoxy-phenyl)-propyl]-methyl-amino}-ethyl)-5-phenyl-bicyclo[2.2.2]oct-5-en-2-ol;

(1R,2R,4R)-2-(2-{[3-(3,4-Diethoxy-phenyl)-propyl]-methyl-amino}-ethyl)-5-phenyl-bicyclo[2.2.2]oct-5-en-2-ol;

(1S,2S,4S)-2-{2-[(3-Furo[2,3-b]pyridin-5-yl-propyl)-methyl-amino]-ethyl}-5-phenyl-bicyclo[2.2.2]oct-5-en-2-ol;

(1R,2R,4R)-2-{2-[(3-Furo[2,3-b]pyridin-5-yl-propyl)-methyl-amino]-ethyl}-5-phenyl-bicyclo[2.2.2]oct-5-en-2-ol;

(1S,2S,4S)-2-(2-{Methyl-[3-(2-methyl-furo[2,3-b]pyridin-5-yl)-propyl]-amino}-ethyl)-5-phenyl-bicyclo[2.2.2]oct-5-en-2-ol;

(1R,2R,4R)-2-(2-{Methyl-[3-(2-methyl-furo[2,3-b]pyridin-5-yl)-propyl]-amino}-ethyl)-5-phenyl-bicyclo[2.2.2]oct-5-en-2-ol;

(1S,2S,4S)-2-{2-[Methyl-(3-pyridin-3-yl-propyl)-amino]-ethyl}-5-phenyl-bicyclo[2.2.2]oct-5-en-2-ol;

(1R,2R,4R)-2-{2-[Methyl-(3-pyridin-3-yl-propyl)-amino]-ethyl}-5-phenyl-bicyclo[2.2.2]oct-5-en-2-ol;

(1S,2S,4S)-2-{2-[(3-Isoquinolin-4-yl-propyl)-methyl-amino]-ethyl}-5-phenyl-bicyclo[2.2.2]oct-5-en-2-ol;

(1R,2R,4R)-2-{2-[(3-Isoquinolin-4-yl-propyl)-methyl-amino]-ethyl}-5-phenyl-bicyclo[2.2.2]oct-5-en-2-ol;

(1S,2S,4S)-2-{2-[Methyl-(3-quinolin-3-yl-propyl)-amino]-ethyl}-5-phenyl-bicyclo[2.2.2]oct-5-en-2-ol;

(1R,2R,4R)-2-{2-[Methyl-(3-quinolin-3-yl-propyl)-amino]-ethyl}-5-phenyl-bicyclo[2.2.2]oct-5-en-2-ol;

(1S,2S,4S)-2-{2-[Methyl-(3-quinolin-4-yl-propyl)-amino]-ethyl}-5-phenyl-bicyclo[2.2.2]oct-5-en-2-ol;

(1R,2R,4R)-2-{2-[Methyl-(3-Quinolin-4-yl-propyl)-amino]-ethyl}-5-phenyl-bicyclo[2.2.2]oct-5-en-2-ol;

(1R,2R,4S)-2-(2-{[3-(1H-Benzoimidazol-2-yl)-propyl]-methyl-amino}-ethyl)-5-methyl-6-phenyl-bicyclo[2.2.2]oct-5-en-2-ol;

(1S,2S,4R)-2-(2-{[3-(1H-Benzoimidazol-2-yl)-propyl]-methyl-amino}-ethyl)-5-methyl-6-phenyl-bicyclo[2.2.2]oct-5-en-2-ol;

N-[2-(3-{[2-((1S,2S,4S)-2-Hydroxy-5-phenyl-bicyclo[2.2.2]oct-5-en-2-yl)-ethyl]-methyl-amino}-propyl)-1H-benzoimidazol-4-yl]-acetamide;

N-[2-(3-{[2-((1R,2R,4R)-2-Hydroxy-5-phenyl-bicyclo[2.2.2]oct-5-en-2-yl)-ethyl]-methyl-amino}-propyl)-1H-benzoimidazol-4-yl]-acetamide;

(1S,2S,4S)-2-(2-{[3-(4-Chloro-1H-benzoimidazol-2-yl)-propyl]-methyl-amino}-ethyl)-5-phenyl-bicyclo[2.2.2]oct-5-en-2-ol;

(1R,2R,4R)-2-(2-{[3-(4-Chloro-1H-benzoimidazol-2-yl)-propyl]-methyl-amino}-ethyl)-5-phenyl-bicyclo[2.2.2]oct-5-en-2-ol;

(1S,2S,4S)-2-(2-{[3-(7-Chloro-4-methoxy-1H-benzoimidazol-2-yl)-propyl]-methyl-amino}-ethyl)-5-phenyl-bicyclo[2.2.2]oct-5-en-2-ol;

(1R,2R,4R)-2-(2-{[3-(7-Chloro-4-methoxy-1H-benzoimidazol-2-yl)-propyl]-methyl-amino}-ethyl)-5-phenyl-bicyclo[2.2.2]oct-5-en-2-ol;

(1S,2S,4S)-2-(2-{[3-(4,6-Dimethoxy-1H-benzoimidazol-2-yl)-propyl]-methyl-amino}-ethyl)-5-phenyl-bicyclo[2.2.2]oct-5-en-2-ol;

(1R,2R,4R)-2-(2-{[3-(4,6-Dimethoxy-1H-benzoimidazol-2-yl)-propyl]-methyl-amino}-ethyl)-5-phenyl-bicyclo[2.2.2]oct-5-en-2-ol;

(1S,2S,4S)-2-(2-{[3-(4,7-Dimethoxy-1H-benzoimidazol-2-yl)-propyl]-methyl-amino}-ethyl)-5-phenyl-bicyclo[2.2.2]oct-5-en-2-ol;

(1R,2R,4R)-2-(2-{[3-(4,7-Dimethoxy-1H-benzoimidazol-2-yl)-propyl]-methyl-amino}-ethyl)-5-phenyl-bicyclo[2.2.2]oct-5-en-2-ol;

(1S,2S,4S)-2-(2-{[3-(4,6-Bis-trifluoromethyl-1H-benzoimidazol-2-yl)-propyl]-methyl-amino}-ethyl)-5-phenyl-bicyclo[2.2.2]oct-5-en-2-ol;

(1R,2R,4R)-2-(2-{[3-(4,6-Bis-trifluoromethyl-1H-benzoimidazol-2-yl)-propyl]-methyl-amino}-ethyl)-5-phenyl-bicyclo[2.2.2]oct-5-en-2-ol;

(1S,2S,4S)-2-[2-({3-[4-(2-Methoxy-ethoxy)-1H-benzoimidazol-2-yl]-propyl}-methyl-amino)-ethyl]-5-phenyl-bicyclo[2.2.2]oct-5-en-2-ol;

(1R,2R,4R)-2-[2-({3-[4-(2-Methoxy-ethoxy)-1H-benzoimidazol-2-yl]-propyl}-methyl-amino)-ethyl]-5-phenyl-bicyclo[2.2.2]oct-5-en-2-ol;

(1S,2S,4S)-2-(2-{[3-(4,5-Dimethoxy-7-methyl-1H-benzoimidazol-2-yl)-propyl]-methyl-amino}-ethyl)-5-phenyl-bicyclo[2.2.2]oct-5-en-2-ol;

(1R,2R,4R)-2-(2-{[3-(4,5-Dimethoxy-7-methyl-1H-benzoimidazol-2-yl)-propyl]-methyl-amino}-ethyl)-5-phenyl-bicyclo[2.2.2]oct-5-en-2-ol;

(1S,5S,6S)-6-(2-{[3-(7-Methoxy-4-methyl-1H-benzoimidazol-2-yl)-propyl]-methyl-amino}-ethyl)-8-phenyl-bicyclo[3.2.2]non-8-en-6-ol;

(1R,5R,6R)-6-(2-{[3-(7-Methoxy-4-methyl-1H-benzoimidazol-2-yl)-propyl]-methyl-amino}-ethyl)-8-phenyl-bicyclo[3.2.2]non-8-en-6-ol;

(1S,2S,4S)-2-(2-{Methyl-[3-(4-trifluoromethoxy-1H-benzoimidazol-2-yl)-propyl]-amino}-ethyl)-5-phenyl-bicyclo[2.2.2]oct-5-en-2-ol;

(1R,2R,4R)-2-(2-{Methyl-[3-(4-trifluoromethoxy-1H-benzoimidazol-2-yl)-propyl]-amino}-ethyl)-5-phenyl-bicyclo[2.2.2]oct-5-en-2-ol;

(1S,5S,6S)-6-(2-{[3-(4,7-Dimethoxy-1H-benzoimidazol-2-yl)-propyl]-methyl-amino}-ethyl)-8-phenyl-bicyclo[3.2.2]non-8-en-6-ol;

(1R,5R,6R)-6-(2-{[3-(4,7-Dimethoxy-1H-benzoimidazol-2-yl)-propyl]-methyl-amino}-ethyl)-8-phenyl-bicyclo[3.2.2]non-8-en-6-ol;
(1R,2R,4R)-2-(2-{[3-(1H-Benzoimidazol-2-yl)-propyl]-methyl-amino}-ethyl)-bicyclo[2.2.2]oct-5-en-2-ol;
(1S,2S,4S)-2-(2-{[3-(1H-Benzoimidazol-2-yl)-propyl]-methyl-amino}-ethyl)-bicyclo[2.2.2]oct-5-en-2-ol;
(1R,2R,4R,5R)-2-(2-{[3-(1H-Benzoimidazol-2-yl)-propyl]-methyl-amino}-ethyl)-5-methoxy-5-phenyl-bicyclo[2.2.2]octan-2-ol;
(1S,2S,4S,5S)-2-(2-{[3-(1H-Benzoimidazol-2-yl)-propyl]-methyl-amino}-ethyl)-5-methoxy-5-phenyl-bicyclo[2.2.2]octan-2-ol;
(1R,2S,4R,5S)-2-(2-{[3-(1H-Benzoimidazol-2-yl)-propyl]-methyl-amino}-ethyl)-5-methoxy-5-phenyl-bicyclo[2.2.2]octan-2-ol;
(1S,2R,4S,5R)-2-(2-{[3-(1H-Benzoimidazol-2-yl)-propyl]-methyl-amino}-ethyl)-5-methoxy-5-phenyl-bicyclo[2.2.2]octan-2-ol;
(1R,2R,4R,5S)-2-(2-{[3-(1H-Benzoimidazol-2-yl)-propyl]-methyl-amino}-ethyl)-5-methoxy-5-phenyl-bicyclo[2.2.2]octan-2-ol;
(1S,2S,4S,5R)-2-(2-{[3-(1H-Benzoimidazol-2-yl)-propyl]-methyl-amino}-ethyl)-5-methoxy-5-phenyl-bicyclo[2.2.2]octan-2-ol;
Isobutyric acid (1S,2S,4S)-2-(2-{[3-(1H-benzoimidazol-2-yl)-propyl]-methyl-amino}-ethyl)-5-phenyl-bicyclo[2.2.2]oct-5-en-2-yl ester;
Isobutyric acid (1R,2R,4R)-2-(2-{[3-(1H-benzoimidazol-2-yl)-propyl]-methyl-amino}-ethyl)-5-phenyl-bicyclo[2.2.2]oct-5-en-2-yl ester;
Isobutyric acid (1S,2S,4S)-2-(2-{[3-(1H-benzoimidazol-2-yl)-propyl]-methyl-amino}-ethyl)-5-(3-methoxy-phenyl)-bicyclo[2.2.2]oct-5-en-2-yl ester;
Isobutyric acid (1R,2R,4R)-2-(2-{[3-(1H-benzoimidazol-2-yl)-propyl]-methyl-amino}-ethyl)-5-(3-methoxy-phenyl)-bicyclo[2.2.2]oct-5-en-2-yl ester;
Isobutyric acid (1S,2S,4S)-2-(2-{[3-(1H-benzoimidazol-2-yl)-propyl]-methyl-amino}-ethyl)-5-(2,6-dimethyl-phenyl)-bicyclo[2.2.2]oct-5-en-2-yl ester;
Isobutyric acid (1R,2R,4R)-2-(2-{[3-(1H-benzoimidazol-2-yl)-propyl]-methyl-amino}-ethyl)-5-(2,6-dimethyl-phenyl)-bicyclo[2.2.2]oct-5-en-2-yl ester;
Isobutyric acid (1S,2S,4S)-2-(2-{[3-(1H-benzoimidazol-2-yl)-propyl]-methyl-amino}-ethyl)-5-o-tolyl-bicyclo[2.2.2]oct-5-en-2-yl ester;
Isobutyric acid (1R,2R,4R)-2-(2-{[3-(1H-benzoimidazol-2-yl)-propyl]-methyl-amino}-ethyl)-5-o-tolyl-bicyclo[2.2.2]oct-5-en-2-yl ester;
Isobutyric acid (1S,2S,4S)-2-(2-{[3-(1H-benzoimidazol-2-yl)-propyl]-methyl-amino}-ethyl)-5-m-tolyl-bicyclo[2.2.2]oct-5-en-2-yl ester;
Isobutyric acid (1R,2R,4R)-2-(2-{[3-(1H-benzoimidazol-2-yl)-propyl]-methyl-amino}-ethyl)-5-m-tolyl-bicyclo[2.2.2]oct-5-en-2-yl ester;
Isobutyric acid (1S,2S,4S)-2-(2-{[3-(1H-benzoimidazol-2-yl)-propyl]-methyl-amino}-ethyl)-5-p-tolyl-bicyclo[2.2.2]oct-5-en-2-yl ester;
Isobutyric acid (1R,2R,4R)-2-(2-{[3-(1H-benzoimidazol-2-yl)-propyl]-methyl-amino}-ethyl)-5-p-tolyl-bicyclo[2.2.2]oct-5-en-2-yl ester;
Isobutyric acid (1S,2S,4S)-2-(2-{[3-(1H-benzoimidazol-2-yl)-propyl]-methyl-amino}-ethyl)-5-(3-fluoro-phenyl)-bicyclo[2.2.2]oct-5-en-2-yl ester;
Isobutyric acid (1R,2R,4R)-2-(2-{[3-(1H-benzoimidazol-2-yl)-propyl]-methyl-amino}-ethyl)-5-(3-fluoro-phenyl)-bicyclo[2.2.2]oct-5-en-2-yl ester;
Isobutyric acid (1S,2S,4S)-2-(2-{[3-(1H-benzoimidazol-2-yl)-propyl]-methyl-amino}-ethyl)-5-(4-fluoro-phenyl)-bicyclo[2.2.2]oct-5-en-2-yl ester;
Isobutyric acid (1R,2R,4R)-2-(2-{[3-(1H-benzoimidazol-2-yl)-propyl]-methyl-amino}-ethyl)-5-(4-fluoro-phenyl)-bicyclo[2.2.2]oct-5-en-2-yl ester;
Isobutyric acid (1S,2S,4S)-2-(2-{[3-(1H-benzoimidazol-2-yl)-propyl]-methyl-amino}-ethyl)-5-pyridin-3-yl-bicyclo[2.2.2]oct-5-en-2-yl ester;
Isobutyric acid (1R,2R,4R)-2-(2-{[3-(1H-benzoimidazol-2-yl)-propyl]-methyl-amino}-ethyl)-5-pyridin-3-yl-bicyclo[2.2.2]oct-5-en-2-yl ester;
Isobutyric acid (1S,2S,4S)-2-(2-{[3-(1H-benzoimidazol-2-yl)-propyl]-methyl-amino}-ethyl)-5-naphthalen-2-yl-bicyclo[2.2.2]oct-5-en-2-yl ester;
Isobutyric acid (1R,2R,4R)-2-(2-{[3-(1H-benzoimidazol-2-yl)-propyl]-methyl-amino}-ethyl)-5-naphthalen-2-yl-bicyclo[2.2.2]oct-5-en-2-yl ester;
Isobutyric acid (1S,2S,4S)-2-(2-{[2-(1H-benzoimidazol-2-yl)-ethyl]-methyl-amino}-ethyl)-5-phenyl-bicyclo[2.2.2]oct-5-en-2-yl ester;
Isobutyric acid (1R,2R,4R)-2-(2-{[2-(1H-benzoimidazol-2-yl)-ethyl]-methyl-amino}-ethyl)-5-phenyl-bicyclo[2.2.2]oct-5-en-2-yl ester;
Isobutyric acid (1S,2S,4S)-2-{2-[(1H-benzoimidazol-2-ylmethyl)-methyl-amino]-ethyl}-5-phenyl-bicyclo[2.2.2]oct-5-en-2-yl ester;
Isobutyric acid (1R,2R,4R)-2-{2-[(1H-benzoimidazol-2-ylmethyl)-methyl-amino]-ethyl}-5-phenyl-bicyclo[2.2.2]oct-5-en-2-yl ester;
Isobutyric acid (1S,2S,4S)-2-{2-[methyl-(3-phenyl-propyl)-amino]-ethyl}-5-phenyl-bicyclo[2.2.2]oct-5-en-2-yl ester;
Isobutyric acid (1R,2R,4R)-2-{2-[methyl-(3-phenyl-propyl)-amino]-ethyl}-5-phenyl-bicyclo[2.2.2]oct-5-en-2-yl ester;
Isobutyric acid (1S,2S,4S)-2-(2-{[3-(1H-benzoimidazol-2-yl)-propyl]-methyl-amino}-ethyl)-6-methyl-5-propyl-bicyclo[2.2.2]oct-5-en-2-yl ester;
Isobutyric acid (1R,2R,4R)-2-(2-{[3-(1H-benzoimidazol-2-yl)-propyl]-methyl-amino}-ethyl)-6-methyl-5-propyl-bicyclo[2.2.2]oct-5-en-2-yl ester;
Isobutyric acid (1S,2S,4S)-2-(2-{[3-(1H-benzoimidazol-2-yl)-propyl]-methyl-amino}-ethyl)-5-methyl-6-phenyl-bicyclo[2.2.2]oct-5-en-2-yl ester;
Isobutyric acid (1R,2R,4R)-2-(2-{[3-(1H-benzoimidazol-2-yl)-propyl]-methyl-amino}-ethyl)-5-methyl-6-phenyl-bicyclo[2.2.2]oct-5-en-2-yl ester;
Isobutyric acid (1S,2R,4S)-2-(2-{[3-(1H-benzoimidazol-2-yl)-propyl]-methyl-amino}-ethyl)-5-methyl-6-phenyl-bicyclo[2.2.2]oct-5-en-2-yl ester;
Isobutyric acid (1R,2S,4R)-2-(2-{[3-(1H-benzoimidazol-2-yl)-propyl]-methyl-amino}-ethyl)-5-methyl-6-phenyl-bicyclo[2.2.2]oct-5-en-2-yl ester;
2-(3-{[2-((1S,2S,4S)-2-Isobutyryloxy-5-phenyl-bicyclo[2.2.2]oct-5-en-2-yl)-ethyl]-methyl-amino}-propyl)-1H-benzoimidazole-4-carboxylic acid methyl ester;
2-(3-{[2-((1R,2R,4R)-2-Isobutyryloxy-5-phenyl-bicyclo[2.2.2]oct-5-en-2-yl)-ethyl]-methyl-amino}-propyl)-1H-benzoimidazole-4-carboxylic acid methyl ester;
2-(3-{[2-((1S,2S,4S)-2-Isobutyryloxy-5-phenyl-bicyclo[2.2.2]oct-5-en-2-yl)-ethyl]-methyl-amino}-propyl)-1H-benzoimidazole-5-carboxylic acid methyl ester;
2-(3-{[2-((1R,2R,4R)-2-Isobutyryloxy-5-phenyl-bicyclo[2.2.2]oct-5-en-2-yl)-ethyl]-methyl-amino}-propyl)-1H-benzoimidazole-5-carboxylic acid methyl ester;

Isobutyric acid (1S,2S,4S)-2-(2-{[3-(1H-benzoimidazol-2-yl)-propyl]-methyl-amino}-ethyl)-5-thiophen-2-yl-bicyclo[2.2.2]oct-5-en-2-yl ester;
Isobutyric acid (1R,2R,4R)-2-(2-{[3-(1H-benzoimidazol-2-yl)-propyl]-methyl-amino}-ethyl)-5-thiophen-2-yl-bicyclo[2.2.2]oct-5-en-2-yl ester;
Isobutyric acid (1S,2S,4S)-2-(2-{[3-(1H-benzoimidazol-2-yl)-propyl]-methyl-amino}-ethyl)-5-(4-methoxy-phenyl)-bicyclo[2.2.2]oct-5-en-2-yl ester;
Isobutyric acid (1R,2R,4R)-2-(2-{[3-(1H-benzoimidazol-2-yl)-propyl]-methyl-amino}-ethyl)-5-(4-methoxy-phenyl)-bicyclo[2.2.2]oct-5-en-2-yl ester;
Isobutyric acid (1S,2S,4S)-2-(2-{[3-(1H-benzoimidazol-2-yl)-propyl]-methyl-amino}-ethyl)-5-(2-methoxy-phenyl)-bicyclo[2.2.2]oct-5-en-2-yl ester;
Isobutyric acid (1R,2R,4R)-2-(2-{[3-(1H-benzoimidazol-2-yl)-propyl]-methyl-amino}-ethyl)-5-(2-methoxy-phenyl)-bicyclo[2.2.2]oct-5-en-2-yl ester;
Isobutyric acid (1S,2S,4S)-2-(2-{[3-(1H-benzoimidazol-2-yl)-propyl]-methyl-amino}-ethyl)-5-thiazol-2-yl-bicyclo[2.2.2]oct-5-en-2-yl ester;
Isobutyric acid (1R,2R,4R)-2-(2-{[3-(1H-benzoimidazol-2-yl)-propyl]-methyl-amino}-ethyl)-5-thiazol-2-yl-bicyclo[2.2.2]oct-5-en-2-yl ester;
Isobutyric acid (1S,2S,4S)-2-(2-{[3-(1H-benzoimidazol-2-yl)-propyl]-methyl-amino}-ethyl)-5-oxazol-2-yl-bicyclo[2.2.2]oct-5-en-2-yl ester;
Isobutyric acid (1R,2R,4R)-2-(2-{[3-(1H-benzoimidazol-2-yl)-propyl]-methyl-amino}-ethyl)-5-oxazol-2-yl-bicyclo[2.2.2]oct-5-en-2-yl ester;
Isobutyric acid (1S,2S,4S)-2-(2-{[3-(4-methoxy-1H-benzoimidazol-2-yl)-propyl]-methyl-amino}-ethyl)-5-phenyl-bicyclo[2.2.2]oct-5-en-2-yl ester;
Isobutyric acid (1R,2R,4R)-2-(2-{[3-(4-methoxy-1H-benzoimidazol-2-yl)-propyl]-methyl-amino}-ethyl)-5-phenyl-bicyclo[2.2.2]oct-5-en-2-yl ester;
Cyclobutanecarboxylic acid (1S,2S,4S)-2-(2-{[3-(4-methoxy-1H-benzoimidazol-2-yl)-propyl]-methyl-amino}-ethyl)-5-phenyl-bicyclo[2.2.2]oct-5-en-2-yl ester;
Cyclobutanecarboxylic acid (1R,2R,4R)-2-(2-{[3-(4-methoxy-1H-benzoimidazol-2-yl)-propyl]-methyl-amino}-ethyl)-5-phenyl-bicyclo[2.2.2]oct-5-en-2-yl ester;
3,3,3-Trifluoro-propionic acid (1S,2S,4S)-2-(2-{[3-(4-methoxy-1H-benzoimidazol-2-yl)-propyl]-methyl-amino}-ethyl)-5-phenyl-bicyclo[2.2.2]oct-5-en-2-yl ester;
3,3,3-Trifluoro-propionic acid (1R,2R,4R)-2-(2-{[3-(4-methoxy-1H-benzoimidazol-2-yl)-propyl]-methyl-amino}-ethyl)-5-phenyl-bicyclo[2.2.2]oct-5-en-2-yl ester;
Isobutyric acid (1S,2S,4S)-2-(2-{[3-(5,6-dichloro-1H-benzoimidazol-2-yl)-propyl]-methyl-amino}-ethyl)-5-phenyl-bicyclo[2.2.2]oct-5-en-2-yl ester;
Isobutyric acid (1R,2R,4R)-2-(2-{[3-(5,6-dichloro-1H-benzoimidazol-2-yl)-propyl]-methyl-amino}-ethyl)-5-phenyl-bicyclo[2.2.2]oct-5-en-2-yl ester;
Cyclopropanecarboxylic acid (1S,2S,4S)-2-(2-{[3-(5,6-dichloro-1H-benzoimidazol-2-yl)-propyl]-methyl-amino}-ethyl)-5-phenyl-bicyclo[2.2.2]oct-5-en-2-yl ester;
Cyclopropanecarboxylic acid (1R,2R,4R)-2-(2-{[3-(5,6-dichloro-1H-benzoimidazol-2-yl)-propyl]-methyl-amino}-ethyl)-5-phenyl-bicyclo[2.2.2]oct-5-en-2-yl ester;
Isobutyric acid (1S,2S,4S)-2-(2-{[3-(5,6-dimethoxy-1H-benzoimidazol-2-yl)-propyl]-methyl-amino}-ethyl)-5-phenyl-bicyclo[2.2.2]oct-5-en-2-yl ester;
Isobutyric acid (1R,2R,4R)-2-(2-{[3-(5,6-dimethoxy-1H-benzoimidazol-2-yl)-propyl]-methyl-amino}-ethyl)-5-phenyl-bicyclo[2.2.2]oct-5-en-2-yl ester;
Isobutyric acid (1S,2S,4S)-2-(2-{[3-(5-methoxy-1H-benzoimidazol-2-yl)-propyl]-methyl-amino}-ethyl)-5-phenyl-bicyclo[2.2.2]oct-5-en-2-yl ester;
Isobutyric acid (1R,2R,4R)-2-(2-{[3-(5-methoxy-1H-benzoimidazol-2-yl)-propyl]-methyl-amino}-ethyl)-5-phenyl-bicyclo[2.2.2]oct-5-en-2-yl ester;
Isobutyric acid (1S,2S,4S)-2-(2-{[3-(7-methoxy-4-methyl-1H-benzoimidazol-2-yl)-propyl]-methyl-amino}-ethyl)-5-phenyl-bicyclo[2.2.2]oct-5-en-2-yl ester;
Isobutyric acid (1R,2R,4R)-2-(2-{[3-(7-methoxy-4-methyl-1H-benzoimidazol-2-yl)-propyl]-methyl-amino}-ethyl)-5-phenyl-bicyclo[2.2.2]oct-5-en-2-yl ester;
Isobutyric acid (1S,2S,4S)-2-(2-{[3-(7-ethoxy-1H-benzoimidazol-2-yl)-propyl]-methyl-amino}-ethyl)-5-phenyl-bicyclo[2.2.2]oct-5-en-2-yl ester;
Isobutyric acid (1R,2R,4R)-2-(2-{[3-(7-ethoxy-1H-benzoimidazol-2-yl)-propyl]-methyl-amino}-ethyl)-5-phenyl-bicyclo[2.2.2]oct-5-en-2-yl ester;
Isobutyric acid (1S,2S,4S)-2-(2-{[2-(7-methoxy-1H-benzoimidazol-2-yl)-ethyl]-methyl-amino}-ethyl)-5-phenyl-bicyclo[2.2.2]oct-5-en-2-yl ester;
Isobutyric acid (1R,2R,4R)-2-(2-{[2-(7-methoxy-1H-benzoimidazol-2-yl)-ethyl]-methyl-amino}-ethyl)-5-phenyl-bicyclo[2.2.2]oct-5-en-2-yl ester;
Isobutyric acid (1S,2S,4S)-2-(2-{[3-(7-isopropoxy-1H-benzoimidazol-2-yl)-propyl]-methyl-amino}-ethyl)-5-phenyl-bicyclo[2.2.2]oct-5-en-2-yl ester;
Isobutyric acid (1R,2R,4R)-2-(2-{[3-(7-isopropoxy-1H-benzoimidazol-2-yl)-propyl]-methyl-amino}-ethyl)-5-phenyl-bicyclo[2.2.2]oct-5-en-2-yl ester;
Isobutyric acid (1S,2S,4S)-2-(2-{[3-(7-isobutyryloxy-1H-benzoimidazol-2-yl)-propyl]-methyl-amino}-ethyl)-5-phenyl-bicyclo[2.2.2]oct-5-en-2-yl ester;
Isobutyric acid (1R,2R,4R)-2-(2-{[3-(7-isobutyryloxy-1H-benzoimidazol-2-yl)-propyl]-methyl-amino}-ethyl)-5-phenyl-bicyclo[2.2.2]oct-5-en-2-yl ester;
Isobutyric acid (1S,2S,4S)-2-(2-{[3-(7-hydroxy-1H-benzoimidazol-2-yl)-propyl]-methyl-amino}-ethyl)-5-phenyl-bicyclo[2.2.2]oct-5-en-2-yl ester;
Isobutyric acid (1R,2R,4R)-2-(2-{[3-(7-hydroxy-1H-benzoimidazol-2-yl)-propyl]-methyl-amino}-ethyl)-5-phenyl-bicyclo[2.2.2]oct-5-en-2-yl ester;
Isobutyric acid (1S,5S,6S)-6-(2-{[3-(7-methoxy-1H-benzoimidazol-2-yl)-propyl]-methyl-amino}-ethyl)-8-phenyl-bicyclo[3.2.2]non-8-en-6-yl ester;
Isobutyric acid (1R,5R,6R)-6-(2-{[3-(7-methoxy-1H-benzoimidazol-2-yl)-propyl]-methyl-amino}-ethyl)-8-phenyl-bicyclo[3.2.2]non-8-en-6-yl ester;
3,3,3-Trifluoro-propionic acid (1S,5S,6S)-6-(2-{[3-(4-methoxy-1H-benzoimidazol-2-yl)-propyl]-methyl-amino}-ethyl)-8-phenyl-bicyclo[3.2.2]non-8-en-6-yl ester;
3,3,3-Trifluoro-propionic acid (1R,5R,6R)-6-(2-{[3-(4-methoxy-1H-benzoimidazol-2-yl)-propyl]-methyl-amino}-ethyl)-8-phenyl-bicyclo[3.2.2]non-8-en-6-yl ester;
Isobutyric acid (1S,2S,4S)-2-(2-{[3-(4-methoxy-1-methyl-1H-benzoimidazol-2-yl)-propyl]-methyl-amino}-ethyl)-5-phenyl-bicyclo[2.2.2]oct-5-en-2-yl ester;

Isobutyric acid (1R,2R,4R)-2-(2-{[3-(4-methoxy-1-methyl-1H-benzoimidazol-2-yl)-propyl]-methyl-amino}-ethyl)-5-phenyl-bicyclo[2.2.2]oct-5-en-2-yl ester;

Isobutyric acid (1S,2S,4S)-2-(2-{[2-(3,4-diethoxy-phenyl)-ethyl]-ethyl-amino}-ethyl)-5-phenyl-bicyclo[2.2.2]oct-5-en-2-yl ester;

Isobutyric acid (1R,2R,4R)-2-(2-{[2-(3,4-diethoxy-phenyl)-ethyl]-ethyl-amino}-ethyl)-5-phenyl-bicyclo[2.2.2]oct-5-en-2-yl ester;

Isobutyric acid (1S,2S,4S)-2-(2-{[3-(3,4-dimethoxy-phenyl)-propyl]-methyl-amino}-ethyl)-5-phenyl-bicyclo[2.2.2]oct-5-en-2-yl ester;

Isobutyric acid (1R,2R,4R)-2-(2-{[3-(3,4-dimethoxy-phenyl)-propyl]-methyl-amino}-ethyl)-5-phenyl-bicyclo[2.2.2]oct-5-en-2-yl ester;

Isobutyric acid (1S,2S,4S)-2-(2-{[3-(3,4-diethoxy-phenyl)-propyl]-methyl-amino}-ethyl)-5-phenyl-bicyclo[2.2.2]oct-5-en-2-yl ester;

Isobutyric acid (1R,2R,4R)-2-(2-{[3-(3,4-diethoxy-phenyl)-propyl]-methyl-amino}-ethyl)-5-phenyl-bicyclo[2.2.2]oct-5-en-2-yl ester;

Isobutyric acid (1S,2S,4S)-2-{2-[(3-furo[2,3-b]pyridin-5-yl-propyl)-methyl-amino]-ethyl}-5-phenyl-bicyclo[2.2.2]oct-5-en-2-yl ester;

Isobutyric acid (1R,2R,4R)-2-{2-[(3-furo[2,3-b]pyridin-5-yl-propyl)-methyl-amino]-ethyl}-5-phenyl-bicyclo[2.2.2]oct-5-en-2-yl ester;

Isobutyric acid (1S,2S,4S)-2-(2-{methyl-[3-(2-methyl-furo[2,3-b]pyridin-5-yl)-propyl]-amino}-ethyl)-5-phenyl-bicyclo[2.2.2]oct-5-en-2-yl ester;

Isobutyric acid (1R,2R,4R)-2-(2-{methyl-[3-(2-methyl-furo[2,3-b]pyridin-5-yl)-propyl]-amino}-ethyl)-5-phenyl-bicyclo[2.2.2]oct-5-en-2-yl ester;

Isobutyric acid (1S,2S,4S)-2-{2-[methyl-(3-pyridin-3-yl-propyl)-amino]-ethyl}-5-phenyl-bicyclo[2.2.2]oct-5-en-2-yl ester;

Isobutyric acid (1R,2R,4R)-2-{2-[methyl-(3-pyridin-3-yl-propyl)-amino]-ethyl}-5-phenyl-bicyclo[2.2.2]oct-5-en-2-yl ester;

Isobutyric acid (1S,2S,4S)-2-(2-{[3-(4,5-diphenyl-1H-imidazol-2-yl)-propyl]-methyl-amino}-ethyl)-5-phenyl-bicyclo[2.2.2]oct-5-en-2-yl ester;

Isobutyric acid (1R,2R,4R)-2-(2-{[3-(4,5-diphenyl-1H-imidazol-2-yl)-propyl]-methyl-amino}-ethyl)-5-phenyl-bicyclo[2.2.2]oct-5-en-2-yl ester;

Isobutyric acid (1S,2S,4S)-2-{2-[(3-isoquinolin-4-yl-propyl)-methyl-amino]-ethyl}-5-phenyl-bicyclo[2.2.2]oct-5-en-2-yl ester;

Isobutyric acid (1R,2R,4R)-2-{2-[(3-isoquinolin-4-yl-propyl)-methyl-amino]-ethyl}-5-phenyl-bicyclo[2.2.2]oct-5-en-2-yl ester;

Isobutyric acid (1S,2S,4S)-2-{2-[methyl-(3-quinolin-3-yl-propyl)-amino]-ethyl}-5-phenyl-bicyclo[2.2.2]oct-5-en-2-yl ester;

Isobutyric acid (1R,2R,4R)-2-{2-[methyl-(3-quinolin-3-yl-propyl)-amino]-ethyl}-5-phenyl-bicyclo[2.2.2]oct-5-en-2-yl ester;

Isobutyric acid (1S,2S,4S)-2-{2-[methyl-(3-quinolin-4-yl-propyl)-amino]-ethyl}-5-phenyl-bicyclo[2.2.2]oct-5-en-2-yl ester;

Isobutyric acid (1R,2R,4R)-2-{2-[methyl-(3-quinolin-4-yl-propyl)-amino]-ethyl}-5-phenyl-bicyclo[2.2.2]oct-5-en-2-yl ester;

2,2-Dimethyl-propionic acid (1S,2S,4S)-2-(2-{[3-(4-methoxy-1H-benzoimidazol-2-yl)-propyl]-methyl-amino}-ethyl)-5-phenyl-bicyclo[2.2.2]oct-5-en-2-yl ester;

2,2-Dimethyl-propionic acid (1R,2R,4R)-2-(2-{[3-(4-methoxy-1H-benzoimidazol-2-yl)-propyl]-methyl-amino}-ethyl)-5-phenyl-bicyclo[2.2.2]oct-5-en-2-yl ester;

Isopropyl-carbamic acid (1S,2S,4S)-2-(2-{[3-(4-methoxy-1H-benzoimidazol-2-yl)-propyl]-methyl-amino}-ethyl)-5-phenyl-bicyclo[2.2.2]oct-5-en-2-yl ester;

Isopropyl-carbamic acid (1R,2R,4R)-2-(2-{[3-(4-methoxy-1H-benzoimidazol-2-yl)-propyl]-methyl-amino}-ethyl)-5-phenyl-bicyclo[2.2.2]oct-5-en-2-yl ester;

2-Methoxy-2-methyl-propionic acid (1S,2S,4S)-2-(2-{[3-(4-methoxy-1H-benzoimidazol-2-yl)-propyl]-methyl-amino}-ethyl)-5-phenyl-bicyclo[2.2.2]oct-5-en-2-yl ester;

2-Methoxy-2-methyl-propionic acid (1R,2R,4R)-2-(2-{[3-(4-methoxy-1H-benzoimidazol-2-yl)-propyl]-methyl-amino}-ethyl)-5-phenyl-bicyclo[2.2.2]oct-5-en-2-yl ester;

Carbonic acid isopropyl ester (1S,2S,4S)-2-(2-{[3-(4-methoxy-1H-benzoimidazol-2-yl)-propyl]-methyl-amino}-ethyl)-5-phenyl-bicyclo[2.2.2]oct-5-en-2-yl ester;

Carbonic acid isopropyl ester (1R,2R,4R)-2-(2-{[3-(4-methoxy-1H-benzoimidazol-2-yl)-propyl]-methyl-amino}-ethyl)-5-phenyl-bicyclo[2.2.2]oct-5-en-2-yl ester;

Isobutyric acid (1S,2S,4S)-2-(2-{[3-(4-acetylamino-1H-benzoimidazol-2-yl)-propyl]-methyl-amino}-ethyl)-5-phenyl-bicyclo[2.2.2]oct-5-en-2-yl ester;

Isobutyric acid (1R,2R,4R)-2-(2-{[3-(4-acetylamino-1H-benzoimidazol-2-yl)-propyl]-methyl-amino}-ethyl)-5-phenyl-bicyclo[2.2.2]oct-5-en-2-yl ester;

Isobutyric acid (1S,2S,4S)-2-(2-{[3-(4-chloro-1H-benzoimidazol-2-yl)-propyl]-methyl-amino}-ethyl)-5-phenyl-bicyclo[2.2.2]oct-5-en-2-yl ester;

Isobutyric acid (1R,2R,4R)-2-(2-{[3-(4-chloro-1H-benzoimidazol-2-yl)-propyl]-methyl-amino}-ethyl)-5-phenyl-bicyclo[2.2.2]oct-5-en-2-yl ester;

Isobutyric acid (1S,2S,4S)-2-(2-{[3-(7-chloro-4-methoxy-1H-benzoimidazol-2-yl)-propyl]-methyl-amino}-ethyl)-5-phenyl-bicyclo[2.2.2]oct-5-en-2-yl ester;

Isobutyric acid (1R,2R,4R)-2-(2-{[3-(7-chloro-4-methoxy-1H-benzoimidazol-2-yl)-propyl]-methyl-amino}-ethyl)-5-phenyl-bicyclo[2.2.2]oct-5-en-2-yl ester;

Isobutyric acid (1S,2S,4S)-2-(2-{[3-(4,6-dimethoxy-1H-benzoimidazol-2-yl)-propyl]-methyl-amino}-ethyl)-5-phenyl-bicyclo[2.2.2]oct-5-en-2-yl ester;

Isobutyric acid (1R,2R,4R)-2-(2-{[3-(4,6-dimethoxy-1H-benzoimidazol-2-yl)-propyl]-methyl-amino}-ethyl)-5-phenyl-bicyclo[2.2.2]oct-5-en-2-yl ester;

Isobutyric acid (1S,2S,4S)-2-(2-{[3-(4,7-dimethoxy-1H-benzoimidazol-2-yl)-propyl]-methyl-amino}-ethyl)-5-phenyl-bicyclo[2.2.2]oct-5-en-2-yl ester;

Isobutyric acid (1R,2R,4R)-2-(2-{[3-(4,7-dimethoxy-1H-benzoimidazol-2-yl)-propyl]-methyl-amino}-ethyl)-5-phenyl-bicyclo[2.2.2]oct-5-en-2-yl ester;

Isobutyric acid (1S,2S,4S)-2-(2-{[3-(4,6-bis-trifluoromethyl-1H-benzoimidazol-2-yl)-propyl]-methyl-amino}-ethyl)-5-phenyl-bicyclo[2.2.2]oct-5-en-2-yl ester;

Isobutyric acid (1R,2R,4R)-2-(2-{[3-(4,6-bis-trifluoromethyl-1H-benzoimidazol-2-yl)-propyl]-methyl-amino}-ethyl)-5-phenyl-bicyclo[2.2.2]oct-5-en-2-yl ester;

Isobutyric acid (1S,2S,4S)-2-[2-({3-[4-(2-methoxy-ethoxy)-1H-benzoimidazol-2-yl]-propyl}-methyl-amino)-ethyl]-5-phenyl-bicyclo[2.2.2]oct-5-en-2-yl ester;

Isobutyric acid (1R,2R,4R)-2-[2-({3-[4-(2-methoxy-ethoxy)-1H-benzoimidazol-2-yl]-propyl}-methyl-amino)-ethyl]-5-phenyl-bicyclo[2.2.2]oct-5-en-2-yl ester;

Isobutyric acid (1S,2S,4S)-2-(2-{[3-(4,5-dimethoxy-7-methyl-1H-benzoimidazol-2-yl)-propyl]-methyl-amino}-ethyl)-5-phenyl-bicyclo[2.2.2]oct-5-en-2-yl ester;

Isobutyric acid (1R,2R,4R)-2-(2-{[3-(4,5-dimethoxy-7-methyl-1H-benzoimidazol-2-yl)-propyl]-methyl-amino}-ethyl)-5-phenyl-bicyclo[2.2.2]oct-5-en-2-yl ester;

Isobutyric acid (1S,5S,6S)-6-(2-{[3-(7-methoxy-4-methyl-1H-benzoimidazol-2-yl)-propyl]-methyl-amino}-ethyl)-8-phenyl-bicyclo[3.2.2]non-8-en-6-yl ester;

Isobutyric acid (1R,5R,6R)-6-(2-{[3-(7-methoxy-4-methyl-1H-benzoimidazol-2-yl)-propyl]-methyl-amino}-ethyl)-8-phenyl-bicyclo[3.2.2]non-8-en-6-yl ester;

Isobutyric acid (1S,2S,4S)-2-(2-{methyl-[3-(4-trifluoromethoxy-1H-benzoimidazol-2-yl)-propyl]-amino}-ethyl)-5-phenyl-bicyclo[2.2.2]oct-5-en-2-yl ester;

Isobutyric acid (1R,2R,4R)-2-(2-{methyl-[3-(4-trifluoromethoxy-1H-benzoimidazol-2-yl)-propyl]-amino}-ethyl)-5-phenyl-bicyclo[2.2.2]oct-5-en-2-yl ester;

Isobutyric acid (1S,5S,6S)-6-(2-{[3-(4,7-dimethoxy-1H-benzoimidazol-2-yl)-propyl]-methyl-amino}-ethyl)-8-phenyl-bicyclo[3.2.2]non-8-en-6-yl ester;

Isobutyric acid (1R,5R,6R)-6-(2-{[3-(4,7-dimethoxy-1H-benzoimidazol-2-yl)-propyl]-methyl-amino}-ethyl)-8-phenyl-bicyclo[3.2.2]non-8-en-6-yl ester;

Isobutyric acid (1S,2S,4S)-2-(2-{methyl-[3-(4-methyl-5-phenyl-1H-imidazol-2-yl)-propyl]-amino}-ethyl)-5-phenyl-bicyclo[2.2.2]oct-5-en-2-yl ester;

Isobutyric acid (1R,2R,4R)-2-(2-{methyl-[3-(4-methyl-5-phenyl-1H-imidazol-2-yl)-propyl]-amino}-ethyl)-5-phenyl-bicyclo[2.2.2]oct-5-en-2-yl ester;

Isobutyric acid (1S,2S,4S)-2-[2-({3-[5-(2-methoxy-phenyl)-1H-imidazol-2-yl]-propyl}-methyl-amino)-ethyl]-5-phenyl-bicyclo[2.2.2]oct-5-en-2-yl ester;

Isobutyric acid (1R,2R,4R)-2-[2-({3-[5-(2-methoxy-phenyl)-1H-imidazol-2-yl]-propyl}-methyl-amino)-ethyl]-5-phenyl-bicyclo[2.2.2]oct-5-en-2-yl ester;

Isobutyric acid (1R,2R,4R,5R)-2-(2-{[3-(1H-benzoimidazol-2-yl)-propyl]-methyl-amino}-ethyl)-5-phenyl-bicyclo[2.2.2]oct-2-yl ester;

Isobutyric acid (1S,2S,4S,5R)-2-(2-{[3-(1H-benzoimidazol-2-yl)-propyl]-methyl-amino}-ethyl)-5-phenyl-bicyclo[2.2.2]oct-2-yl ester;

Isobutyric acid (1R,2R,4R,5S)-2-(2-{[3-(1H-benzoimidazol-2-yl)-propyl]-methyl-amino}-ethyl)-5-phenyl-bicyclo[2.2.2]oct-2-yl ester;

Isobutyric acid (1S,2S,4S,5S)-2-(2-{[3-(1H-benzoimidazol-2-yl)-propyl]-methyl-amino}-ethyl)-5-phenyl-bicyclo[2.2.2]oct-2-yl ester;

Isobutyric acid (1R,2R,4R)-2-(2-{[3-(1H-benzoimidazol-2-yl)-propyl]-methyl-amino}-ethyl)-bicyclo[2.2.2]oct-5-en-2-yl ester;

Isobutyric acid (1S,2S,4S)-2-(2-{[3-(1H-benzoimidazol-2-yl)-propyl]-methyl-amino}-ethyl)-bicyclo[2.2.2]oct-5-en-2-yl ester;

Isobutyric acid (1R,2R,4R,5R)-2-(2-{[3-(1H-benzoimidazol-2-yl)-propyl]-methyl-amino}-ethyl)-5-methoxy-5-phenyl-bicyclo[2.2.2]oct-2-yl ester;

Isobutyric acid (1S,2S,4S,5S)-2-(2-{[3-(1H-benzoimidazol-2-yl)-propyl]-methyl-amino}-ethyl)-5-methoxy-5-phenyl-bicyclo[2.2.2]oct-2-yl ester;

Isobutyric acid (1R,2S,4R,5S)-2-(2-{[3-(1H-benzoimidazol-2-yl)-propyl]-methyl-amino}-ethyl)-5-methoxy-5-phenyl-bicyclo[2.2.2]oct-2-yl ester; and Isobutyric acid (1S,2R,4S,5R)-2-(2-{[3-(1H-benzoimidazol-2-yl)-propyl]-methyl-amino}-ethyl)-5-methoxy-5-phenyl-bicyclo[2.2.2]oct-2-yl ester;

in a free or pharmaceutically acceptable salt form.

24. The method according to claim 23, wherein the disease or disorder is hypertension.

25. The method according to claim 21 wherein the compound is a compound of formula (I)

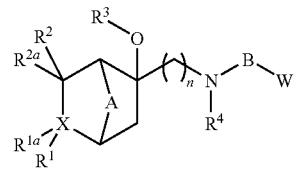

Formula (I)

wherein

X represents a carbon atom; $R^{1a}$ and $R^{2a}$ together form a bond; $R^1$ represents unsubstituted aryl; $R^2$ represents hydrogen; and A represents —$(CH_2)_p$—, wherein p represents the integer 2 or 3;

wherein the configuration of the bridged cyclohexene moiety is such that the $R^3$—O— substituent and the bridge A of the cyclohexene moiety are in cis relation;

$R^3$ represents —CO—$R^{31}$; and $R^{31}$ represents $(C_{1-5})$alkyl;

B represents a group —$(CH_2)_m$—, and m represents the integer 3;

n represents the integer 2;

$R^4$ represents $(C_{1-5})$alkyl; and

W represents

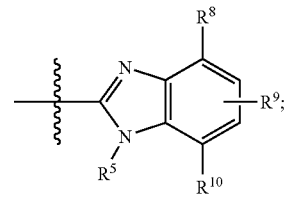

wherein $R^9$ and $R^{10}$ are independently $(C_{1-5})$alkoxy, and $R^5$ and $R^8$ represent hydrogen;

in a free or pharmaceutically acceptable salt form.

26. The method according to claim 21 wherein the compound is isobutyric acid (1R,2R,4R)-2-(2-{[3-(4,7-dimethoxy-1H-benzoimidazol-2-yl)-propyl]-methyl-amino}-ethyl)-5-phenyl-bicyclo[2.2.2]oct-5-en-2-yl ester in a free or pharmaceutically acceptable salt form.

27. The method according to claim 21 wherein the compound is isobutyric acid (1S,2S,4S)-2-(2-{[3-(4,7-dimethoxy-1H-benzoimidazol-2-yl)-propyl]-methyl-amino}-ethyl)-5-phenyl-bicyclo[2.2.2]oct-5-en-2-yl ester in a free or pharmaceutically acceptable salt form.

\* \* \* \* \*

UNITED STATES PATENT AND TRADEMARK OFFICE
CERTIFICATE OF CORRECTION

PATENT NO. : 8,202,885 B2  
APPLICATION NO. : 12/597817  
DATED : June 19, 2012  
INVENTOR(S) : Kurt Hilpert et al.

It is certified that error appears in the above-identified patent and that said Letters Patent is hereby corrected as shown below:

IN THE CLAIMS:

Column 122, Claim 11, lines 38-40 which reads "(1R,2S,4S)-2-(2-{[3-(1H-Benzoimidazol-2-yl)-propyl]-methyl-amino)-ethyl)-5-(3-methoxy-phenyl)-bicyclo[2.2.2]oct-5-en-2-ol;" should be corrected to read "(1S,2S,4S)-2-(2-{[3-(1H-Benzoimidazol-2-yl)-propyl]-methyl-amino)-ethyl)-5-(3-methoxy-phenyl)-bicyclo[2.2.2]oct-5-en-2-ol;"

Column 122, Claim 11, lines 44-46 which reads "(1R,2S,4S)-2-(2-{[3-(1H-Benzoimidazol-2-yl)-propyl]-methyl-amino)-ethyl)-5-(2,6-dimethyl-phenyl)-bicyclo[2.2.2]oct-5-en-2-ol;" should be corrected to read "(1S,2S,4S)-2-(2-{[3-(1H-Benzoimidazol-2-yl)-propyl]-methyl-amino}-ethyl)-5-(2,6-dimethyl-phenyl)-bicyclo[2.2.2]oct-5-en-2-ol;"

Column 126, Claim 11, lines 8-10 which reads "(1S,2S,4R)-2-(2-{[3-(1H-Benzoimidazol-2-yl)-propyl]-methyl-amino}-ethyl)-5-methyl-6-phenyl-bicyclo[2.2.2]oct-5-en-2-ol;" should be corrected to read "(1R,2S,4R)-2-(2-{[3-(1H-Benzoimidazol-2-yl)-propyl]-methyl-amino}-ethyl)-5-methyl-6-phenyl-bicyclo[2.2.2]oct-5-en-2-ol;"

Column 127, Claim 11, lines 20-22 which reads "(1S,2S,4R,5S)-2-(2-{[341H-Benzoimidazol-2-yl)-propyl]-methyl-amino}-ethyl)-5-methoxy-5-phenyl-bicyclo[2.2.2]octan-2-ol;" should be corrected to read "(1R,2S,4R,5S)-2-(2-{[3-(1H-Benzoimidazol-2-yl)-propyl]-methyl-amino}-ethyl)-5-methoxy-5-phenyl-bicyclo[2.2.2]octan-2-ol;"

Column 127, Claim 11, lines 23-25 which reads "(1R,2R,4S,5R)-2-(2-{[3-(1H-Benzoimidazol-2-yl)-propyl]-methyl-amino}-ethyl)-5-methoxy-5-phenyl-bicyclo[2.2.2]octan-2-ol;" should be corrected to read "(1S,2R,4S,5R)-2-(2-{[3-(1H-Benzoimidazol-2-yl)-propyl]-methyl-amino}-ethyl)-5-methoxy-5-phenyl-bicyclo[2.2.2]octan-2-ol;"

Signed and Sealed this  
Ninth Day of October, 2012

David J. Kappos  
*Director of the United States Patent and Trademark Office*

CERTIFICATE OF CORRECTION (continued)
U.S. Pat. No. 8,202,885 B2

Column 129, Claim 11, lines 36-38 which reads "Isobutyric acid (1R,2R,4R)-2-(2-{[341H-benzoimidazol-2-yl)-propyl]-methyl-amino}-ethyl)-5-oxazol-2-yl-bicyclo[2.2.2]oct-5-en-2-yl ester;" should be corrected to read "Isobutyric acid (1R,2R,4R)-2-(2-{[3-(1H-benzoimidazol-2-yl)-propyl]-methyl-amino}-ethyl)-5-oxazol-2-yl-bicyclo[2.2.2]oct-5-en-2-yl ester;"

Column 135, Claim 18, line 65 which reads "wherein R9 and R19 are independently (C1-5)alkoxy," should be corrected to read "wherein R8 and R10 are independently (C1-5)alkoxy,"

Column 136, Claim 23, lines 53-55 which reads "(1S,2S,4S)-2-(2-{[3-(1H-Benzoimidazol-2-yl)-propyl]-methyl-amino}-ethyl)-5-o-tolyl-bicyclo[2.2.2]oct-5-en-2-ol;" should be corrected to read "(1S,2S,4S)-2-(2-{[3-(1H-Benzoimidazol-2-yl)-propyl]-methyl-amino}-ethyl)-5-p-tolyl-bicyclo[2.2.2]oct-5-en-2-ol;"

Column 136, Claim 23, lines 56-58 which reads "(1R,2R,4R)-2-(2-{[3-(1H-Benzoimidazol-2-yl)-propyl]-methyl-amino}-ethyl)-5-O-tolyl-bicyclo[2.2.2]oct-5-en-2-ol;" should be corrected to read "(1R,2R,4R)-2-(2-{[3-(1H-Benzoimidazol-2-yl)-propyl]-methyl-amino}-ethyl)-5-p-tolyl-bicyclo[2.2.2]oct-5-en-2-ol;"

Column 137, Claim 23, lines 41-43 which reads "(1S,2R,4R)-2-(2-{[3-(1H-Benzoimidazol-2-yl)-propyl]-methyl-amino}-ethyl)-5-methyl-6-phenyl-bicyclo[2.2.2]oct-5-en-2-ol;" should be corrected to read "(1R,2R,4R)-2-(2-{[3-(1H-Benzoimidazol-2-yl)-propyl]-methyl-amino}-ethyl)-5-methyl-6-phenyl-bicyclo[2.2.2]oct-5-en-2-ol;"

Column 139, Claim 23, lines 65-67 which reads "(1R,2R,4S)-2-(2-{[3-(1H-Benzoimidazol-2-yl)-propyl]-methyl-amino}-ethyl)-5-methyl-6-phenyl-bicyclo[2.2.2]oct-5-en-2-ol;" should be corrected to read "(1S,2R,4S)-2-(2-{[3-(1H-Benzoimidazol-2-yl)-propyl]-methyl-amino}-ethyl)-5-methyl-6-phenyl-bicyclo[2.2.2]oct-5-en-2-ol;"

Column 140, Claim 23, lines 1-3 which reads "(1S,2S,4R)-2-(2-{[3-(1H-Benzoimidazol-2-yl)-propyl]-methyl-amino}-ethyl)-5-methyl-6-phenyl-bicyclo[2.2.2]oct-5-en-2-ol;" should be corrected to read "(1R,2S,4R)-2-(2-{[3-(1H-Benzoimidazol-2-yl)-propyl]-methyl-amino}-ethyl)-5-methyl-6-phenyl-bicyclo[2.2.2]oct-5-en-2-ol;"

Column 148, Claim 25, line 52 which reads "wherein R9 and R10 are independently (C1-5)alkoxy," should be corrected to read "wherein R8 and R10 are independently (C1-5)alkoxy,"